US012584174B2

(12) United States Patent
Horowitz et al.

(10) Patent No.: US 12,584,174 B2
(45) Date of Patent: Mar. 24, 2026

(54) TREATMENT OF PSORIASIS WITH INTERFERON INDUCED HELICASE C DOMAIN 1 (IFIH1) INHIBITORS

(71) Applicant: Regeneron Pharmaceuticals, Inc., Tarrytown, NY (US)

(72) Inventors: Julie E. Horowitz, Tarrytown, NY (US); Manuel Allen Revez Ferreira, Tarrytown, NY (US); Katherine Siminovitch, Tarrytown, NY (US); Aris Baras, Tarrytown, NY (US); Lori Khrimian, Tarrytown, NY (US); Katia Karalis, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 841 days.

(21) Appl. No.: 17/836,735

(22) Filed: Jun. 9, 2022

(65) Prior Publication Data

US 2023/0037582 A1      Feb. 9, 2023

Related U.S. Application Data

(60) Provisional application No. 63/209,075, filed on Jun. 10, 2021.

(51) Int. Cl.
| | |
|---|---|
| *C12Q 1/6883* | (2018.01) |
| *A61K 31/7105* | (2006.01) |
| *A61K 38/46* | (2006.01) |
| *A61K 45/06* | (2006.01) |
| *C12N 15/113* | (2010.01) |

(52) U.S. Cl.
CPC ........ *C12Q 1/6883* (2013.01); *A61K 31/7105* (2013.01); *A61K 38/465* (2013.01); *A61K 45/06* (2013.01); *C12N 15/1138* (2013.01); *C12N 2310/11* (2013.01); *C12N 2310/14* (2013.01); *C12N 2310/531* (2013.01); *C12N*

*2320/31* (2013.01); *C12Q 2600/118* (2013.01); *C12Q 2600/156* (2013.01)

(58) Field of Classification Search
CPC ............ C12Q 1/6883; C12Q 2600/118; C12Q 2600/156; A61K 31/7105; A61K 38/465; A61K 45/06; A61K 31/713; A61K 31/7088; A61K 48/00; C12N 15/1138; C12N 2310/11; C12N 2310/14; C12N 2310/531; C12N 2320/31; C12N 2310/20; C12N 15/1137; C12N 15/113; C12N 9/22; C12Y 306/04013; C12Y 203/02; A61P 17/06
See application file for complete search history.

(56) References Cited

U.S. PATENT DOCUMENTS

| | | | |
|---|---|---|---|
| 2021/0254056 A1* | 8/2021 | Liu | G16B 20/50 |
| 2023/0181466 A1* | 6/2023 | Staufer | A61K 9/1272 |
| | | | 424/450 |

OTHER PUBLICATIONS

Asgari et al (Date Published: Aug. 1, 2017, Biological Sciences) {herein Asgari}. (Year: 2017).*
Racz et al. (2011, Journal of Investigative Dermatology) {herein Racz} (Year: 2011).*
Singh et al. (Current Protein and Peptide Science, 2017) (Year: 2017).*
Zhang et al. (Structure, 2018) (Year: 2018).*
Cananzi et al (2021, Hum. Genet.) {herein Cananzi} (Year: 2021).*
Genecards et al (2025, The Human Gene Database) {herein GeneCards} (Year: 2025).*

* cited by examiner

*Primary Examiner* — Manjunath N Rao
*Assistant Examiner* — Erica Nicole Jones-Foster
(74) *Attorney, Agent, or Firm* — Armstrong Teasdale LLP

(57) ABSTRACT

The present disclosure provides methods of treating subjects having psoriasis, and methods of identifying subjects having an increased risk of developing psoriasis.

3 Claims, 5 Drawing Sheets

Specification includes a Sequence Listing.

B)

C)

TREATMENT OF PSORIASIS WITH INTERFERON INDUCED HELICASE C DOMAIN 1 (IFIH1) INHIBITORS

REFERENCE TO SEQUENCE LISTING

This application includes a Sequence Listing submitted electronically as a text file named 18923800301SEQ, created on Jun. 9, 2022, with a size of 228 kilobytes. The Sequence Listing is incorporated herein by reference.

FIELD

The present disclosure relates generally to the treatment of subjects having psoriasis with Interferon Induced Helicase C Domain 1 (IFIH1) inhibitors and/or Tripartite Motif Containing 65 (TRIM65) inhibitors, and methods of identifying subjects having an increased risk of developing psoriasis.

BACKGROUND

Psoriasis is an autoimmune skin disease marked by the presence of small elevations of the skin as well as silvery scales. These psoriatic lesions occur most often on the elbows, knees, trunk and scalp. In the area where scales have been shed, tiny bleeding points called "Auspitz sign" appear. The major pathophysiological events involved in the disease process are accelerated epidermal proliferation and metabolic activity, proliferation of capillaries in the dermal region, and invasion of the dermis and epidermis by inflammatory cells. Coal tar and salicylic acid are the only two Category I drugs mentioned in the Final Monograph for dandruff, seborrheic and psoriatic drugs. There are a number of prescription products that are also useful, such as theophylline, which arrests the proliferation of cells during the metaphase stage of cell division.

Psoriasis is believed to be a genetic disease that is triggered by environmental factors. For example, symptoms often worsen during winter and with certain medications, such as beta blockers or NSAIDs. Infections and psychological stress may also be triggers. These periods of increased disease are called flare-ups. There are five main types of psoriasis: plaque, guttate, inverse, pustular, and erythrodermic. Plaque psoriasis, also known as psoriasis vulgaris, is the most common, making up about 90 percent of cases. It typically presents as red patches with white scales on top. Areas of the body most commonly affected are the back of the for psoriasis, shins, navel area, and scalp. Guttate psoriasis has drop-shaped lesions. Pustular psoriasis presents as small non-infectious pus-filled blisters. Erythrodermic psoriasis occurs when the rash becomes very widespread, and can develop from any of the other types. In most affected people, changes in color of fingernails and toenails often occur.

The underlying mechanism of psoriasis involves the immune system reacting to skin cells. Skin cells are replaced every three to five days in psoriasis rather than the usual 28 to 30 days. These changes are believed to stem from the premature maturation of keratinocytes induced by an inflammatory cascade in the dermis involving dendritic cells, macrophages, and T cells. These immune cells move from the dermis to the epidermis and secrete inflammatory chemical signals (cytokines) such as interleukins, tumor necrosis factor-a, interleukin-1b, interleukin-6, and interleukin-22. These secreted inflammatory signals are believed to stimulate keratinocytes to proliferate.

Interferon Induced Helicase C Domain 1 (IFIH1) encodes an innate immune receptor which acts as a cytoplasmic sensor of viral nucleic acids and plays a major role in sensing viral infection and in the activation of a cascade of antiviral responses including the induction of type I interferons and proinflammatory cytokines. Its ligands include mRNA lacking 2'-O-methylation at their 5' cap and long-dsRNA (>1 kb in length). Upon ligand binding, IFIH1 associates with mitochondria antiviral signaling protein (MAVS/IPS1) which activates the IKK-related kinases TBK1 and IKBKE which phosphorylate interferon regulatory factors IRF3 and IRF7, which in turn activate transcription of antiviral immunological genes, including interferons (IFNs), IFN-alpha and IFN-beta. IFIH1 is responsible for detecting the Picornaviridae family members such as encephalomyocarditis virus (EMCV) and mengo encephalomyocarditis virus (ENMG). IFIH1 also plays an important role in amplifying innate immune signaling through recognition of RNA metabolites that are produced during virus infection by ribonuclease L (RNase L). IFIH1 may play a role in enhancing natural killer cell function and may be involved in growth inhibition and apoptosis in several tumor cell lines.

Tripartite Motif Containing 65 (TRIM65) is an E3 ubiquitin ligase and a regulator of a variety of cellular processes, as well as tumor progression. By sequence consensus, TRIM65 belongs to the tripartite motif family. TRIM65 was originally identified as a gene with SNPs associated with cerebral white matter lesions, but was later shown to be a cofactor for the regulation of microRNA function. TRIM65 regulates microRNA activity by ubiquitination of TNRC6 while establishing its E3 ubiquitin ligase activity. Like other TRIM members that are involved in the immune response, TRIM65 also participates in the virus-induced innate immune response by ubiquitination of substrate proteins.

SUMMARY

The present disclosure provides methods of treating a subject having psoriasis, the methods comprising administering an IFIH1 inhibitor to the subject.

The present disclosure also provides methods of treating a subject having guttate psoriasis, the methods comprising administering an IFIH1 inhibitor to the subject.

The present disclosure also provides methods of treating a subject having plaque psoriasis, the methods comprising administering an IFIH1 inhibitor to the subject.

The present disclosure also provides methods of treating a subject having inverse psoriasis, the methods comprising administering an IFIH1 inhibitor to the subject.

The present disclosure also provides methods of treating a subject having pustular psoriasis, the methods comprising administering an IFIH1 inhibitor to the subject.

The present disclosure also provides methods of treating a subject having erythrodermic psoriasis, the methods comprising administering an IFIH1 inhibitor to the subject.

The present disclosure also provides methods of treating a subject with a therapeutic agent that treats or inhibits psoriasis, wherein the subject has psoriasis, the methods comprising the steps of: determining whether the subject has an IFIH1 missense variant nucleic acid molecule encoding an IFIH1 predicted loss-of-function polypeptide by: obtaining or having obtained a biological sample from the subject; and performing or having performed a sequence analysis on the biological sample to determine if the subject has a genotype comprising the IFIH1 missense variant nucleic acid molecule; and administering or continuing to administer the therapeutic agent that treats or inhibits psoriasis in a standard dosage amount to a subject that is IFIH1 reference, and/or administering an IFIH1 inhibitor to the subject; administering or continuing to administer the therapeutic agent that treats or inhibits psoriasis in an amount that is the same as or less than a standard dosage amount to a subject that is heterozygous for the IFIH1 missense variant nucleic acid molecule, and/or administering an IFIH1 inhibitor to the subject; or administering or continuing to administer the therapeutic agent that treats or inhibits psoriasis in an amount that is the same as or less than a standard dosage amount to a subject that is homozygous for the IFIH1 missense variant nucleic acid molecule; wherein the presence of a genotype having the IFIH1 missense variant nucleic acid molecule encoding the IFIH1 predicted loss-of-function polypeptide indicates the subject has a decreased risk of developing psoriasis.

The present disclosure also provides methods of identifying a subject having an increased risk for developing psoriasis, the methods comprising: determining or having determined the presence or absence of an IFIH1 missense variant nucleic acid molecule encoding an IFIH1 predicted loss-of-function polypeptide in a biological sample obtained from the subject; wherein: when the subject is IFIH1 reference, then the subject has an increased risk for developing psoriasis; and when the subject is heterozygous or homozygous for the IFIH1 missense variant nucleic acid molecule encoding an IFIH1 predicted loss-of-function polypeptide, then the subject has a decreased risk for developing psoriasis.

The present disclosure also provides therapeutic agents that treat or inhibit psoriasis for use in the treatment of psoriasis in a subject having a genomic nucleic acid molecule having a nucleotide sequence encoding an IFIH1 polypeptide, wherein the nucleotide sequence comprises a cytosine at a position corresponding to position 38,690 according to SEQ ID NO:2, or the complement thereof.

The present disclosure also provides IFIH1 inhibitors for use in the treatment of psoriasis in a subject that is IFIH1 reference or that is heterozygous for an IFIH1 missense variant nucleic acid molecule encoding an IFIH1 predicted loss-of-function polypeptide.

The present disclosure also provides methods of treating a subject having psoriasis, the methods comprising administering a TRIM65 inhibitor to the subject.

The present disclosure also provides methods of treating a subject with a therapeutic agent that treats or inhibits psoriasis, wherein the subject has psoriasis, the methods comprising the steps of: determining whether the subject has a TRIM65 missense variant nucleic acid molecule encoding a TRIM65 predicted loss-of-function polypeptide by: obtaining or having obtained a biological sample from the subject; and performing or having performed a sequence analysis on the biological sample to determine if the subject has a genotype comprising the TRIM65 missense variant nucleic acid molecule; and administering or continuing to administer the therapeutic agent that treats or inhibits psoriasis in a standard dosage amount to a subject that is TRIM65 reference, and/or administering a TRIM65 inhibitor to the subject; administering or continuing to administer the therapeutic agent that treats or inhibits psoriasis in an amount that is the same as or less than a standard dosage amount to a subject that is heterozygous for the TRIM65 missense variant nucleic acid molecule, and/or administering an TRIM65 inhibitor to the subject; or administering or continuing to administer the therapeutic agent that treats or inhibits psoriasis in an amount that is the same as or less than a standard dosage amount to a subject that is homozygous for the TRIM65 missense variant nucleic acid molecule; wherein the presence of a genotype having the TRIM65 missense variant nucleic acid molecule encoding the TRIM65 predicted loss-of-function polypeptide indicates the subject has a decreased risk of developing psoriasis.

The present disclosure also provides methods of identifying a subject having an increased risk for developing psoriasis, the methods comprising: determining or having determined the presence or absence of a TRIM65 missense variant nucleic acid molecule encoding a TRIM65 predicted loss-of-function polypeptide in a biological sample obtained from the subject; wherein: when the subject is TRIM65 reference, then the subject has an increased risk for developing psoriasis; and when the subject is heterozygous or homozygous for the TRIM65 missense variant nucleic acid molecule encoding a TRIM65 predicted loss-of-function polypeptide, then the subject has a decreased risk for developing psoriasis.

The present disclosure also provides therapeutic agents that treat or inhibit psoriasis for use in the treatment of psoriasis in a subject having a TRIM65 missense variant nucleic acid molecule encoding a TRIM65 predicted loss-of-function polypeptide.

The present disclosure also provides TRIM65 inhibitors for use in the treatment of psoriasis in a subject that is TRIM65 reference or that is heterozygous for a TRIM65 missense variant nucleic acid molecule encoding a TRIM65 predicted loss-of-function polypeptide.

BRIEF DESCRIPTION OF THE DRAWINGS

The accompanying figures, which are incorporated in and constitute a part of this specification, illustrate several features of the present disclosure.

DESCRIPTION

Figure 1:
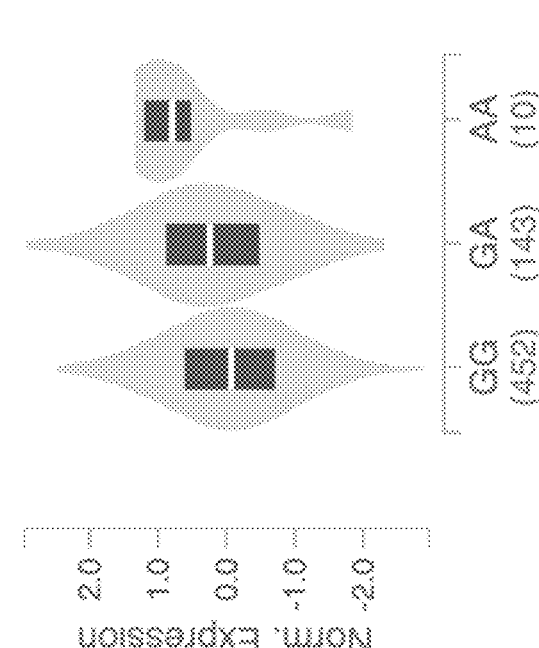
FIG. 1 shows common TRIM65 psoriasis variant is an eQTL for increased TRIM65 expression in skin.

Various terms relating to aspects of the present disclosure are used throughout the specification and claims. Such terms are to be given their ordinary meaning in the art, unless otherwise indicated. Other specifically defined terms are to be construed in a manner consistent with the definitions provided herein.

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-expressed basis for interpretation, including matters of logic with respect to arrangement of steps or operational flow, plain meaning derived from grammatical organization or punctuation, or the number or type of aspects described in the specification.

As used herein, the singular forms "a," "an" and "the" include plural referents unless the context clearly dictates otherwise.

As used herein, the term "about" means that the recited numerical value is approximate and small variations would not significantly affect the practice of the disclosed embodiments. Where a numerical value is used, unless indicated otherwise by the context, the term "about" means the numerical value can vary by ±10% and remain within the scope of the disclosed embodiments.

As used herein, the term "comprising" may be replaced with "consisting" or "consisting essentially of" in particular embodiments as desired.

As used herein, the term "isolated", in regard to a nucleic acid molecule or a polypeptide, means that the nucleic acid molecule or polypeptide is in a condition other than its native environment, such as apart from blood and/or animal tissue. In some embodiments, an isolated nucleic acid molecule or polypeptide is substantially free of other nucleic acid molecules or other polypeptides, particularly other nucleic acid molecules or polypeptides of animal origin. In some embodiments, the nucleic acid molecule or polypeptide can be in a highly purified form, i.e., greater than 95% pure or greater than 99% pure. When used in this context, the term "isolated" does not exclude the presence of the same nucleic acid molecule or polypeptide in alternative physical forms, such as dimers or Alternately phosphorylated or derivatized forms.

As used herein, the terms "nucleic acid", "nucleic acid molecule", "nucleic acid sequence", "polynucleotide", or "oligonucleotide" can comprise a polymeric form of nucleotides of any length, can comprise DNA and/or RNA, and can be single-stranded, double-stranded, or multiple stranded. One strand of a nucleic acid also refers to its complement.

As used herein, the term "subject" includes any animal, including mammals. Mammals include, but are not limited to, farm animals (such as, for example, horse, cow, pig), companion animals (such as, for example, dog, cat), laboratory animals (such as, for example, mouse, rat, rabbits), and non-human primates. In some embodiments, the subject is a human. In some embodiments, the human is a patient under the care of a physician.

A rare variant in the IFIH1 gene associated with a decreased risk of developing psoriasis in humans has been identified in accordance with the present disclosure. For example, a genetic alteration that changes the guanine of position 38,690 in the human IFIH1 reference (see, SEQ ID NO:1) to cytosine has been observed to indicate that the human having such an alteration may have a decreased risk of developing psoriasis. Altogether, the genetic analyses described herein surprisingly indicate that the IFIH1 gene and, in particular, a variant in the IFIH1 gene, associates with a decreased risk of developing psoriasis. Therefore, subjects that are IFIH1 reference that have an increased risk of developing psoriasis may be treated such that psoriasis is prevented, the symptoms thereof are reduced, and/or development of symptoms is repressed. Accordingly, the present disclosure provides methods of leveraging the identification of such variants in subjects to identify or stratify risk in such subjects of developing psoriasis, such as plaque psoriasis, guttate psoriasis, inverse psoriasis, pustular psoriasis and/or erythrodermic psoriasis, or to diagnose subjects as having an increased risk of developing psoriasis, such as plaque psoriasis, guttate psoriasis, inverse psoriasis, pustular psoriasis and/or erythrodermic psoriasis, such that subjects at risk or subjects with active disease may be treated accordingly.

A TRIM65 Gly382Arg variant has been observed to alter the cellular localization and expression levels of TRIM65. TRIM65 Gly382Arg displays reduced colocalization with its binding partner IFIH1. This observation, along with reduced interferon-stimulated response element (ISRE) activity in response to stimulation by IFN-α or poly(i:c) in cells transfected with a TRIM65 Gly382Arg construct, suggest that this variant likely leads to reduced interferon pathway activation, which may in turn be protective against psoriasis.

It has been further observed in accordance with the present disclosure that an aggregate burden of variations in IFIH1 associate with a lower risk of developing psoriasis. It has been also observed in accordance with the present disclosure that an aggregate burden of IFIH1 missense variant nucleic acid molecules encoding IFIH1 predicted loss-of-function polypeptides have a cumulative protective effect in reducing the risk of developing psoriasis, such as plaque psoriasis, guttate psoriasis, inverse psoriasis, pustular psoriasis and/or erythrodermic psoriasis. Therefore, it is believed that humans having psoriasis may be treated with molecules that inhibit IFIH1. Accordingly, the present disclosure provides methods for leveraging the identification of such variants, and an aggregation burden of having such variants, in subjects to identify or stratify risk in such subjects of psoriasis, or to diagnose subjects as having psoriasis, such that subjects at risk or subjects with active disease may be treated.

For purposes of the present disclosure, any particular subject can be categorized as having one of three IFIH1 genotypes: i) IFIH1 reference; ii) heterozygous for an IFIH1 missense variant nucleic acid molecule encoding IFIH1 predicted loss-of-function polypeptide; or iii) homozygous for an IFIH1 missense variant nucleic acid molecule encoding IFIH1 predicted loss-of-function polypeptide. A subject is IFIH1 reference when the subject does not have a copy of an IFIH1 missense variant nucleic acid molecule encoding IFIH1 predicted loss-of-function polypeptide. A subject is heterozygous for an IFIH1 missense variant nucleic acid molecule encoding IFIH1 predicted loss-of-function polypeptide when the subject has a single copy of an IFIH1 missense variant nucleic acid molecule encoding IFIH1 predicted loss-of-function polypeptide. An IFIH1 missense variant nucleic acid molecule encoding IFIH1 predicted loss-of-function polypeptide is any IFIH1 nucleic acid molecule (such as, a genomic nucleic acid molecule, an mRNA molecule, or a cDNA molecule) encoding an IFIH1 polypeptide having a partial loss-of-function, a complete loss-of-function, a predicted partial loss-of-function, or a predicted complete loss-of-function. A subject who has an IFIH1 polypeptide having a partial loss-of-function (or predicted partial loss-of-function) is hypomorphic for IFIH1. In some embodiments, the IFIH1 missense variant nucleic acid molecule encoding IFIH1 predicted loss-of-function polypeptide is an IFIH1 genomic nucleic acid molecule comprising a cytosine at a position corresponding to position 38,690 according to SEQ ID NO:2. A subject is homozygous for an IFIH1 missense variant nucleic acid molecule encoding IFIH1 predicted loss-of-function polypeptide when the subject has two copies of an IFIH1 missense variant nucleic acid molecule encoding IFIH1 predicted loss-of-function polypeptide.

For subjects that are genotyped or determined to be IFIH1 reference, such subjects have an increased risk of developing psoriasis, such as plaque psoriasis, guttate psoriasis, inverse psoriasis, pustular psoriasis, and/or erythrodermic psoriasis. For subjects that are genotyped or determined to be either IFIH1 reference or heterozygous for an IFIH1 missense variant nucleic acid molecule encoding IFIH1 predicted loss-of-function polypeptide, such subjects can be treated with an IFIH1 inhibitor.

In any of the embodiments described herein, the IFIH1 missense variant nucleic acid molecule encoding IFIH1 predicted loss-of-function polypeptide can be any IFIH1 nucleic acid molecule (such as, for example, genomic nucleic acid molecule, mRNA molecule, or cDNA molecule) encoding an IFIH1 polypeptide having a partial loss-of-function, a complete loss-of-function, a predicted partial loss-of-function, or a predicted complete loss-of-function. For example, the IFIH1 missense variant nucleic acid molecule encoding IFIH1 predicted loss-of-function polypeptide comprises a cytosine at a position corresponding to position 38,690 according to SEQ ID NO:2.

In any of the embodiments described herein, the IFIH1 predicted loss-of-function polypeptide can be any IFIH1 polypeptide having a partial loss-of-function, a complete loss-of-function, a predicted partial loss-of-function, or a predicted complete loss-of-function. In any of the embodiments described herein, the IFIH1 predicted loss-of-function polypeptide can be any of the IFIH1 polypeptides described herein.

For purposes of the present disclosure, any particular subject can be categorized as having one of three TRIM65 genotypes: i) TRIM65 reference; ii) heterozygous for a TRIM65 missense variant nucleic acid molecule encoding a TRIM65 predicted loss-of-function polypeptide; or iii) homozygous for a TRIM65 missense variant nucleic acid molecule encoding a TRIM65 predicted loss-of-function polypeptide. A subject is TRIM65 reference when the subject does not have a copy of a TRIM65 missense variant nucleic acid molecule encoding a TRIM65 predicted loss-of-function polypeptide. A subject is heterozygous for a TRIM65 missense variant nucleic acid molecule encoding a TRIM65 predicted loss-of-function polypeptide when the subject has a single copy of a TRIM65 missense variant nucleic acid molecule encoding a TRIM65 predicted loss-of-function polypeptide. A TRIM65 missense variant nucleic acid molecule encoding A TRIM65 predicted loss-of-function polypeptide is any TRIM65 nucleic acid molecule (such as, a genomic nucleic acid molecule, an mRNA molecule, or a cDNA molecule) encoding a TRIM65 polypeptide having a partial loss-of-function, a complete loss-of-function, a predicted partial loss-of-function, or a predicted complete loss-of-function. A subject who has a TRIM65 polypeptide having a partial loss-of-function (or predicted partial loss-of-function) is hypomorphic for TRIM65. In some embodiments, the TRIM65 predicted loss-of-function polypeptide is TRIM65 Gly382Arg. A subject is homozygous for a TRIM65 missense variant nucleic acid molecule encoding a TRIM65 predicted loss-of-function polypeptide when the subject has two copies of a TRIM65 missense variant nucleic acid molecule encoding a TRIM65 predicted loss-of-function polypeptide.

For subjects that are genotyped or determined to be TRIM65 reference, such subjects have an increased risk of developing psoriasis, such as plaque psoriasis, guttate psoriasis, inverse psoriasis, pustular psoriasis, and/or erythrodermic psoriasis. For subjects that are genotyped or determined to be either TRIM65 reference or heterozygous for a TRIM65 missense variant nucleic acid molecule encoding a TRIM65 predicted loss-of-function polypeptide, such subjects can be treated with a TRIM65 inhibitor.

In any of the embodiments described herein, the TRIM65 missense variant nucleic acid molecule encoding a TRIM65 predicted loss-of-function polypeptide can be any TRIM65 nucleic acid molecule (such as, for example, genomic nucleic acid molecule, mRNA molecule, or cDNA molecule) encoding a TRIM65 polypeptide having a partial loss-of-function, a complete loss-of-function, a predicted partial loss-of-function, or a predicted complete loss-of-function. For example, the TRIM65 missense variant nucleic acid molecule encoding a TRIM65 predicted loss-of-function polypeptide can encode TRIM65 Gly382Arg.

In any of the embodiments described herein, the TRIM65 predicted loss-of-function polypeptide can be any TRIM65 polypeptide having a partial loss-of-function, a complete loss-of-function, a predicted partial loss-of-function, or a predicted complete loss-of-function. In any of the embodiments described herein, the TRIM65 predicted loss-of-function polypeptide can be any of the TRIM65 polypeptides described herein.

In any of the embodiments described herein, psoriasis is plaque psoriasis, guttate psoriasis, inverse psoriasis, pustular psoriasis, or erythrodermic psoriasis, or any combination thereof. In any of the embodiments described herein, the psoriasis is guttate psoriasis. In any of the embodiments described herein, the psoriasis is plaque psoriasis. In any of the embodiments described herein, the psoriasis is inverse psoriasis. In any of the embodiments described herein, the psoriasis is pustular psoriasis. In any of the embodiments described herein, the psoriasis is erythrodermic psoriasis.

Symptoms of plaque psoriasis include raised, inflamed, red lesions on the skin covered with scaly, silvery plaques, typically occurring on elbows, knees, scalp, back, and lower back. Plaque psoriasis is also found on nails, legs, hands, genitals, and breasts. Symptoms of guttate psoriasis include small, pink, individual spots, typically occurring on torso, arms, and legs. Symptoms of inverse psoriasis include bright red lesions that are smooth and shiny, typically occurring on armpits, groin, under the breasts, and skin folds around the genitals and buttocks. Symptoms of pustular psoriasis include yellowish blisters of noninfectious pus surrounded by red skin, either localized to certain areas, such as hands and feet, or covering the body. Symptoms of erythrodermic psoriasis include widespread, fiery redness of the skin and shedding of scales in sheet typically covering most of the body surface.

The present disclosure provides methods of treating a subject having psoriasis, the methods comprising administering an IFIH1 inhibitor to the subject.

The present disclosure also provides methods of treating a subject having guttate psoriasis, the methods comprising administering an IFIH1 inhibitor to the subject.

The present disclosure also provides methods of treating a subject having plaque psoriasis, the methods comprising administering an IFIH1 inhibitor to the subject.

The present disclosure also provides methods of treating a subject having inverse psoriasis, the methods comprising administering an IFIH1 inhibitor to the subject.

The present disclosure also provides methods of treating a subject having pustular psoriasis, the methods comprising administering an IFIH1 inhibitor to the subject.

The present disclosure also provides methods of treating a subject having erythrodermic psoriasis, the methods comprising administering an IFIH1 inhibitor to the subject.

In some embodiments, the IFIH1 inhibitor comprises an inhibitory nucleic acid molecule. Examples of inhibitory nucleic acid molecules include, but are not limited to, antisense nucleic acid molecules, small interfering RNAs (siRNAs), and short hairpin RNAs (shRNAs). Such inhibitory nucleic acid molecules can be designed to target any region of an IFIH1 nucleic acid molecule. In some embodiments, the antisense RNA, siRNA, or shRNA hybridizes to a sequence within an IFIH1 genomic nucleic acid molecule or mRNA molecule and decreases expression of the IFIH1 polypeptide in a cell in the subject. In some embodiments, the IFIH1 inhibitor comprises an antisense molecule that hybridizes to an IFIH1 genomic nucleic acid molecule or mRNA molecule and decreases expression of the IFIH1 polypeptide in a cell in the subject. In some embodiments, the IFIH1 inhibitor comprises an siRNA that hybridizes to an IFIH1 genomic nucleic acid molecule or mRNA molecule and decreases expression of the IFIH1 polypeptide in a cell in the subject. In some embodiments, the IFIH1 inhibitor comprises an shRNA that hybridizes to an IFIH1 genomic nucleic acid molecule or mRNA molecule and decreases expression of the IFIH1 polypeptide in a cell in the subject.

The present disclosure also provides methods of treating a subject having psoriasis, the method comprising administering a TRIM65 inhibitor to the subject. In some embodiments, the psoriasis is guttate psoriasis, plaque psoriasis, inverse psoriasis, pustular psoriasis, or erythrodermic psoriasis. In some embodiments, the psoriasis is guttate psoriasis. In some embodiments, the psoriasis is plaque psoriasis. In some embodiments, the psoriasis is inverse psoriasis. In some embodiments, the psoriasis is pustular psoriasis. In some embodiments, the psoriasis is erythrodermic psoriasis.

In some embodiments, the TRIM65 inhibitor comprises an inhibitory nucleic acid molecule. Examples of inhibitory nucleic acid molecules include, but are not limited to, antisense nucleic acid molecules, small interfering RNAs (siRNAs), and short hairpin RNAs (shRNAs). Such inhibitory nucleic acid molecules can be designed to target any region of a TRIM65 nucleic acid molecule. In some embodiments, the antisense RNA, siRNA, or shRNA hybridizes to a sequence within a TRIM65 genomic nucleic acid molecule or mRNA molecule and decreases expression of the TRIM65 polypeptide in a cell in the subject. In some embodiments, the TRIM65 inhibitor comprises an antisense molecule that hybridizes to a TRIM65 genomic nucleic acid molecule or mRNA molecule and decreases expression of the TRIM65 polypeptide in a cell in the subject. In some embodiments, the TRIM65 inhibitor comprises an siRNA that hybridizes to a TRIM65 genomic nucleic acid molecule or mRNA molecule and decreases expression of the TRIM65 polypeptide in a cell in the subject. In some embodiments, the TRIM65 inhibitor comprises an shRNA that hybridizes to a TRIM65 genomic nucleic acid molecule or mRNA molecule and decreases expression of the TRIM65 polypeptide in a cell in the subject.

The inhibitory nucleic acid molecules can comprise RNA, DNA, or both RNA and DNA. The inhibitory nucleic acid molecules can also be linked or fused to a heterologous nucleic acid sequence, such as in a vector, or a heterologous label. For example, the inhibitory nucleic acid molecules can be within a vector or as an exogenous donor sequence comprising the inhibitory nucleic acid molecule and a heterologous nucleic acid sequence. The inhibitory nucleic acid molecules can also be linked or fused to a heterologous label. The label can be directly detectable (such as, for example, fluorophore) or indirectly detectable (such as, for example, hapten, enzyme, or fluorophore quencher). Such labels can be detectable by spectroscopic, photochemical, biochemical, immunochemical, or chemical means. Such labels include, for example, radiolabels, pigments, dyes, chromogens, spin labels, and fluorescent labels. The label can also be, for example, a chemiluminescent substance; a metal-containing substance; or an enzyme, where there occurs an enzyme-dependent secondary generation of signal. The term "label" can also refer to a "tag" or hapten that can bind selectively to a conjugated molecule such that the conjugated molecule, when added subsequently along with a substrate, is used to generate a detectable signal. For example, biotin can be used as a tag along with an avidin or streptavidin conjugate of horseradish peroxidate (HRP) to bind to the tag, and examined using a calorimetric substrate (such as, for example, tetramethylbenzidine (TMB)) or a fluorogenic substrate to detect the presence of HRP. Exemplary labels that can be used as tags to facilitate purification include, but are not limited to, myc, HA, FLAG or 3×FLAG, 6×His or polyhistidine, glutathione-S-transferase (GST), maltose binding protein, an epitope tag, or the Fc portion of immunoglobulin. Numerous labels include, for example, particles, fluorophores, haptens, enzymes and their calorimetric, fluorogenic and chemiluminescent substrates and other labels.

The inhibitory nucleic acid molecules can comprise, for example, nucleotides or non-natural or modified nucleotides, such as nucleotide analogs or nucleotide substitutes. Such nucleotides include a nucleotide that contains a modified base, sugar, or phosphate group, or that incorporates a non-natural moiety in its structure. Examples of non-natural nucleotides include, but are not limited to, dideoxynucleotides, biotinylated, aminated, deaminated, alkylated, benzylated, and fluorophor-labeled nucleotides.

The inhibitory nucleic acid molecules can also comprise one or more nucleotide analogs or substitutions. A nucleotide analog is a nucleotide which contains a modification to either the base, sugar, or phosphate moieties. Modifications to the base moiety include, but are not limited to, natural and synthetic modifications of A, C, G, and T/U, as well as different purine or pyrimidine bases such as, for example, pseudouridine, uracil-5-yl, hypoxanthin-9-yl (1), and 2-aminoadenin-9-yl. Modified bases include, but are not limited to, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo (such as, for example, 5-bromo), 5-trifluoromethyl and other 5-substituted uracils and cytosines, 7-methylguanine, 7-methyladenine, 8-azaguanine, 8-azaadenine, 7-deazaguanine, 7-deazaadenine, 3-deazaguanine, and 3-deazaadenine.

Nucleotide analogs can also include modifications of the sugar moiety. Modifications to the sugar moiety include, but are not limited to, natural modifications of the ribose and deoxy ribose as well as synthetic modifications. Sugar modifications include, but are not limited to, the following modifications at the 2' position: OH; F; O-, S-, or N-alkyl; O-, S-, or N-alkenyl; O-, S- or N-alkynyl; or O-alkyl-O-alkyl, wherein the alkyl, alkenyl, and alkynyl may be substituted or unsubstituted $C_{1-10}$alkyl or $C_{2-10}$alkenyl, and $C_{2-10}$alkynyl. Exemplary 2' sugar modifications also include, but are not limited to, —O[(CH$_2$)$_n$O]$_m$CH$_3$, —O(CH$_2$)$_n$OCH$_3$, —O(CH$_2$)$_n$NH$_2$, —O(CH$_2$)$_n$CH$_3$, —O(CH$_2$)$_n$—ONH$_2$, and —O(CH$_2$)$_n$ON[(CH$_2$)$_n$CH$_3$)]$_2$, where n and m, independently, are from 1 to about 10. Other modifications at the 2' position include, but are not limited to, $C_{1-10}$alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars can also include those that contain modifications at the bridging ring oxygen, such as CH$_2$ and S. Nucleotide sugar analogs can also have sugar mimetics, such as cyclobutyl moieties in place of the pentofuranosyl sugar.

Nucleotide analogs can also be modified at the phosphate moiety. Modified phosphate moieties include, but are not limited to, those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. These phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts, and free acid forms are also included. Nucleotide substitutes also include peptide nucleic acids (PNAs).

In some embodiments, the antisense nucleic acid molecules are gapmers, whereby the first one to seven nucleotides at the 5' and 3' ends each have 2'-methoxyethyl (2'-MOE) modifications. In some embodiments, the first five nucleotides at the 5' and 3' ends each have 2'-MOE modifications. In some embodiments, the first one to seven nucleotides at the 5' and 3' ends are RNA nucleotides. In some embodiments, the first five nucleotides at the 5' and 3' ends are RNA nucleotides. In some embodiments, each of the backbone linkages between the nucleotides is a phosphorothioate linkage.

In some embodiments, the siRNA molecules have termini modifications. In some embodiments, the 5' end of the antisense strand is phosphorylated. In some embodiments, 5'-phosphate analogs that cannot be hydrolyzed, such as 5'-(E)-vinyl-phosphonate are used.

In some embodiments, the siRNA molecules have backbone modifications. In some embodiments, the modified phosphodiester groups that link consecutive ribose nucleosides have been shown to enhance the stability and in vivo bioavailability of siRNAs The non-ester groups (—OH, =O) of the phosphodiester linkage can be replaced with sulfur, boron, or acetate to give phosphorothioate, boranophosphate, and phosphonoacetate linkages. In addition, substituting the phosphodiester group with a phosphotriester can facilitate cellular uptake of siRNAs and retention on serum components by eliminating their negative charge. In some embodiments, the siRNA molecules have sugar modifications. In some embodiments, the sugars are deprotonated (reaction catalyzed by exo- and endonucleases) whereby the 2'-hydroxyl can act as a nucleophile and attack the adjacent phosphorous in the phosphodiester bond. Such alternatives include 2'-O-methyl, 2'-O-methoxyethyl, and 2'-fluoro modifications.

In some embodiments, the siRNA molecules have base modifications. In some embodiments, the bases can be substituted with modified bases such as pseudouridine, 5'-methylcytidine, N6-methyladenosine, inosine, and N7-methylguanosine.

In some embodiments, the siRNA molecules are conjugated to lipids. Lipids can be conjugated to the 5' or 3' termini of siRNA to improve their in vivo bioavailability by allowing them to associate with serum lipoproteins. Representative lipids include, but are not limited to, cholesterol and vitamin E, and fatty acids, such as palmitate and tocopherol.

In some embodiments, a representative siRNA has the following formula:

```
Sense:
mN*mN*/i2FN/mN/i2FN/mN/i2FN/mN/i2FN/mN/i2FN/mN/ i2FN/mN/i2FN/mN/i2FN/*mN*/32FN/

Antisense:
/52FN/*/i2FN/*mN/i2FN/mN/i2FN/mN/i2FN/mN/i2FN/ mN/i2FN/mN/i2FN/mN/i2FN/mN/i2FN/mN*N*N
``` wherein: "N" is the base; "2F" is a 2'-F modification; "m" is a 2'-O-methyl modification, "I" is an internal base; and "*" is a phosphorothioate backbone linkage.

The present disclosure also provides vectors comprising any one or more of the inhibitory nucleic acid molecules. In some embodiments, the vectors comprise any one or more of the inhibitory nucleic acid molecules and a heterologous nucleic acid. The vectors can be viral or nonviral vectors capable of transporting a nucleic acid molecule. In some embodiments, the vector is a plasmid or cosmid (such as, for example, a circular double-stranded DNA into which additional DNA segments can be ligated). In some embodiments, the vector is a viral vector, wherein additional DNA segments can be ligated into the viral genome. Expression vectors include, but are not limited to, plasmids, cosmids, retroviruses, adenoviruses, adeno-associated viruses (AAV), plant viruses such as cauliflower mosaic virus and tobacco mosaic virus, yeast artificial chromosomes (YACs), Epstein-Barr (EBV)-derived episomes, and other expression vectors known in the art.

The present disclosure also provides compositions comprising any one or more of the inhibitory nucleic acid molecules. In some embodiments, the composition is a pharmaceutical composition. In some embodiments, the compositions comprise a carrier and/or excipient. Examples of carriers include, but are not limited to, poly(lactic acid) (PLA) microspheres, poly(D,L-lactic-coglycolic-acid) (PLGA) microspheres, liposomes, micelles, inverse micelles, lipid cochleates, and lipid microtubules. A carrier may comprise a buffered salt solution such as PBS, HBSS, etc.

In some embodiments, the IFIH1 inhibitor or TRIM65 inhibitor comprises a nuclease agent that induces one or more nicks or double-strand breaks at a recognition sequence(s) or a DNA-binding protein that binds to a recognition sequence within an IFIH1 genomic nucleic acid molecule or a or TRIM65 genomic nucleic acid molecule. The recognition sequence can be located within a coding region of the IFIH1 gene or TRIM65 gene, or within regulatory regions that influence the expression of the gene. A recognition sequence of the DNA-binding protein or nuclease agent can be located in an intron, an exon, a promoter, an enhancer, a regulatory region, or any non-protein coding region. The recognition sequence can include or be proximate to the start codon of the IFIH1 gene or TRIM65 gene. For example, the recognition sequence can be located about 10, about 20, about 30, about 40, about 50, about 100, about 200, about 300, about 400, about 500, or about 1,000 nucleotides from the start codon. As another example, two or more nuclease agents can be used, each targeting a nuclease recognition sequence including or proximate to the start codon. As another example, two nuclease agents can be used, one targeting a nuclease recognition sequence including or proximate to the start codon, and one targeting a nuclease recognition sequence including or proximate to the stop codon, wherein cleavage by the nuclease agents can result in deletion of the coding region between the two nuclease recognition sequences. Any nuclease agent that induces a nick or double-strand break into a desired recognition sequence can be used in the methods and compositions disclosed herein. Any DNA-binding protein that binds to a desired recognition sequence can be used in the methods and compositions disclosed herein.

Suitable nuclease agents and DNA-binding proteins for use herein include, but are not limited to, zinc finger protein or zinc finger nuclease (ZFN) pair, Transcription Activator-Like Effector (TALE) protein or Transcription Activator-Like Effector Nuclease (TALEN), or Clustered Regularly Interspersed Short Palindromic Repeats (CRISPR)/CRISPR-associated (Cas) systems. The length of the recognition sequence can vary, and includes, for example, recognition sequences that are about 30-36 bp for a zinc finger protein or ZFN pair, about 15-18 bp for each ZFN, about 36 bp for a TALE protein or TALEN, and about 20 bp for a CRISPR/Cas guide RNA.

In some embodiments, CRISPR/Cas systems can be used to modify an IFIH1 or TRIM65 genomic nucleic acid molecule within a cell. The methods and compositions disclosed herein can employ CRISPR-Cas systems by utilizing CRISPR complexes (comprising a guide RNA (gRNA) complexed with a Cas protein) for site-directed cleavage of IFIH1 or TRIM65 nucleic acid molecules.

Cas proteins generally comprise at least one RNA recognition or binding domain that can interact with gRNAs. Cas proteins can also comprise nuclease domains (such as, for example, DNase or RNase domains), DNA binding domains, helicase domains, protein-protein interaction domains, dimerization domains, and other domains. Suitable Cas proteins include, for example, a wild type Cas9 protein and a wild type Cpf1 protein (such as, for example, FnCpf1). A Cas protein can have full cleavage activity to create a double-strand break in an IFIH1 or TRIM65 genomic nucleic acid molecule or it can be a nickase that creates a single-strand break in an IFIH1 or TRIM65 genomic nucleic acid molecule. Additional examples of Cas proteins include, but are not limited to, Cas1, Cas1B, Cas2, Cas3, Cas4, Cas5, Cas5e (CasD), Cas6, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof. Cas proteins can also be operably linked to heterologous polypeptides as fusion proteins. For example, a Cas protein can be fused to a cleavage domain, an epigenetic modification domain, a transcriptional activation domain, or a transcriptional repressor domain. Cas proteins can be provided in any form. For example, a Cas protein can be provided in the form of a protein, such as a Cas protein complexed with a gRNA. Alternately, a Cas protein can be provided in the form of a nucleic acid molecule encoding the Cas protein, such as an RNA or DNA.

In some embodiments, targeted genetic modifications of IFIH1 or TRIM65 genomic nucleic acid molecules can be generated by contacting a cell with a Cas protein and one or more gRNAs that hybridize to one or more gRNA recognition sequences within a target genomic locus in the IFIH1 or TRIM65 genomic nucleic acid molecule. For example, a gRNA recognition sequence can be located within a region of SEQ ID NO:1. The gRNA recognition sequence can also include or be proximate to a position corresponding to position 38,690 according to SEQ ID NO:1. For example, the gRNA recognition sequence can be located from about 1000, from about 500, from about 400, from about 300, from about 200, from about 100, from about 50, from about 45, from about 40, from about 35, from about 30, from about 25, from about 20, from about 15, from about 10, or from about 5 nucleotides of a position corresponding to position 38,690 according to SEQ ID NO:1. The gRNA recognition sequence can include or be proximate to the start codon of an IFIH1 or TRIM65 genomic nucleic acid molecule or the stop codon of an IFIH1 genomic nucleic acid molecule. For example, the gRNA recognition sequence can be located from about 10, from about 20, from about 30, from about 40, from about 50, from about 100, from about 200, from about 300, from about 400, from about 500, or from about 1,000 nucleotides of the start codon or the stop codon.

The gRNA recognition sequences within a target genomic locus in an IFIH1 or TRIM65 genomic nucleic acid molecule are located near a Protospacer Adjacent Motif (PAM) sequence, which is a 2-6 base pair DNA sequence immediately following the DNA sequence targeted by the Cas9 nuclease. The canonical PAM is the sequence 5'-NGG-3' where "N" is any nucleobase followed by two guanine ("G") nucleobases. gRNAs can transport Cas9 to anywhere in the genome for gene editing, but no editing can occur at any site other than one at which Cas9 recognizes PAM. In addition, 5'-NGA-3' can be a highly efficient non-canonical PAM for human cells. Generally, the PAM is about 2-6 nucleotides downstream of the DNA sequence targeted by the gRNA. The PAM can flank the gRNA recognition sequence. In some embodiments, the gRNA recognition sequence can be flanked on the 3' end by the PAM. In some embodiments, the gRNA recognition sequence can be flanked on the 5' end by the PAM. For example, the cleavage site of Cas proteins can be about 1 to about 10, about 2 to about 5 base pairs, or three base pairs upstream or downstream of the PAM sequence. In some embodiments (such as when Cas9 from *S. pyogenes* or a closely related Cas9 is used), the PAM sequence of the non-complementary strand can be 5'-NGG-3', where N is any DNA nucleotide and is immediately 3' of the gRNA recognition sequence of the non-complementary strand of the target DNA. As such, the PAM sequence of the complementary strand would be 5'-CCN-3', where N is any DNA nucleotide and is immediately 5' of the gRNA recognition sequence of the complementary strand of the target DNA.

A gRNA is an RNA molecule that binds to a Cas protein and targets the Cas protein to a specific location within an IFIH1 or TRIM65 genomic nucleic acid molecule. An exemplary gRNA is a gRNA effective to direct a Cas enzyme to bind to or cleave an IFIH1 or TRIM65 genomic nucleic acid molecule, wherein the gRNA comprises a DNA-targeting segment that hybridizes to a gRNA recognition sequence within the IFIH1 or TRIM65 genomic nucleic acid molecule that includes or is proximate to a position corresponding to position 38,690 according to SEQ ID NO:1 (for IFIH1). For example, a gRNA can be selected such that it hybridizes to a gRNA recognition sequence that is located from about 5, from about 10, from about 15, from about 20, from about 25, from about 30, from about 35, from about 40, from about 45, from about 50, from about 100, from about 200, from about 300, from about 400, from about 500, or from about 1,000 nucleotides of a position corresponding to position 38,690 according to SEQ ID NO:1. Other exemplary gRNAs comprise a DNA-targeting segment that hybridizes to a gRNA recognition sequence present within an IFIH1 or TRIM65 genomic nucleic acid molecule that includes or is proximate to the start codon or the stop codon. For example, a gRNA can be selected such that it hybridizes to a gRNA recognition sequence that is located from about 5, from about 10, from about 15, from about 20, from about 25, from about 30, from about 35, from about 40, from about 45, from about 50, from about 100, from about 200, from about 300, from about 400, from about 500, or from about 1,000 nucleotides of the start codon or located from about 5, from about 10, from about 15, from about 20, from about 25, from about 30, from about 35, from about 40, from about 45, from about 50, from about 100, from about 200, from about 300, from about 400, from about 500, or from about 1,000 nucleotides of the stop codon. Suitable gRNAs can comprise from about 17 to about 25 nucleotides, from about 17 to about 23 nucleotides, from about 18 to about 22 nucleotides, or from about 19 to about 21 nucleotides. In some embodiments, the gRNAs can comprise 20 nucleotides.

Examples of suitable gRNA recognition sequences located within the human IFIH1 reference gene are set forth in Table 1 as SEQ ID NOs:24-34.

TABLE 1

| Guide RNA Recognition Sequences Near IFIH1 Variation(s) | | |
| --- | --- | --- |
| Strand | gRNA Recognition Sequence | SEQ ID NO: |
| − | GCAATGGCAAACTTCTTGCA*TGG* | 24 |
| + | AGATGCAACCAGAGAAGTAT*GGG* | 25 |
| + | CAGATGCAACCAGAGAAGTA*TGG* | 26 |
| + | TACTACATTCAGTAGAAAGA*TGG* | 27 |
| + | TCAACTGAAAAACCAAATAC*AGG* | 28 |
| − | TTCTCTGGTTGCATCTGCAA*TGG* | 29 |
| + | ATTCAGTAGAAAGATGGCAA*AGG* | 30 |

TABLE 1-continued

| Guide RNA Recognition Sequences Near IFIH1 Variation(s) | | |
| --- | --- | --- |
| Strand | gRNA Recognition Sequence | SEQ ID NO: |
| − | ACATTAAGCCCATACTTCTCTGG | 31 |
| − | TCTTGCATGGCTCCTGTATTTGG | 32 |
| − | TTTGGTTTTTCAGTTGATCAAGG | 33 |
| − | TTTAAATAATATTTTTCAGATGG | 34 |

The Cas protein and the gRNA form a complex, and the Cas protein cleaves the target IFIH1 or TRIM65 genomic nucleic acid molecule. The Cas protein can cleave the nucleic acid molecule at a site within or outside of the nucleic acid sequence present in the target IFIH1 or TRIM65 genomic nucleic acid molecule to which the DNA-targeting segment of a gRNA will bind. For example, formation of a CRISPR complex (comprising a gRNA hybridized to a gRNA recognition sequence and complexed with a Cas protein) can result in cleavage of one or both strands in or near (such as, for example, within 1, 2, 3, 4, 5, 6, 7, 8, 9, 10, 20, 50, or more base pairs from) the nucleic acid sequence present in the IFIH1 or TRIM65 genomic nucleic acid molecule to which a DNA-targeting segment of a gRNA will bind.

Such methods can result, for example, in an IFIH1 or TRIM65 genomic nucleic acid molecule in which a region of the gene is disrupted, the start codon is disrupted, the stop codon is disrupted, or the coding sequence is disrupted or deleted. Optionally, the cell can be further contacted with one or more additional gRNAs that hybridize to additional gRNA recognition sequences within the target genomic locus in the IFIH1 or TRIM65 genomic nucleic acid molecule. By contacting the cell with one or more additional gRNAs (such as, for example, a second gRNA that hybridizes to a second gRNA recognition sequence), cleavage by the Cas protein can create two or more double-strand breaks or two or more single-strand breaks.

In some embodiments, the methods of treatment further comprise detecting the presence or absence of an IFIH1 missense variant nucleic acid molecule encoding an IFIH1 predicted loss-of-function polypeptide in a biological sample from the subject. As used throughout the present disclosure, an "IFIH1 missense variant nucleic acid molecule encoding an IFIH1 predicted loss-of-function polypeptide" is any IFIH1 nucleic acid molecule (such as, for example, genomic nucleic acid molecule, mRNA molecule, or cDNA molecule) encoding an IFIH1 polypeptide having a partial loss-of-function, a complete loss-of-function, a predicted partial loss-of-function, or a predicted complete loss-of-function.

The present disclosure also provides methods of treating a subject with a therapeutic agent that treats or inhibits psoriasis, wherein the subject has psoriasis. In some embodiments, the methods comprise determining whether the subject has an IFIH1 missense variant nucleic acid molecule encoding an IFIH1 predicted loss-of-function polypeptide by obtaining or having obtained a biological sample from the subject, and performing or having performed a sequence analysis on the biological sample to determine if the subject has a genotype comprising the IFIH1 missense variant nucleic acid molecule encoding an IGIH1 predicted loss-of-function polypeptide. In some embodiments, the methods further comprise administering or continuing to administer the therapeutic agent that treats or inhibits psoriasis in a standard dosage amount to a subject that is IFIH1 reference, and/or administering an IFIH1 inhibitor to the subject. In some embodiments, the methods further comprise administering or continuing to administer the therapeutic agent that treats or inhibits psoriasis in an amount that is the same as or less than a standard dosage amount to a subject that is heterozygous for the IFIH1 missense variant nucleic acid molecule, and/or administering an IFIH1 inhibitor to the subject. In some embodiments, the methods further comprise administering or continuing to administer the therapeutic agent that treats or inhibits psoriasis in an amount that is the same as or less than a standard dosage amount to a subject that is homozygous for the IFIH1 missense variant nucleic acid molecule. The presence of a genotype having the IFIH1 missense variant nucleic acid molecule encoding the IFIH1 predicted loss-of-function polypeptide indicates the subject has a decreased risk of developing psoriasis. In some embodiments, the subject is IFIH1 reference. In some embodiments, the subject is heterozygous for a IFIH1 missense variant nucleic acid molecule encoding an IFIH1 predicted loss-of-function polypeptide.

For subjects that are genotyped or determined to be either IFIH1 reference or heterozygous for an IFIH1 missense variant nucleic acid molecule encoding an IFIH1 predicted loss-of-function polypeptide, such subjects can be treated with an IFIH1 inhibitor, as described herein.

Detecting the presence or absence of an IFIH1 missense variant nucleic acid molecule encoding an IFIH1 predicted loss-of-function polypeptide in a biological sample from a subject and/or determining whether a subject has an IFIH1 missense variant nucleic acid molecule encoding an IFIH1 predicted loss-of-function polypeptide can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a cell obtained from the subject.

In some embodiments, the treatment methods further comprise detecting the presence or absence of an IFIH1 predicted loss-of-function polypeptide in a biological sample from the subject. In some embodiments, when the subject does not have an IFIH1 predicted loss-of-function polypeptide, the subject is also administered a therapeutic agent that treats or inhibits psoriasis in a standard dosage amount. In some embodiments, when the subject has an IFIH1 predicted loss-of-function polypeptide, the subject is also administered a therapeutic agent that treats or inhibits psoriasis in a dosage amount that is the same as or less than a standard dosage amount.

The present disclosure also provides methods of treating a subject with a therapeutic agent that treats or inhibits psoriasis, wherein the subject has psoriasis. In some embodiments, the method comprises determining whether the subject has an IFIH1 predicted loss-of-function polypeptide by obtaining or having obtained a biological sample from the subject, and performing or having performed an assay on the biological sample to determine if the subject has an IFIH1 predicted loss-of-function polypeptide. When the subject does not have an IFIH1 predicted loss-of-function polypeptide, the therapeutic agent that treats or inhibits psoriasis is administered or continued to be administered to the subject in a standard dosage amount, and/or an IFIH1 inhibitor is administered to the subject. When the subject has an IFIH1 predicted loss-of-function polypeptide, the therapeutic agent that treats or inhibits psoriasis is administered or continued to be administered to the subject in an amount that is the same as or less than a standard dosage amount, and/or an IFIH1 inhibitor is administered to the subject. The presence of an IFIH1 predicted loss-of-function polypeptide indicates the subject has a decreased risk of developing psoriasis. In some embodiments, the subject has an IFIH1 predicted loss-of-function polypeptide. In some embodiments, the subject does not have an IFIH1 predicted loss-of-function polypeptide.

Detecting the presence or absence of an IFIH1 predicted loss-of-function polypeptide in a biological sample from a subject and/or determining whether a subject has an IFIH1 predicted loss-of-function polypeptide can be carried out by any of the methods described herein. In some embodiments, these methods can be carried out in vitro. In some embodiments, these methods can be carried out in situ. In some embodiments, these methods can be carried out in vivo. In any of these embodiments, the polypeptide can be present within a cell obtained from the subject.

In some embodiments, the IFIH1 inhibitor is a paramyxovirus V protein. In some embodiments, the IFIH1 inhibitor comprises a small molecule.

In any embodiment where a subject that is genotyped or determined to be either IFIH1 reference or heterozygous for an IFIH1 missense variant nucleic acid molecule encoding an IFIH1 predicted loss-of-function polypeptide, such subject can be treated with an inhibitor of type 1 interferon pathway. In some embodiments, the inhibitor of type 1 interferon pathway is an agonist of Adenosine Deaminase RNA Specific (ADAR). In some embodiments, the ADAR agonist is ADAR protein. In some embodiments, the ADAR agonist is an ADAR agonist antibody. In some embodiments, the inhibitor of type 1 interferon pathway is an inhibitor of TRIM65. In some embodiments, the TRIM65 inhibitor comprises a small molecule. In some embodiments, the inhibitor of type 1 interferon pathway is an inhibitor of DEAD-box polypeptide 58 ("DDX58") (i.e., RIG-1). DDX58 inhibitors include, but are not limited to, epigallocatechin gallate (EGCG) and BX795 (InvivoGen).

In some embodiments, the methods of treatment further comprise detecting the presence or absence of a TRIM65 missense variant nucleic acid molecule encoding a TRIM65 predicted loss-of-function polypeptide in a biological sample from the subject. As used throughout the present disclosure, a "TRIM65 missense variant nucleic acid molecule encoding a TRIM65 predicted loss-of-function polypeptide" is any TRIM65 nucleic acid molecule (such as, for example, genomic nucleic acid molecule, mRNA molecule, or cDNA molecule) encoding a TRIM65 polypeptide having a partial loss-of-function, a complete loss-of-function, a predicted partial loss-of-function, or a predicted complete loss-of-function.

The present disclosure also provides methods of treating a subject with a therapeutic agent that treats or inhibits psoriasis, wherein the subject has psoriasis. In some embodiments, the methods comprise determining whether the subject has a TRIM65 missense variant nucleic acid molecule encoding a TRIM65 predicted loss-of-function polypeptide by obtaining or having obtained a biological sample from the subject, and performing or having performed a sequence analysis on the biological sample to determine if the subject has a genotype comprising the TRIM65 missense variant nucleic acid molecule encoding a TRIM65 predicted loss-of-function polypeptide. In some embodiments, the methods further comprise administering or continuing to administer the therapeutic agent that treats or inhibits psoriasis in a standard dosage amount to a subject that is TRIM65 reference, and/or administering a TRIM65 inhibitor to the subject. In some embodiments, the methods further comprise administering or continuing to administer the therapeutic agent that treats or inhibits psoriasis in an amount that is the same as or less than a standard dosage amount to a subject that is heterozygous for the TRIM65 missense variant nucleic acid molecule, and/or administering a TRIM65 inhibitor to the subject. In some embodiments, the methods further comprise administering or continuing to administer the therapeutic agent that treats or inhibits psoriasis in an amount that is the same as or less than a standard dosage amount to a subject that is homozygous for the TRIM65 missense variant nucleic acid molecule. The presence of a genotype having the TRIM65 missense variant nucleic acid molecule encoding the TRIM65 predicted loss-of-function polypeptide indicates the subject has a decreased risk of developing psoriasis. In some embodiments, the subject is TRIM65 reference. In some embodiments, the subject is heterozygous for a TRIM65 missense variant nucleic acid molecule encoding a TRIM65 predicted loss-of-function polypeptide.

For subjects that are genotyped or determined to be either TRIM65 reference or heterozygous for a TRIM65 missense variant nucleic acid molecule encoding a TRIM65 predicted loss-of-function polypeptide, such subjects can be treated with a TRIM65 inhibitor, as described herein.

Detecting the presence or absence of a TRIM65 missense variant nucleic acid molecule encoding a TRIM65 predicted loss-of-function polypeptide in a biological sample from a subject and/or determining whether a subject has a TRIM65 missense variant nucleic acid molecule encoding a TRIM65 predicted loss-of-function polypeptide can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a cell obtained from the subject.

In some embodiments, the treatment methods further comprise detecting the presence or absence of a TRIM65 predicted loss-of-function polypeptide in a biological sample from the subject. In some embodiments, when the subject does not have a TRIM65 predicted loss-of-function polypeptide, the subject is also administered a therapeutic agent that treats or inhibits psoriasis in a standard dosage amount. In some embodiments, when the subject has a TRIM65 predicted loss-of-function polypeptide, the subject is also administered a therapeutic agent that treats or inhibits psoriasis in a dosage amount that is the same as or less than a standard dosage amount.

The present disclosure also provides methods of treating a subject with a therapeutic agent that treats or inhibits psoriasis, wherein the subject has psoriasis. In some embodiments, the method comprises determining whether the subject has a TRIM65 predicted loss-of-function polypeptide by obtaining or having obtained a biological sample from the subject, and performing or having performed an assay on the biological sample to determine if the subject has a TRIM65 predicted loss-of-function polypeptide. When the subject does not have a TRIM65 predicted loss-of-function polypeptide, the therapeutic agent that treats or inhibits psoriasis is administered or continued to be administered to the subject in a standard dosage amount, and/or a TRIM65 inhibitor is administered to the subject. When the subject has a TRIM65 predicted loss-of-function polypeptide, the therapeutic agent that treats or inhibits psoriasis is administered or continued to be administered to the subject in an amount that is the same as or less than a standard dosage amount, and/or a TRIM65 inhibitor is administered to the subject. The presence of a TRIM65 predicted loss-of-function polypeptide indicates the subject has a decreased risk of developing psoriasis. In some embodiments, the subject has a TRIM65 predicted loss-of-function polypeptide. In some embodiments, the subject does not have a TRIM65 predicted loss-of-function polypeptide.

Detecting the presence or absence of a TRIM65 predicted loss-of-function polypeptide in a biological sample from a subject and/or determining whether a subject has a TRIM65 predicted loss-of-function polypeptide can be carried out by any of the methods described herein. In some embodiments, these methods can be carried out in vitro. In some embodiments, these methods can be carried out in situ. In some embodiments, these methods can be carried out in vivo. In any of these embodiments, the polypeptide can be present within a cell obtained from the subject.

In some embodiments, the TRIM65 inhibitor is a peptide that blocks the interaction between TRIM65 and IFIH1. In some embodiments, the TRIM65 inhibitor comprises a small molecule.

In any embodiment where a subject that is genotyped or determined to be either TRIM65 reference or heterozygous for a TRIM65 missense variant nucleic acid molecule encoding a TRIM65 predicted loss-of-function polypeptide, such subject can be treated with an inhibitor of type 1 interferon pathway and/or an IFIH1 inhibitor. In some embodiments, the inhibitor of type 1 interferon pathway is an agonist of Adenosine Deaminase RNA Specific (ADAR). In some embodiments, the ADAR agonist is ADAR protein. In some embodiments, the ADAR agonist is an ADAR agonist antibody. In some embodiments, the TRIM65 inhibitor comprises a small molecule. In some embodiments, the inhibitor of type 1 interferon pathway is an inhibitor of DEAD-box polypeptide 58 ("DDX58") (i.e., RIG-1). DDX58 inhibitors include, but are not limited to, epigallocatechin gallate (EGCG) and BX795 (InvivoGen).

Examples of therapeutic agents that treat or inhibit psoriasis include, but are not limited to, an anthralin (dihydroxyanthralin), azarabine, colchicine, fluorouracil, methotrexate, methoxsalen (8-methoxypsoralen), resorcinol, retinoids (such as retinoic acid), corticosteroids (such as clobetasol propionate, triamcinolone acetonide, and the like), cyclosporin, iodochlorhydroxyquin, salicylic acid, vitamin D, dapsone, somatostatin, sulfur, tars, zinc oxide, hydroxycarbamide, fumarates (such as dimethyl fumarate), and ultra-violet light. In some embodiments, the therapeutic agent that treats or inhibits psoriasis is an anthralin (such as dihydroxyanthralin). In some embodiments, the therapeutic agent that treats or inhibits psoriasis is azarabine. In some embodiments, the therapeutic agent that treats or inhibits psoriasis is colchicine. In some embodiments, the therapeutic agent that treats or inhibits psoriasis is fluorouracil. In some embodiments, the therapeutic agent that treats or inhibits psoriasis is methotrexate. In some embodiments, the therapeutic agent that treats or inhibits psoriasis is methoxsalen (such as 8-methoxypsoralen). In some embodiments, the therapeutic agent that treats or inhibits psoriasis is resorcinol. In some embodiments, the therapeutic agent that treats or inhibits psoriasis is a retinoid (such as retinoic acid). In some embodiments, the therapeutic agent that treats or inhibits psoriasis is a corticosteroid (such as clobetasol propionate or triamcinolone acetonide). In some embodiments, the therapeutic agent that treats or inhibits psoriasis is cyclosporin. In some embodiments, the therapeutic agent that treats or inhibits psoriasis is iodochlorhydroxyquin. In some embodiments, the therapeutic agent that treats or inhibits psoriasis is salicylic acid. In some embodiments, the therapeutic agent that treats or inhibits psoriasis is vitamin D. In some embodiments, the therapeutic agent that treats or inhibits psoriasis is dapsone. In some embodiments, the therapeutic agent that treats or inhibits psoriasis is somatostatin. In some embodiments, the therapeutic agent that treats or inhibits psoriasis is sulfur. In some embodiments, the therapeutic agent that treats or inhibits psoriasis is a tar. In some embodiments, the therapeutic agent that treats or inhibits psoriasis is zinc oxide. In some embodiments, the therapeutic agent that treats or inhibits psoriasis is hydroxycarbamide. In some embodiments, the therapeutic agent that treats or inhibits psoriasis is a fumarate (such as dimethyl fumarate). In some embodiments, the therapeutic agent that treats or inhibits psoriasis is ultra-violet light.

In some embodiments, the dose of the therapeutic agents that treat or inhibit psoriasis can be reduced by about 10%, by about 20%, by about 30%, by about 40%, by about 50%, by about 60%, by about 70%, by about 80%, or by about 90% for subjects that are heterozygous for an IFIH1 or TRIM65 missense variant nucleic acid molecule encoding an IFIH1 or TRIM65 predicted loss-of-function polypeptide (i.e., a lower than the standard dosage amount) compared to subjects that are IFIH1 reference or TRIM65 reference (who may receive a standard dosage amount). In some embodiments, the dose of the therapeutic agents that treat or inhibit psoriasis can be reduced by about 10%, by about 20%, by about 30%, by about 40%, or by about 50%. In addition, the dose of therapeutic agents that treat or inhibit psoriasis in subjects that are heterozygous for an IFIH1 or TRIM65 missense variant nucleic acid molecule encoding an IFIH1 or TRIM65 predicted loss-of-function polypeptide can be administered less frequently compared to subjects that are IFIH1 reference or TRIM65 reference.

Administration of the therapeutic agents that treat or inhibit psoriasis and/or IFIH1 inhibitors/TRIM65 inhibitors/ type 1 interferon pathway inhibitors can be repeated, for example, after one day, two days, three days, five days, one week, two weeks, three weeks, one month, five weeks, six weeks, seven weeks, eight weeks, two months, or three months. The repeated administration can be at the same dose or at a different dose. The administration can be repeated once, twice, three times, four times, five times, six times, seven times, eight times, nine times, ten times, or more. For example, according to certain dosage regimens a subject can receive therapy for a prolonged period of time such as, for example, 6 months, 1 year, or more.

Administration of the therapeutic agents that treat or inhibit psoriasis and/or IFIH1 inhibitors/TRIM65 inhibitors/ type 1 interferon pathway inhibitors can occur by any suitable route including, but not limited to, parenteral, intravenous, oral, subcutaneous, intra-arterial, intracranial, intrathecal, intraperitoneal, topical, intranasal, or intramuscular. Pharmaceutical compositions for administration are desirably sterile and substantially isotonic and manufactured under GMP conditions. Pharmaceutical compositions can be provided in unit dosage form (i.e., the dosage for a single administration). Pharmaceutical compositions can be formulated using one or more physiologically and pharmaceutically acceptable carriers, diluents, excipients or auxiliaries. The formulation depends on the route of administration chosen. The term "pharmaceutically acceptable" means that the carrier, diluent, excipient, or auxiliary is compatible with the other ingredients of the formulation and not substantially deleterious to the recipient thereof.

The terms "treat", "treating", and "treatment" and "prevent", "preventing", and "prevention" as used herein, refer to eliciting the desired biological response, such as a therapeutic and prophylactic effect, respectively. In some embodiments, a therapeutic effect comprises one or more of a decrease/reduction in psoriasis, a decrease/reduction in the severity of psoriasis (such as, for example, a reduction or inhibition of development or psoriasis), a decrease/reduction in symptoms and psoriasis-related effects, delaying the onset of symptoms and psoriasis-related effects, reducing the severity of symptoms of psoriasis-related effects, reducing the severity of an acute episode, reducing the number of symptoms and psoriasis-related effects, reducing the latency of symptoms and psoriasis-related effects, an amelioration of symptoms and psoriasis-related effects, reducing secondary symptoms, reducing secondary infections, preventing relapse to psoriasis, decreasing the number or frequency of relapse episodes, increasing latency between symptomatic episodes, increasing time to sustained progression, expediting remission, inducing remission, augmenting remission, speeding recovery, or increasing efficacy of or decreasing resistance to alternative therapeutics, and/or an increased survival time of the affected host animal, following administration of the agent or composition comprising the agent. A prophylactic effect may comprise a complete or partial avoidance/inhibition or a delay of psoriasis development/ progression (such as, for example, a complete or partial avoidance/inhibition or a delay), and an increased survival time of the affected host animal, following administration of a therapeutic protocol. Treatment of psoriasis encompasses the treatment of subjects already diagnosed as having any form of psoriasis at any clinical stage or manifestation, the delay of the onset or evolution or aggravation or deterioration of the symptoms or signs of psoriasis, and/or preventing and/or reducing the severity of psoriasis.

The present disclosure also provides methods of diagnosing psoriasis in a subject, the methods comprising determining the subject's aggregate burden of having a plurality of IFIH1 missense variant nucleic acid molecule encoding an IFIH1 predicted loss-of-function polypeptide. When the subject has a lower aggregate burden, and has one or more symptoms of psoriasis, then the subject is diagnosed as having psoriasis. When the subject has a greater aggregate burden, and does not have one or more symptoms of psoriasis, then the subject is diagnosed as not having psoriasis.

The present disclosure also provides methods of identifying a subject having an increased risk for developing psoriasis. In some embodiments, the method comprises determining or having determined in a biological sample obtained from the subject the presence or absence of an IFIH1 missense variant nucleic acid molecule (such as a genomic nucleic acid molecule, mRNA molecule, and/or cDNA molecule) encoding an IFIH1 predicted loss-of-function polypeptide. When the subject lacks an IFIH1 missense variant nucleic acid molecule encoding an IFIH1 predicted loss-of-function polypeptide (i.e., the subject is genotypically categorized as an IFIH1 reference), then the subject has an increased risk for developing psoriasis. When the subject has an IFIH1 missense variant nucleic acid molecule encoding an IFIH1 predicted loss-of-function polypeptide (i.e., the subject is heterozygous for an IFIH1 missense variant nucleic acid molecule encoding an IFIH1 predicted loss-of-function polypeptide), then the subject has a decreased risk for developing psoriasis.

Having a single copy of an IFIH1 missense variant nucleic acid molecule encoding an IFIH1 predicted loss-offunction polypeptide is more protective of a subject from developing psoriasis than having no copies of an IFIH1 missense variant nucleic acid molecule encoding an IFIH1 predicted loss-of-function polypeptide. Without intending to be limited to any particular theory or mechanism of action, it is believed that a single copy of an IFIH1 missense variant nucleic acid molecule encoding an IFIH1 predicted loss-of-function polypeptide (i.e., heterozygous for an IFIH1 missense variant nucleic acid molecule encoding an IFIH1 predicted loss-of-function polypeptide) is protective of a subject from developing psoriasis, and it is also believed that having two copies of an IFIH1 missense variant nucleic acid molecule encoding an IFIH1 predicted loss-of-function polypeptide (i.e., homozygous for an IFIH1 missense variant nucleic acid molecule encoding an IFIH1 predicted loss-of-function polypeptide) may be more protective of a subject from developing psoriasis, relative to a subject with a single copy. Thus, in some embodiments, a single copy of an IFIH1 missense variant nucleic acid molecule encoding an IFIH1 predicted loss-of-function polypeptide may not be completely protective, but instead, may be partially or incompletely protective of a subject from developing psoriasis. While not desiring to be bound by any particular theory, there may be additional factors or molecules involved in the development of psoriasis that are still present in a subject having a single copy of an IFIH1 missense variant nucleic acid molecule encoding an IFIH1 predicted loss-of-function polypeptide, thus resulting in less than complete protection from the development of psoriasis.

Determining whether a subject has an IFIH1 missense variant nucleic acid molecule encoding an IFIH1 predicted loss-of-function polypeptide in a biological sample from a subject and/or determining whether a subject has an IFIH1 missense variant nucleic acid molecule encoding an IFIH1 predicted loss-of-function polypeptide can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a cell obtained from the subject.

The present disclosure also provides methods of identifying a subject having an increased risk for developing psoriasis. In some embodiments, the method comprises determining or having determined in a biological sample obtained from the subject the presence or absence of a TRIM65 missense variant nucleic acid molecule (such as a genomic nucleic acid molecule, mRNA molecule, and/or cDNA molecule) encoding a TRIM65 predicted loss-of-function polypeptide. When the subject lacks a TRIM65 missense variant nucleic acid molecule encoding a TRIM65 predicted loss-of-function polypeptide (i.e., the subject is genotypically categorized as TRIM65 reference), then the subject has an increased risk for developing psoriasis. When the subject has a TRIM65 missense variant nucleic acid molecule encoding a TRIM65 predicted loss-of-function polypeptide (i.e., the subject is heterozygous for a TRIM65 missense variant nucleic acid molecule encoding a TRIM65 predicted loss-of-function polypeptide), then the subject has a decreased risk for developing psoriasis.

Having a single copy of a TRIM65 missense variant nucleic acid molecule encoding a TRIM65 predicted loss-of-function polypeptide is more protective of a subject from developing psoriasis than having no copies of a TRIM65 missense variant nucleic acid molecule encoding a TRIM65 predicted loss-of-function polypeptide. Without intending to be limited to any particular theory or mechanism of action, it is believed that a single copy of a TRIM65 missense variant nucleic acid molecule encoding a TRIM65 predicted loss-of-function polypeptide (i.e., heterozygous for a TRIM65 missense variant nucleic acid molecule encoding a TRIM65 predicted loss-of-function polypeptide) is protective of a subject from developing psoriasis, and it is also believed that having two copies of a TRIM65 missense variant nucleic acid molecule encoding a TRIM65 predicted loss-of-function polypeptide (i.e., homozygous for a TRIM65 missense variant nucleic acid molecule encoding a TRIM65 predicted loss-of-function polypeptide) may be more protective of a subject from developing psoriasis, relative to a subject with a single copy. Thus, in some embodiments, a single copy of a TRIM65 missense variant nucleic acid molecule encoding a TRIM65 predicted loss-of-function polypeptide may not be completely protective, but instead, may be partially or incompletely protective of a subject from developing psoriasis. While not desiring to be bound by any particular theory, there may be additional factors or molecules involved in the development of psoriasis that are still present in a subject having a single copy of a TRIM65 missense variant nucleic acid molecule encoding a TRIM65 predicted loss-of-function polypeptide, thus resulting in less than complete protection from the development of psoriasis.

Determining whether a subject has a TRIM65 missense variant nucleic acid molecule encoding a TRIM65 predicted loss-of-function polypeptide in a biological sample from a subject and/or determining whether a subject has a TRIM65 missense variant nucleic acid molecule encoding a TRIM65 predicted loss-of-function polypeptide can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a cell obtained from the subject.

In some embodiments, any of the methods described herein can further comprise determining the subject's aggregate burden of having an IFIH1 missense variant nucleic acid molecule encoding an IFIH1 predicted loss-of-function polypeptide, and/or an IFIH1 predicted loss-of-function variant polypeptide associated with a decreased risk of developing psoriasis. The aggregate burden is the sum of all variants in the IFIH1 gene, which can be carried out in an association analysis with psoriasis. In some embodiments, the subject is homozygous for one or more IFIH1 missense variant nucleic acid molecules encoding an IFIH1 predicted loss-of-function polypeptide associated with a decreased risk of developing psoriasis. In some embodiments, the subject is heterozygous for one or more IFIH1 missense variant nucleic acid molecules encoding an IFIH1 predicted loss-of-function polypeptide associated with a decreased risk of developing psoriasis. The result of the association analysis suggests that IFIH1 missense variant nucleic acid molecules encoding an IFIH1 predicted loss-of-function polypeptide are associated with decreased risk of developing psoriasis. When the subject has a lower aggregate burden, the subject is at a higher risk of developing psoriasis and the subject is administered or continued to be administered the therapeutic agent that treats or inhibits psoriasis in a standard dosage amount. When the subject has a greater aggregate burden, the subject is at a lower risk of developing psoriasis and the subject is administered or continued to be administered the therapeutic agent that treats or inhibits psoriasis in an amount that is the same as or less than the standard dosage amount. The greater the aggregate burden, the lower the risk of developing psoriasis. Table 2 lists exemplary IFIH1 variant nucleic acid molecules that can be used in an aggregate burden analysis.

TABLE 2

| Variant | rsID | Effect | HGVS.c | HGVS.p |
|---|---|---|---|---|
| 2:162279995:C:G | rs35337543 | splice_donor | c.1641 + 1G > C | |
| 2:162268086:C:T | rs35732034 | splice_donor | c.2807 + 1G > A | |
| 2:162277580:C:A | rs35744605 | stop_gained | c,1879G > T | p.Glu627* |
| 2:162278205:C:CT | rs553669430 | frameshift | c.l764dupA | p.Ala589fs |
| 2:162277435:AATCT:A | rs569337014 | frameshift | c.2020_2023delAGAT | p.Arg674fs |
| 2:162277442:CT:C | rs773033563 | frameshift | c.2016delA | p.Asp673fs |
| 2:162267515:A:C | rs750063177 | stop_gained | c.2862T > G | p.Tyr954* |
| 2:162273932:C:A | rs201472224 | stop_gained | c.2317G > T | p.Glu773* |
| 2:162276691:GT:G | rs759430873 | frameshift | c.2299delA | p.Thr767fs |
| 2:162277422:TAA:T | rs774076578 | frameshift | c.2035_2036delTT | p.Leu679fs |
| 2:162277651:TG:T | | frameshift | c.l807delC | p.His603fs |
| 2:162280040:G:A | | stop_gained | c.1597OT | p.Gln533* |
| 2:162280047:GT:G | rs779192156 | frameshift | c.l589delA | p.Asn530fs |
| 2:162267201:TA:T | | frameshift | c.3076delT | p.Terl026fs |
| 2:162267202:A:T | | stop_lost | c.3076T > A | p.TerlO26Lyse xt*? |
| 2:162267213:CTAAA:C | | frameshift | c.3061_3064delTTTA | p.Phel021fs |
| 2:162267222:CA:C | rsl392296770 | frameshift | c.3055delT | p.Cysl019fs |
| 2:162267270:C:T | | stop_gained | c.3008G > A | p.Trpl003* |
| 2:162267271:AC:A | | frameshift | c.3006delG | p.Lysl002fs |
| 2:162267274:T:A | | stop_gained | c.3004A > T | p.Lysl002* |
| 2:162267278:G:T | rsl51037370 | stop_gained | c.3000C > A | p.Tyr1000* |
| 2:162267304:T:A | | stop_gained | c.2974A > T | p.Lys992* |
| 2:162267324:CTTATT:C | | frameshift | c.2949_2953delAATAA | p.lle984fs |
| 2:162267335:A:T | | stop_gained | c.2943T > A | p.Cys981* |
| 2:162267336:CA:C | | frameshift | c.2941delT | p.Cys981fs |
| 2:162267348:A:C | | stop_gained | c.2930T > G | p.Leu977* |
| 2:162267375:C:T | | stop_gained | c.2903G > A | p.Trp968* |
| 2:162267381:T:C | | splice_acceptor | c.2899-2A > G | |
| 2:162267478:C:A | | splice_donor | c.2898 + 1G > T | |
| 2:162267485:AC:A | rs761697569 | frameshift | c.2891delG | p.Cys964fs |
| 2:162267491:G:T | rsl423577496 | stop_gained | c.2886OA | p.Cys962* |
| 2:162267514:G:A | rsl44455277 | stop_gained | c.2863OT | p.Gln955* |
| 2:162267541:CT:C | | frameshift | c.2835delA | p.Ala946fs |
| 2:162267544:TG:T | | frameshift | c.2832delC | p.Asn944fs |
| 2:162267550:C:A | | stop_gained | c.2827G > T | p.Glu943* |
| 2:162267560:G:T | | stop_gained | c.2817OA | p.Tyr939* |
| 2:162267564:AG:A | | frameshift | c.2812delC | p.Leu938fs |
| 2:162267568:CCCTA:C | | frameshift | c.2808-3_2808delTAGG | p.Glu937fs |
| 2:162267570:C:T | | splice_acceptor | c.2808-1G > A | |
| 2:162268086:C:G | | splice_donor | c.2807 + lG > C | |
| 2:162268164:G:T | rs775467204 | stop_gained | c.2730OA | p.Cys910* |
| 2:162268192:G:C | | stop_gained | c.2702OG | p.Ser901* |
| 2:162268206:G:T | rs946205846 | stop_gained | c.2688OA | p.Tyr896* |
| 2:162268207:TA:T | | frameshift | c.2686delT | p.Tyr896fs |
| 2:162268229:T:A | rsl252022173 | stop_gained | c.2665A > T | p.Lys889* |
| 2:162268254: ACTTTGCAT:A | | frameshift | c.2632_2639delATGCAAAG | p.Met878fs |
| 2:162268259:G:A | | stop_gained | c.2635OT | p.Gln879* |
| 2:162268263:CT:C | | frameshift | c.2630delA | p.Gln877fs |
| 2:162268265:G:GT | | frameshift | c.2628dupA | p.Gln877fs |
| 2:162268265:G:A | | stop_gained | c.2629OT | p.Gln877* |
| 2:162268271:C:A | | stop_gained | c.2623G > T | p.Glu875* |
| 2:162268272:CA:C | | frameshift | c.2621delT | p.Leu874fs |
| 2:162268278:C:A | | splice_acceptor | c.2617-1G > T | |
| 2:162272225:C:T | rsl428749026 | splice_donor | c.2616 + 1G > A | |
| 2:162272225:C:A | | splice_donor | c.2616 + 1G > T | |
| 2:162272260:AC:A | | frameshift | c.2581delG | p.Val861fs |
| 2:162272271:AGCTT:A | rs764990040 | frameshift | c.2567_2570delAAGC | p.Lys856fs |
| 2:162272277:A:T | | stop_gained | c.2565T > A | p.Tyr855* |
| 2:162272287:TTCTC:T | | frameshift | c.2551_2554delGAGA | p.Glu851fs |
| 2:162272294:G:A | rs750804689 | stop_gained | c.2548OT | p.Arg850* |
| 2:162272299:TC:T | | frameshift | c.2542delG | p.Asp848fs |
| 2:162272306:CT:C | | frameshift | c.2535delA | p.Val846fs |
| 2:162272312:C:A | | stop_gained | c.2530G > T | p.Glu844* |
| 2:162272336:T:TGTGA | | frameshift | c.2502_2505dupTCAC | p.Gly837fs |
| 2:162272352:G:T | | stop_gained | c.2490OA | p.Tyr830* |
| 2:162272378:G:A | rs747926684 | stop_gained | c.2464OT | p.Arg822* |
| 2:162272389:T:G | | splice_acceptor | c.2455-2A > C | |
| 2:162273793:A:G | | splice_donor | c.2454 + 2T > C | |
| 2:162273793:A:T | | splice_donor | c.2454 + 2T > A | |
| 2:162273794:C:G | | splice_donor | c.2454 + 1G > C | |
| 2:162273794:C:A | rs778780074 | splice_donor | c.2454 + 1G > T | |
| 2:162273801:CA:C | rsl349369420 | frameshift | c.2447delT | p.Met816fs |
| 2:162273806:CTATT:C | | frameshift | c.2439_2442delAATA | p.lle814fs |
| 2:162273812:C:A | | stop_gained | c.2437G > T | p.Glu813* |
| 2:162273818:TGACG:T | | frameshift | c.2427_2430delCGTC | p.Val810fs |
| 2:162273828:A:C | rsl84259770 | stop_gained | c.2421T > G | p.Tyr807* |
| 2:162273851:C:A | rsl444920926 | stop_gained | c.2398G > T | p.Glu800* |

TABLE 2-continued

| Variant | rsID | Effect | HGVS.c | HGVS.p |
|---|---|---|---|---|
| 2:162273901:A:AT | rs765769492 | frameshift | c.2347dupA | p.Ile783fs |
| 2:162273901:AT:A | rs751055123 | frameshift | c.2347delA | p.Ile783fs |
| 2:162273931:TC:T | rs746375033 | frameshift | c.2317delG | p.Glu773fs |
| 2:162273946:T:C | rsl99696786 | splice_acceptor | c.2305-2A > G | |
| 2:162276686:C:T | rs762865950 | splice_donor | c.2304 + lG > A | |
| 2:162276686:C:A | rs762865950 | splice_donor | c.2304 + lG > T | |
| 2:162276687:C:CT | | frameshift | c.2303dupA | p.Asn769fs |
| 2:162276704:ACT:A | | frameshift | c.2285_2286delAG | p.Glu762fs |
| 2:162276710:TG:T | rs771155568 | frameshift | c.2280delC | p.Ser760fs |
| 2:162276733:TG:T | rs778910754 | frameshift | c.2257delC | p.His753fs |
| 2:162276739:GC:G | | frameshift | c.2251delG | p.Ala751fs |
| 2:162276768:ATTTTCAG:A | rs745948096 | frameshift | c.2216_2222delCTGAAAA | p.Thr739fs |
| 2:162276780:C:T | | stop_gained | c.2211G > A | p.Trp737* |
| 2:162276795:A:T | rsl47175706 | stop_gained | c.2196T > A | p.Tyr732* |
| 2:162276795:A:C | | stop_gained | c.2196T > G | p.Tyr732* |
| 2:162276804:CT:C | | frameshift | c.2186delA | p.Gln729fs |
| 2:162276809:GT:G | | frameshift | c.2181delA | p.Arg728fs |
| 2:162276809:G:A | rs201193151 | stop_gained | c.2182OT | p.Arg728* |
| 2:162276830:C:A | | stop_gained | c.2161G > T | p.Gly721* |
| 2:162276833:G:A | rs761864966 | stop_gained | c.2158OT | p.Arg720* |
| 2:162276860:G:A | | stop_gained | c.2131OT | p.Gln711* |
| 2:162276871:G:GT | | frameshift | c.2119dupA | p.Thr707fs |
| 2:162276884:TG:T | | frameshift | c.2106delC | p.Lys703fs |
| 2:162276889:AG:A | | frameshift | c.2101delC | p.Leu701fs |
| 2:162276903:A:T | rs761764756 | stop_gained | c.2088T > A | p.Tyr696* |
| 2:162276910:GGGTTTTCA:G | | frameshift | c.2073_2080delTGAAAACC | p.Glu692fs |
| 2:162276922:AG:A | | frameshift | c.2068delC | p.Leu690fs |
| 2:162276923:GC:G | | frameshift | c.2067delG | p.Arg689fs |
| 2:162276925:CT:C | rsll90347967 | frameshift | c.2065delA | p.Arg689fs |
| 2:162276934:AT:A | | frameshift | c.2056delA | p.Met686fs |
| 2:162276947:C:T | rs748813106 | splice_acceptor | c.2045-lG > A | |
| 2:162276947:C:A | rs748813106 | splice_acceptor | c.2045-lG > T | |
| 2:162277413:AC:A | | splice_donor | c.2044 + ldelG | |
| 2:162277413:A:G | rs201026962 | splice_donor | c.2044 + 2T > C | |
| 2:162277414:C:T | | splice_donor | c.2044 + lG > A | |
| 2:162277415:C:CA | rsl475939758 | frameshift | c.2043dupT | p.Glu682fs |
| 2:162277422:T:TA | | frameshift | c.2036dupT | p.Leu679fs |
| 2:162277438:CTA:C | | frameshift | c.2019_2020delTA | p.Asp673fs |
| 2:162277439:T:A | | stop_gained | c.2020A > T | p.Arg674* |
| 2:162277440:ATC:A | | frameshift | c.2017_2018delGA | p.Asp673fs |
| 2:162277466:T:A | | stop_gained | c.1993A > T | p.Lys665* |
| 2:162277471:A:T | | stop_gained | c.1988T > A | |
| 2:162277515:AC:A | rs751231371 | frameshift | c.1943delG | p.Gly648fs |
| 2:162277535:CTA:C | | frameshift | c.l922_1923delTA | p.lle641fs |
| 2:162277539:G:GT | | frameshift | c.l919_1920insA | p.lle641fs |
| 2:162277562:C:A | | stop_gained | c,1897G > T | p.Glu633* |
| 2:162277590:A:T | | stop_gained | c,1869T > A | p.Tyr623* |
| 2:162277607:GA:G | | frameshift | c.l851delT | p.Arg618fs |
| 2:162277607:G:A | rs745937740 | stop_gained | c.1852OT | p.Arg618* |
| 2:162277612:GT:G | | frameshift | c.l846delA | p.Thr616fs |
| 2:162277661:AAACACG I IUI 1:A | rs766039450 | frameshift | c.l787_1797delAA GAACGTGTT | p.Lys596fs |
| 2:162277663:AC:A | rs773795297 | frameshift | c.l795delG | p.Val599fs |
| 2:162277664:C:CA | | frameshift | c.l794dupT | p.Val599fs |
| 2:162277665:AC:A | | frameshift | c.l793delG | p.Arg598fs |
| 2:162277670:CT:C | | frameshift | c.l788delA | p.Glu597fs |
| 2:162277682:C:A | | stop_gained | c.1777G > T | p.Gly593* |
| 2:162277685:C:A | rsl025854546 | stop_gained | c.1774G > T | p.Glu592* |
| 2:162277694:C:T | | splice_acceptor | c.1766-1G > A | |
| 2:162277695:T:A | | splice_acceptor | c.1766-2A > T | |
| 2:162278203:A:G | rs995063479 | splice_donor | c.1765 + 2T > C | |
| 2:162278203:AC:A | rsl227440828 | splice_donor | c.1765 + ldelG | |
| 2:162278204:C:T | rsl292220162 | splice_donor | c.1765 + 1G > A | |
| 2:162278205:CT:C | rs753152979 | frameshift | c.l764delA | p.Ala589fs |
| 2:162278227:C:T | rsl370550497 | stop_gained | c.1743G > A | p.Trp581* |
| 2:162278232:G:A | rs774888783 | stop_gained | c.1738OT | p.Gln580* |
| 2:162278244:G:A | | stop_gained | c.1726OT | p.Gln576* |
| 2:162278248:TC:T | | frameshift | c.l721delG | p.Gly574fs |
| 2:162278250:CA:C | | frameshift | c.l719delT | p.Phe573fs |
| 2:162278258:G:C | | stop_gained | c.1712OG | p.Ser571* |
| 2:162278265:GA:G | | frameshift | c.l704delT | p.Pro569fs |
| 2:162278279:TAA:T | rsl464362256 | frameshift | c.l689_1690delTT | p.Tyr564fs |
| 2:162278286:GA:G | | frameshift | c.l683delT | p.Gln562fs |
| 2:162278297:AT:A | | frameshift | c.l672delA | p.Met558fs |
| 2:162278319:TA:T | | frameshift | c.l650delT | p.Phe550fs |
| 2:162278319:T:A | | stop_gained | c.1651A > T | p.Lys551* |
| 2:162278326:AT:A | | frameshift | c.l643delA | p.Asp548fs |
| 2:162278330:T:G | | splice_acceptor | c.1642-2A > C | |

TABLE 2-continued

| Variant | rsID | Effect | HGVS.c | HGVS.p |
|---|---|---|---|---|
| 2:162278330:T:C | | splice_acceptor | c.1642-2A > G | |
| 2:162279994:A:C | | splice_donor | c.1641 + 2T > G | |
| 2:162279994:A:G | rs747781178 | splice_donor | c.1641 + 2T > C | |
| 2:162279995:C:T | rs35337543 | splice_donor | c.1641 + 1G > A | |
| 2:162279995:C:A | | splice_donor | c.1641 + 1G > T | |
| 2:162280001:TG:T | | frameshift | c.l635delC | p.Arg546fs |
| 2:162280004:TTG:T | | frameshift | c.l631_1632delCA | p.Ala544fs |
| 2:162280011:TG:T | | frameshift | c.l625delC | p.Ala542fs |
| 2:162280016:TG:T | | frameshift | c.l620delC | p.lle541fs |
| 2:162280047:G:GT | | frameshift | c.l589dupA | p.Asn530fs |
| 2:162280055:G:GT | | frameshift | c.l581dupA | p.Leu528fs |
| 2:162280058:G:A | | stop_gained | c.15790T | p.Gln527* |
| 2:162280066:TTTTC:T | | frameshift | c.l567_1570delGAAA | p.Glu523fs |
| 2:162280073:T:A | | stop_gained | c.1564A > T | p.Lys522* |
| 2:162280076:CA:C | | frameshift | c.l560delT | p.Val521fs |
| 2:162280078:GTT:G | rsl466828817 | frameshift | c.l557_1558delAA | p.Lys519fs |
| 2:162280082:T:A | rsll90299758 | stop_gained | c.1555A > T | p.Lys519* |
| 2:162280088:TA:T | | frameshift | c.l548delT | p.Phe516fs |
| 2:162280105:GCA:G | | frameshift | c.l530_1531delTG | p.Ala511fs |
| 2:162280109:A:AGC | | frameshift | c.l527_1528insGC | p.Cys510fs |
| 2:162280113:C:G | | splice_acceptor | c.1525-1G > C | |
| 2:162280113:C:T | rs774035953 | splice_acceptor | c.1525-1G > A | |
| 2:162280114:T:C | | splice_acceptor | c.l525-2A > G | |
| 2:162280114:T:A | | splice_acceptor | c.l525-2A > T | |
| 2:162281326:A:T | rs865898522 | splice_donor | c,1524 + 2T > A | |
| 2:162281326:A:C | rs865898522 | splice_donor | c.1524 + 2T > G | |
| 2:162281327:C:T | rs898118498 | splice_donor | c.1524 + 1G > A | |
| 2:162281327:C:A | rs898118498 | splice_donor | c.1524 + 1G > T | |
| 2:162281331:T:TA | | frameshift | c,1520dupT | p.Leu507fs |
| 2:162281332:A:T | | stop_gained | c.1520T > A | p.Leu507* |
| 2:162281342:C:A | rs772032662 | stop_gained | c.1510G > T | p.Glu504* |
| 2:162281348:CT:C | | frameshift | c.l503delA | p.Ala502fs |
| 2:162281352:GGCTT:G | rs758450641 | frameshift | c.l496_1499delAAGC | p.Gln499fs |
| 2:162281361:CG:C | rs781305209 | frameshift | c.l490delC | p.Thr497fs |
| 2:162281365:GCCCCTCCA:G | | frameshift | c.l479_1486delTGGAGGGG | p.Gly494fs |
| 2:162281375:C:CT | | frameshift | c.l476_1477insA | p.Val493fs |
| 2:162281401:A:AAGGGGAT | rs748061170 | frameshift | c.l450_1451insATCCCCT | p.Ile484fs |
| 2:162281405:G:A | rs763638412 | stop_gained | c.14470T | p.Gln483* |
| 2:162281426:T:A | rs778487639 | stop_gained | c.1426A > T | p.Lys476* |
| 2:162281432:CT:C | | frameshift | c.l419delA | p.Glu474fs |
| 2:162281434:1ILIIGAGTCTA:T | | frameshift | c.1407_1417delTAGACTCAAGA | p.Asn469fs |
| 2:162281436:CTT:C | | frameshift | c.l414_1415delAA | p.Lys472fs |
| 2:162281445:AT:A | | frameshift | c.l406delA | p.Asn469fs |
| 2:162281453:TC:T | | frameshift | c.l398delG | p.Asn468fs |
| 2:162281467:A:T | rs779927507 | stop_gained | c.1385T > A | p.Leu462* |
| 2:162281488:T:TTA | | frameshift | c.l362_1363dupTA | p.Asn455fs |
| 2:162281490:A:C | | stop_gained | c.1362T > G | p.Tyr454* |
| 2:162281498:CT:C | | frameshift | c.l353delA | p.Ala452fs |
| 2:162281501:CT:C | | frameshift | c.l350delA | p.Glu451fs |
| 2:162281508:GGT:G | rsll95101187 | frameshift | c.l342_1343delAC | p.Thr448fs |
| 2:162281519:AT:A | rs773197026 | frameshift | c.l332delA | p.Glu444fs |
| 2:162281539:GAA:G | | frameshift | c.l311_1312delTT | p.Ser438fs |
| 2:162281546:C:A | rs779764925 | splice_acceptor | c.1307-1G > T | |
| 2:162282365:C:T | | splice_donor | c.1306 + 1G > A | |
| 2:162282365:C:A | rsl002771119 | splice_donor | c.1306 + 1G > T | |
| 2:162282399:C:A | rsl054159671 | stop_gained | c.1273G > T | p.Glu425* |
| 2:162282400:CA:C | rsll80019447 | frameshift | c.l271delT | p.Leu424fs |
| 2:162282468:C:A | | stop_gained | c.1204G > T | p.Glu402* |
| 2:162282514:AC:A | | frameshift | c.H57delG | p.Arg386fs |
| 2:162282517:A:T | | stop_gained | c.H55T > A | p.Tyr385* |
| 2:162282520:C:T | rsl99917968 | stop_gained | c.1152G > A | p.Trp384* |
| 2:162282521:C:T | rs752544919 | stop_gained | c.H51G > A | p.Trp384* |
| 2:162282561:G:A | rsl285685926 | stop_gained | c.11110T | p.Gln371* |
| 2:162282570:GC:G | | frameshift | c.HOldelG | p.Leu368fs |
| 2:162282577:CT:C | | splice_acceptor | c.lO96-2delA | |
| 2:162282577:C:T | | splice_acceptor | c.1096-1G > A | |
| 2:162288134:C:T | rsl40125523 | splice_donor | c.1095 + 1G > A | |
| 2:162288134:C:A | rsl40125523 | splice_donor | c.1095 + 1G > T | |
| 2:162288154:AC:A | | frameshift | c.lO75delG | p.Val359fs |
| 2:162288167:C:A | | stop_gained | c.lO63G > T | p.Glu355* |
| 2:162288183:CTTGT:C | | frameshift | c.l043_1046delACAA | p.Asp348fs |
| 2:162288189:TA:T | | frameshift | c,1040delT | p.Leu347fs |
| 2:162288236:CT:C | | frameshift | c.993delA | p.Ser333fs |
| 2:162288281:G:A | rs74162079 | stop_gained | c.9490T | p.Gln317* |
| 2:162288292:A:AC | | frameshift | c.937_938insG | p.Met313fs |
| 2:162288292:AT:A | rs757577285 | frameshift | c.937delA | p.Met313fs |
| 2:162288297:G:C | | stop_gained | c.9330G | p.Tyr311* |
| 2:162288297:G:T | rsl057520076 | stop_gained | c.9330A | p.Tyr311* |

TABLE 2-continued

| Variant | rsID | Effect | HGVS.c | HGVS.p |
|---|---|---|---|---|
| 2:162288300:AG:A | rsl212715492 | frameshift | c.929delC | p.Pro310fs |
| 2:162288311:G:A | rs762821474 | stop_gained | c.919OT | p.Gln307* |
| 2:162288324:CG:C | | frameshift | c.905delC | p.Pro302fs |
| 2:162288342:CA:C | | frameshift | c.887delT | p.Val296fs |
| 2:162288343:AC:A | rsl259622346 | frameshift | c.886delG | p.Val296fs |
| 2:162288356:C:G | | splice_acceptor | c.875-lG > C | |
| 2:162293562:ACCTGAA TCACTTCCCATGGTG:A | rsll95353990 | frameshift | c.855_874 + IdelCA CCATGGGAAGTGATTCAGG | p.Thr286fs |
| 2:162293562:A:G | | splice_donor | c.874 + 2T > C | |
| 2:162293563:C:T | | splice_donor | c.874 + lG > A | |
| 2:162293583:G:GCCTGAAT | | frameshift | c.848_854dupATTCAGG | p.Thr286fs |
| 2:162293643:TC:T | rs758585876 | frameshift | c.794delG | p.Gly265fs |
| 2:162293669:C:T | | splice_acceptor | c.770-lG > A | |
| 2:162306706:T:TACCTG | rsl323841528 | splice_donor | c.769 + 2_769 + 3insCAGGT | |
| 2:162306708:C:A | | splice_donor | c.769 + 1G > T | |
| 2:162306742:C:A | rs373854773 | stop_gained | c.736G > T | p.Glu246* |
| 2:162306744:G:T | | stop_gained | c.734OA | p.Ser245* |
| 2:162306747:GA:G | | frameshift | c.730delT | p.Ser244fs |
| 2:162306708:G:GC | | frameshift | c.716dupG | p.Met240fs |
| 2:162306790:G:A | rs771251917 | stop_gained | c.688OT | p.Gln230* |
| 2:162306811:G:A | rsl463635016 | stop_gained | c.667OT | p.Gln223* |
| 2:162306823:G:A | | stop_gained | c.655OT | p.Gln219* |
| 2:162306851:AAT:A | | frameshift | c.625_626delAT | p.lle209fs |
| 2:162310723:AG:A | | frameshift | c.663delC | p.Ter222fs |
| 2:162310723:A:T | | stop_lost | c.664T > A | p.Ter222Lysex t*? |
| 2:162310733:TG:T | | frameshift | c.653delC | p.Ser218fs |
| 2:162310741:CT:C | | frameshift | c.645delA | p.Asp216fs |
| 2:162310750:TA:T | | frameshift | c.636delT | p.Phe212fs |
| 2:162310765:C:A | | stop_gained | c.622G > T | p.Glu208* |
| 2:162310777:C:A | | stop_gained | c.610G > T:c.610G > T | p.Glu204*:p.GI u204* |
| 2:162310822:C:A | | stop_gained | c.565G > T:c.565G > T | p.Glyl89*:p.GI yl89* |
| 2:162310855:AC:A | | frameshift | c.531delG:c.531delG | p.Trpl77fs:p.T rpl77fs |
| 2:162310857:C:T | | stop_gained | c.530G > A:c.530G > A | p.Trpl77*:p.Tr pl77* |
| 2:162310868:CT:C | rsl348521704 | frameshift | c.518delA:c.518delA | p.Glnl73fs:p.G lnl73fs |
| 2:162310878:CT:C | | frameshift | c.508delA:c.508delA | p.Argl70fs:p.A rgl70fs |
| 2:162310882:T:A | rs201495678 | stop_gained | c.505A > T:c.505A > T | p.Lysl69*:p.Ly sl69* |
| 2:162310891:C:A | | stop_gained | c.496G > T:c.496G > T | p.Glul66*:p.GI ul66* |
| 2:162310902:G:T | rsl455983191 | stop_gained | c.485C > A:c.485C > A | p.Serl62*:p.Se rl62* |
| 2:162310903:A:AT | | frameshift | c.483dupA:c.483du pA | p.Serl62fs:p.S erl62fs |
| 2:162310906:C:A | | stop_gained | c.481G > T:c.481G > T | p.Glul61*:p.GI U161* |
| 2:162310924:CA:C | | frameshift | c.462delT:c.462delT | p.Alal55fs:p.A lal55fs |
| 2:162310934:C:A | rsl48590996 | splice_acceptor | c.454-lG > T:c.454-1G > T | |
| 2:162317853:AC:A | | splice_donor | c.453 + ldelG:c.453 + ldelG | |
| 2:162317854:C:T | rs967571395 | splice_donor | c.453 + 1G > A:c.453 + 1G > A | |
| 2:162317869:C:A | | stop_gained | c.439G > T:c.439G > T | p.Glul47*:p.GI ul47* |
| 2:162317881:GT:G | | frameshift | c.426delA:c.426delA | p.Glul42fs:p.G lul42fs |
| 2:162317890:C:A | | stop_gained | c.418G > T:c.418G > T | p.Glul40*:p.GI ul40* |
| 2:162317901:TC:T | rsl261022198 | frameshift | c.406delG:c.406delG | p.Aspl36fs:p. Aspl36fs |
| 2:162317944:G:A | | stop_gained | c.364C > T:c.364C > T | p.Glnl22*:p.GI nl22* |
| 2:162317962:G:A | | stop_gained | c.346C > T:c.346C > T | p.Glnll6*:p.GI nll6* |
| 2:162317965:GAT:G | | frameshift | c.341_342delAT:c.341_342delAT | p.Tyrll4fs:p.T yrll4fs |
| 2:162317966:A:C | | stop_gained | c.342T > G:c.342T > G | p.Tyrll4*:p.Ty rll4* |
| 2:162317967:TA:T | | frameshift | c.340delT:c.340delT | p.Tyrll4fs:p.T yrll4fs |
| 2:162317971:C:A | | stop_gained | c.337G > T:c.337G > T | p.Glull3*:p.GI ull3* |

TABLE 2-continued

| Variant | rsID | Effect | HGVS.c | HGVS.p |
|---|---|---|---|---|
| 2:162317986:C:A | | stop_gained | c.322G > T:c.322G > T | p.GluIO8*:p.GIuI08* |
| 2:162317994:GGA:G | rs756183031 | frameshift | c.312_313delTC:c.312_313delTC | p.Pro105fs:p.Pro105fs |
| 2:162318017:A:AG | | frameshift | c.290dupC:c.290dupC | p.Glu98fs:p.GIu98fs |
| 2:162318026:G:T | | stop_gained | c.282C > A:c.282C > A | p.Tyr94*:p.Tyr94* |
| 2:162318055:T:A | | stop_gained | c.253A > T:c.253A > T | p.Arg85*:p.Arg885* |
| 2:162318065:C:CT | | frameshift | c.242dupA:c.242dupA | p.Ala82fs:p.AIa82fs |
| 2:162318069:AC:A | | frameshift | c.238delG:c.238delG | p.Val80fs:p.Val80fs |
| 2:162318073:A:AT | rsll73976772 | frameshift | c.234dupA:c.234dupA | p.Phe79fs:p.Phe79fs |
| 2:162318084:CIT | | stop_gained | c.224G > A:c.224G > A | p.Trp75*:p.Trp75* |
| 2:162318092:GT:G | rsl327398341 | frameshift | c.215delA:c.215delA | p.His72fs:p.His72fs |
| 2:162318145:TC:T | rsl394699072 | frameshift | c.l62delG:c.l62delG | p.Asn55fs:p.Asn55fs |
| 2:162318169:G:A | | stop_gained | c.139C > T:c.139C > T | p.Gln47*:p.GIn47* |
| 2:162318188:TGCAG:T | | frameshift | c.H6_119delCTGC:c.H6_119delCTGC | p.Pro39fs:p.Pro39fs |
| 2:162318254:GAA:G | | frameshift | c.52_53delTT:c.52_53delTT | p.Phel8fs:p.Phel8fs |
| 2:162318254:GA:G | | frameshift | c.53delT:c.53delT | p.Phel8fs:p.Phel8fs |
| 2:162318258:C:CA | | frameshift | c.49dupT:c.49dupT | p.Cysl7fs:p.Cysl7fs |
| 2:162318283:C:A | | stop_gained | c.25G > T:c.25G > T | p.Glu9*:p.Glu9* |
| 2:162318284:GTC:G | | frameshift | c.22_23delGA:c.22_23delGA | p.Asp8fs:p.Asp8fs |
| 2:162318297:CCATTCGA:C | | frameshift | c.4_10delTCGAATG:c.4_10delTCGAATG | p.Ser2fs:p.Ser2fs |

In some embodiments, the subject's aggregate burden of having any one or more IFIH1 missense variant nucleic acid molecules encoding an IFIH1 predicted loss-of-function polypeptide represents a weighted sum of a plurality of any of the IFIH1 missense variant nucleic acid molecules encoding an IFIH1 predicted loss-of-function polypeptide. In some embodiments, the aggregate burden is calculated using at least about 2, at least about 3, at least about 4, at least about 5, at least about 10, at least about 20, at least about 30, at least about 40, at least about 50, at least about 60, at least about 70, at least about 80, at least about 100, at least about 120, at least about 150, at least about 200, at least about 250, at least about 300, at least about 400, at least about 500, at least about 1,000, at least about 10,000, at least about 100,000, or at least about or more than 1,000,000 genetic variants present in or around (up to 10 Mb) the IFIH1 gene where the genetic burden is the number of alleles multiplied by the association estimate with psoriasis or related outcome for each allele (e.g., a weighted polygenic burden score). This can include any genetic variants, regardless of their genomic annotation, in proximity to the IFIH1 gene (up to 10 Mb around the gene) that show a non-zero association with psoriasis-related traits in a genetic association analysis. In some embodiments, when the subject has an aggregate burden above a desired threshold score, the subject has a decreased risk of developing psoriasis. In some embodiments, when the subject has an aggregate burden below a desired threshold score, the subject has an increased risk of developing psoriasis.

In some embodiments, the aggregate burden may be divided into quintiles, e.g., top quintile, intermediate quintile, and bottom quintile, wherein the top quintile of aggregate burden corresponds to the lowest risk group and the bottom quintile of aggregate burden corresponds to the highest risk group. In some embodiments, a subject having a greater aggregate burden comprises the highest weighted aggregate burdens, including, but not limited to the top 10%, top 20%, top 30%, top 40%, or top 50% of aggregate burdens from a subject population. In some embodiments, the genetic variants comprise the genetic variants having association with psoriasis in the top 10%, top 20%, top 30%, top 40%, or top 50% of p-value range for the association. In some embodiments, each of the identified genetic variants comprise the genetic variants having association with psoriasis with p-value of no more than about $10^{-2}$, about $10^{-3}$, about $10^{-4}$, about $10^{-5}$, about $10^{-6}$, about $10^{-7}$, about $10^{-8}$, about $10^{-9}$, about $10^{-10}$, about $10^{-11}$, about $10^{-12}$, about $10^{-13}$, about $10^{-14}$, about or $10^{-15}$. In some embodiments, the identified genetic variants comprise the genetic variants having association with psoriasis with p-value of less than $5 \times 10^{-8}$. In some embodiments, the identified genetic variants comprise genetic variants having association with psoriasis in high-risk subjects as compared to the rest of the reference population with odds ratio (OR) about 1.5 or greater, about 1.75 or greater, about 2.0 or greater, or about 2.25 or greater for the top 20% of the distribution; or about 1.5 or greater, about 1.75 or greater, about 2.0 or greater, about 2.25 or greater, about 2.5 or greater, or about 2.75 or greater. In some embodiments, the odds ratio (OR) may range from about 1.0 to about 1.5, from about 1.5 to about 2.0, from about 2.0 to about 2.5, from about 2.5 to about 3.0, from about 3.0 to about 3.5, from about 3.5 to about 4.0, from about 4.0 to about 4.5, from about 4.5 to about 5.0, from about 5.0 to about 5.5, from about 5.5 to about 6.0, from about 6.0 to about 6.5, from about 6.5 to about 7.0, or greater than 7.0. In some embodiments, high-risk subjects comprise subjects having aggregate burdens in the bottom decile, quintile, or tertile in a reference population. The threshold of the aggregate burden is determined on the basis of the nature of the intended practical application and the risk difference that would be considered meaningful for that practical application.

In some embodiments, when a subject is identified as having an increased risk of developing psoriasis, the subject is further treated with a therapeutic agent that treats or inhibits psoriasis, and/or an IFIH1 inhibitor, and/or a TRIM65 inhibitor, and/or type 1 interferon pathway inhibitor as described herein. For example, when the subject is IFIH1 reference, and therefore has an increased risk of developing psoriasis, the subject is administered an IFIH1 inhibitor. In some embodiments, such a subject is also administered a therapeutic agent that treats or inhibits psoriasis and/or a type 1 interferon pathway inhibitor and/or an IFIH1 inhibitor. In some embodiments, when the subject is heterozygous for an IFIH1 missense variant nucleic acid molecule encoding an IFIH1 predicted loss-of-function polypeptide, the subject is administered the therapeutic agent that treats or inhibits psoriasis in a dosage amount that is the same as or less than a standard dosage amount, and is also administered an IFIH1 inhibitor, and/or type 1 interferon pathway inhibitor, and/or an IFIH1 inhibitor. In some embodiments, the subject is IFIH1 reference. In some embodiments, the subject is heterozygous for an IFIH1 missense variant nucleic acid molecule encoding an IFIH1 predicted loss-of-function polypeptide. Furthermore, when the subject has a lower aggregate burden for having an IFIH1 missense variant nucleic acid molecule encoding an IFIH1 predicted loss-of-function polypeptide, and therefore has an increased risk of developing psoriasis, the subject is administered a therapeutic agent that treats or inhibits psoriasis. In some embodiments, when the subject has a lower aggregate burden for having an IFIH1 missense variant nucleic acid molecule encoding an IFIH1 predicted loss-of-function polypeptide, the subject is administered the therapeutic agent that treats or inhibits psoriasis in a dosage amount that is the same as or greater than the standard dosage amount administered to a subject who has a greater aggregate burden for having an IFIH1 missense variant nucleic acid molecule encoding an IFIH1 predicted loss-of-function polypeptide.

The present disclosure also provides methods of detecting the presence or absence of an IFIH1 or TRIM65 missense genomic variant nucleic acid molecule encoding an IFIH1 predicted loss-of-function polypeptide in a biological sample from a subject, and/or an IFIH1 or TRIM65 missense variant mRNA molecule encoding an IFIH1 or TRIM65 predicted loss-of-function polypeptide in a biological sample from a subject, and/or an IFIH1 or TRIM65 missense variant cDNA molecule encoding an IFIH1 or TRIM65 predicted loss-of-function polypeptide produced from an mRNA molecule in a biological sample from a subject. It is understood that gene sequences within a population and mRNA molecules encoded by such genes can vary due to polymorphisms such as single-nucleotide polymorphisms. The sequences provided herein for the IFIH1 or TRIM65 missense variant genomic nucleic acid molecule, IFIH1 or TRIM65 missense variant mRNA molecule, and IFIH1 or TRIM65 missense variant cDNA molecule are only exemplary sequences. Other sequences for the IFIH1 or TRIM65 missense variant genomic nucleic acid molecule, missense variant mRNA molecule, and missense variant cDNA molecule are also possible.

The biological sample can be derived from any cell, tissue, or biological fluid from the subject. The sample may comprise any clinically relevant tissue, such as a bone marrow sample, a tumor biopsy, a fine needle aspirate, or a sample of bodily fluid, such as blood, gingival crevicular fluid, plasma, serum, lymph, ascitic fluid, cystic fluid, or urine. In some cases, the sample comprises a buccal swab. The sample used in the methods disclosed herein will vary based on the assay format, nature of the detection method, and the tissues, cells, or extracts that are used as the sample. A biological sample can be processed differently depending on the assay being employed. For example, when detecting any IFIH1 missense variant nucleic acid molecule, preliminary processing designed to isolate or enrich the sample for the genomic DNA can be employed. A variety of techniques may be used for this purpose. When detecting the level of any IFIH1 or TRIM65 missense variant mRNA, different techniques can be used enrich the biological sample with mRNA. Various methods to detect the presence or level of an mRNA or the presence of a particular missense variant genomic DNA locus can be used.

In some embodiments, detecting an IFIH1 or TRIM65 missense variant nucleic acid molecule encoding an IFIH1 or TRIM65 predicted loss-of-function polypeptide in a subject comprises assaying or genotyping a biological sample obtained from the subject to determine whether an IFIH1 or TRIM65 genomic nucleic acid molecule in the biological sample, and/or an IFIH1 or TRIM65 mRNA molecule in the biological sample, and/or an IFIH1 or TRIM65 cDNA molecule produced from an mRNA molecule in the biological sample, comprises one or more variations that cause a loss-of-function (partial or complete) or are predicted to cause a loss-of-function (partial or complete).

In some embodiments, the methods of detecting the presence or absence of an IFIH1 or TRIM65 missense variant nucleic acid molecule encoding an IFIH1 or TRIM65 predicted loss-of-function polypeptide (such as, for example, a genomic nucleic acid molecule, an mRNA molecule, and/or a cDNA molecule produced from an mRNA molecule) in a subject, comprise performing an assay on a biological sample obtained from the subject. The assay determines whether a nucleic acid molecule in the biological sample comprises a particular nucleotide sequence. In some embodiments, the IFIH1 nucleotide sequence comprises a cytosine at a position corresponding to position 38,690 according to SEQ ID NO:2 (for genomic nucleic acid molecules).

In some embodiments, the biological sample comprises a cell or cell lysate. Such methods can further comprise, for example, obtaining a biological sample from the subject comprising an IFIH1 or TRIM65 genomic nucleic acid molecule or mRNA molecule, and if mRNA, optionally reverse transcribing the mRNA into cDNA. Such assays can comprise, for example determining the identity of these positions of the particular IFIH1 or TRIM65 nucleic acid molecule. In some embodiments, the method is an in vitro method.

In some embodiments, the determining step, detecting step, or sequencing analysis comprises sequencing at least a portion of the nucleotide sequence of the IFIH1 or TRIM65 genomic nucleic acid molecule, the IFIH1 or TRIM65 mRNA molecule, or the IFIH1 or TRIM65 cDNA molecule in the biological sample, wherein the sequenced portion comprises one or more variations that cause a loss-of-function (partial or complete) or are predicted to cause a loss-of-function (partial or complete).

In some embodiments, the determining step, detecting step, or sequence analysis comprises sequencing at least a portion of the nucleotide sequence of the IFIH1 genomic nucleic acid molecule in the biological sample, wherein the sequenced portion comprises a position corresponding to position 38,690 according to SEQ ID NO:2, or the complement thereof. When the sequenced portion of the IFIH1 nucleic acid molecule in the biological sample comprises a cytosine at a position corresponding to position 38,690 according to SEQ ID NO:2, then the IFIH1 nucleic acid molecule in the biological sample is an IFIH1 missense variant nucleic acid molecule encoding an IFIH1 predicted loss-of-function polypeptide.

In some embodiments, the determining step, detecting step, or sequence analysis comprises: a) contacting the biological sample with a primer hybridizing to a portion of the nucleotide sequence of the IFIH1 genomic nucleic acid molecule that is proximate to a position corresponding to position 38,690 according to SEQ ID NO:2; b) extending the primer at least through the position of the nucleotide sequence of the IFIH1 genomic nucleic acid molecule corresponding to position 38,690 according to SEQ ID NO:2; and c) determining whether the extension product of the primer comprises a cytosine at a position corresponding to position 38,690 according to SEQ ID NO:2.

In some embodiments, the assay comprises sequencing the entire nucleic acid molecule. In some embodiments, only an IFIH1 or TRIM65 genomic nucleic acid molecule is analyzed. In some embodiments, only an IFIH1 or TRIM65 mRNA is analyzed. In some embodiments, only an IFIH1 cDNA obtained from IFIH1 or TRIM65 mRNA is analyzed.

In some embodiments, the determining step, detecting step, or sequence analysis comprises: a) amplifying at least a portion of the nucleic acid molecule that encodes the human IFIH1 polypeptide, wherein the amplified portion comprises a cytosine at a position corresponding to position 38,690 according to SEQ ID NO:2, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising a cytosine at a position corresponding to position 38,690 according to SEQ ID NO:2, or the complement thereof; and d) detecting the detectable label.

In some embodiments, the nucleic acid molecule is mRNA and the determining step further comprises reverse-transcribing the mRNA into a cDNA prior to the amplifying step.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising a cytosine at a position corresponding to position 38,690 according to SEQ ID NO:2, or the complement thereof; and detecting the detectable label.

Alteration-specific polymerase chain reaction techniques can be used to detect mutations such as SNPs in a nucleic acid sequence. Alteration-specific primers can be used because the DNA polymerase will not extend when a mismatch with the template is present.

In some embodiments, the nucleic acid molecule in the sample is mRNA and the mRNA is reverse-transcribed into a cDNA prior to the amplifying step. In some embodiments, the nucleic acid molecule is present within a cell obtained from the human subject.

In some embodiments, the assay comprises contacting the biological sample with a primer or probe, such as an alteration-specific primer or alteration-specific probe, that specifically hybridizes to an IFIH1 or TRIM65 variant genomic sequence, variant mRNA sequence, or variant cDNA sequence and not the corresponding IFIH1 or TRIM65 reference sequence under stringent conditions, and determining whether hybridization has occurred.

In some embodiments, the assay comprises RNA sequencing (RNA-Seq). In some embodiments, the assays also comprise reverse transcribing mRNA into cDNA, such as by the reverse transcriptase polymerase chain reaction (RT-PCR).

In some embodiments, the methods utilize probes and primers of sufficient nucleotide length to bind to the target nucleotide sequence and specifically detect and/or identify a polynucleotide comprising an IFIH1 or TRIM65 missense variant genomic nucleic acid molecule, missense variant mRNA molecule, or missense variant cDNA molecule. The hybridization conditions or reaction conditions can be determined by the operator to achieve this result. The nucleotide length may be any length that is sufficient for use in a detection method of choice, including any assay described or exemplified herein. Such probes and primers can hybridize specifically to a target nucleotide sequence under high stringency hybridization conditions. Probes and primers may have complete nucleotide sequence identity of contiguous nucleotides within the target nucleotide sequence, although probes differing from the target nucleotide sequence and that retain the ability to specifically detect and/or identify a target nucleotide sequence may be designed by conventional methods. Probes and primers can have about 80%, about 85%, about 90%, about 91%, about 92%, about 93%, about 94%, about 95%, about 96%, about 97%, about 98%, about 99%, or 100% sequence identity or complementarity with the nucleotide sequence of the target nucleic acid molecule.

In some embodiments, to determine whether an IFIH1 nucleic acid molecule (genomic nucleic acid molecule, mRNA molecule, or cDNA molecule), or complement thereof, within a biological sample comprises a nucleotide sequence comprising a cytosine at a position corresponding to position 38,690 according to SEQ ID NO:2 (genomic nucleic acid molecule), the biological sample can be subjected to an amplification method using a primer pair that includes a first primer derived from the 5' flanking sequence adjacent to a cytosine at a position corresponding to position 38,690 according to SEQ ID NO:2, and a second primer derived from the 3' flanking sequence adjacent to a cytosine at a position corresponding to position 38,690 according to SEQ ID NO:2 to produce an amplicon that is indicative of the presence of the SNP at positions encoding a cytosine at a position corresponding to position 38,690 according to SEQ ID NO:2. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising a cytosine at a position corresponding to position 38,690 according to SEQ ID NO:2 and at least 1, 2, 3, 4, 5, 6, 7, 8, 9, 10, or more nucleotides on each side of positions comprising a cytosine at a position corresponding to position 38,690 according to SEQ ID NO:2.

Similar amplicons can be generated from the mRNA and/or cDNA sequences. PCR primer pairs can be derived from a known sequence, for example, by using computer programs intended for that purpose, such as the PCR primer analysis tool in Vector NTI version 10 (Informax Inc., Bethesda Md.); PrimerSelect (DNASTAR Inc., Madison, Wis.); and Primer3 (Version 0.4.0.COPYRGT., 1991, Whitehead Institute for Biomedical Research, Cambridge, Mass.). Additionally, the sequence can be visually scanned and primers manually identified using known guidelines.

Illustrative examples of nucleic acid sequencing techniques include, but are not limited to, chain terminator (Sanger) sequencing and dye terminator sequencing. Other methods involve nucleic acid hybridization methods other than sequencing, including using labeled primers or probes directed against purified DNA, amplified DNA, and fixed cell preparations (fluorescence in situ hybridization (FISH)). In some methods, a target nucleic acid molecule may be amplified prior to or simultaneous with detection. Illustrative examples of nucleic acid amplification techniques include, but are not limited to, polymerase chain reaction (PCR), ligase chain reaction (LCR), strand displacement amplification (SDA), and nucleic acid sequence based amplification (NASBA). Other methods include, but are not limited to, ligase chain reaction, strand displacement amplification, and thermophilic SDA (tSDA).

In hybridization techniques, stringent conditions can be employed such that a probe or primer will specifically hybridize to its target. In some embodiments, a polynucleotide primer or probe under stringent conditions will hybridize to its target sequence to a detectably greater degree than to other non-target sequences, such as, at least 2-fold, at least 3-fold, at least 4-fold, or more over background, including over 10-fold over background. In some embodiments, a polynucleotide primer or probe under stringent conditions will hybridize to its target nucleotide sequence to a detectably greater degree than to other nucleotide sequences by at least 2-fold. In some embodiments, a polynucleotide primer or probe under stringent conditions will hybridize to its target nucleotide sequence to a detectably greater degree than to other nucleotide sequences by at least 3-fold. In some embodiments, a polynucleotide primer or probe under stringent conditions will hybridize to its target nucleotide sequence to a detectably greater degree than to other nucleotide sequences by at least 4-fold. In some embodiments, a polynucleotide primer or probe under stringent conditions will hybridize to its target nucleotide sequence to a detectably greater degree than to other nucleotide sequences by over 10-fold over background. Stringent conditions are sequence-dependent and will be different in different circumstances.

Appropriate stringency conditions which promote DNA hybridization, for example, 6× sodium chloride/sodium citrate (SSC) at about 45° C., followed by a wash of 2×SSC at 50° C., are known or can be found in Current Protocols in Molecular Biology, John Wiley & Sons, N.Y. (1989), 6.3.1-6.3.6. Typically, stringent conditions for hybridization and detection will be those in which the salt concentration is less than about 1.5 M Na$^+$ ion, typically about 0.01 to 1.0 M Na$^+$ ion concentration (or other salts) at pH 7.0 to 8.3 and the temperature is at least about 30° C. for short probes (such as, for example, 10 to 50 nucleotides) and at least about 60° C. for longer probes (such as, for example, greater than 50 nucleotides). Stringent conditions may also be achieved with the addition of destabilizing agents such as formamide. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

The present disclosure also provides methods of detecting the presence of an IFIH1 predicted loss-of-function polypeptide comprising performing an assay on a sample obtained from a subject to determine whether an IFIH1 polypeptide in the subject contains one or more variations that causes the polypeptide to have a loss-of-function (partial or complete) or predicted loss-of-function (partial or complete). The IFIH1 predicted loss-of-function polypeptide can be any of the IFIH1 truncated variant polypeptides described herein. In some embodiments, when the subject does not have an IFIH1 predicted loss-of-function polypeptide, then the subject has an increased risk for developing psoriasis. In some embodiments, when the subject has an IFIH1 predicted loss-of-function polypeptide, then the subject has a decreased risk for developing psoriasis.

The present disclosure also provides methods of detecting the presence of a TRIM65 predicted loss-of-function polypeptide comprising performing an assay on a sample obtained from a subject to determine whether a TRIM65 polypeptide in the subject contains one or more variations that causes the polypeptide to have a loss-of-function (partial or complete) or predicted loss-of-function (partial or complete). The TRIM65 predicted loss-of-function polypeptide can be any of the TRIM65 variant polypeptides described herein. In some embodiments, when the subject does not have a TRIM65 predicted loss-of-function polypeptide, then the subject has an increased risk for developing psoriasis. In some embodiments, when the subject has a TRIM65 predicted loss-of-function polypeptide, then the subject has a decreased risk for developing psoriasis.

The present disclosure also provides isolated nucleic acid molecules that hybridize to IFIH1 or TRIM65 missense variant genomic nucleic acid molecules, IFIH1 or TRIM65 missense variant mRNA molecules, and/or IFIH1 or TRIM65 missense variant cDNA molecules (such as any of the genomic variant nucleic acid molecules, mRNA variant molecules, and cDNA variant molecules disclosed herein). In some embodiments, the isolated nucleic acid molecules hybridize to a portion of the IFIH1 nucleic acid molecule that includes a position corresponding to position 38,690 according to SEQ ID NO:2.

In some embodiments, such isolated nucleic acid molecules comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 200, at least about 300, at least about 400, at least about 500, at least about 600, at least about 700, at least about 800, at least about 900, at least about 1000, at least about 2000, at least about 3000, at least about 4000, or at least about 5000 nucleotides. In some embodiments, such isolated nucleic acid molecules comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, or at least about 25 nucleotides. In some embodiments, the isolated nucleic acid molecules comprise or consist of at least about 18 nucleotides. In some embodiments, the isolated nucleic acid molecules comprise or consists of at least about 15 nucleotides. In some embodiments, the isolated nucleic acid molecules consist of or comprise from about 10 to about 35, from about 10 to about 30, from about 10 to about 25, from about 12 to about 30, from about 12 to about 28, from about 12 to about 24, from about 15 to about 30, from about 15 to about 25, from about 18 to about 30, from about 18 to about 25, from about 18 to about 24, or from about 18 to about 22 nucleotides. In some embodiments, the isolated nucleic acid molecules consist of or comprise from about 18 to about 30 nucleotides. In some embodiments, the isolated nucleic acid molecules comprise or consist of at least about 15 nucleotides to at least about 35 nucleotides.

In some embodiments, such isolated nucleic acid molecules hybridize to IFIH1 or TRIM65 missense variant nucleic acid molecules (such as genomic nucleic acid molecules, mRNA molecules, and/or cDNA molecules) under stringent conditions. Such nucleic acid molecules can be used, for example, as probes, primers, alteration-specific probes, or alteration-specific primers as described or exemplified herein, and include, without limitation primers, probes, antisense RNAs, shRNAs, and siRNAs, each of which is described in more detail elsewhere herein, and can be used in any of the methods described herein.

In some embodiments, the isolated nucleic acid molecules hybridize to at least about 15 contiguous nucleotides of a nucleic acid molecule that is at least about 70%, at least about 75%, at least about 80%, at least about 85%, at least about 90%, at least about 95%, at least about 96%, at least about 97%, at least about 98%, at least about 99%, or 100% identical to IFIH1 or TRIM65 missense variant genomic nucleic acid molecules, IFIH1 or TRIM65 missense variant mRNA molecules, and/or IFIH1 or TRIM65 missense variant cDNA molecules. In some embodiments, the isolated nucleic acid molecules consist of or comprise from about 15 to about 100 nucleotides, or from about 15 to about 35 nucleotides. In some embodiments, the isolated nucleic acid molecules consist of or comprise from about 15 to about 100 nucleotides. In some embodiments, the isolated nucleic acid molecules consist of or comprise from about 15 to about 35 nucleotides.

In some embodiments, the isolated alteration-specific probes or alteration-specific primers comprise at least about 15 nucleotides, wherein the alteration-specific probe or alteration-specific primer comprises a nucleotide sequence which is complementary to a portion of an IFIH1 missense variant nucleic acid molecule encoding an IFIH1 predicted loss-of-function polypeptide, wherein the portion comprises a position corresponding to position 38,690 according to SEQ ID NO:2, or the complement thereof.

In some embodiments, the alteration-specific probes and alteration-specific primers comprise DNA. In some embodiments, the alteration-specific probes and alteration-specific primers comprise RNA.

In some embodiments, the probes and primers described herein (including alteration-specific probes and alteration-specific primers) have a nucleotide sequence that specifically hybridizes to any of the nucleic acid molecules disclosed herein, or the complement thereof. In some embodiments, the probes and primers specifically hybridize to any of the nucleic acid molecules disclosed herein under stringent conditions.

In some embodiments, the primers, including alteration-specific primers, can be used in second generation sequencing or high throughput sequencing. In some instances, the primers, including alteration-specific primers, can be modified. In particular, the primers can comprise various modifications that are used at different steps of, for example, Massive Parallel Signature Sequencing (MPSS), Polony sequencing, and 454 Pyrosequencing. Modified primers can be used at several steps of the process, including biotinylated primers in the cloning step and fluorescently labeled primers used at the bead loading step and detection step. Polony sequencing is generally performed using a paired-end tags library wherein each molecule of DNA template is about 135 bp in length. Biotinylated primers are used at the bead loading step and emulsion PCR. Fluorescently labeled degenerate nonamer oligonucleotides are used at the detection step. An adaptor can contain a 5'-biotin tag for immobilization of the DNA library onto streptavidin-coated beads.

The probes and primers described herein can be used to detect a nucleotide variation within any of the IFIH1 or TRIM65 missense variant genomic nucleic acid molecules, IFIH1 or TRIM65 missense variant mRNA molecules, and/or IFIH1 or TRIM65 missense variant cDNA molecules disclosed herein. The primers described herein can be used to amplify IFIH1 or TRIM65 missense variant genomic nucleic acid molecules, IFIH1 or TRIM65 missense variant mRNA molecules, or IFIH1 or TRIM65 missense variant cDNA molecules, or a fragment thereof.

The present disclosure also provides pairs of primers comprising any of the primers described above. For example, if one of the primers' 3'-ends hybridizes to a guanine at a position corresponding to position 38,690 according to SEQ ID NO:1 (rather than cytosine) in a particular IFIH1 nucleic acid molecule, then the presence of the amplified fragment would indicate the presence of an IFIH1 reference genomic nucleic acid molecule. Conversely, if one of the primers' 3'-ends hybridizes to a cytosine at a position corresponding to position 38,690 according to SEQ ID NO:2 (rather than guanine) in a particular IFIH1 nucleic acid molecule, then the presence of the amplified fragment would indicate the presence of the IFIH1 missense variant genomic nucleic acid molecule. In some embodiments, the nucleotide of the primer complementary to the cytosine at a position corresponding to position 38,690 according to SEQ ID NO:2 can be at the 3' end of the primer.

In the context of the disclosure "specifically hybridizes" means that the probe or primer (such as, for example, the alteration-specific probe or alteration-specific primer) does not hybridize to a nucleic acid sequence encoding an IFIH1 or TRIM65 reference genomic nucleic acid molecule, an IFIH1 or TRIM65 reference mRNA molecule, and/or an IFIH1 or TRIM65 reference cDNA molecule.

In some embodiments, the probes (such as, for example, an alteration-specific probe) comprise a label. In some embodiments, the label is a fluorescent label, a radiolabel, or biotin.

The present disclosure also provides supports comprising a substrate to which any one or more of the probes disclosed herein is attached. Solid supports are solid-state substrates or supports with which molecules, such as any of the probes disclosed herein, can be associated. A form of solid support is an array. Another form of solid support is an array detector. An array detector is a solid support to which multiple different probes have been coupled in an array, grid, or other organized pattern. A form for a solid-state substrate is a microtiter dish, such as a standard 96-well type. In some embodiments, a multiwell glass slide can be employed that normally contains one array per well.

The nucleotide sequence of an IFIH1 reference genomic nucleic acid molecule is set forth in SEQ ID NO:1. This sequence corresponds to chromosome 2 positions 162,267, 074-162,318,684 according to GRCh38/hg38 human genome assembly (Gencode gene ENSG00000115267.8). Referring to SEQ ID NO:1, position 38,690 is a guanine.

A variant genomic nucleic acid molecule of IFIH1 exists, wherein the guanine at position 38,690 is replaced with cytosine. The nucleotide sequence of this IFIH1 variant genomic nucleic acid molecule is set forth in SEQ ID NO:2.

The nucleotide sequence of an IFIH1 reference mRNA molecule is set forth in SEQ ID NO:3. The nucleotide sequence of another IFIH1 reference mRNA molecule is set forth in SEQ ID NO:4. The nucleotide sequence of another IFIH1 reference mRNA molecule is set forth in SEQ ID NO:5. The nucleotide sequence of another IFIH1 reference mRNA molecule is set forth in SEQ ID NO:6. The nucleotide sequence of another IFIH1 reference mRNA molecule is set forth in SEQ ID NO:7. The nucleotide sequence of another IFIH1 reference mRNA molecule is set forth in SEQ ID NO:8. The nucleotide sequence of another IFIH1 reference mRNA molecule is set forth in SEQ ID NO:9 The nucleotide sequence of another IFIH1 reference mRNA molecule is set forth in is set forth in SEQ ID NO:10.

The nucleotide sequence of an IFIH1 reference cDNA molecule is set forth in SEQ ID NO:11. The nucleotide sequence of another IFIH1 reference cDNA molecule is set forth in SEQ ID NO:12. The nucleotide sequence of another IFIH1 reference cDNA molecule is set forth in SEQ ID NO:13. The nucleotide sequence of another IFIH1 reference cDNA molecule is set forth in SEQ ID NO:14. The nucleotide sequence of another IFIH1 reference cDNA molecule is set forth in SEQ ID NO:15. The nucleotide sequence of another IFIH1 reference cDNA molecule is set forth in SEQ ID NO:16. The nucleotide sequence of another IFIH1 reference cDNA molecule is set forth in SEQ ID NO:17. The nucleotide sequence of another IFIH1 reference cDNA molecule is set forth in SEQ ID NO:18.

The genomic nucleic acid molecules, mRNA molecules, and cDNA molecules can be from any organism. For example, the genomic nucleic acid molecules, mRNA molecules, and cDNA molecules can be human or an ortholog from another organism, such as a non-human mammal, a rodent, a mouse, or a rat. It is understood that gene sequences within a population can vary due to polymorphisms such as single-nucleotide polymorphisms. The examples provided herein are only exemplary sequences. Other sequences are also possible.

Also provided herein are functional polynucleotides that can interact with the disclosed nucleic acid molecules. Examples of functional polynucleotides include, but are not limited to, antisense molecules, aptamers, ribozymes, triplex forming molecules, and external guide sequences. The functional polynucleotides can act as effectors, inhibitors, modulators, and stimulators of a specific activity possessed by a target molecule, or the functional polynucleotides can possess a de novo activity independent of any other molecules.

The isolated nucleic acid molecules disclosed herein can comprise RNA, DNA, or both RNA and DNA. The isolated nucleic acid molecules can also be linked or fused to a heterologous nucleic acid sequence, such as in a vector, or a heterologous label. For example, the isolated nucleic acid molecules disclosed herein can be within a vector or as an exogenous donor sequence comprising the isolated nucleic acid molecule and a heterologous nucleic acid sequence. The isolated nucleic acid molecules can also be linked or fused to a heterologous label. The label can be directly detectable (such as, for example, fluorophore) or indirectly detectable (such as, for example, hapten, enzyme, or fluorophore quencher). Such labels can be detectable by spectroscopic, photochemical, biochemical, immunochemical, or chemical means. Such labels include, for example, radiolabels, pigments, dyes, chromogens, spin labels, and fluorescent labels. The label can also be, for example, a chemiluminescent substance; a metal-containing substance; or an enzyme, where there occurs an enzyme-dependent secondary generation of signal. The term "label" can also refer to a "tag" or hapten that can bind selectively to a conjugated molecule such that the conjugated molecule, when added subsequently along with a substrate, is used to generate a detectable signal. For example, biotin can be used as a tag along with an avidin or streptavidin conjugate of horseradish peroxidate (HRP) to bind to the tag, and examined using a calorimetric substrate (such as, for example, tetramethylbenzidine (TMB)) or a fluorogenic substrate to detect the presence of HRP. Exemplary labels that can be used as tags to facilitate purification include, but are not limited to, myc, HA, FLAG or 3×FLAG, 6×His or polyhistidine, glutathione-S-transferase (GST), maltose binding protein, an epitope tag, or the Fc portion of immunoglobulin. Numerous labels include, for example, particles, fluorophores, haptens, enzymes and their calorimetric, fluorogenic and chemiluminescent substrates and other labels.

Percent identity (or percent complementarity) between particular stretches of nucleotide sequences within nucleic acid molecules or amino acid sequences within polypeptides can be determined routinely using BLAST programs (basic local alignment search tools) and PowerBLAST programs (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). Herein, if reference is made to percent sequence identity, the higher percentages of sequence identity are preferred over the lower ones.

As used herein, the phrase "corresponding to" or grammatical variations thereof when used in the context of the numbering of a particular nucleotide or nucleotide sequence or position refers to the numbering of a specified reference sequence when the particular nucleotide or nucleotide sequence is compared to a reference sequence (such as, for example, SEQ ID NO:1, SEQ ID NO:3, or SEQ ID NO:12). In other words, the residue (such as, for example, nucleotide or amino acid) number or residue (such as, for example, nucleotide or amino acid) position of a particular polymer is designated with respect to the reference sequence rather than by the actual numerical position of the residue within the particular nucleotide or nucleotide sequence. For example, a particular nucleotide sequence can be aligned to a reference sequence by introducing gaps to optimize residue matches between the two sequences. In these cases, although the gaps are present, the numbering of the residue in the particular nucleotide or nucleotide sequence is made with respect to the reference sequence to which it has been aligned.

For example, a nucleic acid molecule comprising a nucleotide sequence encoding an IFIH1 polypeptide, wherein the nucleotide sequence comprises a cytosine at a position corresponding to position 38,690 according to SEQ ID NO:2 means that if the nucleotide sequence of the IFIH1 genomic nucleic acid molecule is aligned to the sequence of SEQ ID NO:2, the IFIH1 sequence has a guanine residue at the position that corresponds to position 38,690 of SEQ ID NO:2. In other words, these phrases refer to a nucleic acid molecule encoding an IFIH1 polypeptide, wherein the genomic nucleic acid molecule has a nucleotide sequence that comprises a guanine residue that is homologous to the guanine residue at position 38,690 of SEQ ID NO:2.

As described herein, a position within an IFIH1 genomic nucleic acid molecule that corresponds to position 38,690 according to SEQ ID NO:2, for example, can be identified by performing a sequence alignment between the nucleotide sequence of a particular IFIH1 nucleic acid molecule and the nucleotide sequence of SEQ ID NO:2. A variety of computational algorithms exist that can be used for performing a sequence alignment to identify a nucleotide position that corresponds to, for example, position 38,690 in SEQ ID NO:2. For example, by using the NCBI BLAST algorithm (Altschul et al., Nucleic Acids Res., 1997, 25, 3389-3402) or CLUSTALW software (Sievers and Higgins, Methods Mol. Biol., 2014, 1079, 105-116) sequence alignments may be performed. However, sequences can also be aligned manually.

The amino acid sequence of an IFIH1 reference polypeptide is set forth in SEQ ID NO:19, and is 1,025 amino acids in length. The amino acid sequence of another IFIH1 reference polypeptide is set forth in SEQ ID NO:20, and is 986 amino acids in length. The amino acid sequence of another IFIH1 reference polypeptide is set forth in SEQ ID NO:21, and is 468 amino acids in length. The amino acid sequence of another IFIH1 reference polypeptide is set forth in SEQ ID NO:22, and is 772 amino acids in length. The amino acid sequence of another IFIH1 reference polypeptide is set forth in SEQ ID NO:23, and is 221 amino acids in length.

The present disclosure also provides therapeutic agents that treat or inhibit psoriasis for use in the treatment of psoriasis in a subject having a genomic nucleic acid molecule having a nucleotide sequence encoding an IFIH1 predicted loss-of-function polypeptide. In some embodiments, the nucleic acid molecule comprises a nucleotide sequence comprising a cytosine at a position corresponding to position 38,690 according to SEQ ID NO:2, or the complement thereof. The therapeutic agent that treats or inhibits psoriasis can be any of the therapeutic agents described herein.

The present disclosure also provides therapeutic agents that treat or inhibit psoriasis for use in the preparation of a medicament for treating psoriasis in a subject having a genomic nucleic acid molecule having a nucleotide sequence encoding an IFIH1 predicted loss-of-function polypeptide. In some embodiments, the nucleic acid molecule comprises a nucleotide sequence comprising a cytosine at a position corresponding to position 38,690 according to SEQ ID NO:2, or the complement thereof. The therapeutic agent that treats or inhibits psoriasis can be any of the therapeutic agents described herein.

The present disclosure also provides IFIH1 inhibitors for use in the treatment of psoriasis in a subject that is IFIH1 reference or heterozygous for an IFIH1 missense variant nucleic acid molecule encoding an IFIH1 predicted loss-of-function polypeptide. In some embodiments, the nucleic acid molecule comprises a nucleotide sequence comprising a cytosine at a position corresponding to position 38,690 according to SEQ ID NO:2, or the complement thereof. The IFIH1 inhibitor can be any of the IFIH1 inhibitors described herein.

The present disclosure also provides IFIH1 inhibitors for use in the preparation of a medicament for treating psoriasis in a subject that is IFIH1 reference or heterozygous for an IFIH1 missense variant nucleic acid molecule encoding an IFIH1 predicted loss-of-function polypeptide. In some embodiments, the nucleic acid molecule comprises a nucleotide sequence comprising a cytosine at a position corresponding to position 38,690 according to SEQ ID NO:2, or the complement thereof. The IFIH1 inhibitor can be any of the IFIH1 inhibitors described herein.

The present disclosure also provides therapeutic agents that treat or inhibit psoriasis for use in the treatment of psoriasis in a subject that is TRIM65 reference or heterozygous for a TRIM65 missense variant nucleic acid molecule encoding a TRIM65 predicted loss-of-function polypeptide. In some embodiments, the TRIM65 predicted loss-of-function polypeptide is TRIM65 Gly382Arg. The therapeutic agent that treats or inhibits psoriasis can be any of the therapeutic agents described herein.

The present disclosure also provides therapeutic agents that treat or inhibit psoriasis for use in the preparation of a medicament for treating psoriasis in a subject that is TRIM65 reference or heterozygous for a TRIM65 missense variant nucleic acid molecule encoding a TRIM65 predicted loss-of-function polypeptide. In some embodiments, the TRIM65 predicted loss-of-function polypeptide is TRIM65 Gly382Arg. The therapeutic agent that treats or inhibits psoriasis can be any of the therapeutic agents described herein.

The present disclosure also provides TRIM65 inhibitors for use in the treatment of psoriasis in a subject that is TRIM65 reference or heterozygous for a TRIM65 missense variant nucleic acid molecule encoding a TRIM65 predicted loss-of-function polypeptide. In some embodiments, the TRIM65 predicted loss-of-function polypeptide is TRIM65 Gly382Arg. The TRIM65 inhibitor can be any of the TRIM65 inhibitors described herein.

The present disclosure also provides TRIM65 inhibitors for use in the preparation of a medicament for treating psoriasis in a subject that is TRIM65 reference or heterozygous for a TRIM65 missense variant nucleic acid molecule encoding a TRIM65 predicted loss-of-function polypeptide. In some embodiments, the TRIM65 predicted loss-of-function polypeptide is TRIM65 Gly382Arg. The TRIM65 inhibitor can be any of the TRIM65 inhibitors described herein.

All patent documents, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the present disclosure can be used in combination with any other feature, step, element, embodiment, or aspect unless specifically indicated otherwise. Although the present disclosure has been described in some detail by way of illustration and example for purposes of clarity and understanding, it will be apparent that certain changes and modifications may be practiced within the scope of the appended claims.

The following examples are provided to describe the embodiments in greater detail. They are intended to illustrate, not to limit, the claimed embodiments. The following examples provide those of ordinary skill in the art with a disclosure and description of how the compounds, compositions, articles, devices and/or methods described herein are made and evaluated, and are intended to be purely exemplary and are not intended to limit the scope of any claims. Efforts have been made to ensure accuracy with respect to numbers (such as, for example, amounts, temperature, etc.), but some errors and deviations may be accounted for. Unless indicated otherwise, parts are parts by weight, temperature is in ° C. or is at ambient temperature, and pressure is at or near atmospheric.

EXAMPLES

Example 1: A Haplotype Carrying a Common Missense Variant in IFIH1 is Associated with Psoriasis Phenotypes in a Protective Direction A meta analysis of several genetic cohorts (Table 3) was carried out to identify novel genetic associations.

TABLE 3

| Number of Psoriasis cases/controls sequenced and analyzed, to date (EUR) | | |
|---|---|---|
| Cohort | Number of Cases | Number of Controls |
| UK Biobank | 10,715 | 458,650 |
| GHS 145K Mega | 4,044 | 122,132 |
| Kiel | 1,390 | 1,206 |
| Sinai BioMe | 361 | 22,417 |
| Penn Med BioBank | 212 | 15,276 |
| Michigan (J.T. Elder) | 4,088 | 3,478 |
| Total | 20,810 | 623,159 |

Significant common variant associations were found in known loci, including IFIH1; in total 5 common, independent/novel signals in known loci (data not shown). In addition, independent and potentially novel common variant signals in/near known GWAS regions have been identified (Table 4; gene=IFIH1; phenotype=psoriasis meta). Row 1: variant=2:162267541:C:T; rsID=rs1990760; and HGVS=missense Ala946Thr. Row 2: variant=2:162268127:T:C; rsID=rs35667974; and HGVS=missense Ile923Val. Row 3: variant=2:162279995:C:G; rsID=rs35337543; and HGVS=splice_donor c.1641+1G>C). Row 4: variant=2:162352383:T:G; rsID=rs17783344; and HGVS=missense Ser80Ala.

TABLE 4

| Independent and potentially novel common variant signals in/near psoriasis GWAS loci | | | | | | |
|---|---|---|---|---|---|---|
| Effect (95% CI) | P-value | Cases RR\|RA\|AA | Controls RR\|RA\|AA | AAF | Heterozygote OR (95% CI) | Homozygote OR (95% CI) |
| 0.850 (0.832, 0.867) | 5.18e−15 | 7798\|9064\|2974 | 202572\|271656\|106593 | 0.412 | 0.867 (0.840, 0.894) | 0.725 (0.694, 0.757) |
| 0.718 (0.659, 0.782) | 3.02e−11 | 19141\|536\|6 | 558537\|21952\|227 | 0.019 | 0.712 (0.653, 0.777) | 0.771 (0.343, 1.735) |
| 0.676 (0.606, 0.753) | 2.64e−8 | 19337\|333\|2 | 565784\|14433\|112 | 0.012 | 0.675 (0.605, 0.753) | 0.522 (0.129, 2.115) |
| 0.938 (0.910, 0.967) | 1.73e−7 | 15201\|4265\|312 | 438987\|129943\|10769 | 0.130 | 0.948 (0.916, 0.981) | 0.837 (0.747, 0.937) |

Specifically, the analysis revealed a protective IFIH1 splice variant association to psoriasis that is both novel and independent of IFIH missense variants known to associate with reduced odds of psoriasis.

The psoriasis meta-analysis also shown significant associations of IFIH1 gene burden results reduced odds of psoriasis: additional IFIH1 pLoFs and rare missense variants contribute to protection (Table 5; gene=IFIH1).

TABLE 5

| Additional rare pLoFs/deleterious missense variants in IFIH1 associations with reduced odds of psoriasis | | | | | |
|---|---|---|---|---|---|
| Mask | Effect (95% CI) | P-value | Cases RR\|RA\|AA | Controls RR\|RA\|AA | AAF |
| M1.1 | 0.742 (0.683, 0.808) | 4.05E−12 | 19196\|619\|3 | 558193\|22548\|7 | 0.019 |
| M1.01 | 0.673 (0.523, 0.866) | 2.05E−3 | 19519\|57\|0 | 566202\|2501\|0 | 0.002 |
| M1.001 | 0.705 (0.501, 0.994) | 4.60E−2 | 18159\|26\|0 | 566202\|1295\|0 | 0.001 |
| M3.1 | 0.793 (0.738, 0.852) | 2.92E−19 | 18928\|887\|3 | 548960\|31761\|100 | 0.027 |

TABLE 5-continued

Additional rare pLoFs/deleterious missense variants in IFIH1 associations with reduced odds of psoriasis

| Mask | Effect (95% CI) | P-value | Cases RR|RA|AA | Controls RR|RA|AA | AAF |
|---|---|---|---|---|---|
| M3.01 | 0.851 (0.746, 0.971) | 1.66E−2 | 19435|276|0 | 559785|9034|7 | 0.008 |
| M3.001 | 0.743 (0.606,0.911) | 4.36E−3 | 19494|82|0 | 565096|3610|0 | 0.003 |

Functional Prediction=pLoFs, <1% AAF (data row 1); pLoFs, <0.1% AAF (data row 2); pLoFs, <0.01% AAF (data row 3); pLoFs and deleterious missense, <1% AAF (data row 4); pLoFs and deleterious missense, <0.1% AAF (data row 5); and pLoFs and deleterious missense, <0.01% AAF (data row 6).

Moreover, significant gene-burden associations for three genes in the Type 1 interferon pathway: IFIH1, ADAR, TRIM65 were also shown. (Table 6; gene=IFIH1 (data rows 1 and 2), ADAR (data rows 3 and 4), and TRIM65 (data rows 5 and 6)).

TABLE 6

Significant M1/M3 gene-burden associations for genes in Type 1 interferon pathway

| Effect (95% CI) | P-value | Cases RR|RA|AA | Controls RR|RA|AA | AAF |
|---|---|---|---|---|
| 0.742 (0.683, 0.808) | 4.05E−12 | 19196|619|3 | 558193|22548|7 | 0.019 |
| 0.793 (0.738, 0.852) | 2.92E−10 | 18928|887|3 | 548960|3176|100 | 0.027 |
| 3.741 (1.866, 7.501) | 2.02E−4 | 17863|16|0 | 539839|162|0 | 0.0002 |
| 2.292 (1.683, 3.120) | 1.36E−7 | 18218|74|0 | 578560|933|0 | 0.0008 |
| 0.697 (0.524, 0.926) | 1.28E−2 | 18253|39|0 | 577669|1824|0 | 0.002 |
| 0.628 (0.502, 0.786) | 4.78E−5 | 18350|77|0 | 575397|4214|0 | 0.004 |

Functional Prediction=pLoFs, <1% AAF (M1) (data row 1); pLoFs and deleterious missense, <1% AAF (M3) (data row 2); pLoFs, <1% AAF (MA) (data row 3); pLoFs and deleterious missense, <1% AAF (M3) (data row 4); pLoFs, <1% AAF (M1) (data row 5); and pLoFs and deleterious missense, <1% AAF (M3) (data row 6).

Furthermore, additional rare pLoFs/deleterious missense variants in TRIM65 associate with reduced odds of psoriasis (Table 7).

TABLE 7

Additional rare pLoFs/deleterious missense variants in TRIM65 associate with reduced odds of psoriasis

| Effect (95% CI) | P-value | Cases RR|RA|AA | Controls RR|RA|AA | AAF |
|---|---|---|---|---|
| 0.697 (0.525, 0.926) | 1.28E−2 | 18253|39|0 | 577669|1824|0 | 0.002 |
| 0.628 (0.502, 0.786) | 4.78E−5 | 18350|77|0 | 575397|4214|2 | 0.004 |
| 0.413 (0.262, 0.652) | 1.47E−4 | 18107|11|0 | 568492|1074|1 | 0.0009 |

Functional Prediction=pLoFs, <1% AAF (M1) (data row 1); pLoFs and deleterious missense, <1% AAF (M3) (data row 2); and Missense p.Gly382Arg; 17:75891189:C:T (data row 3).

Finally, the data suggests that TRIM65 inhibition may be protective in psoriasis (Table 8; Variant=17:75894282:G:A (data row 1) and 17:75891189:C:T (data row 2); rsID=rs55823223 (data row 1) and rs202175254 (data row 2); and HGVS=Intronic c.415-1432C>T (data row 1) and Missense p.Gly382Arg (data row 2); and FIG. 1).

TABLE 8

Common TRIM65 psoriasis variant is an eQTL for increased TRIM65 expression

| Effect (95% CI) | P-value | AAF | Heterozygote OR (95% CI) | Homozygote OR (95% CI) |
|---|---|---|---|---|
| 1.11 (1.07, 1.16) | 4.09E−6 | 0.14 | 1.12 (1.07, 1.17) | 1.22 (1.07, 1.38) |
| 0.413 (0.262, 0.652) | 1.47E−4 | 0.0009 | NA | NA |

Cases RR IRAIAA=7092126031247 (data row 1), and 1810711110 (data row 2).

Controls RR IRAIAA=313749110265518980 (data row 1), and 5684921107411 (data row 2).

The meta analysis also revealed a significant associations for rare pLoFs/deleterious heterozygous missense variants in ADAR1 and psoriasis (Table 9).

TABLE 9

Significant associations for rare pLoFs/deleterious heterozygous missense variants in ADARI and psoriasis

| Effect (95% CI) | P-value | Cases RR|RA|AA | Controls RR|RA|AA | AAF |
|---|---|---|---|---|
| 3.741 (1.866, 7.501) | 2.02E−4 | 17863|16|0 | 539839|162|0 | 0.0002 |
| 2.292 (1.683, 3.120) | 1.36E−7 | 18218|74|0 | 578560|933|0 | 0.0008 |

Functional Prediction=pLoFs, <1% AAF (M1) (data row 1); and pLoFs and deleterious missense, <1% AAF (M3) (data row 2).

Figure 2:
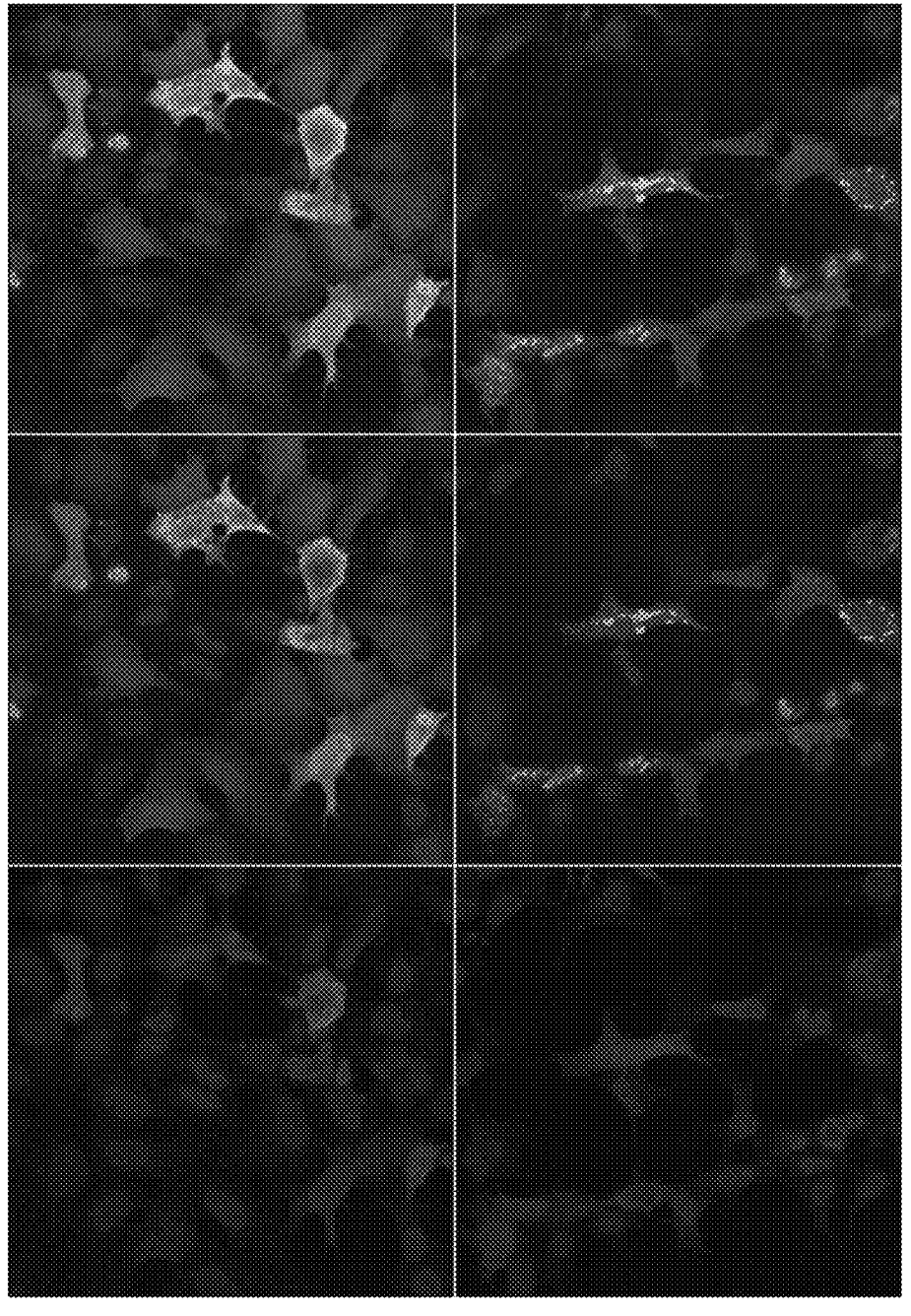
FIG. 2 shows immunofluorescence analysis of HEK293-HZ cells transiently transfected with N-HA-IFIH1 and N-FlagTRIM65-WT (top) or N-FlagTRIM65-G382R (bottom) which reveals aberrant expression of TRIM65-G382R protein (Panel A); N-HA-IFIH1% colocalization with WT vs TRIM65-G382R (Panel B); % colocalization of WT TRIM65 and TRIM65-G382R with IFIH1 (Panel C); Manders Overlap Coefficient (ranges from 0.0 for no colocalization to 1.0 for full colocalization) between N-HA-IFIH1 and N-FlagTRIM65-WT or N-FlagTRIM65-G382R, which reveals significantly reduced colocalization between IFIH1 and TRIM65-G382R (Panel D); Western blot analysis, which reveals reduced expression of N-Flag-TRIM65-G382R compared to N-Flag-TRIM65-WT (Panel E); and HEK-ISRE-Luc reporter cells transfected with empty vector, N-eGFP-TRIM65-WT, or N-eGFP-TRIM65-G382R (Panels F and G)—ISRE activation was measured by luciferase reporter activity in a 96-well plate in response to 0.05 μg poly(i:c) (Panel F); and 5000 U IFN-α (Panel G); N-eGFP-TRIM65-G382R-transfected cells have reduced ISRE activation compared to N-eGFP-TRIM65-WT in response to poly(i:c) and IFN-α.
Figure 2:
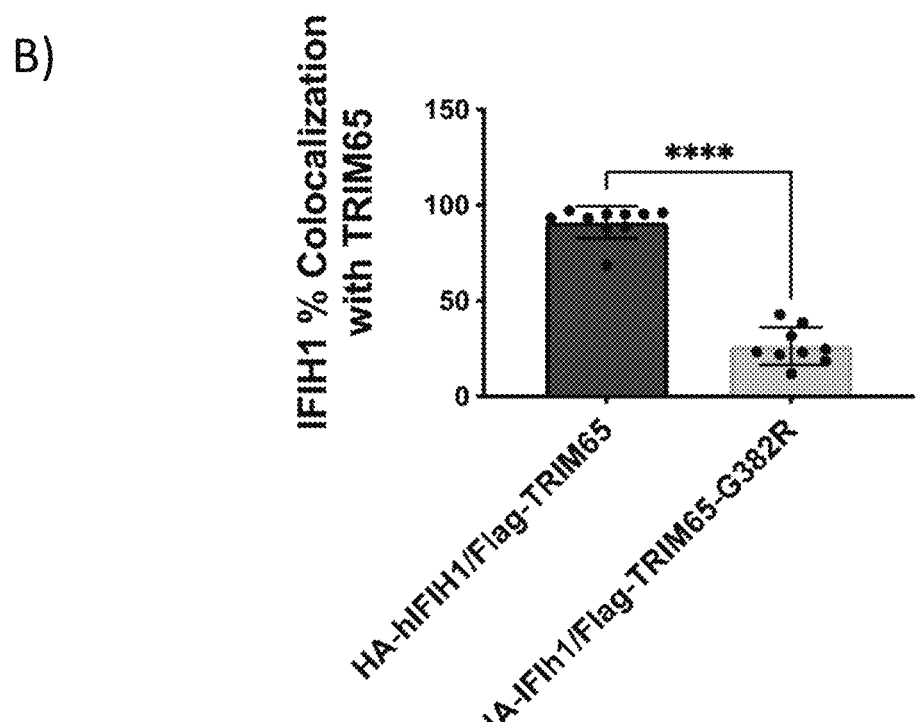
Figure 2:
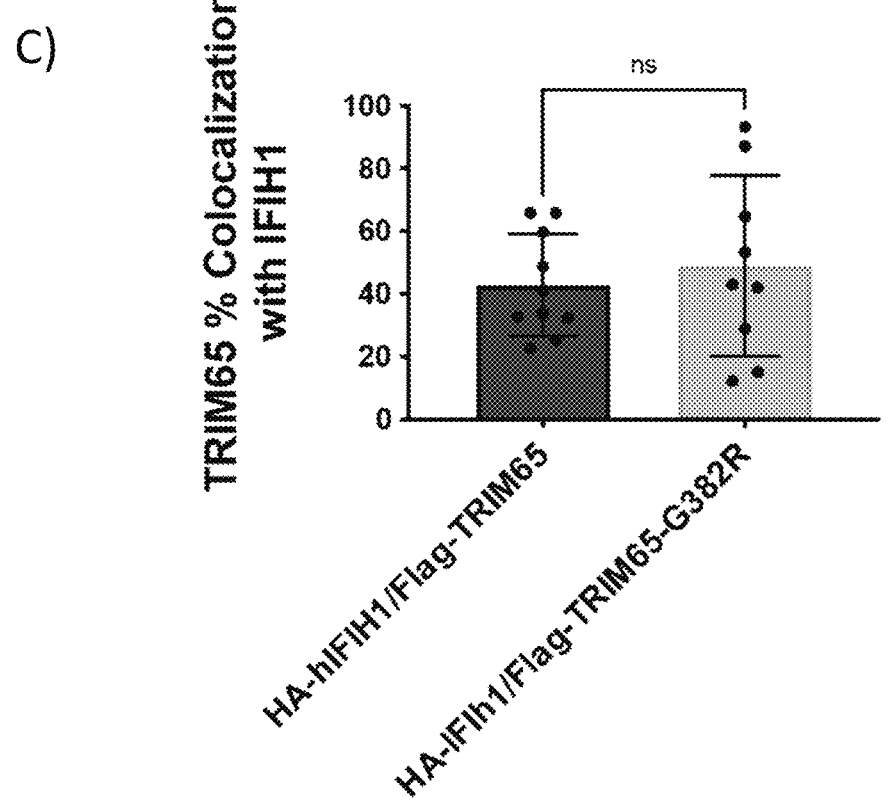
Figure 2:
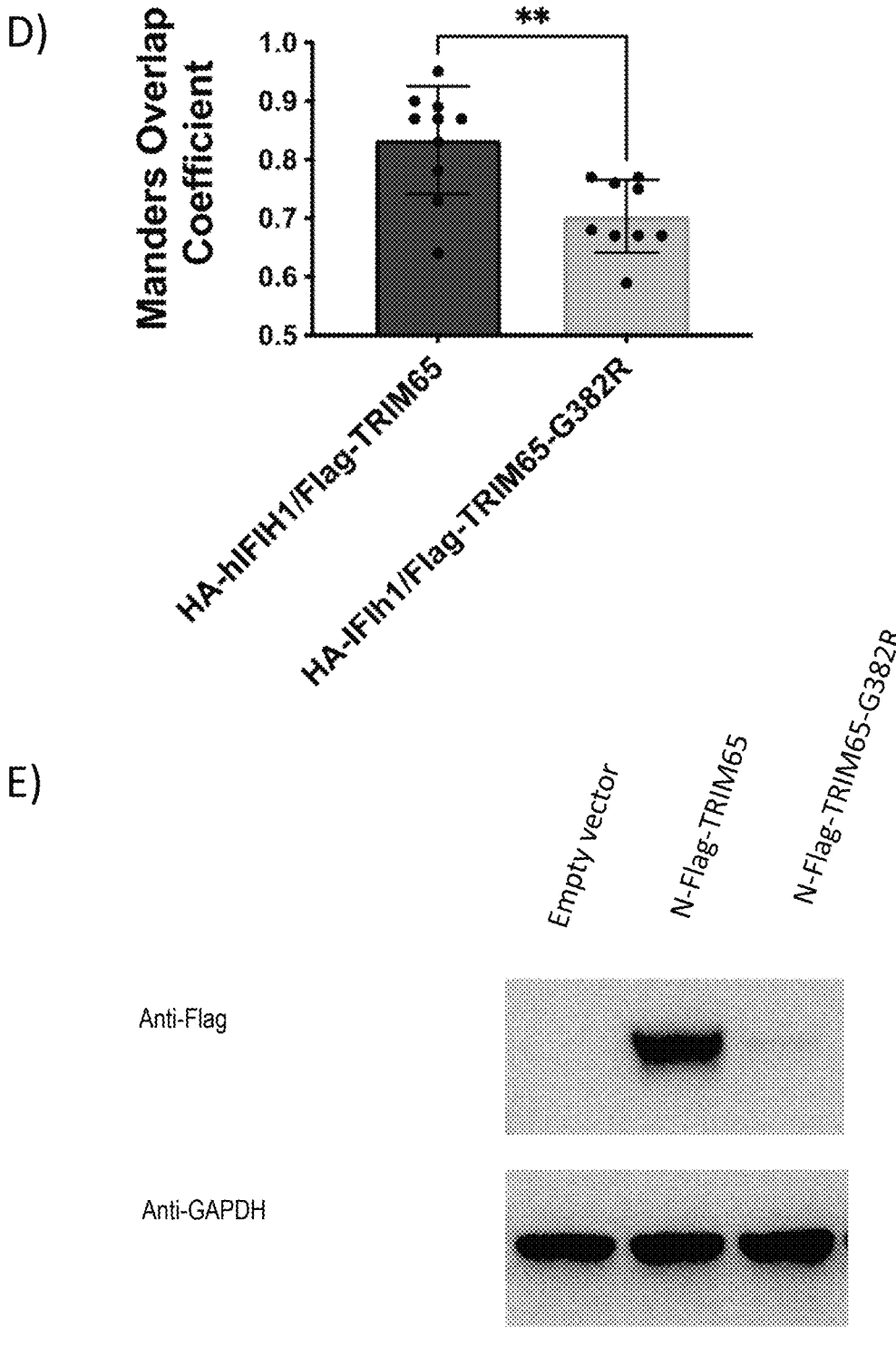
Figure 2:
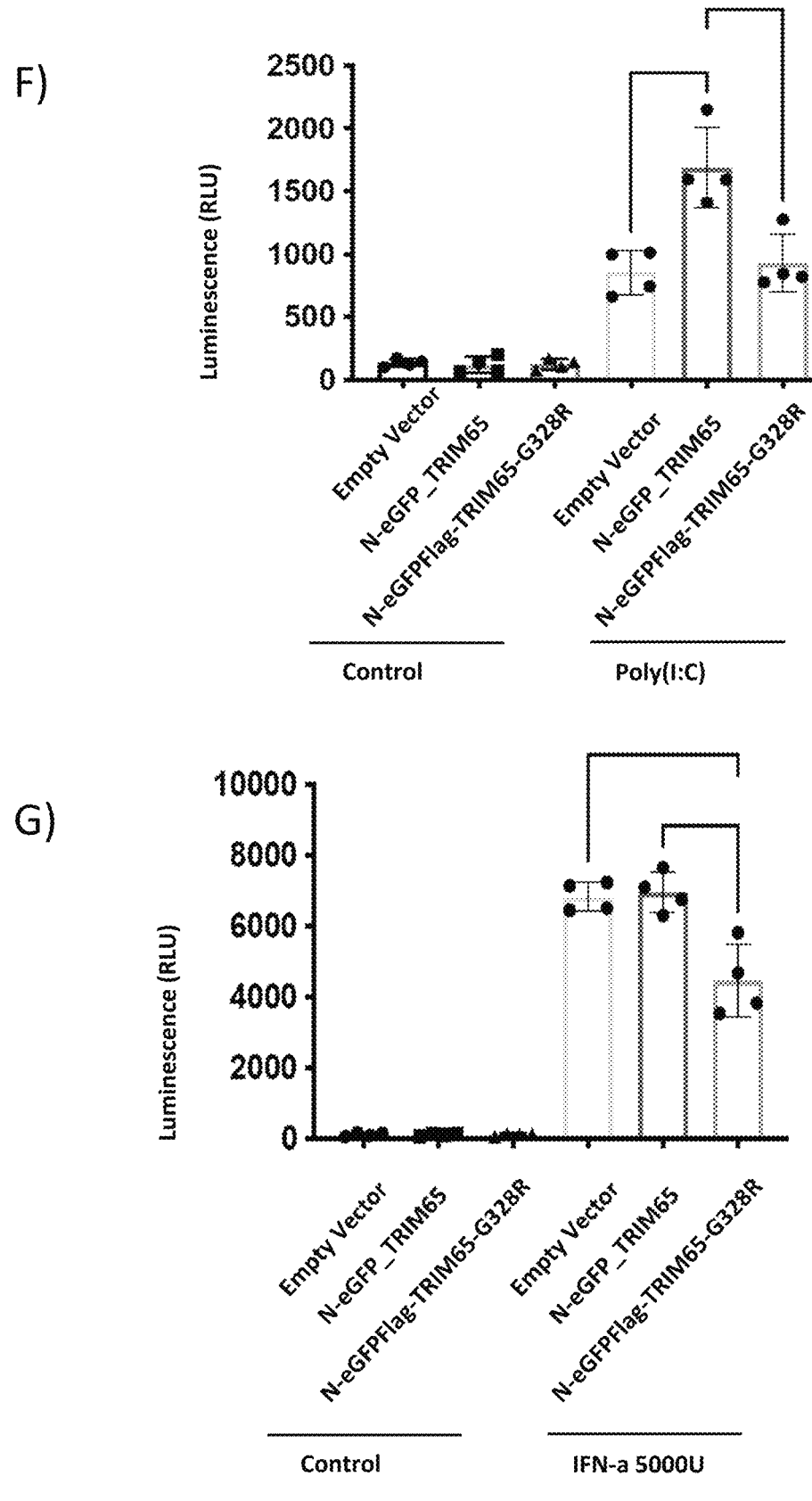

Example 2: TRIM65-G382R Variant Alters the Cellular Localization and Expression Levels of TRIM65 (FIG. 2)

Cell Culture, Plasmids and Cell Transfection:

HEK293-HZ cells were maintained in Dulbecco's modified Eagle's medium supplemented with 10% fetal bovine serum, and antibiotics (50 units/mL penicillin and 50 µg/mL streptomycin; Thermo Fisher Scientific). pcDNA 3.1 plasmids encoding for N-terminus Flag-tagged wild-type TRIM65 or TRIM65-G382R, and N-terminally HA-tagged wild-type IFIH1 were synthesized by GenScript (USA). Cells at approximately 60-70% confluence were transiently transfected using FuGENE 6 (Promega) according to the manufacturer's protocol, at a ratio of 1 µg DNA:5 ul FuGENE transfection reagent. After 48 hours, cells were washed with 1×DPBS (Thermo Fisher Scientific) and collected for downstream analysis.

Immunofluorescence Assays:

For immunofluorescence assays, cells were seeded onto open 8-well μ-Slides (chamber slide) with a glass bottom (Ibidi, cat #80827). The following day, cells were transfected with pcDNA 3.1 plasmids encoding for N-terminally Flag-tagged wild-type TRIM65 or TRIM65-G382R constructs, with or without co-transfection of N-terminally HA-tagged WT IFIH1. At 48 hours post-transfection, cells were fixed in ice-cold 4% PFA for 10 minutes at RT and washed 3× with ice-cold 1×DPBS (all subsequent wash steps performed 3 times with ice-cold 1×DPBS for 5 minutes per wash). Cells were blocked using 10% normal donkey serum (NDS) with 0.1% Triton X-100 (Jackson Immunoresearch Laboratories, #017-000-121). Cells were incubated with 1:2000 anti-Flag antibody (Sigma) and anti-HA antibody (Cell Signaling) O/N, washed and then incubated for 1 hour with 1:1000 Alexa Fluor 594-conjugated anti-mouse secondary antibody and 1:1000 Alexa Fluor 647-conjugated anti-rabbit secondary antibody (Thermo Fisher Scientific). Wells were then washed, and slides were mounted with ProLong® Gold Antifade Reagent with DAPI (Cell Signaling, #8961). Slides were imaged using Zeiss confocal LSM880. Colocalization coefficients and the Mander's Overlap Coefficient were calculated using ZEN Blue. Thresholds for each channel were estimated from single-labeled control wells.

Western Blotting:

48 hours after transfection in 10 cm² cell culture plates, HEK293HZ cells were pelleted and lysed in RIPA buffer supplemented with protease and kinase inhibitors. The following primary antibodies were used: anti-Flag M2 (mouse monoclonal, Sigma) and GAPDH 14C10 (Rabbit mAb, Cell Signaling Cat #2118). The appropriate LI-COR secondary IRDye antibodies (anti-rabbit (926-32211) and anti-mouse (926-32210)) were used to detect and quantify immunoblots using a LI-COR Odyssey Infrared Imaging System (LI-COR, Lincoln, Nebr.).

Quantification of ISRE Activity:

HEK293-ISRE-luc cells were maintained in Dulbecco's modified Eagle's medium supplemented with 10% fetal bovine serum (FBS), and antibiotics (50 units/mL penicillin and 50 μg/mL streptomycin; Thermo Fisher Scientific), 1×NEAA, and 1×L-Glutamine. pcDNA 3.1 plasmids encoding for N-terminus eGFP-tagged wild-type TRIM65 or TRIM65-G382R were synthesized by GenScript (USA). Cells at approximately 60-70% confluence were transiently transfected using FuGENE 6 (Promega) according to the manufacturer's protocol, at a ratio of 1 μg DNA:5 μl FuGENE transfection reagent. The following day, serum in the media was reduced to 0.5% FBS, and 24 hours after transfection, cells were stimulated with HMW 0.05 μg poly(i:c) (Invivogen) or 5000 U human IFN-α (R&D Systems) overnight. Luciferase activity was assessed using the Bright-Glo Luciferase Assay System (Promega) according to the manufacturer's protocol and read on a SpectraMax© i3x Multi-Mode Microplate Reader.

The obtained results suggest that the TRIM65-G382R variant alters the cellular localization and expression levels of TRIM65. TRIM65-G382R displays reduced colocalization with its binding partner IFIH1. This observation, along with reduced interferon-stimulated response element (ISRE) activity in response to stimulation by IFN-α or poly(i:c) (an analog for dsRNA which is known to activate IFIH1 in vitro) in cells transfected with a TRIM65-G382R construct, suggest that this variant likely leads to reduced interferon pathway activation, which may in turn be protective against psoriasis.

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

---

What is claimed is:

1. A method of treating a subject with a therapeutic agent that treats or inhibits psoriasis, wherein the subject has psoriasis, the method comprising the steps of:
- determining whether the subject has a Tripartite Motif Containing 65 (TRIM65) missense variant nucleic acid molecule encoding a TRIM65 predicted loss-of-function polypeptide by:
  - obtaining or having obtained a biological sample from the subject; and
  - performing or having performed a sequence analysis on the biological sample to determine if the subject has a genotype comprising the TRIM65 missense variant nucleic acid molecule; and
- administering or continuing to administer the therapeutic agent that treats or inhibits psoriasis in a standard dosage amount and/or administering a TRIM65 inhibitor to the subject that is TRIM65 reference;
- administering or continuing to administer the therapeutic agent that treats or inhibits psoriasis in an amount that is the same as or less than a standard dosage amount and/or administering a TRIM65 inhibitor to the subject that is heterozygous for the TRIM65 missense variant nucleic acid molecule; or
- administering or continuing to administer the therapeutic agent that treats or inhibits psoriasis in an amount that is the same as or less than a standard dosage amount to a subject that is homozygous for the TRIM65 missense variant nucleic acid molecule;

wherein the presence of a genotype having the TRIM65 missense variant nucleic acid molecule encoding the TRIM65 polypeptide indicates the subject has a decreased risk of developing psoriasis; and wherein the TRIM65 inhibitor comprises an inhibitory nucleic acid molecule comprising an antisense nucleic acid molecule, a small interfering RNA (siRNA), or a short hairpin RNA (shRNA) that hybridizes to a TRIM65 nucleic acid molecule.

2. The method according to claim 1, wherein the subject is TRIM65 reference, and the subject is administered or continued to be administered the therapeutic agent that treats or inhibits psoriasis in a standard dosage amount, and/or is administered an TRIM65 inhibitor.

3. The method according to claim 1, wherein the subject is heterozygous for a TRIM65 missense variant nucleic acid molecule, and the subject is administered or continued to be administered the therapeutic agent that treats or inhibits psoriasis in an amount that is the same as or less than a standard dosage amount, and/or is administered a TRIM65 inhibitor.

\*  \*  \*  \*  \*

SEQUENCE LISTING

```
<160> NUMBER OF SEQ ID NOS: 34

<210> SEQ ID NO 1
<211> LENGTH: 51611
<212> TYPE: DNA
<213> ORGANISM: homo sapien

<400> SEQUENCE: 1
caaactctgt aagaactgcc tgacagaaag ctggactcaa agctcctacc cgagtgtgca        60
gcaggatcgc cccggtccgg gaccccaggc gcacaccgca gagtccaaag tgccgcgcct       120
gccggccgca cctgcctgcc gcggccccgc gcgccgcccc gctgcccacc tgcccgcctg       180
cccacctgcc caggtgcgag tgcagccccg cgcgccggcc tgagagccct gtggacaacc       240
tcgtcattgt caggcacaga gcggtagacc ctgcttctct aagtgggcag cggacagcgg       300
cacgcacatt tcacctgtcc cgcagacaac agcaccatct gcttgggaga accctctccc       360
ttctctgaga aagaaagatg tcgaatgggt attccacaga cgagaatttc cgctatctca       420
tctcgtgctt cagggccagg gtgaaaatgt acatccaggt ggagcctgtg ctggactacc       480
tgacctttct gcctgcagag gtgaaggagc agattcagag gacagtcgcc acctccggga       540
```

-continued

```
acatgcaggc agttgaactg ctgctgagca ccttggagaa gggagtctgg caccttggtt      600
ggactcggga attcgtggag gccctccgga gaaccggcag ccctctggcc gcccgctaca      660
tgaaccctga gctcacggac ttgccctctc catcgtttga gaacgctcat gatgaatatc      720
tccaactgct gaacctcctt cagcccactc tggtggacaa gcttctagtt agagacgtct      780
tggataagtg catggaggag gaactgttga caattgaaga cagaaaccgg gtaggtgtct      840
gttcagatgg agctagcctt ttaggcagat tttgcaaagc aggcttcctt gtgcgtttgc      900
ccctttccaa atgtgcttga cctctttggg caaatctagt ttcttccttt gagaagacaa      960
catctaggca ctttaagaca attttaaaaa tttaaacaca aaagaactac ttttctaatg     1020
ttttcactga agtaaaaagg agttaactct agaatcgtaa tgtgtattaa caggtaactt     1080
ttattgaaca cttactatgt gcagttggta tcattttcaa aatgtattac tacagttcat     1140
gttcagagta acccactgag gctcctaatg ttattaactc cattttacag atgagaaacc     1200
tgaggcaggt aaataatttt gtccaaggtc tcccaggaaa aacagtggca gagctaagaa     1260
tttagcttgt gatagtgttg aatgtttttc ttatttaatg tagttccatg gagcaggggt     1320
tagtaaacta cggcccatgg gctaaatcaa gcctgctact gtttttttca ggcccacagg     1380
ctaagaatgg tcttcagatt tttcaatttt taattttcag tgttcataaa gttttattgg     1440
aacacagtca tgctcgtttg tttacatatt gcttgtggct gcttttctac tccaaaggca     1500
attggatgga gactgtgtgc ccttaaagcc aaaaatattt attatctggc attttagaga     1560
aaaagttttc caatctttgc cctacattac actttgtgcc atttagtctt agcccaaatg     1620
ggtaaattgc aatcacacac acacacacac acacacacac acacacaccc ttttttcttta     1680 atcaaagttt caacattctt tgagaatcaa aatttagaaa caattcattg aaagaatgtg     1740
ttgctagttt cagttttttca tgttagtgaa gaaactcatt tttcttaagg tagcattttg     1800
acagggcgaa ttttactgat gactttacat tgaatgtgat atgaattatt ttttgataag     1860
tgaagatgta ctgtgatgtg tataaatgct gacctgtttg aatgtgactt attcaggctc     1920
gtaagtcaaa agtcttgttt tggaagacat gtagacaaat aaagccatga ctaaaagtca     1980
aaggctttgt ctacaccact ctatgatttt cacatggttt ttttctctct ctctcttttg     2040
ggtcatccat tgtttgtata ttcatacaaa cttctgggca tttgattgat ttgctatagc     2100
ctatgatgca atttagtctt tagtgaataa agttagtgat cttttgtaga cttgacagac     2160
acagggcctg tccaaagacc caaacatgca tctaattttg atggccagtt ttcccaacaa     2220
gtaaattact ttgcactgtt gtctgtaatg tttatgtcgt tttgtgtatt gagaaccagc     2280
tagaacgcat tatagtagtc cagctggata tgacaaatgt gtacatcact gtggcagaat     2340
cttaatttgg aagaaagtat gcagccttca agccagctgg agatggaaga tggcatttcc     2400
agccacagta gctgttagaa gtccagaagc aacagagtcc agtaacacca caaagctgtt     2460
tatgtttggt gggtatgatg tcccgattgc cagcgaaaca gcacttctcc ctatttactc     2520
taaatacttc tgcctatcag catcactttt gtcttgcctg gattgaattt ccgccagcta     2580
gattttatcc aagttcttga ttctggcaag cttggaggca gctagcagta atgcaaggga     2640
tttgacacaa agaagatata gagtaacggg acttttgtgt actggtagca gttaaggcca     2700
aaacaaccca aattctccct ctgattcaca tttcaaagga ggccccaaaa gactgagcag     2760
ctataaattt gaggctctct aggaagcaat agtttctctg tgagagtgtg aataaatttt     2820
tgtgtgcatc atttacatgt attatcagtt ccaaaactaa gatatggtgg acaatgagac     2880
ggaagcatta agtttggtag aataatctat attgaggtgg tggtcattga caaatgttta     2940
```

-continued

```
tcttacagca gcaaagtgtg ataagactgt agaaggggaa cacatggatt tgaggtccat   3000
cttggcttct tactatatgc gttactttgg gccaaattac tgaagttccc tgatgctaca   3060
tttacctgtg aaaatggaca tcataaaatt tctcacagta tttagtcaa catcaaatca   3120 gaaatagtgt ttatgaaaaa gcttataaat cagagctatt tgatatgata atggtgttga   3180
cttttgtaac cattcatctg gttacatttc tgtgtaaatt taagtttgag agattgaggt   3240
aaattcccca tgtcgcaatt gagatatact tcttaaagtc cctagattat actgatttga   3300
aaaagaaatt acctctttca tcccagaacc taactaggat taggtagagg gttggtgttt   3360
agtaagcatt gattacttga ttgatagact aattgaattt atttctgaaa gtgtctggaa   3420
taagcgttga aaacacatga cgtattgaat tgtgttgcca ggcgttagag aatggatgaa   3480
tgatgaaaat aagatttcca aatttgcttt tttgaaggct taaaatagca tttaactaag   3540
taatcaagac ttctataaaa tggtcttgta ttttcattct ttttctgttt ccccatagac   3600
attttctact tgatctatta ttttaatta ggattcccac cccatttcct agccctgcc   3660 cgtaattaca gcaggccttc tgaaaatgac tttatacata ggtttgtgtc cagcaagtac   3720
ccaaaaactt attcattcat tcactcattc attcagtttg aatttattga gtggcatctt   3780
tgtgccggat gccatgctag tggtgaaaag ataggagaaa aacacagaga ctgttttgtc   3840
ctttcgtgaa gttgtgttgt agtgttaatt agtgttgata aaagaatgtc tactgtaggc   3900
cagtcatggt ggcttacgcc tgtaatccca gcactttggg aggccgagga gggtggctct   3960
cgaggtcagg agatggagac catcctggct aacacggtaa aactccgtct ctactaaaaa   4020
tacaaaaaaa ttagctgggt gtggtggtgg gagcctgtag tcccagttac tcgggaggct   4080
gaggcaggag aatggcatga acctgggagg cggagcttgc agtgagctga gatggcgcca   4140
ctgcactcca ccctggtgac agagcgagac tccatctaat aagaaagaga gaaagaaaaa   4200
gaaagaaaga aagaaagaaa gaaagaaaga aagaaagaaa gaaagaaaga agaaagaaa   4260 gaaagaaaag aaagaaagaa agaaaggagg gagggaggga gggagggagg gagggaagga   4320
aggaagaaag gaaggaagga aagaagaatg tctactgtat acaagggact attctaaata   4380
ctagagtttc agcaataaat atatgccatt ttatcaatca ttataataaa gcaatcctta   4440
atggtaaggg ggtacccctg tactgccttg ctcctctttt aggatgctaa gttacaattt   4500
ggcattgtta catcttagtt ataactaagt acaacttgg cacacccatc aatttaggca   4560
gtcatgaact ctgggaacga aagtgatcat ataaacattt ccatagtgtc ttaataatca   4620
agctgaacag ctaaagagag atgcatgttt catccctggc cagttcagaa cacaatgcat   4680
ctgtagtcct ggagactcca cacaccttcc atttacacag aagaaccaga gatgccatga   4740
ctagtccacc taagaacagt ccagttctcc caacatgaag ttgagcaccc aagtcaatct   4800
ccccaggaac attgtattgt ctggcaaatt aggaaagata agaatttcat ctgcaaaaaa   4860
aaaagtatga ataagaaatt agctatgtca atgtgacaat aaatattcat tgggttaaga   4920
cattaacttt ttgtgggaaa ctggttcttt aaaattcttt tttaacatac aggttttgcc   4980
tcctgattta ctttttatctg agagttgaac tctgctgggt taaaaaaatc accattatat   5040
ttaaatagct atctaaggtt attataaagg gaagaaaaca ttttcattaa actgtacaat   5100
tgtgttggta agccagtgct ttatggaaat gtcattggtt tcttcactga tttctgttgg   5160
aaagaaaaaa catatcaaag aatttagaat atgaaagcat tgagttgtat tattaccaaa   5220
ttaattttat ttcgtatttc ataaattagt taacaatgta ttaatagact acatagtgaa   5280
```

-continued

```
aacatccatc catttttaac ttcacagaga aaacttcgag tgggggaggg gcatgggtga    5340
gaattgtttt atgacttgtt gcagtctcaa atgtaaatat tcacctccca cgaatttctg    5400
taattgtgtt tacatattgg gatcaatatc tttacaatgt tttaggagaa catattaaat    5460 tttttaaaatt atataattgc ttcaaaggga gctgatgtac tttccagcac caaaactgag    5520
aagatttctt aaaaattcag catcttgatg aggctgctaa aattgcacag atatatgtag    5580
ttccacattc aaattgtaag aatatgttta ggaaataatg acatcatgat ccttatatgc    5640
ttggactcaa taacggcaaa gaaagcttga aaaatatgat tccacagtaa aagttgactt    5700
aatagaatag tggttgaaga aaattttgtg gatagaatat gcttagggat ttttaataac    5760
agcatttgtt gcctcactgg ttctttttaa ggaaatcctt cctgattgct tcagtcaaat    5820
atatttaaag ctgattaaag gatggggtaa taaaatatga gaatggctga gttaaaagaa    5880
gacactgaaa ccagtcttat ttacatctat agcaattact tgttaaatta gcagatgata    5940
ataaagatgt tacaacatca gggaagccaa agaatttcca ttaggagact aagagagcta    6000
gaaaaaaatg gtaaaaaatg agcaaaaatc tgcttagaaa atgttgtggg tgacatggac    6060
tgaattcact tgaaatttac tgagttcaaa tagttatttt taaccacttc ttgccagaaa    6120
atgaatttaa aattggagaa aattataagc tataattata gttcaagaag gcaggattca    6180
gcctctaaat tcaactgcct gggatcaaat tctacttctg ccacttactc actttgtgac    6240
ctcagagagg tacctaaaca tctctgtgcc tcggatttct gatctgtaaa tgagttaata    6300
ttggtaccta tttctgggct gctgggttaa tatattcaag ttccctagaa cagcatgctt    6360
aactactaga tgctaagacg gaaatatccc ttgggtagag accatgctgt atgtgcttgt    6420
gcaggtgagg tgtttgtaac aataactctt cccaatcatc cataatagtt ctaacactga    6480
attagtgcca gacattgttc caaaaatgtt aacaaatttc tgacataaaa ggttatggaa    6540
tatatttata gaactagaaa atacataaat ttgtaggaaa gaactaaaca atccaaatga    6600
tacatgtgga agattggcaa atgttgagaa ggacctttga taatatcaaa gtcaatattt    6660
cttatctggg aggctgatag aatcacatga gatgttttac ttttttcttta atatctgagt    6720 tcctaacata gacaaaataa atcataatct tttaggggtg tttcctagac atcagtattt    6780
tttaaggctt tacggttgtt tctaacatgc agctaagata tagaaactct gaaatttctt    6840
ttcagctgcc ttgtaaccac atattgtaac caaggtctag ggagatgaag taaattgcct    6900
aatgccacag aaagctaatg atgtcctgcc taacttcttt catgtctaaa catggcttga    6960
gttactcttt cctccaaatc cttattgcta tattaggacc tagggaaatg cactgtgaca    7020
atgattacac aaaagatcca catttaaaag aaatttacta atctaaaaga gaaaataaaa    7080
gaaggctaaa gactctaatg aatggatata aaaataattc tgccccatat ttccaaaaaa    7140
aagatataac aataaatttc ccataacatt aaaaaaacac aaatttgaga aaaattgatt    7200
atagtaataa tcaactatgc aaatattaca taggaaaaaa tataaatctg cagtagtaat    7260
tacttatttc ataatgataa tcatgaagaa aggagataag aaatgtttga tttcccattt    7320
acagactcca tagattgaaa aaatatagcc agccctagat atacagaaag aaattggtga    7380
aaatagacat aacatggctg cagactaaag atactttctc ttctatcctt tattcaggaa    7440
tggctgaggt aaaatttatt ttctaggtgt caggtttgaa taattcaata gcttttaaaa    7500
aaaatggttc atatttaaaa ggacacttgg tccagagatt tttgttgttg ttgttgttgt    7560
tgtcccggag atttttttcc ctgccgactt cagaattgct acaggtaaca ttgctatttt    7620
cttcaatgtt tcaatgtaag cctttatttta tacttatgct taattgctca gttttttctaa    7680
```

-continued

```
agggtatttc ctgtttaagg ttattcagaa gatgtttgat cttacttaat tctaattttc   7740
tcttacaaca gattgctgct gcagaaaaca atggaaatga atcaggtgta agagagctac   7800
taaaaaggat tgtgcagaaa gaaaactggt tctctgcatt tctgaatgtt cttcgtcaaa   7860
caggaaacaa tgaacttgtc caagagttaa caggctctga ttgctcagaa agcaatgcag   7920
gtatttgtaa ttttactgag gaagattctt caaattctgc ctagtgattg agaattcaat   7980
aaagcagaaa gacacaatgc taaacaccaa gatttttaga atcaaaattt taagagtgga   8040
acatatgtga tagatcatct attttatcac cttaacaaat gaggaaattg atgcctggga   8100
aaatatcaac tgatcaaaga ccattttttca tccaaccaac actctttcta ctaccttatt   8160
ttaaaaacaa tatgactacc agaaatttta tcaagattat gtaacattaa atatacacaa   8220
atacattgga agaaagtatt ttagtggtta taaaaaatct gctgcatatt cttctgaaca   8280
tttttataca ttttaagcaa tgtattaagc atttgataaa aggattgttt tgtcaatata   8340
tctcaacctt acctaatgtg agattttaaa cagcattcaa taatagtaat aacataaacat  8400 tttatagctc cttctcctac attatttgta aatctcactt aaactgctat cttatttttc   8460
ttttcgtagt atgcatccta tgtttccaaa aatatcatat gaaagacaaa ttgaaagtta   8520
actattaatt aattataatc attgcagttt tgttctggtg accctaacta atgaaaactt   8580
tgctgtaaaa agtggggtgc tgctgtaaca aacacctaaa cgtgtggaag tggctttgga   8640
actgggtaat tgatagagac tgtaagagtt ttgggtgaat ggtagaaata tgggtgttca   8700
gggtgattct ggtgaggtca cagagagaaa tgagaaaaat gtcattggaa actggaagaa   8760
aggtgatcct tgttataaaa tgggataaaa cttgatctca caagtaatgg atttggatat   8820
ttggctgaga aaatttctta gcaaaatgct gaaggagcag cttgatttcc cctaactgct   8880
tatagtaaaa tgcaaaagaa gagaaattaa ttgaaggagt tgttatgcaa aaaggaacca   8940
aaatttaaat atctggaaaa ttctcagcct atccatatgg caaaaaatga gaaattgtgt   9000
tataaagaga acaaccaatt gataacaaga tcatgggtgc tactgatgga cttaatcagc   9060
catttcagca gaaggtagga gtagagatat attataccag caaatacact tccagtttga   9120
actgaaggag acagagaaag caggacagaa tgagaaaagg atactggact ttctggattc   9180
tacagaacca gaccatagag ctatttggct gtgaatgtgt actattcttc agggaaagga   9240
aagaatgccc ccaaaagtga tacagaagtc atcagggttg ccacttccac cacagaccca   9300
gaggccaagg cagtttcctt tttggtttca aagggcaaaa ctgtctctct ggttttagtg   9360
agccctcagg atgaccctgc ctagtgtctc agaagcagag ctatcctcac agaaagctgt   9420
gtggatggag cccttagaga gagcaggctg tcttgcagag ccctagaacc tgccattccg   9480
tggacctgga aggcagagca tcaaaccaaa cagagctatt ctcaagcctt ataagcctta   9540
agatgtgaca gaatttacct taataagttt tggatttgct tgggacccat cacccttgct   9600
ttctttccta tatctccttt ttggaataag acgtccatcc tatgcctgtc ccaccattgt   9660
attatggaaa agaaacatgt agctcaactg gtttcacaag ttcacagctg gtgatgaatt   9720
tgccttatca tgaatcacac ctctagtctc atctacgtct gatttggaca atgtttaggt   9780 gagactttttg actttagact tagagttcat gcttcagtga gttaaggcac ttgggctgat   9840
gagatgagat gaatgtattt tgtatgtagt aaagatatga attttgggaa gccaatggta   9900
aaatgctaca gatggaattt tgtcctccta atactcatat gttggaacct aatatgactc   9960
tatctggaga cagtgatagt aggagatagt taagattaaa tgagccaggc caagcgtggt  10020
```

-continued

```
ggctcacgcc tgtaatccca gcactttggg aggccaagac gggtggatca cctgaggtca  10080
ggagtttgag accagcctgg ccaacatggc gaaaccgcat ctctactaag aatacaaaaa  10140
ttagctgggg tggtggcatg cagctataat cccagctact tggaaggctg aggcagaaga  10200
atcacttgaa ccaggaggct gaggttgcag tgagccgaga tcatgccact gcactctggc  10260
ctgggtgtca gagcaagact ccgtctcaaa aaaaaaaaa aaagattaaa tgaatcataa  10320
gaatggggcc ttaatctgat agaattgtgg ccttttaaga agaggaagaa agagaaaaag  10380
agaaacatct gtctctttct ctctcttaac cgtgtgagga cgcagggaga acgtggccat  10440
ctgcaaatca aggagagagt cctcatcaga cattgaccct gctgtcacct tgatcttgga  10500
cttccagtgc ccagaactgt gagaaaagaa gtgtctgttg tttcagccac tcagttgatg  10560 gtgtttatt atggcagcat aaacagacta ctgtaggagc ttagactctg ggtcctgata  10620
catatcggat cctgatgctt atcaaatcca ggctccttcc ttgaatgtgt gacctttggc  10680
caggttctcg acttctctat gcctcagttt actcctcagt aaaatggaga taataatatt  10740
acttatcacc tcagtaaaat ggagacaata atattactta ccatctaggt ttattttgag  10800
acttaaataa cttaatgtat gtaaagtatt tatattgtga gtgcaaaata aattaactat  10860
tataatagtc cctaatgtac ttaatatcta actgcaaaca ttgccaagtt ttcttcttgt  10920
ccaaagtcac aacagttttc tttaggaaat tttccataca aagtggggca cattttcact  10980
gggttcttta agatgagata ataaaaaatg atacgttaga aaattttcct tatggcatca  11040
gtcttctctg acagattgca gcttcataaa ggcaaaaact cttgatttc tttttaaccc  11100 acataagccc ttaataaaat acccattaca tgtagttgaa gtaagaaaag ctggaagtga  11160
ggaatggagg aaagaagaaa agaggggcac aaaatatttc attaaatgtt ttaaaaatcc  11220
ccagaaattc agaatacatg aatataggct gacattaaag cagatgtacg tctcgtgcag  11280
aacacacagt gaggaaacaa aatggcaaga gcaaagctaa agaaaactac caaatttgca  11340
ttttcattaa ttcagcctta aatgtaactt tgtgtcactg aataagtgac ttacttccta  11400
aacatgacgg tcagacagga aatcacttt cttgtgatta gcataatgct tatattgttt  11460
ttttagctac agtctaatca ttacaaagaa ctactcgttg tgtccatatt aaaattaaaa  11520
gtaccttgcc ataacaaaag cacattctaa gcctttcgaa atgtcaacat attaaaatat  11580
attaaagcaa tctctattgc gggctctcca ttttgttttc aaaataacaa taacagctat  11640
ttatattgta taaaatcttg cattgcaata caatttacat tctattcaga acttcaaagt  11700
atttaaatat attcaggcaa tctctattag gaacctctag tttgtttca aaataacaat  11760 aacagttatg tatgctctac aaaaacttgt atggcactat gatttgcatt ctaatactgt  11820
tattcacaga gattgagaat ttatcacaag ttgatggtcc tcaagtggaa gagcaacttc  11880
tttcaaccac agttcagcca aatctggaga aggaggtctg gggcatggag aataactcat  11940
cagaatcatc ttttgcagat tcttctgtag tttcaggtac ttgaaacaca tacgtacttt  12000
aatacagtaa ttactacttc cagaaaaacc aactgggcag aacctattaa tcagagggag  12060
aaaatgtggg cattaaggtt agtaaacatt tatattaaaa taatatttt agaggagatt  12120 aaattaaaat aattcttggc caaaatgctt tctaaaacta atccaatatc gatgtgttat  12180
aaatatgaac acaattgcat ctaatttaa tttataagaa atccatagtc attgtaagat  12240
aagtataaga atgccttata tttcctggtt ttcaaagtac ttataaatag atcagtcaat  12300
ttaattcacc caaaaccctg aaaataaaat agattcattg cttttttct ctggtttaaa  12360 ctgggatggc tcagagaggt tcaactgtgt cgtaaaaatt aaaatcaaag ctataaaaag  12420
```

-continued

```
gaagatgaac agatgctgaa ctagggttgg cttgaattgc attaactaat cggtgaggac   12480
tgaagactac catgtccacc tttttgatac tgaaacagcc ctggcagaaa caaattattt   12540
aattattttt tccctttcta atctgctcgt gataggagaa tccacctctc cccttctctg   12600
ccaaaaggac ttattctgtt ttcacaagaa atagttgctt aaagcctgtg gtgtgctggt   12660
gaatgtaaca agtaactctg gggaaaagaa aaagccctag tttgtagcat ttgctagtct   12720
ctgtggttta aatattctca ttcaggctta tttcaagctt ccaacataag atcactgaac   12780
acaaagctgg gaagagctgt gcagtggcac atctttatac agcattccca ccgtacagat   12840
gcaaaagacg gagatagcct ccagatcaaa gatgatagtt aaatgattag gtgatgagtt   12900
ttaaatactt acaacctttg cctgaaaata atttctttta tggtaagttt atacaattta   12960
atttttgtaa tggctgtggt taaaaactca gaaaattcct gaaaagttac cagttagctc   13020
ctgtgagccc atataaacta actctagcac accactgcaa agtttattat ttttattttt   13080
ttaatttcat tttattttat tttattttat ttttggagat ggaatctcac tcagtcacac   13140
aggctggagt gcagtggcat gctcttggct cactgcatcc ttcacctccc gggttcaagt   13200
gattctcctg cctcagcctc ccaagtagct gggattacag gcacccacca ccatgcccgg   13260
ctaatttttg tattttttagt agagacaggg tttcaccatg ttggccagga ttgtcttgaa   13320
ctcctgacct caggtgatcc cccccactcg gcctcccaaa gtgctgggat tacaggcatg   13380
agccactccg cctggccttg ttattttgta cttagataag taatatgcat gcattgcaag   13440
aaatctgtaa tacacagaaa cacacaaaga agtcaccaat attcccagaa tgtggatatt   13500
acacttaaca tttgggtatg tgtgcttctg ggctttttac atacctgaat gtgtatatat   13560
agtgtcattt ctcttatgtt cattaaatat tcttctacag cctggttttt aatgactaaa   13620
taatggtccc accatttgga tgcagtatga ttaattgacc aattgttgaa catttaaata   13680
atgcctcgat agctctcttt gtacttatgt cacagtttgc tttttaaaaa catattatat   13740
aattggaatt tctgggtcaa atgatttata ctattttaac acatttgata cttaatgtca   13800
aatctcactc caggaacttg taccaattta catgttctcc aagagtatgg gatatgagtg   13860
cttatttccc tgaattctct tctacgagaa tgaataatat tatcatgttc aatcttttca   13920
atttggctgc tattaaaaat ggtatttcgt tatttgaatt tacattttca tatttctgct   13980
gaaaaagaat ttcacaaatt cattctcttt gttttgttaa ttatcaatac ttttaaaatt   14040
cacttttcta ttagggtatt catcttcttt ttgctgactt atatgaacta tctaagtata   14100
taagatatca attcattgtc ataaatagta ccattttttt tcacagttgg cttgcttttt   14160
agcctgtttg tggattttttc tcttttttctt tttttggggg ttctgggggc aggcggggac   14220
agggtcttgc tctgtctctc tgtcgcccag gctggagtac agtggcacaa acacagctca   14280
ctgcagcctt gacctcccag gcgcaagtga tcctcccacc tcagtctccc aagtagctgg   14340
catcacgggc gtgcgccacc atacccagct aattttttgta tttttttttag agaatggggt   14400 ttcaccatgt tgtcaagact tgtctggaaa ctcctgggct caaggaatcc tcctgccttg   14460
gcctcccaaa gtgctgggat tataggcttg agctgctgtt tgttttttaa tgtaatgcga   14520 ttccacctttt ctcataaact ctggtgctgc tgctgctgct aatagcaaag cttatacagg   14580 atagttttttt ttgttgttgt tgttgttttt catttgagca gctgcacctt cctttagaaa   14640
tcatgattct ataggaatgc caaaattcac tatctgagtg tggagttttc atgttttaat   14700
aaatgtcctt tacaagctac tcgacatctc tatgagttac tggccatttt ctgtaaatcc   14760
```

-continued

```
acactagaaa gaagggaaga tggagctact gctgagagat gaccctgcat cttaaatgag   14820
ggtttatcat caaagattac cagactaatg cattgcatta gcttgtagtt aatctgctct   14880
gaacttctag tgaacaaaat taaaggcaaa gttttaaatt tttttaaatt tttacttctt   14940
agtataaaac ttaaagatgt atcttgtgaa aaaaatttta ataatgatat tagggggacag   15000 aaaagctttt tatttttttt tttcctcttg ggttccttcc tctctatctc cctccttccc   15060
ttcccttcct ttcaccctaa cttccttccc tctcttcctt tcacttcttt catttaacaa   15120
ctattttcca aactcctatc atgtgccagg caccttgttg tatactgtga actcaggaac   15180
ataacagaaa tggcttcatg gccatgggagc ctaatatgac tctatctgga gattgtgatg   15240
gtaagagata attaagagta aatgagtcag gccaggcgtg gtggctcaca cctgtaatcc   15300
caggactttg ggaggacgag gcgggtggat cacctgaggc caggagttca agaccagcct   15360
gaccaccatg gtgaagccct atctgtatta aaaatacaaa aacttagccg agcatggtgg   15420
cagatgcctg taatcccagc tacttggaag gctgaggcag gggaatcact tgaacccaag   15480
aggcagaggt tgcagtgagc caagattgca ccattgcact ccagcctgag caataagaac   15540
aaaaaaactc cgtctcaaaa aaaaagaaat gacttcagcc cccatggagc tttccactga   15600
gggaggtgtc ggcccagcag tagtaactgt atagctacac ttttagtaag tgccatgaaa   15660
gagtagtaca gagtattaaa atatataata gtctgagagc atgtaagagt atacagtaaa   15720
ctgcacagta atccgaggat ccatccaatt cacaaacatc ttaatggtct tctagtccat   15780
aggttcttta tgatatctgg atttctcatg tggatttgaa agcaggttag tttaatccat   15840
tctggccctt tccagagcac tagcaaagag tcacttattt atgaaaatgt agtgtgtttg   15900
cttcagacct ttgctttaga ctgctgctgt cattccaggt atctgtttgt ttccttgtta   15960
tcttaaggac taagaattac tgatattaat aacttataaa gtaccattag tccagagaaa   16020
ttattgagtt cttttgattg aagttttttgt tgcagaattt actatggaag ggttttgcct   16080
gcataggcat tttctgacag aagtaacaat caaggtaaat gtgaaagtgc tccatagctt   16140
ctaatatgca tttgtgtagt tttgtttttgt gtatcttctt gatattgata atgtttagtc   16200 tttatttttga attccattat attaggttaa agtttcaaat agttgccaag atagcactga   16260
aaaaaacttg tcacaaagtc tgtaaatatg attttttatgt gtataaagaa aagactcaaa   16320
ttatttgtaa ttttaaatta agatatttat aattattatt tctgaaccag tttatcaaat   16380
attttctcag tgcatagtag tcttagtgca tgcaaatatt aattatttat agctttaatg   16440
caaagattat gtgtgtgtgt gtgtttttagc acctttacc ccttaacaca tctgatggat   16500
aagacacact accatcagta acagtggccc accttgaaac taattttaaa cacatatccc   16560
tttggcacta gaggtgacat atcagagttc tctagtggat tgttctagag agtgatttca   16620
tcatatctcc aaacttgcgg gttgatatgt gtcctttttc ctcctcccac ctatgtttac   16680
aaatcaattg cttctcatta aaaaagtggt tagtaattga tatatcaatt tttttatttgc   16740 cctttttccaa attaccaaaa caatttctaa acaaaatttg aacagttctc agactattaa   16800
tggcaattta atgctggatg ctatagttct gctttctgaa gtcactggtc gtcttataac   16860
aaaagataac tgcaaaactt tggtgtttct ctagatcaga tttccctagg aaacatcaga   16920
gagacactaa gcctgctttc attttctatt aaaagcattt taattatagc aaataattga   16980
cttctatata gcaaatattt tacttctaaa agcgaacagt taaattagtt gtgcagtcag   17040
tctttgtctg ctactgctgc tttgtcaaaa caagtgaata gttacttcac attaaccttt   17100
tttcattata ctattttagg aattaatgca ttacaataaa atcaaaggaa attaagtgac   17160
```

-continued

```
atttaaaact aagtcaactt tattgcattt ggtataaact tttatgcaga atggagcaga   17220
aaatcccccc aaacttcttt aatcattgtg ttacagctgc cctattgtga aaactagaaa   17280
atgcaaatgc ctcagattgg ccagcagagg gcgcctttac atttataaag ccaatggaat   17340
ttcactgttt cagcgtgaaa gattataatg taactgtaga gtgtgccatg tgtgaatata   17400
cagtgcgcat gactgtgatt gcatgtgtat attttgattt atatattcgt tcacgtgaag   17460
attttaaaat tccaccccag ctaatgagct taccaacctg cttgttttca gactttaata   17520
ccttctttct catatttccc catatgttcc actccttagg tttatccggt gacattatgc   17580
tttggaatat attgtggata tattttgcat agatcatgtt ctgtaggagg ggtttaaaaa   17640
ttgaccttta caaaacagcc ttcttctccc tggtccaatc tgttatagca ctttttttgt   17700
tgttgttttg ttttgccttt ttatagacta aagtccaatc ttagatttgg tctatactaa   17760
tttctgtaaa agtgccacaa aatttatcct tgcacttgag gaccagaata atgttctgta   17820
gcactaacct ctagaaatct agagattttt agaatctcta gaaataaaac catagcattt   17880
gaaacctaag tggaaaaaaa taattgatac agtagtttac aataagactg tttcagaatc   17940
attcatgcta tatcaggact ggtttgaagt aagagcactc ctttactttt taatttttct   18000
aaacttagtt atcattaatt attgagaact agcagtacta ctgaggcaat ccaaaagaca   18060
catattaatt tgagctgaga gaaagagaga gatgctgatg ctgacactga tattggtact   18120
tgttaaagga ttatgtaagt ttgtatttta tttgaaacct agcatgaggt atctgggtca   18180
gttatatggc ttacagttgc ataatagtcc taggaggatt accattcata cctcaggaat   18240
ggggacataa atattatgac agaaagacag aaagaaatct ccccagtgtg cagttaatac   18300
atgttggatt tattttcatg atatctgttt atgactacaa acataaagct gtttttttag   18360
cagagtttta acaaaagcag tgattttaat tttgactatc agatcttccc ttcacaattt   18420
taggatgtga atgaggtcag aagccagaga aataggaaga aggaggtgag ttggtcagat   18480
aatacagtat cattgagaga accaagcact gaggaattgc gttcactctc aaaaagttta   18540
tactctaatg aaggaaaaca agtgacatgc ctccacaaag aaactgtaat ctagccatgg   18600
taaaagagat gcaagatcta tattacagga tgaagagaga agatctgtaa aagaaggaag   18660
actgacgaga gaaagcttac cagatgagga atatcagata tttcatctga gccttgagag   18720
cactatgctg gatttgtaaa tagaagtggc aggcaacatt tcaggtttca gaggcatcat   18780
gagcaaaagc acaagcacaa gagagctcaa aatgtgttca gaggaacagt ctgatgagag   18840
aggagcattt gtggaggagg gcggtaggat ttaagacttc taagatcagt gaaagttaac   18900
gagtttctct aacagtaatt tttacaatgc tttttctcac acacacacac ttttaaaagt   18960
acaccattta tcatttggat aattatacaa tgccagcaca atgcatgtgt gtacaagcat   19020
catctcagat gatgattgta ggaaagtcct taggtagagg aatatatcta gcagagcgct   19080
ggaactggat cttactggct tgtaagaccc cagtgtgcac atctctttcc agctccacac   19140
aggacatcat gctggaaatt ggccacggtg tgaatattta caccatggaa attgacaaac   19200
ctttaaaaaa tcctgtctcc ccccaccaaa gggccagttg ttgaacattt acctgggcac   19260
ccttagtgta ttcgtatctc cctccattct ttcatgtctg cttaagtttg cttaactcct   19320
acagcctttc ctgaaaagtg cttaccagcc aaagaggttt ctaattcaca ttctaccttg   19380
ccgtctccaa accttgttat tgccaagatt tacttcccat gtggttacct ggcttctcac   19440
tattaactga ctctactcta ggactttttg cctccattac tgactggcag tgaatgaatg   19500
```

-continued

```
ggtcattctg gtgtgtgttg ttatccttgc aacctgtgct ttaataacta cctctcttta   19560
ttagaaccta agtgcaaagg ctaaagggca tagatgatac aatctaagcc aacctcatta   19620
cacacaattc aaatttaatt ctgttagaaa catttcagca gtagaaattc tataaacagg   19680
agcagaggag ctccatggat agccatgtgg gcctgtggct ctaggagagt gattttttctc   19740 gttggggaac tcatttccta gaagcttgga tccaggagag aatatgcaag gtgggtggag   19800
gtggcttctc tccattctgt gggaacacat gttccctggc acggagagga aaatctgaca   19860
gaccaaaatg tgagtgtgtg tgtgtgtgtg tgtgcgcgcg cgcgtgcgtg tgtgtgtaga   19920
tccatataca tagagctgaa aataaaagtg atctatttcc tctcaaaaaa gattaagtta   19980
tttcaaaagg aaaggaaata tatattatta gcagtatgag tgtaagccca cttgagaagc   20040
ccatgcagtc tttgtgtgtg tgcccaaacg tgcacacatg tttcaagctt tcggggtagc   20100
ttggaccttc caggcgtgag gattatgaaa ctggagggaa ggtgggggata gctgcaaagg   20160 tgaagctaaa atgcatcaca aggtcagaac tagaataaac atgaaattac catgaaaagt   20220
gaaattggac taaagacctt gtcaccactg actcgcagga gaacaggagc agttggtgct   20280
gttctttctc aatatgcaca gaggcccttt cccctcgcgt ttcctgctgt aatgcaaaac   20340
cacttttcgg gaaaaatagt gtgtggcaga ctgaagccag gggaagaaa cgaaagatat   20400 tctgtggggt gataaatgcc tctaggccaa aaatagaaga ggtactacct ggtaggaata   20460
gaagcaagaa tcaatttgaa ttttacctaa tggagcttag ctctttgaat aaagaatgcc   20520
tacttgtcca ctacttgcca tgttagcttt ttccagcaga gggcagactt tacattgaaa   20580
tagatctaaa aaggccttca acctcttgct ttatttattt attttttttg gtttgaatat   20640
tttaaagttc aatatttttg gtttctaaat gatttaaaaa tattttaaag tatttaaggt   20700
ctagagtatg ttaaataaga aatttcttgg atttcagtta atatttctgc cttattagca   20760
aaatactcaa gatgtgattg caaaataagg ctttttttttt ccatggcttt tgggctggtc   20820
ttaggcactt gctgtcattg taggcaaggc tgttctttttt tgtgttgttt acaaaattat   20880
gaaagaaaat cctatctctt aactggatgg ttataatttt cattcattcc aatagctttt   20940
gatataaata actgctttttc tttaacagtt caattactac catcttctaa tctgtttcat   21000
agttagcttt gatattttcc ctagaggaaa tgacacctat ataaaactta actaaactta   21060
ttatacaata taacttcaat attcaaagcc ctttttaatga gaatttaaaa tttgtttctc   21120
ttcgagtttc attttcttgg tctaaccgaa tcattctcac aataagtgag aaaatagaga   21180
ctactatctc tctctatata ttttttaaaa cagaaggtta atttgcttgt aagtcgtggc   21240
tacgttcgat ctggagactt atctgttgga ctccaaagca caaattttttt tcatagcaag   21300 gcctgcctcc aattaactcc atgcgatcta cttataaaat cataaacgca ggactttatt   21360
cattaggact taaatccaga ctgacatagt ttgaaaaata caaagaacaa aacaagataa   21420
acctaaataa atcaatttca gaaattcttg gcatttaaac tcaataggtc ggtttaattt   21480
tggcttcacg caaacacttt cttgatctca cttttttttggg agtgtgtgtg tgtttgtgtg   21540
taatacggtt tttaaagtga atgcaggagg aagatctctg gggaaggcat tctccctatt   21600
ataagaaata caatatattt tctttttatta ttaaatttta cttatatttc tatgaaagca   21660
aaaacgtata tcaaaatgca taagaatttg ctgcctagga aacaaaatta tttttatgtg   21720
gagaaactga agatttatat acccttaaaa tgacaaagaa atcgagctcc atatattcac   21780
tttcattttc ataataatct ctacaggatt actgcaatta attttatgta acgagaacag   21840
aggtgttctt tttatttgag tgcagaaaaa agtttaaaaa gaggtgtgga cacttaaatg   21900
```

-continued

```
taaagttagt gaaatctat caatgaaacc agaaatgtta gcaaagcaaa atcatctctc  21960
taagttcttt tcttggaaag ataagctctg tttcaagatg gatagaaatg tgacaataca  22020
atgaaaatgt ctcttgctgt tgaaaaacac caccaccaca gctcttaatt cagttaacac  22080
tgtgtttaca aaacttcacc caaatcatca gccatgctta gtgttagcgg aaaaagcact  22140
ggaacactgg acttggattc agaaatgagg attctgcccc actgtagctg tgtgatctgg  22200
atatatcagt taacctctca gcgccttggt ttctcaccta tgaaacagga gataaatatgt  22260 atctaccaca cagaatgttg agagattaaa atgaaattta cattacatct gtgaaaactc  22320
tgagttcagt gtcttcctga cacattggtg attggtttgt tagatcaaaa taatccagat  22380
aatagacttt attaataata ccctattttg ggtagcaact tttaaaacaa ttcatcaatt  22440
attcgtgcac attgcataaa tagctccctc ccaaaactta cggatgttag aacaaagctt  22500
gggagaaatc ttgactctac atgtagatga agtaggttta agattaaagt ttaactgcta  22560
gtgattagaa aatgaagtgg aaatcaaata taattttcat ttttattata cttggaaaat  22620
ttaatgatac agtcttagat tttagatatt tgttagtatt ttttcagtaa ttttggtatt  22680
ctcttcagtt ctcaatatta catttaaaac agcaaatgaa aagcatgtca aaattcactt  22740
ttttgcctca aaaatcttag cctatatttc tagatctaga attactcttg caatgacatt  22800
ttccccatct cattttacac cttgcctttt ccttacaaat catattctct tttcatcagt  22860
acatctgccc aaaacgctct tctacttgac agttctatcc cacattcgcc tctgagcttc  22920
taacaagaca tacctctggg aattgcgagg tgccatattt taaatctctc agtgagatat  22980
acaggttttc ccgtgtgatc ataagggatt cctcaaatct gagtttttaga actaatctgc  23040 gacaactgat aagcacagta ttttcacatt agtatattta tgttgtgcta atatacttaa  23100
acagtatgta tgtccattga gaattttict acaaatttct tatcagctta cttttaattt  23160
ttaagaaaga taccttacat atttgattgg cattggctgt aattctgtta tagctcttaa  23220
actaaatagg ctcatccaaa ttggatggga gatgtaaatg tcacagattc tcagtggaat  23280
actagtcagc aataaaaagg aacaaattag taatacacac aacaacgtag atgaatcaca  23340
attactataa actaagtttt aaaagacaga cataaaggct acatattgca tgaatccatt  23400
catatgacat cctggaaaag gaaaaactat tggaacagaa accagatcag tggttgccac  23460
tggttgtctg atgtggaaca gaaaccagat tagataacca gagggattta ctacaaagag  23520
gcttgaggag acttttgggg tgctggaaat accttaactg tgatggtagt tgcgtaactg  23580
tatacatatg tcaacctctt caaagttgca aaactgtata catttgtcaa acttctcaaa  23640
ctataaacat aaaaagtaat cttttttagta agtaaattat atcttaatat agctgacttg  23700
aaaaaattaa ctacttaagg aaaaaggaaa tatttgcagt tttgagttgt atatcatctc  23760
ttttcagaga agtttattta aaacatacta tgtgtctatt ttttcatcca ttttttatttc  23820 cagccataaa tatgacactc agactagttt taaatagcta agagctacct cattggtgtg  23880
ttaagaggct ttaggatgaa atattatcta agtataaata ttataaaata tttttaatta  23940
aaagaagaac attatctaat ggaactccta tcctaagaat atatcatttc ttgattttta  24000
tttcattttc taattgccag caattaaagt cctgtgccaa gagcttgttg tacctaatat  24060
tacttaaaga ttatcaaggg ctgtgaagta agtgggatta gcctcacttt aaaacaaggg  24120
gaacttgtta ggttcagagc aaagtgaata gcaaattttg caagtccttc tgattccaaa  24180
gccaatatta gtaaccacca ttgctttatt tttaccagtt taacgatagt tctggtgctt  24240
```

-continued

```
gaggatgagg ttgtgtaagt gtttggaaat aaactgtaag aaaagaattc ttctctgagg   24300
gaaagaaggt tttcaaaaag aattgatcct gagttctgaa aacagaatgt caggattcat   24360
aaatgaagga tgtgcactgc tattcatcca tattaaccat aactctttga tagaggctta   24420
atctaattat agtaaagaaa aacagttatt tccaacctca catgagcttc tagtacaact   24480
gtgatgccag gctttagtga tattctttt gaacaaattc tctttgagat tttacatcta   24540
tgtttatcac caaactatca ttttcataac tgatcagtag atccaggtac tttattaatt   24600
tttgtacttt attaattccc tatcatttta aatgaaaaga cctcaaaggt ttctatgtat   24660 tatttttgt ttaaaagaca tatcaaacct aaatagtgtt ttcttgggca acatttacat   24720
gtagaagggc aataaaagtt ataaaccctt aggaatttgc tttagctctc atactggatg   24780
tgtagtactt taagtaggta atatgtattt gaatcactac ccagcagctg ctcatccata   24840
gtggattttt cttaatgtag cctgccagaa gcgcttacct tttattcata attgtctggg   24900
tgtgccttcc ccacttgaat tgaactgtat gtactgtgtg ctgtagaggt gtgcagttaa   24960
aatacgttta ttctcagaaa tattttaaaa atattttaaa atgttttcct ttgcagaatc   25020
agacacaagt ttggcagaag gaagtgtcag ctgcttagat gaaagtcttg gacataacag   25080
caacatgggc agtgattcag gcaccatggg aagtgattca ggtactgcct aactgttgtg   25140
taaaccttaa aaagtgtgaa ataagacgcc atatagtgga agcatggggg ctgttcatac   25200
cctccctaat gtatttatgc aattaaagca attctttct acagtgaaat agtttggaa   25260 ctttgccatt cactttcttt aaaagtgtaa cttacaaact cttagaacca aactctctaa   25320
ttttgatcca gtacatatct ttctggtctg gcatatgcca cattccatag agtcatgtca   25380
tctattttat ttatgggatc tgtttcaatt aatttgactg catttaaata gactgtattc   25440
aatttggtac atttatttac ttccaaattc tacttttaa attaaaatac ttttttaaata   25500 aaaaattgat actatcaata agagaagtat gactaactag aaattacata tgtaagtaaa   25560
agaagtcaag tttgtataag tatcttttga ataggagtag agttggcaaa atatttcggt   25620
cactaaatga aaattttacc aggttttttcc caaattactt tcaatatcag ttgtatattc   25680
caccagcaat aaatgagagt gcctcttcct aattccccac accttaatta ttacttcctg   25740
ttatcagttt tccaatttgt tagtctgata gatttcaaat tgtttctttc ttttctttga   25800
gtgtatattt ccatgatgac tactaagcta aaatgttaac attattaaat gtaggtgatg   25860
ggttagtggg tttctattac ataccttct atatttgcct acctgtttga agtatttcac   25920
aattaaaatg aacaaatcac aaacaaaaat aaaatgcttt gcaaggggcc agctaagaag   25980
cattggaaaa atgataaatt aagaaacaca ttactttatt cttcatttgt gattgagttg   26040
tttcccctaa gaatatatta tataattcag attatcctgc attgtcagaa gaattataaa   26100
aattgatatc cacaagaggc ctaaggtggc aaaatagttt atagaaagat tgtcatcaat   26160
cctaaatgct ttccaaatta gattgtagca cctctttttt catatatcct tttatcacaa   26220
tgacactcct gaatccctta gaacaaatta gtttgaggaa acccaattca ccaaatgtca   26280
ttcacaactt taatcttcat ttaaaagggt gaattcattt tctgttcaat tcagtcagtg   26340
tttattgagt tcttgccatg tgcttatttc tgtggattat atttgttttt tctatccttg   26400
tcataaaatt gttcaattta ataattaaca tttctattac atgctatgct agaactcaaa   26460
atagataatc tagctaatat ttaacatcat tataggttgt tttaagtttt tggagatcat   26520
gctaattttc atttgtctaa gtaagggctt ttcaataata tccattcatt caataaatat   26580
ttaatgtgta ccttctatgt gcagggcatc ttgcctattt agagctgtta acaaatgtat   26640
```

```
ttgctgattt ttagtcctca atgtggcatg aaacacatga taagtctgaa cgcaatctac  26700 tttttgaaaag caaatacatt ttcaaaggca aatacatatt tgaagacaaa cacatcagaa  26760
cgaacaccac ttgaagttct agatggatca gtacttagga gcaaagaatt actttgccta  26820
gtgggtagtc aatttccgaa atggtaaaat tatgaaattc cttgcccaca agtgcctggt  26880
ataagctaaa atagaaacca attcaaaagg aggtttagat aaattggtga actgttaaac  26940
acatattgag gcactgaaaa gtattataga atttgcaatt gtgtttttaat ctttgaagtt  27000 gacatcaaaa gggacttcat tctatatgtc cttcctcctc ctccagaggt catatatggg  27060
ccataaggtg tgacccaaaa caatcatatt atattccttt gtggaagtgt tatgccatag  27120
tagacatgat taccggtact tttaaagtat aaatattcta attatattat gagaggcttt  27180 ttttttttctg tttcccattt tcagaaagat atattgcctc tcaaaaagtg gcaatgtttt  27240
tggcaataca tattggcctg atatgtagaa agtgtttcct tactatttca agataatgcc  27300
tattaatatt tgtccagctg gaatggtgta ttttttctgtg gttacatacc ataggtaaag  27360
gaatactttg tagatttcaa acacatgcag tgacagacct tttctctcca agaataactc  27420
agctgtcaaa atcaatgtga gaatgaaatt tgccacatgg tgtagttcca atagaatatt  27480
attatttaag ccttatttga ttttcttttt tgaccattta tatggtagaa tataatttta  27540
aggtctttaa tcaatacttg ttgtagaggg agggcacagt gttattcaaa gcttgtgcat  27600
attttaactg ctattttcat ttaattgatt atgcttttca gagaaagcca aaaacaaaca  27660
aacaacaaac aatcaaaaac ccaaacattt cttttataaa ggaaattggc tcctggctca  27720
ttgataccag cccagttctc tccttctgct gacacagaag agaaaactct cttttcattg  27780
cttctgtgga taaattcttc catccctgtg tcagaggatg tgataaggca agaatcaggc  27840
tgaatattta gcactcaccc agcttttatt ctttggatgc tagtctcaca ttgaatccaa  27900
ctctaatttt ttcctgtatc cacactgtgc ttctttttaa acttagggcc acctatcaaa  27960
tctcctagtc ttaaatcaaa aatatggaag attattgagc tatctgtcta accaggtatt  28020
tttgtgtgca taacagcggt atagtgtcct agactctaaa gtccttcagg acaacaacta  28080
tattattgag agtgcctggc atataatagg tgtccagtca atattgactg aagaataaat  28140
ttgtggtaca tgcctactta agtagcagta aaacctcatg acttcagttc tgaagttaaa  28200
ttgtaaacac aatagtcctt ttaacattct cgctcttctt aaatgtatca gcttaataaa  28260
tgattagaat gcatgagtaa tattaatatt ttactcattt gatttggttc tggattctcg  28320
ggaaagagac ttaggaaatt gctatatctt tctctttgta atatttctta ttcaaggata  28380
tagtagtaag catgaaaaat gggggaaatt attattaaaa tgtactcttt taatagttta  28440
ttctgcaact attatgaagg aaggagcatt ttattagtat tcttaaaatc tacgcaaaaa  28500
tgaaactcag atgaaattaa acaaagagga tttattccta tattttaaca aacttcctag  28560
atcaaacaaa aatttagcag tagtaaattt ctgggtcttt gtttagacac tttataatgc  28620
atcttccttt gcaaatatac tggctctttt ggaaaagtta gatgacaaac tatcctaata  28680
gaggtgaaat atcatggttt tgatagtcta tgaaagctac agagggctaa cattgttctt  28740
aaataaatca gagccttaca taaatataat acaagatgaa ctattgtaaa tattgtagag  28800
ttcaaaacaa gcatggaaac ttataaaggt atattttaaa tgctggtgat tttaaatgag  28860
tttttcataa aaatcatatt gaatgaatca gcagatgatc caacgatagc ttaaatgtat  28920
tgcatctgtt tttactcatc catacaaaag gcaaatttcc tgccaggtta gtagatgatc  28980
```

-continued

```
ctaagtggta tttggtgtga attttcctac ctgttcagat agtactatca caacaagtta    29040
aaactcactc aaatagaatt atccaggggc tgaaatggag ccatcagcaa gttttttgaa    29100
gttaatggga ttatgttagt ttagttttat tgcaaacatt gataagaaaa agaagttatt    29160
tcatgtgtga tgaaatatgg ataaatactg ttatttcatt ttttcttctt attatataag    29220
tcataaaatg ggctttaaa ttggtataat atttatgtta cttcatttca cattataagc    29280
tatgcatttt ttgatctttt tcccctggta atataggtca atatggtcac ttctaaataa    29340
aatatattct atctaaaaca agacatatta taataatttt attttaatat acataaagtt    29400
tatgttagaa cttattttat cagtatttta aatttaaaat ccatgttaat tgaaaatatt    29460
tttaatatat tatactttgg attttagaaa aagttggaat atgtggagcc ataaacataa    29520
ggaagtaata aagataacaa ttcacaaata aatggcaaaa gtagtcatga tttagtttaa    29580
accaacaaaa ttatttttac ctttcaagga aaacctacca attaaaggct agcataggaa    29640
gagttttttc ctctactctc taaataacac ttctgtacaa cgtagttgcc tcagatggaa    29700
aaaggaactt gagatagata gggtgtctgt gtgtgtgtgt gtgtgtgtgt gtgtgtgtgt    29760
gtgtgtgctt tttggtattt ggttgtcaga taaagtttct acaaacgaaa gaaaatagta    29820
tcagccataa taccttcttt gcaattaaaa aaaggggaaa tacggaattg ggaggactaa    29880
tgattccaac tttctcagct cctcttgatt ttgtaggtgg aagggctaag tgaaacaagc    29940
agggcatagt ggctccacaa agaaatggga agtctgatgc cttaacaact agacctgcca    30000
atcccgcacc acagcccttt ctacaaattc gccttggctt cacccactct gtgaaaacac    30060
tcccccatgt tgctccttcc agtcctctta attagttgac tccctctgca cccccacacc    30120
cccagactcc ttctgtgaga gggagcctgt gttgtattct gcagatgcag agagcagaca    30180
ttaattggta cagaaaagag aaaatgaatt ggtttggacc acatgtgaaa aggagtttaa    30240
agcacaagag gcctacgttc agtttcaggc ttcctaagct ctgttatttt gttgtccctt    30300
ctcttatttt tcttttcaac cttcttcaga tgaagagaat gtggcagcaa gagcatcccc    30360
ggagccagaa ctccagctca ggccttacca aatggaagtt gcccagccag ccttggaagg    30420
gaagaatatc atcatctgcc tccctacagg gagtggaaaa accagagtgg ctgtttacat    30480
tgccaaggat cacttagaca agaagaaaaa agcatctgag cctggaaaag ttatagttct    30540
tgtcaataag gtattcaaag aacacataac actagttgat cattttcatt gtattattct    30600
gaaactttta tatgatggca tttgtgtcat tgactcacac atgtttagtt taattaagag    30660
taatgtcaaa ataagctctt tattttatct ttaatctttt ttaggtatat gtaatatcta    30720
agtgatgaac ctgaaaatag aaatttttca ataaaactag gacattatac caaatagcta    30780
taacttatgt agccccaaca cctgggagtt agttttgatt catctgcttc ctttatttcc    30840
cttatctggt cacaggttat atttacccag atatacttta aggttaacta gctaatttat    30900
cattgcaaat gaatatgaat gaccccaaaa tatcactgga atcaaggatc aaatattgtt    30960
ttttactttc tctttagctg ttgaccctta gtcaaagatg gcaagtcctc tttctccaga    31020
atacatataa tgtggtttgg agataaaatt aagtgaaggt ttggtatcta catcaagtta    31080
aatagatttt aaaatgctca agaagtatac atatatatat ataaaatata cacatattac    31140
attaaatgca actgaagttt tccttcaata atttatatct tagggtattt gaaggccatc    31200
ttcataagta aatatgtctg cttcaccgta aaacaaaatc tagtcatttg agctttattc    31260
agataaatga cagtttatta atttataaat atacaaattg gggatatgaa tatttactat    31320
tttatggaat aaaaatgagc atacttttcc ttgatcagaa agtctttttt ctgttcttat    31380
```

-continued

```
ctattccttt ataaaaaaaa gcagtagact gtaaaatatt ctattttta tttctattat   31440 gctaaaagtt ttagttacat cctgtttttc agtacttaga atccatgatt tgaatgattc   31500
ctatcatgta gttccaaatg cattttgtgt gcatctgcta agtccaaaga gctctccttt   31560
atacttgtat acttactatt aaaacacttt tatttatttt gctggtaatg gtgacacatt   31620
caaatttgtt tgccgataga cttgcatatg tattcccttt gtacaggata ttattttttt   31680
aaatgaaata ggtttgaatc ctatttctac ctaccggtac tttgaattag acaaattagt   31740
aacttctcta actttaattt cttcatctgc aaaatgaaca aaataataac taccctgctc   31800
tgaaatttca attggattat atatggccta gtaatgactc ctgcttttac tcttaaatac   31860
tagctttctc ctgctccttt ctcttcacct tcataactca tgaaactaag taacataacc   31920
agggaggctt ttaagtgcca aatccaaaga aaagaaccaa gttaactgga ttcaaagcta   31980
cttaaactga taattttgaa accatttgag catctgccat tttctcaaac tcagcctcac   32040
catctaccct cccaaaggct cctcttcccc atttacctgt ctctttgtga gtaataccac   32100
ctcctccaaa gcatgcagcc cccacaccta ggagttagtt ttaattcatc tacttccttt   32160
atttccctta tctggtcaca gggacatagg ctaatagagt tgaaaagggg cttcgagatt   32220
cagctttctt cctttgcaga gtggttctct cacttctgca gggtaacttc ctaatatcaa   32280
ggaggtcccc ctactaacaa gacactgaca ctcttagaaa gccctatttg tattcatcca   32340
aatctgtttc tctggaatcc cacaatcacc ggttagagtt ccttcctctg caaccacacg   32400
aagtcctaat tctccagcct aatgacagcc cttcacatag acaaggcagc atcatgtggc   32460
tcctaagtta ctttttttg ttgttccttg gaataaatgt ccacagttcc tttaactgtt   32520
ttccatataa catggtttct aaacctgtca tcattcctag tgctcatact ccttcagaca   32580
tttttctggg acactcttaa atgcggtgtc cagagttggg caaaatacta cagataagat   32640
cataccagtg cagagcgtag gagacatgag atatgacacc cagcttatga ccgcatttgc   32700
ctctggcatc cacagactta tctggacctt gtcatagaat caaaatcctc agttcctttt   32760
tatttgaaaa tctcttaaac tagaacattc ttaatttatt tttgtgcagt cagtttctga   32820
gcctaaattc aaatacttag gtttatttct ttaactattg atcttttcaa gtctcatatt   32880
tttgtatgtg tctgatgcat cttcctttct ataatattcc cttctcttct caatgctata   32940
ttctagccag gaatctttca ttgcattgga tctacatgat tcttcggaat gcacatttat   33000
ggctatgttt aaatattaat ttatcctcat taattattca cattcactgc attgttgtgt   33060
ggacacctgg ggacttgact ctaattcctt attgcttttc tattgttttt ctccttagaa   33120
ttactagaaa tccctccact aattcttcca tctatgtcat aattgtttac tataccatct   33180
ttttgaattt taaattaatt tcagtttaa ttctttttga ttgagtcaga acacctctgg    33240
cccagtaagt ctaagtaacc tgaatcttgt gtttggccca acaacaaggt attgttaccc   33300
ttgatctaga aaaagaaat cctgttctct aacaccattt actttcatct cccttcctcc    33360
gtcctttcca aagttatagc cttcgaatgc agagagaaat gaaaacacca cctgtgttcc   33420
cagactttcc atttcctatc tagggcttca acatcatgag agataaatcc caggttcctt   33480
cagatgctgc aatgcagccc catatgattc agcagaagtg ggtagcagtt gggtttgatt   33540
agtcttggca ggcactctgt cacatctcaa gaaaaggctc caagaggacc acacacctcc   33600
caattagcca tgtcagactt gcatctggct ttctctgtgt ccttcagtag gaagtcaaca   33660
ccacccagag cgagtatcag gatttccagc atctgctatc tcctgtgaca acttcttttt   33720
```

-continued

```
gttctgtaca tcagaaggtg cggcttcttt tgaagatttt tgactcacct tttatgggca   33780
gaattttgtg gtgcaatgtc actccataat acagagattc ttaattaaat cattcagcat   33840
gagtgtattt aaagacaaat caaatgtaga tcttgtcctc acgaaatata cagtctagaa   33900
gaaagatgag agatatatgt tgataatatg ataattaata ttttattgca ctttataaag   33960
cactctcaga tatattatct cattaaatct acacagcaac cccataaggt agtctttatt   34020
attctcattt tttcccatca gaaaactgaa gtttcaagac tttaattggc aattcaggga   34080
tcatccagcc aagaaacagc agaaatgaga cacgaacttt tatcttctga gtccactggt   34140
cttcctttgc cactgcaccc tccttctaga ataaaaggat tggtgaaata tcgtggaagt   34200
tttagtactg acaatacagc atcctctatt tcatttaatt ttcacaaccc tataataggt   34260
taacattatc ctcattttat taatctggaa attgagagca ttaagatgat tgagaccttg   34320
tccaaggtac aaagaagtaa gtggctggag tagctgtttt cagggctttc ttccctctgc   34380
atcatgctgt ctctttccac taaacttaat ttccattctt ttcctcagaa gccttctgtc   34440
ttgcataaat gaaatggaaa gaatacttct agaaaatgat tcaagaacgg ctttgtggaa   34500
gagagagaga agagcagagc tgtgactctc aaattttaaa ggcttaaatg tcattaaagt   34560
gaaggtttca agcctctgcc ccccagagat tgtccctaga ttcagtaatt cttgagtggg   34620
acttaggagt ctgcattttc taaacttctc aagcgtgttt gtaacaggta gattagagag   34680
actttacttt gaaaaaaaaa aagaactaaa tgaaagtttc tcttcttact ctttctaccc   34740
tttccacctt gtggtaaggt aatgttcttt cactcaccaa cttgattact gattttaagt   34800
ccactttgct tccttagaat ttatggattt cattttaact cttccccacc ccttcttcca   34860 gcccccccaga cacctacttt tggaagcctc catcatttcc actaaataat aaagtaaacc   34920
agtgttcttc ataaggtagc tgttcccttt agccaggggg atcagccatt ccttatttaa   34980
cacctaagtg ggacttacct caagtaaaaa gatgaataac acaaaccta cagactagga   35040 gaaaggtaac cactgattgc atttctggta gaattatgga gagtgaataa tataatgggc   35100
attctttgaa gcttgcccct gaaactcttc ctgccaactc tctgtttccc atattgtaca   35160
ctgctgggct tccattgcat aaatcttcct aggatatgac cttcaagatg gccttatatt   35220
ttttctccta atccagaagg tattttgagt gactagtaat gtgtagcatt gaggtgtcaa   35280
cccagctacc ttcagcagat gttataacat acagaatcag ctgagaagga cccgaagttt   35340
ccacttcttt tgccaggtct actttcgggt ttgttctttc tcagccacca cagctattcc   35400
agcagctcat ttcttcactt cacatctgtt ctcctagtca atgccctaac tcctcacttg   35460
tggttccctg attcttccgg tcctgtgggc ctgttgcttc tggtctaatc caaaacaaac   35520
aacaggaata aatcacttca acagtacaac ttgtagggat cctgtaaact gttatactac   35580
atgtaaaata ctctgcttga tgtttgcagc cctttataac ctggcactgc tctacaaatt   35640
taaaaatgta tttcttattc aaccttagct tcagtttatc ttttcactga ctcatggctt   35700
actagattca aattccttca aattcccctt ttttgagtcg tcagttgctt cttctcttaa   35760
ctgtcacttt gtgtgtgttt ctaggtgagc attattacat tgtgttgtaa taatttgtct   35820
tgctttgttt agtcttggtc tgtatgatca gctagacaga gttcctcaga gttgtcaacc   35880
atatgttaaa tatctttgtg tcccagacat aaatgcccac acctaacaag ggtataatca   35940
gtgcttattg acagatgaat gaaaggagtg atgggaacgt tgttatgcct gattcactga   36000
taatgtaaac acctctttc atgctggatg ccaaacaggc ctttgatcaa cactcttttg   36060
gcttcgacta actttctctc ttttaaaaaa tcttcacatt tttttaaggt actgctagtt   36120
```

-continued

```
gaacagctct tccgcaagga gttccaacca tttttgaaga aatggtatcg tgttattgga   36180
ttaagtggtg atacccaact gaaaatatca tttccagaag ttgtcaagtc ctgtgatatt   36240
attatcagta cagctcaaat ccttgaaaac tccctcttaa acttggaaaa tggagaagat   36300
gctggtgttc aattgtcagg tcagtttaag tgtttatttt tttaaaaaaa ttaatagtaa   36360
tattgatgat aacaaaggct gtatttgtta attttttaaa tgttcgtggc ttaaattgtc   36420
ttttattgct tatggtttta ttaaaatcct tctacttcct ggaggaaaca aaaaaagtaa   36480
gtttttaatt agaccacttt attctgcata agaataccat tattaaggca agcactcgct   36540
ggactttcca tttattctga caagttcctt tatttgctat tgaatgttgt tagatctgct   36600
tccctttccc atagaataaa aatacaaatc ttgtcttta tggggtatag gatgagaagg    36660
taggagaaag aatggaaaaa aataaaaata atttataata actaaatgca atgttaaaac   36720
aaggcaaaat tttccctctt taaatagtgt gttttttcact tgatgtaata aaaataaaat   36780
tcaccaacct aaaattaaat attttattaa agaacaaaag taaaatcctg agatttgttt    36840
tgtaataagc cagggtgtga attccacatc taacgctttt tagctctgta aactttctga    36900
atcttatcta ttaaagaagg agaatgtcta acagggagtt tcatgattag tatatacgaa    36960
cgtctgtgtg tacaggtgct agtatagtta gatttccctc ctaaaaactg aaagtggact    37020
gctcttgtgt cgtgcccaag agaaggcatc cccaaggcag ctcaattact ggtctaaagc    37080
tattttctca ctgtagtgtg ctgatatgga gaaatgaact ctttgaattt tcttttaaga    37140
cttttccctc attatcattg atgaatgtca tcacaccaac aaagaagcag tgtataataa    37200
catcatgagg cattatttga tgcagaagtt gaaaaacaat agactcaaga aagaaaacaa    37260
accagtgatt cccccttcctc agatactggg actaacagct tcacctggtg ttggaggggc   37320
cacgaagcaa gccaaagctg aagaacacat tttaaaagta agtcataatt ttatgtataa    37380
ccaatgaaag caaagctaaa acaaatgcca ggacttcttg gtcttattaa ataagattga    37440
gttcaagtgc tgtgatcatc agttaagtga aatctgtttg ctttagtaca ataaatatac    37500
tcagtcttct acagaatact aatatgcctt aataaatatc aataacacaa aatcatatca    37560
taaaaatgat ggagagtgat ataattaatg ggaagttgag ataaatagaa tgccttcttt    37620
tgaacatcta ctcttatggt taaatttaat gatctacctg atatagaaat atgcataaac    37680
tatgaaagtt tctagttgtc acacataata aagtcttact ccatgagttt caaaactgcg    37740
tattttctgt ccttcatatg ttattctagg aatctaggta attcaaatta aagggaaata    37800
gggatatgaa gatctttaaa gatgagcttg tcagctgccc cctaatggta acaccacata    37860
cagtgctact gttaatcttg agtgttaagt aaatcagagt agcccaagaa gtattttggt    37920
accaaggcaa ttgcatttga attttaagtc ccttacttta agttgaattc aatacaaatt    37980
atgtagagta gacacaacat tcagagatgc aattataggc tccaaaatat aatttattac    38040
tgggattaag gactaattcc aatctaataa tcaaggaaca tgactaagga tgctcccagc    38100
tttatgtgta gatgcctgct ttatgtgtag aagaaggtgg tagtatgatc cacggatgtc    38160
aagttgacct ttgatatgcc tcatgtaaca tggttatctc aaaatcattc tctgtcaatg    38220
atggtaaatt gttatactct ttccatgtca gtttttccact tggaaaatgg aatttaagga   38280
atgaatatca atacacctttt ttctctgtta ttacaccaac ttgatttaga agctcctttt    38340
tcctatatta ggacaaatgt tgctgattgt gggttaatga gatccataat aaaacaatgt    38400
taaaatgcta tatttagcaa gcaatgctac atattacttt catgaaattt tataccacat    38460
```

-continued

```
atttatgcta caatttaatg ctacatattt tttacatgaa aaagagttct acgttgaata  38520
aagtgaaagg gaaaaataat tgcataaata ttgaaaaatg tctctttcc agctatgtgc   38580 caatcttgat gcatttacta ttaaaactgt taaagaaaac cttgatcaac tgaaaaacca   38640
aatacaggag ccatgcaaga agtttgccat tgcagatgca accagagaag tatgggctta   38700 atgtttata tctattgatt gacaatacta cattcagtag aaagatggca aaggctattt     38760
tatactgacc atctgaaaaa tattatttaa aaattttagc aaacaagttt caggtttttt    38820
tttaattgat gttaggcagt aaagcactac agtgaattct cgcctctaga cctctttttag   38880 ttttctaatt tacatgagga atagcttatt cattgtttgt acatatgagt taaaagggac    38940
agtgaggggc catgggcaga gggatgtgta actaagctgg aggggttatg acagttcgtt     39000
ttagcctttt taattttctt cgtgaattcc aggattgatt ttctgacatt ccacagagcc     39060
attttgttgc tatcaaatta catttggcaa tgataatggg aatcctatct aatttgcata    39120
cttgcatatt tactttctta ggaaaacagt gcaatggtaa agaagtgaaa tatttactt     39180 aatgatgctt ttctgatgaa tttttcagga attataagaa taaactgaga gtcaatttgg    39240
acattatggc cagtaaatta tgtcaatact ttattttgta aaatttagaa agcattacaa    39300
attctggcca tatgtacttg ataataccat tgaaaataag aatgttggga tcaaatgata   39360
tgaaatatgc atagtagata aaacaatgct tgaaatatag taggcactaa accaatgtta    39420
gtaactagcc tccgtatatc tcttttttta aattctgaaa aagactgcta tctactccag    39480
ctgcactagc acagttgaat atattttatt cactttcctt ttttttgttac ttatttggtt    39540 ttacttgata attttaaatg catgtttcta ctcataaaga tttttaaaac taaatttctc    39600
aggtacattt tttaaaagaa tttgccattt tttaaactta ctttaatttt tttatatacc    39660
ttgaagcata acatacatac agaaaagtac aaattcatat gtgtactgat tgctgaattt    39720
tcctaaactg aatacacata tgtaaacaaa atccaaatca agagacagca cactgccagt    39780
atcctaaaag ctcctggctc ccccttccag tcaccatgcc ccaggaatca ctactatctt    39840
gacttctaaa acaaaaaatg agttttcact gattctgaac tttatataaa tggaatcata    39900
tagcatgcac tcctttattt ctggctttat tcagactcta cttcaacttt ttattttggt     39960
cgaaataata ctgaaaccag ttttacaaag gaggaatgtt tcttaaatta cactgtaagc    40020
tttctaaata attgtggcat taatgcaata tgtgtttttct aagttacctt taacatacaa    40080
ggtttatata attcattaac tttacttttg ttaacctttt aagttggaga ttccagcaga    40140
ggtaacaggg tgttggtgtg ggtgtggctt gatggcaggc ttaaaagaga agctgacaaa    40200
aataaatgta cagacaagtg atgggacact aacctgttac tttgtctaaa caaagatgaa    40260
tcagatttat tataacctag aaattattct aacaaagata atgttattcc tttaacaata    40320
agaatacata agaataagtg tgtactttat ttttaggatc catttaaaga gaaacttcta    40380
gaaataatga caaggattca aacttattgt caaatgagtc caatgtcaga ttttggaact    40440
caaccctatg aacaatgggc cattcaaatg gaaaaaaaag gtaatttagg tttggaccta    40500
acacttagtt tatcccatgt ttataccaag attttagatg actatatcac agattccca    40560 aaaaatggaa agcaaaagta gttccaaata gaatttctgt gttctctgta ggacaagcat    40620
aataaacatg ttctaattcc ttttctaagg agagagattc caatgctatc caattttctc    40680
tttgtctcca gagtcttgag ataaacttta atagctctgt ctccaaaggc aaactcaact    40740
aatatatttt catgccattt ctctgtgcat cagctacatg ttttttgctga ggcagaactc    40800 aagcagcaag tctaggagtt ggaaaacttg ccctgtttca gagctcagga cacattttga    40860
```

```
gccttaactt gcccatttta aaaccaaggt gaagccagtt ttgcagttag taacatatat    40920
tcaagtccat ggcacaattt tagggggttt atatgcttat tatttcactt acataatata    40980
ttttttcaca gctgcaaaag aaggaaatcg caaagaacgt gtttgtgcag aacatttgag    41040
gaagtacaat gaggccctac aaattaatga cacaattcga atgatagatg cgtatactca    41100
tcttgaaact ttctataatg aagagaaaga taagaagttt gcagtcatag aagatgatag    41160
tgatgagggt ggtgatgatg agtattgtga tggtgatgaa gatgaggatg atttaaagaa    41220
acctttgaaa ctggatgaaa cagatagatt tctcatgact ttattttttg gtaagattca    41280
aagtaacata tactggtgtc attcatttac cttttcaaca tgaacttact gcttctcata    41340
agctctccaa aaagagaaat atcttttgaa agaagaaatc ccactcagat tggaactatt    41400
tctaatgata tgaccagatt agctaccagt tgtatgatca cagtcagtca tttggtcatt    41460
cagttttatt gtcaagacaa ttgtaatgaa tttatttatt aaaccatcct aattattaga    41520
tatagcgcaa gattgtagat gagccacaat tcatgaaacc ttctagtgta attcgttgta    41580
tgttttacta atttatactt ccaaatagtt tttaaattaa ttaattttta atcaataaaa    41640
ctgtatattt ttggtgtaca aaatgtttga tatatctgta cattgtggag tggctaaatc    41700
aagcttgtta acatatcaac tctaattatt tcttaaagaa aacaataaaa tgttgaaaag    41760
gctggctgaa aacccagaat atgaaaatga aaagctgacc aaattaagaa ataccataat    41820
ggagcaatat actaggactg aggaatcagc acgaggaata atctttacaa aaacacgaca    41880
gagtgcatat gcgctttccc agtggattac tgaaaatgaa aaatttgctg aagtaggagt    41940
caaagcccac catctgattg gagctggaca cagcagtgag ttcaaaccca tgacacaggt    42000
ataaatatcc ttttggacga cttctttttct tttctttctc ttttcttctt ctcttctctt    42060
cttctcttct tctttttcttt cagacgaggc ctcgctctgt cactcaggct gaagagcagt    42120
ggcatgatca agattcactg cacccttgac ctcctaggct caagcaatcc tccagcccca    42180
gcctcctgag cagctgggac tctaggtgtg caccaccaca cccaactaat ttttttatct    42240
tttttgtaga aaaggtgtcc cactatgttg tcctggcttg tcttaaactc ctgggctcaa    42300
gccatccttc tgcctctgcc ttccaaagta ttgagattat aggcacgagc cactgcgctc    42360
agcctggact tctttctta tgctgttatt actcttctca aattgttttt agtcttttc    42420 taccaatcct ctcaccaccc atgaatacat ttacaggata aaacacctgt tcttgaaata    42480
aaatctaagg ctaatagcaa tcaaatctgt ggttttgag aggttaagtg ttgtttagg    42540 agtcatttt cccacataat aattggaaga actttctaag tttcccttgc aaaaataagt    42600
gacatgtaag cttaacaaca aagttcagaa atgattgcca tgtagtatca agtggaaaat    42660
tcaaactccc acaaaatgt gttcgttata actagaacta tgcaaaatat atttacatag    42720
aatgagacct ctagggaaac ttgaaaaaac taaagaattt gatatattag agatttggga    42780
ttctggtaag taggttttct gttccatttt aaggtgtttt gttttacttt gtttacatgt    42840
tgcttactgt gggcatagta aaaaaacact tgggtaagaa aaaaaggcac tagtagacat    42900
tacaagcatg catgaagcaa tgatgccttg ttagagtaaa atattcttct gagggctaaa    42960
atcacattga ccctgagtct ttctggacaa atggatactt cctttctatt atagttatca    43020
ctattcaagc caatggagca aattaattct gtttcagtgt ttgctggaaa aaaattcttg    43080
aaatggttca ctataactct ttatataccc tctacatgca ctcctgtgag cattgccaat    43140
aaaattaatg ccagagaaag tactgttttc cttgggtaac aagtttgctt ccttcttttt    43200
```

-continued

```
gatgagatgt agtttgcttt atatgttttt cttttttgcct tagcttccag aaagctagca   43260
ggaaaaactc aagttcagtc tcacagcctc tgtgttgatt cttatgagtt ctgtttttaa   43320
atttctatta tattaacttt agcgttgtga cttttattgt aagagggcta agcttctctg   43380
taaaaagagg tagagtgcaa atgaaaagcc tatgttcaag ctactttctg ctccttattc   43440
atttcaaacc aaggggctgt gtgccaaaat acagaacata ttcccttcct tccccactcc   43500
ttgtatcctc accttgtaaa ctggggtgga caaactcctt agcaatggtg ttaggcatct   43560
atgtgatgtg acttgaagat ctgacactgt ctggaatttt tgttattaaa gttactcctt   43620
caaattaaga cacaggcatc ttctgctaaa atccaagaac atgtaagttt ttatcgggag   43680
atgtgagggc cggagggaga aattttcaga gaagactcaa gagaggcctt tctacagggt   43740
tctccgacag ttaggagtag gagtcaaata aggactcaca ctgcctctga gaagaaaggg   43800
aaggggatgg aagaacatac ttttggtctg gcagctttat ttttgtttaa tgtatggggg   43860
caatagacag tgtggatgtg caccaaatgc caactggacc aacagctttg atgagagtgg   43920
ttatgaaaat aaaaccacat tgtccatatc aagctaggtt tgtgctcact catttctccc   43980
atgtaaggat gagaggtcat attttaattt atttatattg actttcaaaa ttcagagttt   44040
tttcatttga aaatagtttt atttacagtt gcataacctc ttctttcatt tttatttata   44100
ttgtcccttt gaattgataa tatatttacc tcattcaaaa ttaatgaggc acaaggcata   44160
ccactgacct ctagtcttcc agctcccctc cctagatgca gctgatgttt tcagtttctc   44220
ttgtgtcctt ttgggaatat tccatagctt ctaactcaaa tgattcttaa agtgaccaaa   44280
tgcatataca gtgtgcattt tctctgtgac tgaaaacaat atatcaaagc atctctgcat   44340
cttatcctct aaatagcaaa gattctgaag ttaatgtagt gggggaaaaa agcccatttt   44400
agcttctgat tgtcatatcc tcttctcaac cgacagctcc tcctttcttc ctctggagtc   44460
acccatcaat ttatttcctt ggcataaaat gtggtcttcc cacctccaga ctggatgatg   44520
gaaatatttt tgttattgtg tggtaatccc agattggaaa tcaaatgttg tctcaccatt   44580
atgtctttgt tcaatgccaa aaacagatgg caacaaatcc atgtatgatc taatcctttg   44640
atttacactg accagttgca atttattatt tcttcctcta attagaagat tttaatgtgt   44700
ttagcatcac aaaatttaat ttattaaaat gtttctacag aatgaacaaa aagaagtcat   44760
tagtaaattt cgcactggaa aaataaatct gcttatcgct accacagtgg cagaagaagg   44820
tctggatatt aaagaatgta acattgttat ccgttatggt ctcgtcacca atgaaatagc   44880
catggtccag gtacattcaa atacctctac ttactatgtt aatttttatt tgttgtgttc   44940
ctattttaat tgctttcttt tagttaaaca gcaaaaacat cttttttagtt tttaaaacaa   45000 agccttttc ctgttaaaag agcatttta aaatgctgtg cactgttgcc tttcatattg   45060
ctgtcaattc atataataac cagatacctg ttgtatgttt aaacaacaac tcctctttag   45120
ctatttctgt accctaaggc tttccaggac catgacacta gccccatttg taagagtcaa   45180
aagcagcctc ctcttcctca ggatgtctgt gagcccccag ctggaccagg aatctaaagt   45240
acactgtccc acaaatgtct gatgaagtaa catgcccaaa cctgagggag ccctgctgtt   45300
tctgcatttt cttcccttat cctttccaat tttctgtgtg tttagaagtt ttcatgataa   45360
aatgttggtt gggggcagac ttataaatgt aaaaataaat aaaagagtga aatgttctgt   45420
tttcattcag atttcacttt atctcttacc cacctatgtt aatggcatta ttgtaacctg   45480
ttgagtaggc ataggtgtta tgctgattaa tagatacact attcttccta taaaattaac   45540
taaagggatt tttaaataac ttaaattgca tccttgaata aaaggcaagt catagaagac   45600
```

-continued

```
taagataacc agactgccat caaattagca aataattta  tttcaggagt ctatttgtaa  45660
gtcagtgata agcttagtaa tcaaacttag aatacatttt tccttgagga tacttttata  45720
gttgataggc tcctgggcca ggccacagaa gtttctatta atcaaaatat acctgaatat  45780
cactttcata aagaggcttg tagaaagtta tcaccatgtt aaatatgttc ccatgggaaa  45840
atgtgctaag aatgtaatgt aggatgccag aaactgacct gccttctcac cagccctagt  45900
gtcaaggtca gagatgaccc ttctctccat tcattcctcc cagcttccta ccaagaaaga  45960
cgactcctca gtccaagtca ttgatcgtgg ttctcatagt ttgagagaga agttctgaga  46020
gcaaaaagcc tggacaggat gatattatgt cattgaggcc taaccatcat cactctagaa  46080
cactttttct gtattaaagc atattataag tttcaaagag ctgacttaca agtaatggat  46140
taataactaa ctttactaac tttacccatt tgaagactgg catgctgaac aacccaatat  46200
catttcattc tgagcaagaa tatcattccc agaaaaaacc aggaggattt gtatcacaac  46260 gtacccttc  atttacttga tttatttgtg ttttcaggcc cgtggtcgag ccagagctga  46320
tgagagcacc tacgtcctgg ttgctcacag tggttcagga gttatcgaac atgagacagt  46380
taatgatttc cgagagaaga tgatgtataa agctatacat tgtgttcaaa atatgaaacc  46440
agaggagtat gctcataagg tattgttggt cacctctgaa tttgattttc atttaaaaat  46500
ggcggcatgt ggttgccatt gatatctctg tgactcattc tccagacaaa aattgtgctg  46560
aattataagt ttctgtttag tgaactgtgc ttaatccaga ttcacatgca gagaatcaag  46620
atccatggtg ggcaggaaat tatcagggag ccattcctca ttccagtaaa accaaccata  46680
aatttggata atataaattt agcctgcctt gttccagaaa gactgctgca actcactgat  46740
tcaatccaac atggtaattt tggtttgatc caatttgttt gtaaaggcac agttttttaa  46800
tttcagaaat gtagatgaaa cgcctactgt gtgccaggta accttatagg aacagccaac  46860
agaggaaaca aaacacataa gactcctgct gcacgaagtt tatatttcta gtgtgtgcct  46920
ggtgaagttt ggaggacaga aacagtaaac aaacattaaa agacaagaaa tataatatat  46980
caagataagt gaagagaatt agaataggat gatatgaaac aactgactag atggatactt  47040
tcttgttttt agtagttttt gaaattcttt tttttcttat tatactttaa gttctagcgt  47100
acatgtgcac aacgtgcagg tctgttacat atgtatacat gtgccatgtt ggtgtgctgt  47160
acccatttac ttgtcattta cattaggtat ttctcttaat gctatccctc tcccctcccc  47220
ccaccccacg acaggccctg gtgtgtaatg ttcccagccc tgtgtccaag tgttctcatt  47280
gttcaatttc cacctatgag tgagaacatg cggggtttgg ttttctgtcc ttgtgatagt  47340
ttgctcagaa tgatggtttt cagtttcatc catgtcccta caaaggacat gaactcatcc  47400 tttttatgg  ctgcatagac tagatggata cttttcaactg ggtggttgag gaaggtctct  47460
tagaaggagt gacagggaag ctgcatctga atgataagaa aatacagaat atgtcatcta  47520
gctacatctc aatttactaa cacacagtta tttgagttgt gcaaaggaat gcagtgaaga  47580
aagaatgtat ttctatagta tttcaggaaa tcccccatac cactgaatta aaaactgtaa  47640
ctactataat agcaaacaat ccatttagaa gaaaattcac acccttgcat atgggtgtga  47700
atgttagttt cttaacattg gaattggctc taccttaaat agagtttcac taaagggatg  47760
ctttcaaatt ggtgtgcatt gctattacca actccaaggt ttcctgacca ggtttctgca  47820
caaaacttta ttttaaaacc cctttaaata caaggcaaag caaatatttt agagtatcaa  47880
atcaaacttt tgtcaccaaa ttatgccact ggaaagttac tgcctcccag ttaatgtcct  47940
```

-continued

```
aagagaatta atcaagtaga tgtttacaaa gactgatgtt ttaagagtag ttttttgggg   48000
gtcaacacta ggacaatctc tggagtttaa gggtcaaatt cttccagaca ttctttagaa   48060
taagactctg tccctttggg tgccccagaa tggactatat ttttaggtct cctttggcca   48120
agaaacctgc cctcctaaaa ctacttcagg tagatgaact tagagtagga gtggcaatgg   48180
ggaaggaggg ctacatgcca ccagtaatct gttcaaagcc tgtagaaaac attgctactg   48240
ggaagatgtt tactttcttc taatttgagc atctttctca acacaatctt cagacaacca   48300
ctaatgaatg atgagaattg acagataaga tgaaatcttt cttccatgtc ataaacacag   48360
tttaaacata acagagcttc ttaaaattaa atcagacttc taggagcaag ttgatcatca   48420
taaatgtttt tctctagcat tgattcaatt tttttgctac attattacac tttatttgga   48480
cttaggctga ttgtagctgt gcctcctgta tatttattat gagttctttt ttttgtttgt   48540
ttacccctct agttacttca aattcctta ctattttaga gttagtcttt tagcttctga   48600
tgtcctgatt acaaatccat acacttacct tggctttatt ttttttctga ctcattcata   48660
cacatttctt aattcccaca tgtatgtgat cctataatta ccttatcagc tcattgaact   48720
gtaaatgtct tataaaagta acctattaaa acttttaggg aaaaatattt cagtgtatta   48780
ttttgctata atttacatag gaaattaatc ttggtacttg tctgattaat ctattatata   48840
gcctccaggc ttgcttgcaa ggtttttattc tcttttctat gctatatatg gctgccttga   48900
agggagatct aaaatgtaga gttagaagcc aaagagatgg gctttgttca actgcactga   48960
tgacttactt ttactgaaaa tttctccctc ggtcttaaag aaaacaatta attcttccat   49020
aatttaatat aaatatgtca tctatgagag gtcagtttgg cggtaaatta ttcaagaacc   49080 agattttct accgtgaagt tgtgttggta taaacactgt tcagtcccta tgtcaacttt   49140
catatgttac ataaactaga ttatttccat tataaaataa gtgctgctgc tagtcacaga   49200
gcatagaata aagaggttga tgggcatatt ctctcacaga aggaatctag gcagtattgg   49260
ctccatgaag ttatgaggaa tccaggcctt ttctctcctt tttatgctgt tatagcattg   49320
ggctttcatt ctcatggtcg aagatggctt ttagaatttc agctgccaca tcctcattct   49380
aggcaggaag taagaggaga atggaaaggg cgaaaggtac acatgccagc tatctaattt   49440
ttaagaagat tttctgaaaa ttccactcaa cagcttttta catgtcattg actgctggtt   49500
tggaaatgta gtcatttagc tagcatattt ccacccagaa taaaattatg gttcgtgttag   49560 gaaaaatgga cactgaatga aaaactagtg gtttctgcta caaatgtgta aagagtagac   49620
tgattaagat ggtgaagggt ctgaaaatta taaagcatga aaaaagatta aaggcatttg   49680
ggtgcttagc atagattaga gaagacttgg taatgtaata acagtgttta gtaaagagat   49740
tccatgtgga aggaagttta gacctatttt atggaacaga attaaaacaa atgggtaggc   49800
tggcgcagtg gctcacacct gcaatcccag cactttgaga ggctgaggca ggtggatcac   49860
tgagatcaag aatttgagat cagcctgggc aacatggcaa aactccatct ctactaaaaa   49920
tatgaaaatt agctgagcat ggtggcaggt gcctggaatc ccagctactt gggagtctaa   49980
ggcagaagaa tcccttgaac ccaggagatg gaggttgcag tgacccgaga tagtaccaac   50040
acactccagc ctgggcagca gagcaagact ccatctcaat aaataaataa ataaataaat   50100
aacaaatggg taggctagac agagaatttt tgttgaatat tgctaaggac tttctcacaa   50160
tagaactttt ctgaaatgga atgggctact ttttgaatac ctgaagactg cacattttca   50220
tggttacagg agatgattat ataccaaatt ctttgggggg tcattacctc attattttta   50280
tttcctagac cataagctaa gggtatattt tcacaactaa gacctccaaa tttcaggaga   50340
```

```
cttacttcta tgaaactgaa aaaagaaaac aaacctgaaa ccactaacta ttcctttctc   50400
tgtccagatt ttggaattac agatgcaaag tataatggaa aagaaaatga aaaccaagag   50460
aaatattgcc aagcattaca agaataaccc atcactaata actttccttt gcaaaaactg   50520
cagtgtgcta gcctgttctg gggaagatat ccatgtaatt gagaaaatgc atcacgtcaa   50580
tatgacccca gaattcaagt gagtccagaa agacccattt ttacattttt ccacaagggg   50640
tgaagcaggt tgcattgtaa atgttctttc aaaatagtgc aaatgagatt catttatttt   50700
acaacttcct ctcctttagc ctctcaatta tattcctatt ttaaatgtct atgttttaaa   50760
taaactgcac tggggcagga aaagagaagt gtaagaacca aagccatttt gatccaaggc   50820
acgtattttt gtatgctcat catttgttct caaattttttg aacaactaaa gtcaagttaa   50880
tataaccaac agacttgaaa gaagttatga aaggcaacat gccccttgag aggtatgtgt   50940
agaagagaag cattgcctta gttgcaataa caagcctggg aagcaggagg gaaggaagga   51000
atgccgtgta gaataccgca ggcatgcgga tgagctccag gtccaataac ccatgaacta   51060
cacactggta ttttgtcagt tctccatgat gattctttcc ctttgatact tatagggaac   51120
tttacattgt aagagaaaac aaagcactgc aaaagaagtg tgccgactat caaataaatg   51180
gtgaaatcat ctgcaaatgt ggccaggtga gtaaattgct gtgggccaga ttttacttta   51240
gccaacagga atgtttaatt gcatgtacat ttaattttcc tcttgctctc tcttttgttt   51300
tccaggcttg gggaacaatg atggtgcaca aaggcttaga tttgccttgt ctcaaaataa   51360
ggaattttgt agtggttttc aaaaataatt caacaaagaa acaatacaaa aagtgggtag   51420
aattacctat cacatttccc aatcttgact attcagaatg ctgtttattt agtgatgagg   51480
attagcactt gattgaagat tcttttaaaa tactatcagt taaacattta atatgattat   51540
gattaatgta ttcattatgc tacagaactg acataagaat caataaaatg attgttttac   51600
tctgcattga a                                                       51611
```

<210> SEQ ID NO 2
<211> LENGTH: 51611
<212> TYPE: DNA
<213> ORGANISM: homo sapien

<400> SEQUENCE: 2

```
caaactctgt aagaactgcc tgacagaaag ctggactcaa agctcctacc cgagtgtgca    60
gcaggatcgc cccggtccgg accccaggc gcacaccgca gagtccaaag tgccgcgcct   120
gccggccgca cctgcctgcc gcggccccgc gcgccgcccc gctgcccacc tgcccgcctg   180
cccacctgcc caggtgcgag tgcagccccg cgcgccggcc tgagagccct gtggacaacc   240
tcgtcattgt caggcacaga gcggtagacc ctgcttctct aagtgggcag cggacagcgg   300
cacgcacatt tcacctgtcc cgcagacaac agcaccatct gcttgggaga accctctccc   360
ttctctgaga aagaaagatg tcgaatgggt attccacaga cgagaatttc cgctatctca   420
tctcgtgctt cagggccagg gtgaaaatgt acatccaggt ggagcctgtg ctggactacc   480
tgacctttct gcctgcagag gtgaaggagc agattcagag gacagtcgcc acctccggga   540
acatgcaggc agttgaactg ctgctgagca ccttgggaga gggagtctgg caccttggtt   600
ggactcggga attcgtggag gccctccgga gaaccggcag ccctctggcc gcccgctaca   660
tgaaccctga gctcacggac ttgccctctc catcgtttga gaacgctcat gatgaatatc   720
tccaactgct gaacctcctt cagcccactc tggtggacaa gcttctagtt agagacgtct   780
```

```
tggataagtg catggaggag gaactgttga caattgaaga cagaaaccgg gtaggtgtct    840
gttcagatgg agctagcctt ttaggcagat tttgcaaagc aggcttcctt gtgcgtttgc    900
ccctttccaa atgtgcttga cctctttggg caaatctagt ttcttccttt gagaagacaa    960
catctaggca ctttaagaca attttaaaaa tttaaacaca aaagaactac ttttctaatg   1020
ttttcactga agtaaaaagg agttaactct agaatcgtaa tgtgtattaa caggtaactt   1080
ttattgaaca cttactatgt gcagttggta tcattttcaa aatgtattac tacagttcat   1140
gttcagagta acccactgag gctcctaatg ttattaactc cattttacag atgagaaacc   1200
tgaggcaggt taaataattt gtccaaggtc tcccaggaaa aacagtggca gagctaagaa   1260
tttagcttgt gatagtgttg aatgtttttc ttatttaatg tagttccatg gagcaggggt   1320
tagtaaacta cggcccatgg gctaaatcaa gcctgctact gttttttttca ggcccacagg   1380 ctaagaatgg tcttcagatt tttcaatttt taattttcag tgttcataaa gttttattgg   1440
aacacagtca tgctcgtttg tttacatatt gcttgtggct gctttttctac tccaaaggca   1500 attggatgga gactgtgtgc ccttaaagcc aaaaatattt attatctggc attttagaga   1560
aaaagttttc caatctttgc cctacattac actttgtgcc atttagtctt agcccaaatg   1620
ggtaaattgc aatcacacac acacacacac acacacacac acacacaccc tttttctta   1680 atcaaagttt caacattctt tgagaatcaa aatttagaaa caattcattg aaagaatgtg   1740
ttgctagttt cagtttttca tgttagtgaa gaaactcatt tttcttaagg tagcattttg   1800
acagggcgaa ttttactgat gactttacat tgaatgtgat atgaattatt ttttgataag   1860
tgaagatgta ctgtgatgtg tataaatgct gacctgtttg aatgtgactt attcaggctc   1920
gtaagtcaaa agtcttgttt tggaagacat gtagacaaat aaagccatga ctaaaagtca   1980
aaggctttgt ctacaccact ctatgatttt cacatggttt ttttctctct ctctcttttg   2040
ggtcatccat tgtttgtata ttcatacaaa cttctgggca tttgattgat ttgctatagc   2100
ctatgatgca atttagtctt tagtgaataa agttagtgat cttttgtaga cttgacagac   2160
acagggcctg tccaaagacc caaacatgca tctaattttg atggccagtt ttcccaacaa   2220
gtaaattact ttgcactgtt gtctgtaatg tttatgtcgt tttgtgtatt gagaaccagc   2280
tagaacgcat tatagtagtc cagctggata tgacaaatgt gtacatcact gtggcagaat   2340
cttaatttgg aagaaagtat gcagccttca agccagctgg agatggaaga tggcatttcc   2400
agccacagta gctgttagaa gtccagaagc aacagagtcc agtaacacca caaagctgtt   2460
tatgtttggt gggtatgatg tcccgattgc cagcgaaaca gcacttctcc ctatttactc   2520
taaatacttc tgcctatcag catcactttt gtcttgcctg gattgaattt ccgccagcta   2580
gattttatcc aagttcttga ttctggcaag cttggaggca gctagcagta atgcaaggga   2640
tttgacacaa agaagatata gagtaacggg acttttgtgt actggtagca gttaaggcca   2700
aaacaaccca aattctccct ctgattcaca tttcaaagga ggccccaaaa gactgagcag   2760
ctataaattt gaggctctct aggaagcaat agtttctctg tgagagtgtg gaataatttt   2820
tgtgtgcatc atttacatgt attatcagtt ccaaaactaa gatatggtgg acaatgagac   2880
ggaagcatta agtttggtag aataatctat attgaggtgg tggtcattga caaatgttta   2940
tcttacagca gcaaagtgtg ataagactgt agaaggggaa cacatggatt tgaggtccat   3000
cttggcttct tactatatgc gttactttgg gccaaattac tgaagttccc tgatgctaca   3060
tttacctgtg aaaatggaca tcataaaatt tctcacagta ttttagtcaa catcaaatca   3120
gaaatagtgt ttatgaaaaa gcttataaat cagagctatt tgatatgata atggtgttga   3180
```

```
cttttgtaac cattcatctg gttacatttc tgtgtaaatt taagtttgag agattgaggt    3240
aaattcccca tgtcgcaatt gagatatact tcttaaagtc cctagattat actgatttga    3300
aaaagaaatt acctctttca tcccagaacc taactaggat taggtagagg gttggtgttt    3360
agtaagcatt gattacttga ttgatagact aattgaattt atttctgaaa gtgtctggaa    3420
taagcgttga aaacacatga cgtattgaat tgtgttgcca ggcgttagag aatggatgaa    3480
tgatgaaaat aagatttcca aatttgcttt tttgaaggct taaaatagca tttaactaag    3540
taatcaagac ttctataaaa tggtcttgta ttttcattct ttttctgttt ccccatagac    3600
attttctact tgatctatta ttttaattta ggattcccac cccatttcct agcccctgcc    3660
cgtaattaca gcaggccttc tgaaaatgac tttatacata ggtttgtgtc cagcaagtac    3720
ccaaaaactt attcattcat tcactcattc attcagtttg aatttattga gtggcatctt    3780
tgtgccggat gccatgctag tggtgaaaag ataggagaaa aacacagaga ctgttttgtc    3840
ctttcgtgaa gttgtgttgt agtgttaatt agtgttgata aaagaatgtc tactgtaggc    3900
cagtcatggt ggcttacgcc tgtaatccca gcactttggg aggccgagga gggtggctct    3960
cgaggtcagg agatggagac catcctggct aacacggtaa aactccgtct ctactaaaaa    4020
tacaaaaaaa ttagctgggt gtggtggtgg gagcctgtag tcccagttac tcgggaggct    4080
gaggcaggag aatggcatga acctgggagg cggagcttgc agtgagctga gatgcgccca    4140
ctgcactcca ccctggtgac agagcgagac tccatctaat aagaaagaga gaaagaaaaa    4200
gaaagaaaga aagaaagaaa gaaagaaaga aagaaagaaa gaaagaaaga agaaagaaa    4260 gaaagaaaag aaagaaagaa agaaaggagg gagggaggga gggagggagg gagggaagga    4320
aggaagaaag gaaggaagga aagaagaatg tctactgtat acaagggact attctaaata    4380
ctagagtttc agcaataaat atatgccatt ttatcaatca ttataataaa gcaatcctta    4440
atggtaaggg ggtaccccctg tactgccttg ctcctctttt aggatgctaa gttacaattt    4500
ggcattgtta catcttagtt ataactaagt tacaacttgg cacacccatc aatttaggca    4560
gtcatgaact ctgggaacga aagtgatcat ataaacattt ccatagtgtc ttaataatca    4620
agctgaacag ctaaagagag atgcatgttt catccctggc cagttcagaa cacaatgcat    4680
ctgtagtcct ggagactcca cacaccttcc atttacacag aagaaccaga gatgccatga    4740
ctagtccacc taagaacagt ccagttctcc caacatgaag ttgagcaccc aagtcaatct    4800
ccccaggaac attgtattgt ctggcaaatt aggaaagata agaatttcat ctgcaaaaaa    4860
aaaagtatga ataagaaatt agctatgtca atgtgacaat aaatattcat tgggttaaga    4920
cattaacttt ttgtgggaaa ctggttcttt aaaattcttt tttaacatac aggttttgcc    4980
tcctgattta cttttatctg agagttgaac tctgctgggt taaaaaaatc accattatat    5040
ttaaatagct atctaaggtt attataaagg gaagaaaaca ttttcattaa actgtacaat    5100
tgtgttggta agccagtgct ttatggaaat gtcattggtt tcttcactga tttctgttgg    5160
aaagaaaaaa catatcaaag aatttagaat atgaaagcat tgagttgtat tattaccaaa    5220
ttaattttat ttcgtatttc ataaattagt taacaatgta ttaatagact acatagtgaa    5280
aacatccatc cattttaac ttcacagaga aaacttcgag tggggagggg gcatgggtga    5340
gaattgtttt atgacttgtt gcagtctcaa atgtaaatat tcacctccca cgaatttctg    5400
taattgtgtt tacatattgg gatcaatatc tttacaatgt tttaggagaa catattaaat    5460
tttaaaaatt atataattgc ttcaaaggga gctgatgtac tttccagcac caaaactgag    5520
```

-continued

```
aagatttctt aaaaattcag catcttgatg aggctgctaa aattgcacag atatatgtag     5580
ttccacattc aaattgtaag aatatgttta ggaaataatg acatcatgat ccttatatgc     5640
ttggactcaa taacggcaaa gaaagcttga aaaatatgat tccacagtaa aagttgactt     5700
aatagaatag tggttgaaga aaattttgtg gatagaatat gcttagggat ttttaataac     5760
agcatttgtt gcctcactgg ttcttttttaa ggaaatcctt cctgattgct tcagtcaaat     5820
atatttaaag ctgattaaag gatggggtaa taaaatatga gaatggctga gttaaaagaa     5880
gacactgaaa ccagtcttat ttacatctat agcaattact tgttaaatta gcagatgata     5940
ataaagatgt tacaacatca gggaagccaa agaatttcca ttaggagact aagagagcta     6000
gaaaaaaatg gtaaaaaatg agcaaaaatc tgcttagaaa atgttgtggg tgacatggac     6060
tgaattcact tgaaatttac tgagttcaaa tagttatttt taaccacttc ttgccagaaa     6120
atgaatttaa aattggagaa aattataagc tataattata gttcaagaag gcaggattca     6180
gcctctaaat tcaactgcct gggatcaaat tctacttctg ccacttactc actttgtgac     6240
ctcagagagg tacctaaaca tctctgtgcc tcggatttct gatctgtaaa tgagttaata     6300
ttggtaccta tttctgggct gctgggttaa tatattcaag ttccctagaa cagcatgctt     6360
aactactaga tgctaagacg gaaatatccc ttgggtagag accatgctgt atgtgcttgt     6420
gcaggtgagg tgtttgtaac aataactctt cccaatcatc cataatagtt ctaacactga     6480
attagtgcca gacattgttc caaaaatgtt aacaaatttc tgacataaaa ggttatggaa     6540
tatatttata gaactagaaa atacataaat ttgtaggaaa gaactaaaca atccaaatga     6600
tacatgtgga agattggcaa atgttgagaa ggacctttga taatatcaaa gtcaatattt     6660
cttatctggg aggctgatag aatcacatga gatgttttac ttttttcttta atatctgagt     6720 tcctaacata gacaaaataa atcataatct tttaggggtg tttcctagac atcagtattt     6780
tttaaggctt tacggttgtt tctaacatgc agctaagata tagaaactct gaaatttctt     6840
ttcagctgcc ttgtaaccac atattgtaac caaggtctag ggagatgaag taaattgcct     6900
aatgccacag aaagctaatg atgtcctgcc taacttcttt catgtctaaa catggcttga     6960
gttactcttt cctccaaatc cttattgcta tattaggacc tagggaaatg cactgtgaca     7020
atgattacac aaaagatcca catttaaaag aaatttacta atctaaaaga gaaaataaaa     7080
gaaggctaaa gactctaatg aatggatata aaaataattc tgccccatat ttccaaaaaa     7140
aagatataac aataaatttc ccataacatt aaaaaaacac aaatttgaga aaaattgatt     7200
atagtaataa tcaactatgc aaatattaca taggaaaaaa tataaatctg cagtagtaat     7260
tacttatttc ataatgataa tcatgaagaa aggagataag aaatgtttga tttcccattt     7320
acagactcca tagattgaaa aaatatagcc agccctagat atacagaaag aaattggtga     7380
aaatagacat aacatggctg cagactaaag atactttctc ttctatcctt tattcaggaa     7440
tggctgaggt aaaatttatt ttctaggtgt caggtttgaa taattcaata gctttttaaaa     7500 aaaatggttc atatttaaaa ggacacttgg tccagagatt tttgttgttg ttgttgttgt     7560
tgtcccggag attttttttcc ctgccgactt cagaattgct acaggtaaca ttgctatttt     7620
cttcaatgtt tcaatgtaag cctttatttta tacttatgct taattgctca gtttttctaa     7680
agggtatttc ctgtttaagg ttattcagaa gatgtttgat cttacttaat tctaattttc     7740
tcttacaaca gattgctgct gcagaaaaca atggaaatga atcaggtgta agagagctac     7800
taaaaaggat tgtgcagaaa gaaaactggt tctctgcatt tctgaatgtt cttcgtcaaa     7860
caggaaacaa tgaacttgtc caagagttaa caggctctga ttgctcagaa agcaatgcag     7920
```

-continued

```
gtatttgtaa ttttactgag gaagattctt caaattctgc ctagtgattg agaattcaat    7980
aaagcagaaa gacacaatgc taaacaccaa gatttttaga atcaaaattt taagagtgga    8040
acatatgtga tagatcatct attttatcac cttaacaaat gaggaaattg atgcctggga    8100
aaatatcaac tgatcaaaga ccatttttca tccaaccaac actctttcta ctaccttatt    8160
ttaaaaacaa tatgactacc agaaatttta tcaagattat gtaacattaa atatacacaa    8220
atacattgga agaaagtatt ttagtggtta taaaaaatct gctgcatatt cttctgaaca    8280
tttttataca ttttaagcaa tgtattaagc atttgataaa aggattgttt tgtcaatata    8340
tctcaacctt acctaatgtg agattttaaa cagcattcaa taatagtaat aacataacat    8400
tttatagctc cttctcctac attatttgta aatctcactt aaactgctat cttatttttc    8460
ttttcgtagt atgcatccta tgtttccaaa aatatcatat gaaagacaaa ttgaaagtta    8520
actattaatt aattataatc attgcagttt tgttctggtg accctaacta atgaaaactt    8580
tgctgtaaaa agtggggtgc tgctgtaaca aacacctaaa cgtgtggaag tggctttgga    8640
actgggtaat tgatagagac tgtaagagtt ttgggtgaat ggtagaaata tgggtgttca    8700
gggtgattct ggtgaggtca cagagagaaa tgagaaaaat gtcattggaa actggaagaa    8760
aggtgatcct tgttataaaa tgggataaaa cttgatctca caagtaatgg atttggatat    8820
ttggctgaga aaatttctta gcaaaatgct gaaggagcag cttgatttcc cctaactgct    8880
tatagtaaaa tgcaaaagaa gagaaattaa ttgaaggagt tgttatgcaa aaaggaacca    8940
aaatttaaat atctggaaaa ttctcagcct atccatatgg caaaaaatga gaaattgtgt    9000
tataaagaga acaaccaatt gataacaaga tcatgggtgc tactgatgga cttaatcagc    9060
catttcagca gaaggtagga gtagagatat attataccag caaatacact tccagtttga    9120
actgaaggag acagagaaag caggacagaa tgagaaaagg atactggact ttctggattc    9180
tacagaacca gaccatagag ctatttggct gtgaatgtgt actattcttc agggaaagga    9240
aagaatgccc ccaaaagtga tacagaagtc atcagggttg ccacttccac cacagaccca    9300
gaggccaagg cagtttcctt tttggtttca aagggcaaaa ctgtctctct ggttttagtg    9360
agccctcagg atgaccctgc ctagtgtctc agaagcagag ctatcctcac agaaagctgt    9420
gtggatggag cccttagaga gagcaggctg tcttgcagag ccctagaacc tgccattccg    9480
tggacctgga aggcagagca tcaaaccaaa cagagctatt ctcaagcctt ataagcctta    9540
agatgtgaca gaatttacct taataagttt tggatttgct tgggacccat cacccttgct    9600
ttctttccta tatctccttt ttggaataag acgtccatcc tatgcctgtc ccaccattgt    9660
attatggaaa agaaacatgt agctcaactg gtttcacaag ttcacagctg gtgatgaatt    9720
tgccttatca tgaatcacac ctctagtctc atctacgtct gatttggaca atgtttaggt    9780
gagacttttg actttagact tagagttcat gcttcagtga gttaaggcac ttgggctgat    9840
gagatgagat gaatgtattt tgtatgtagt aaagatatga attttgggaa gccaatggta    9900
aaatgctaca gatggaattt tgtcctccta atactcatat gttggaacct aatatgactc    9960
tatctggaga cagtgatagt aggagatagt taagattaaa tgagccaggc caagcgtggt   10020
ggctcacgcc tgtaatccca gcactttggg aggccaagac gggtggatca cctgaggtca   10080
ggagtttgag accagcctgg ccaacatggc gaaaccgcat ctctactaag aatacaaaaa   10140
ttagctgggg tggtggcatg cagctataat cccagctact tggaaggctg aggcagaaga   10200
atcacttgaa ccaggaggct gaggttgcag tgagccgaga tcatgccact gcactctggc   10260
```

-continued

```
ctgggtgtca gagcaagact ccgtctcaaa aaaaaaaaaa aaagattaaa tgaatcataa  10320
gaatggggcc ttaatctgat agaattgtgg ccttttaaga agaggaagaa agagaaaaag  10380
agaaacatct gtctctttct ctctcttaac cgtgtgagga cgcagggaga acgtggccat  10440
ctgcaaatca aggagagagt cctcatcaga cattgaccct gctgtcacct tgatcttgga  10500
cttccagtgc ccagaactgt gagaaaagaa gtgtctgttg tttcagccac tcagttgatg  10560 gtgtttatt atggcagcat aaacagacta ctgtaggagc ttagactctg ggtcctgata  10620
catatcggat cctgatgctt atcaaatcca ggctccttcc ttgaatgtgt gacctttggc  10680
caggttctcg acttctctat gcctcagttt actcctcagt aaaatggaga taataatatt  10740
acttatcacc tcagtaaaat ggagacaata atattactta ccatctaggt ttattttgag  10800
acttaaataa cttaatgtat gtaaagtatt tatattgtga gtgcaaaata aattaactat  10860
tataatagtc cctaatgtac ttaatatcta actgcaaaca ttgccaagtt ttcttcttgt  10920
ccaaagtcac aacagttttc tttaggaaat tttccataca aagtggggca cattttcact  10980
gggttcttta agatgagata ataaaaaatg atacgttaga aaattttcct tatggcatca  11040
gtcttctctg acagattgca gcttcataaa ggcaaaaact cttgattttc tttttaaccc  11100
acataagccc ttaataaaat acccattaca tgtagttgaa gtaagaaaag ctggaagtga  11160
ggaatggagg aaagaagaaa agaggggcac aaaatatttc attaaatgtt ttaaaaatcc  11220
ccagaaattc agaatacatg aatataggct gacattaaag cagatgtacg tctcgtgcag  11280
aacacacagt gaggaaacaa aatggcaaga gcaaagctaa agaaaactac caaatttgca  11340
ttttcattaa ttcagcctta aatgtaactt tgtgtcactg aataagtgac ttacttccta  11400
aacatgacgg tcagacagga aatcactttt cttgtgatta gcataatgct tatattgttt  11460
ttttagctac agtctaatca ttacaaagaa ctactcgttg tgtccatatt aaaattaaaa  11520
gtaccttgcc ataacaaaag cacattctaa gcctttcgaa atgtcaacat attaaaatat  11580
attaaagcaa tctctattgc gggctctcca ttttgttttc aaaataacaa taacagctat  11640
ttatattgta taaaatcttg cattgcaata caatttacat tctattcaga acttcaaagt  11700
atttaaatat attcaggcaa tctctattag gaacctctag tttgtttca aaataacaat  11760 aacagttatg tatgctctac aaaaacttgt atggcactat gatttgcatt ctaatactgt  11820
tattcacaga gattgagaat ttatcacaag ttgatggtcc tcaagtggaa gagcaacttc  11880
tttcaaccac agttcagcca aatctggaga aggaggtctg gggcatggag aataactcat  11940
cagaatcatc ttttgcagat tcttctgtag tttcaggtac ttgaaacaca tacgtacttt  12000
aatacagtaa ttactacttc cagaaaaacc aactgggcag aacctattaa tcagagggag  12060
aaaatgtggg cattaaggtt agtaaacatt tatattaaaa taatattttt agaggagatt  12120
aaattaaaat aattcttggc caaatgctt tctaaaacta atccaatatc gatgtgttat  12180
aaatatgaac acaattgcat ctaattttaa tttataagaa atccatagtc attgtaagat  12240
aagtataaga atgccttata tttcctggtt ttcaaagtac ttataaatag atcagtcaat  12300
ttaattcacc caaaaccctg aaaataaaat agattcattg cttttttttct ctggtttaaa  12360 ctgggatggc tcagagaggt tcaactgtgt cgtaaaaatt aaaatcaaag ctataaaaag  12420
gaagatgaac agatgctgaa ctagggttgg cttgaattgc attaactaat cggtgaggac  12480
tgaagactac catgtccacc tttttgatac tgaaacagcc ctggcagaaa caaattattt  12540
aattattttt tccctttcta atctgctcgt gataggagaa tccacctctc cccttctctg  12600
ccaaaaggac ttattctgtt ttcacaagaa atagttgctt aaagcctgtg gtgtgctggt  12660
```

-continued

```
gaatgtaaca agtaactctg gggaaaagaa aaagccctag tttgtagcat ttgctagtct   12720
ctgtggttta aatattctca ttcaggctta tttcaagctt ccaacataag atcactgaac   12780
acaaagctgg gaagagctgt gcagtggcac atctttatac agcattccca ccgtacagat   12840
gcaaaagacg gagatagcct ccagatcaaa gatgatagtt aaatgattag gtgatgagtt   12900
ttaaatactt acaacctttg cctgaaaata atttcttta tggtaagttt atacaattta   12960 attttgtaa tggctgtggt taaaaactca gaaaattcct gaaaagttac cagttagctc   13020
ctgtgagccc atataaacta actctagcac accactgcaa agtttattat ttttattttt   13080
ttaatttcat tttattttat tttattttat ttttggagat ggaatctcac tcagtcacac   13140
aggctggagt gcagtggcat gctcttggct cactgcatcc ttcacctccc gggttcaagt   13200
gattctcctg cctcagcctc ccaagtagct gggattacag gcacccacca ccatgcccgg   13260
ctaatttttg tattttagt agagacaggg tttcaccatg ttggccagga ttgtcttgaa   13320
ctcctgacct caggtgatcc cccccactcg gcctcccaaa gtgctgggat tacaggcatg   13380
agccactccg cctggccttg ttattttgta cttagataag taatatgcat gcattgcaag   13440
aaatctgtaa tacacagaaa cacacaaaga agtcaccaat attcccagaa tgtggatatt   13500
acacttaaca tttgggtatg tgtgcttctg ggctttttac atacctgaat gtgtatatat   13560
agtgtcattt ctcttatgtt cattaaatat tcttctacag cctggttttt aatgactaaa   13620
taatggtccc accatttgga tgcagtatga ttaattgacc aattgttgaa catttaaata   13680
atgcctcgat agctctcttt gtacttatgt cacagtttgc tttttaaaaa catattatat   13740
aattggaatt tctgggtcaa atgatttata ctattttaac acatttgata cttaatgtca   13800
aatctcactc caggaacttg taccaattta catgttctcc aagagtatgg gatatgagtg   13860
cttatttccc tgaattctct tctacgagaa tgaataatat tatcatgttc aatcttttca   13920
atttggctgc tattaaaaat ggtatttcgt tatttgaatt tacattttca tatttctgct   13980
gaaaaagaat ttcacaaatt cattctcttt gttttgttaa ttatcaatac ttttaaaatt   14040
cacttttcta ttagggtatt catcttcttt ttgctgactt atatgaacta tctaagtata   14100
taagatatca attcattgtc ataaatagta ccaatttttt tcacagttgg cttgcttttt   14160
agcctgtttg tggattttttc tcttttttctt tttttggggg ttctgggggc aggcggggac   14220
agggtcttgc tctgtctctc tgtcgcccag gctggagtac agtggcacaa acacagctca   14280
ctgcagcctt gacctcccag gcgcaagtga tcctcccacc tcagtctccc aagtagctgg   14340
catcacgggc gtgcgccacc atacccagct aattttttgta tttttttttag agaatggggt   14400 ttcaccatgt tgtcaagact tgtctggaaa ctcctgggct caaggaatcc tcctgccttg   14460
gcctcccaaa gtgctgggat tataggcttg agctgctgtt tgtttttttaa tgtaatgcga   14520 ttccaccttt ctcataaact ctggtgctgc tgctgctgct aatagcaaag cttatacagg   14580
atagtttttt ttgttgttgt tgttgttttt catttgagca gctgcacctt cctttagaaa   14640
tcatgattct ataggaatgc caaaattcac tatctgagtg tggagttttc atgttttaat   14700
aaatgtcctt tacaagctac tcgacatctc tatgagttac tggccatttt ctgtaaatcc   14760
acactagaaa gaagggaaga tggagctact gctgagagat gaccctgcat cttaaatgag   14820
ggtttatcat caaagattac cagactaatg cattgcatta gcttgtagtt aatctgctct   14880
gaacttctag tgaacaaaat taaaggcaaa gtttttaaatt tttttaaatt tttacttctt   14940
agtataaaac ttaaagatgt atcttgtgaa aaaaatttta ataatgatat taggggacag   15000
```

-continued

```
aaaagctttt tatttttttt tttcctcttg ggttccttcc tctctatctc cctccttccc   15060
ttcccttcct ttcaccctaa cttccttccc tctcttcctt tcacttcttt catttaacaa   15120
ctattttcca aactcctatc atgtgccagg caccttgttg tatactgtga actcaggaac   15180
ataacagaaa tggcttcatg gccatggagc ctaatatgac tctatctgga gattgtgatg   15240
gtaagagata attaagagta aatgagtcag gccaggcgtg gtggctcaca cctgtaatcc   15300
caggactttg ggaggacgag gcgggtggat cacctgaggc caggagttca agaccagcct   15360
gaccaccatg gtgaagccct atctgtatta aaaatacaaa aacttagccg agcatggtgg   15420
cagatgcctg taatcccagc tacttggaag gctgaggcag gggaatcact tgaacccaag   15480
aggcagaggt tgcagtgagc caagattgca ccattgcact ccagcctgag caataagaac   15540
aaaaaaactc cgtctcaaaa aaaaagaaat gacttcagcc cccatggagc tttccactga   15600
gggaggtgtc ggcccagcag tagtaactgt atagctacac ttttagtaag tgccatgaaa   15660
gagtagtaca gagtattaaa atatataata gtctgagagc atgtaagagt atacagtaaa   15720
ctgcacagta atccgaggat ccatccaatt cacaaacatc ttaatggtct tctagtccat   15780
aggttcttta tgatatctgg atttctcatg tggatttgaa agcaggttag tttaatccat   15840
tctggccctt tccagagcac tagcaaagag tcacttattt atgaaaatgt agtgtgtttg   15900
cttcagacct ttgctttaga ctgctgctgt cattccaggt atctgtttgt ttccttgtta   15960
tcttaaggac taagaattac tgatattaat aacttataaa gtaccattag tccagagaaa   16020
ttattgagtt cttttgattg aagttttgt tgcagaattt actatggaag ggttttgcct   16080
gcataggcat tttctgacag aagtaacaat caaggtaaat gtgaaagtgc tccatagctt   16140
ctaatatgca tttgtgtagt tttgtttgt gtatcttctt gatattgata atgtttagtc   16200
tttattttga attccattat attaggttaa agtttcaaat agttgccaag atagcactga   16260
aaaaaacttg tcacaaagtc tgtaaatatg attttttatgt gtataaagaa aagactcaaa   16320
ttatttgtaa ttttaaatta agatatttat aattattatt tctgaaccag tttatcaaat   16380
attttctcag tgcatagtag tcttagtgca tgcaaatatt aattatttat agctttaatg   16440
caaagattat gtgtgtgtgt gtgtttttagc accttttacc ccttaacaca tctgatggat   16500
aagacacact accatcagta acagtggccc accttgaaac taattttaaa cacatatccc   16560
tttggcacta gaggtgacat atcagagttc tctagtggat tgttctagag agtgatttca   16620
tcatatctcc aaacttgcgg gttgatatgt gtccttttc ctcctcccac ctatgtttac   16680
aaatcaattg cttctcatta aaaagtggt tagtaattga tatatcaatt ttttatttgc   16740
ccttttccaa attaccaaaa caatttctaa acaaaatttg aacagttctc agactattaa   16800
tggcaattta atgctggatg ctatagttct gctttctgaa gtcactggtc gtcttataac   16860
aaaagataac tgcaaaactt tggtgtttct ctagatcaga tttccctagg aaacatcaga   16920
gagacactaa gcctgctttc attttctatt aaaagcattt taattatagc aaataattga   16980
cttctatata gcaaatattt tacttctaaa agcgaacagt taaattagtt gtgcagtcag   17040
tctttgtctg ctactgctgc tttgtcaaaa caagtgaata gttacttcac attaacctt   17100 tttcattata ctatttttagg aattaatgca ttacaataaa atcaaaggaa attaagtgac   17160
atttaaaact aagtcaactt tattgcattt ggtataaact tttatgcaga atggagcaga   17220
aaatcccccc aaacttcttt aatcattgtg ttacagctgc cctattgtga aaactagaaa   17280
atgcaaatgc ctcagattgg ccagcagagg gcgcctttac atttataaag ccaatggaat   17340
ttcactgttt cagcgtgaaa gattataatg taactgtaga gtgtgccatg tgtgaatata   17400
```

```
cagtgcgcat gactgtgatt gcatgtgtat attttgattt atatattcgt tcacgtgaag   17460
attttaaaat tccaccccag ctaatgagct taccaacctg cttgttttca gactttaata   17520
ccttctttct catatttccc catatgttcc actccttagg tttatccggt gacattatgc   17580
tttggaatat attgtggata tattttgcat agatcatgtt ctgtaggagg ggtttaaaaa   17640 ttgacccttta caaaacagcc ttcttctccc tggtccaatc tgttatagca cttttttttgt   17700 tgttgttttg ttttgccttt ttatagacta aagtccaatc ttagatttgg tctatactaa   17760
tttctgtaaa agtgccacaa aatttatcct tgcacttgag gaccagaata atgttctgta   17820
gcactaacct ctagaaatct agagattttt agaatctcta gaaataaaac catagcattt   17880
gaaacctaag tggaaaaaaa taattgatac agtagtttac aataagactg tttcagaatc   17940
attcatgcta tatcaggact ggtttgaagt aagagcactc cttttactttt taattttttct   18000 aaacttagtt atcattaatt attgagaact agcagtacta ctgaggcaat ccaaaagaca   18060
catattaatt tgagctgaga gaaagagaga gatgctgatg ctgacactga tattggtact   18120
tgttaaagga ttatgtaagt ttgtatttta tttgaaacct agcatgaggt atctgggtca   18180
gttatatggc ttacagttgc ataatagtcc taggaggatt accattcata cctcaggaat   18240
ggggacataa atattatgac agaaagacag aaagaaatct ccccagtgtg cagttaatac   18300
atgttggatt tattttcatg atatctgttt atgactacaa acataaagct gtttttttag   18360
cagagtttta acaaaagcag tgattttaat tttgactatc agatcttccc ttcacaattt   18420
taggatgtga atgaggtcag aagccagaga aataggaaga aggaggtgag ttggtcagat   18480
aatacagtat cattgagaga accaagcact gaggaattgc gttcactctc aaaaagttta   18540
tactctaatg aaggaaaaca agtgacatgc ctccacaaag aaactgtaat ctagccatgg   18600
taaaagagat gcaagatcta tattacagga tgaagagaga agatctgtaa aagaaggaag   18660
actgacgaga gaaagcttac cagatgagga atatcagata tttcatctga gccttgagag   18720
cactatgctg gatttgtaaa tagaagtggc aggcaacatt tcaggtttca gaggcatcat   18780
gagcaaaagc acaagcacaa gagagctcaa aatgtgttca gaggaacagt ctgatgagag   18840
aggagcattt gtggaggagg gcggtaggat ttaagacttc taagatcagt gaaagttaac   18900
gagtttctct aacagtaatt tttacaatgc ttttttctcac acacacacac tttttaaaagt   18960 acaccattta tcatttggat aattatacaa tgccagcaca atgcatgtgt gtacaagcat   19020
catctcagat gatgattgta ggaaagtcct taggtagagg aatatatcta gcagagcgct   19080
ggaactggat cttactggct tgtaagaccc cagtgtgcac atctctttcc agctccacac   19140
aggacatcat gctggaaatt ggccacggtg tgaatattta caccatggaa attgacaaac   19200 ctttttaaaaa tcctgtctcc ccccaccaaa gggccagttg ttgaacattt acctgggcac   19260
ccttagtgta ttcgtatctc cctccattct ttcatgtctg cttaagtttg cttaactcct   19320
acagcctttc ctgaaaagtg cttaccagcc aaagaggttt ctaattcaca ttctaccttg   19380
ccgtctccaa accttgttat tgccaagatt tacttcccat gtggttacct ggcttctcac   19440
tattaactga ctctactcta ggactttttg cctccattac tgactggcag tgaatgaatg   19500
ggtcattctg gtgtgtgttg ttatccttgc aacctgtgct ttaataacta cctctcttta   19560
ttagaaccta agtgcaaagg ctaaagggca tagatgatac aatctaagcc aacctcatta   19620
cacacaattc aaatttaatt ctgttagaaa catttcagca gtagaaattc tataaacagg   19680
agcagaggag ctccatggat agccatgtgg gcctgtggct ctaggagagt gattttttctc   19740
```

-continued

```
gttggggaac tcatttccta gaagcttgga tccaggagag aatatgcaag gtgggtggag   19800
gtggcttctc tccattctgt gggaacacat gttccctggc acggagagga aaatctgaca   19860
gaccaaaatg tgagtgtgtg tgtgtgtgtg tgtgcgcgcg cgcgtgcgtg tgtgtgtaga   19920
tccatataca tagagctgaa aataaaagtg atctatttcc tctcaaaaaa gattaagtta   19980
tttcaaaagg aaaggaaata tatattatta gcagtatgag tgtaagccca cttgagaagc   20040
ccatgcagtc tttgtgtgtg tgcccaaacg tgcacacatg tttcaagctt tcggggtagc   20100
ttggaccttc caggcgtgag gattatgaaa ctggagggaa ggtgggggata gctgcaaagg   20160 tgaagctaaa atgcatcaca aggtcagaac tagaataaac atgaaattac catgaaaagt   20220
gaaattggac taaagacctt gtcaccactg actcgcagga gaacaggagc agttggtgct   20280
gttctttctc aatatgcaca gaggcccttt cccctcgcgt ttcctgctgt aatgcaaaac   20340
cacttttcgg gaaaaatagt gtgtggcaga ctgaagccag gggaaagaaa cgaaagatat   20400
tctgtggggt gataaatgcc tctaggccaa aaatagaaga ggtactacct ggtaggaata   20460
gaagcaagaa tcaatttgaa ttttacctaa tggagcttag ctctttgaat aaagaatgcc   20520
tacttgtcca ctacttgcca tgttagcttt ttccagcaga gggcagactt tacattgaaa   20580
tagatctaaa aaggccttca acctcttgct ttatttattt attttttttg gtttgaatat   20640
tttaaagttc aatatttttg gtttctaaat gatttaaaaa tattttaaag tatttaaggt   20700
ctagagtatg ttaaataaga aatttcttgg atttcagtta atatttctgc cttattagca   20760
aaatactcaa gatgtgattg caaaataagg cttttttttt ccatggcttt tgggctggtc   20820
ttaggcactt gctgtcattg taggcaaggc tgttcttttt tgtgttgttt acaaaattat   20880
gaaagaaaat cctatctctt aactggatgg ttataatttt cattcattcc aatagctttt   20940
gatataaata actgcttttc tttaacagtt caattactac catcttctaa tctgtttcat   21000
agttagcttt gatattttcc ctagaggaaa tgacacctat ataaaactta actaaactta   21060
ttatacaata taacttcaat attcaaagcc cttttaatga gaatttaaaa tttgtttctc   21120
ttcgagtttc attttcttgg tctaaccgaa tcattctcac aataagtgag aaaatagaga   21180
ctactatctc tctctatata tttttttaaaa cagaaggtta atttgcttgt aagtcgtggc   21240
tacgttcgat ctggagactt atctgttgga ctccaaagca caattttttt tcatagcaag   21300
gcctgcctcc aattaactcc atgcgatcta cttataaaat cataaacgca ggactttatt   21360
cattaggact taaatccaga ctgacatagt ttgaaaaata caaagaacaa aacaagataa   21420
acctaaataa atcaatttca gaaattcttg gcatttaaac tcaataggtc ggtttaattt   21480
tggcttcacg caaacacttt cttgatctca ctttttttggg agtgtgtgtg tgtttgtgtg   21540
taatacggtt tttaaagtga atgcaggagg aagatctctg gggaaggcat tctccctatt   21600
ataagaaata caatatattt tcttttatta ttaaattttta cttatatttc tatgaaagca   21660
aaaacgtata tcaaaatgca taagaatttg ctgcctagga aacaaaatta tttttatgtg   21720
gagaaactga agatttatat acccttaaaa tgacaaagaa atcgagctcc atatattcac   21780
tttcattttc ataataatct ctacaggatt actgcaatta attttatgta acgagaacag   21840
aggtgttctt tttatttgag tgcagaaaaa agtttaaaaa gaggtgtgga cacttaaatg   21900
taaagttagt gaaaatctat caatgaaacc agaaatgtta gcaaagcaaa atcatctctc   21960
taagttcttt tcttggaaag ataagctctg tttcaagatg gatagaaatg tgacaataca   22020
atgaaaatgt ctcttgctgt tgaaaaacac caccaccaca gctcttaatt cagttaacac   22080
tgtgtttaca aaacttcacc caaatcatca gccatgctta gtgttagcgg aaaaagcact   22140
```

-continued

```
ggaacactgg acttggattc agaaatgagg attctgcccc actgtagctg tgtgatctgg   22200
atatatcagt taacctctca gcgccttggt ttctcaccta tgaaacagga gataatatgt   22260
atctaccaca cagaatgttg agagattaaa atgaaattta cattacatct gtgaaaactc   22320
tgagttcagt gtcttcctga cacattggtg attggtttgt tagatcaaaa taatccagat   22380
aatagacttt attaataata ccctattttg ggtagcaact tttaaaacaa ttcatcaatt   22440
attcgtgcac attgcataaa tagctccctc ccaaaactta cggatgttag aacaaagctt   22500
gggagaaatc ttgactctac atgtagatga agtaggttta agattaaagt ttaactgcta   22560
gtgattagaa aatgaagtgg aaatcaaata taattttcat ttttattata cttggaaaat   22620
ttaatgatac agtcttagat tttagatatt tgttagtatt ttttcagtaa ttttggtatt   22680
ctcttcagtt ctcaatatta catttaaaac agcaaatgaa aagcatgtca aaattcactt   22740
ttttgcctca aaaatcttag cctatatttc tagatctaga attactcttg caatgacatt   22800
ttccccatct cattttacac cttgcctttt ccttacaaat catattctct tttcatcagt   22860
acatctgccc aaaacgctct tctacttgac agttctatcc cacattcgcc tctgagcttc   22920
taacaagaca tacctctggg aattgcgagg tgccatattt taaatctctc agtgagatat   22980
acaggttttc ccgtgtgatc ataagggatt cctcaaatct gagtttttaga actaatctgc   23040 gacaactgat aagcacagta ttttcacatt agtatattta tgttgtgcta atatacttaa   23100
acagtatgta tgtccattga gaatttttct acaaatttct tatcagctta cttttaattt   23160
ttaagaaaga taccttacat atttgattgg cattggctgt aattctgtta tagctcttaa   23220
actaaatagg ctcatccaaa ttggatggga gatgtaaatg tcacagattc tcagtggaat   23280
actagtcagc aataaaaagg aacaaattag taatacacac aacaacgtag atgaatcaca   23340
attactataa actaagtttt aaaagacaga cataaaggct acatattgca tgaatccatt   23400
catatgacat cctggaaaag gaaaaactat tggaacagaa accagatcag tggttgccac   23460
tggttgtctg atgtggaaca gaaaccagat tagataacca gagggattta ctacaaagag   23520
gcttgaggag acttttgggg tgctggaaat accttaactg tgatggtagt tgcgtaactg   23580
tatacatatg tcaacctctt caaagttgca aaactgtata catttgtcaa acttctcaaa   23640
ctataaacat aaaaagtaat cttttttagta agtaaattat atcttaatat agctgacttg   23700
aaaaaattaa ctacttaagg aaaaaggaaa tatttgcagt tttgagttgt atatcatctc   23760
ttttcagaga agtttttatta aaacatacta tgtgtctatt ttttcatcca ttttttatttc   23820 cagccataaa tatgacactc agactagttt taaatagcta agagctacct cattggtgtg   23880
ttaagaggct ttaggatgaa atattatcta agtataaata ttataaaata ttttttaatta   23940 aaagaagaac attatctaat ggaactccta tcctaagaat atatcatttc ttgatttta   24000 tttcatttc taattgccag caattaaagt cctgtgccaa gagcttgttg tacctaatat   24060
tacttaaaga ttatcaaggg ctgtgaagta agtgggatta gcctcacttt aaaacaaggg   24120
gaacttgtta ggttcagagc aaagtgaata gcaaattttg caagtccttc tgattccaaa   24180
gccaatatta gtaaccacca ttgctttatt tttaccagtt taacgatagt tctggtgctt   24240
gaggatgagg ttgtgtaagt gtttggaaat aaactgtaag aaaagaattc ttctctgagg   24300
gaaagaaggt tttcaaaaag aattgatcct gagttctgaa aacagaatgt caggattcat   24360
aaatgaagga tgtgcactgc tattcatcca tattaaccat aactctttga tagaggctta   24420
atctaattat agtaaagaaa aacagttatt tccaacctca catgagcttc tagtacaact   24480
```

-continued

```
gtgatgccag gctttagtga tattcttttt gaacaaattc tctttgagat tttacatcta   24540
tgtttatcac caaactatca tttttcataac tgatcagtag atccaggtac tttattaatt   24600
tttgtacttt attaattccc tatcatttta aatgaaaaga cctcaaaggt ttctatgtat   24660 tatttttgt ttaaaagaca tatcaaacct aaatagtgtt ttcttgggca acatttacat   24720
gtagaagggc aataaaagtt ataaaccctt aggaatttgc tttagctctc atactggatg   24780
tgtagtactt taagtaggta atatgtattt gaatcactac ccagcagctg ctcatccata   24840
gtggattttt cttaatgtag cctgccagaa gcgcttacct tttattcata attgtctggg   24900
tgtgccttcc ccacttgaat tgaactgtat gtactgtgtg ctgtagaggt gtgcagttaa   24960
aatacgttta ttctcagaaa tattttaaaa atattttaaa atgttttcct ttgcagaatc   25020
agacacaagt ttggcagaag gaagtgtcag ctgcttagat gaaagtcttg gacataacag   25080
caacatgggc agtgattcag gcaccatggg aagtgattca ggtactgcct aactgttgtg   25140
taaaccttaa aaagtgtgaa ataagacgcc atatagtgga agcatggggg ctgttcatac   25200
cctccctaat gtatttatgc aattaaagca attctttttct acagtgaaat agttttggaa   25260
ctttgccatt cacttttcttt aaaagtgtaa cttacaaact cttagaacca aactctctaa   25320
ttttgatcca gtacatatct ttctggtctg gcatatgcca cattccatag agtcatgtca   25380
tctattttat ttatgggatc tgtttcaatt aatttgactg catttaaata gactgtattc   25440
aatttggtac atttatttac ttccaaattc tactttttaa attaaaatac tttttaaata   25500
aaaaattgat actatcaata agagaagtat gactaactag aaattacata tgtaagtaaa   25560
agaagtcaag tttgtataag tatcttttga ataggagtag agttggcaaa atatttcggt   25620
cactaaatga aaattttacc aggttttcc caaattactt tcaatatcag ttgtatattc   25680
caccagcaat aaatgagagt gcctcttcct aattccccac accttaatta ttacttcctg   25740
ttatcagttt tccaatttgt tagtctgata gatttcaaat tgtttctttc ttttctttga   25800
gtgtatattt ccatgatgac tactaagcta aaatgttaac attattaaat gtaggtgatg   25860
ggttagtggg tttctattac ataccttct atatttgcct acctgtttga agtatttcac   25920
aattaaaatg aacaaatcac aaacaaaaat aaaatgcttt gcaaggggcc agctaagaag   25980
cattggaaaa atgataaatt aagaaacaca ttactttatt cttcatttgt gattgagttg   26040
tttcccctaa gaatatatta tataattcag attatcctgc attgtcagaa gaattataaa   26100
aattgatatc cacaagaggc ctaaggtggc aaaatagttt atagaaagat tgtcatcaat   26160
cctaaatgct ttccaaatta gattgtagca cctctttttt catatatcct tttatcacaa   26220
tgacactcct gaatcccttaa gaacaaatta gtttgaggaa acccaattca ccaaatgtca   26280
ttcacaactt taatcttcat ttaaaagggt gaattcattt tctgttcaat tcagtcagtg   26340
tttattgagt tcttgccatg tgcttatttc tgtggattat atttgttttt tctatccttg   26400
tcataaaatt gttcaatttta ataattaaca tttctattac atgctatgct agaactcaaa   26460
atagataatc tagctaatat ttaacatcat tataggttgt tttaagtttt tggagatcat   26520
gctaattttc atttgtctaa gtaagggctt ttcaataata tccattcatt caataaatat   26580
ttaatgtgta ccttctatgt gcagggcatc ttgcctattt agagctgtta acaaatgtat   26640
ttgctgattt ttagtcctca atgtggcatg aaacacatga taagtctgaa cgcaatctac   26700
ttttgaaaag caaatacatt ttcaaaggca aatacatatt tgaagacaaa cacatcagaa   26760
cgaacaccac ttgaagttct agatggatca gtacttagga gcaaagaatt actttgccta   26820
gtgggtagtc aatttccgaa atggtaaaat tatgaaattc cttgcccaca agtgcctggt   26880
```

-continued

```
ataagctaaa atagaaacca attcaaaagg aggtttagat aaattggtga actgttaaac   26940
acatattgag gcactgaaaa gtattataga atttgcaatt gtgttttaat ctttgaagtt   27000
gacatcaaaa gggacttcat tctatatgtc cttcctcctc ctccagaggt catatatggg   27060
ccataaggtg tgacccaaaa caatcatatt atattccttt gtggaagtgt tatgccatag   27120
tagacatgat taccggtact tttaaagtat aaatattcta attatattat gagaggcttt   27180 ttttttctg tttcccattt tcagaaagat atattgcctc tcaaaaagtg gcaatgtttt   27240
tggcaataca tattggcctg atatgtagaa agtgtttcct tactatttca agataatgcc   27300
tattaatatt tgtccagctg gaatggtgta tttttctgtg gttacatacc ataggtaaag   27360
gaatactttg tagatttcaa acacatgcag tgacagacct tttctctcca agaataactc   27420
agctgtcaaa atcaatgtga gaatgaaatt tgccacatgg tgtagttcca atagaatatt   27480
attatttaag ccttatttga ttttcttttt tgaccattta tatggtagaa tataatttta   27540
aggtctttaa tcaatacttg ttgtagaggg agggcacagt gttattcaaa gcttgtgcat   27600
attttaactg ctattttcat ttaattgatt atgcttttca gagaaagcca aaaacaaaca   27660
aacaacaaac aatcaaaaac ccaaacattt cttttataaa ggaaattggc tcctggctca   27720
ttgataccag cccagttctc tccttctgct gacacagaag agaaaactct cttttcattg   27780
cttctgtgga taaattcttc catccctgtg tcagaggatg tgataaggca agaatcaggc   27840
tgaatattta gcactcaccc agcttttatt ctttggatgc tagtctcaca ttgaatccaa   27900
ctctaatttt ttcctgtatc cacactgtgc ttcttttaa acttagggcc acctatcaaa   27960
tctcctagtc ttaaatcaaa aatatggaag attattgagc tatctgtcta accaggtatt   28020
tttgtgtgca taacagcggt atagtgtcct agactctaaa gtccttcagg acaacaacta   28080
tattattgag agtgcctggc atataatagg tgtccagtca atattgactg aagaataaat   28140
ttgtggtaca tgcctactta agtagcagta aaacctcatg acttcagttc tgaagttaaa   28200
ttgtaaacac aatagtcctt ttaacattct cgctcttctt aaatgtatca gcttaataaa   28260
tgattagaat gcatgagtaa tattaatatt ttactcattt gatttggttc tggattctcg   28320
ggaaagagac ttaggaaatt gctatatctt tctctttgta atatttctta ttcaaggata   28380
tagtagtaag catgaaaaat gggggaaatt attattaaaa tgtactcttt taatagttta   28440
ttctgcaact attatgaagg aaggagcatt ttattagtat tcttaaaatc tacgcaaaaa   28500
tgaaactcag atgaaattaa acaaagagga tttattccta tattttaaca aacttcctag   28560
atcaaacaaa aatttagcag tagtaaattt ctgggtcttt gtttagacac tttataatgc   28620
atcttccttt gcaaatatac tggctctttt ggaaaagtta gatgacaaac tatcctaata   28680
gaggtgaaat atcatggttt tgatagtcta tgaaagctac agagggctaa cattgttctt   28740
aaataaatca gagccttaca taaatataat acaagatgaa ctattgtaaa tattgtagag   28800
ttcaaaacaa gcatggaaac ttataaaggt atattttaaa tgctggtgat tttaaatgag   28860
tttttcataa aaatcatatt gaatgaatca gcagatgatc caacgatagc ttaaatgtat   28920
tgcatctgtt tttactcatc catacaaaag gcaaatttcc tgccaggtta gtagatgatc   28980
ctaagtggta tttggtgtga attttcctac ctgttcagat agtactatca caacaagtta   29040
aaactcactc aaatagaatt atccaggggc tgaaatggag ccatcagcaa gttttttgaa   29100
gttaatggga ttatgttagt ttagttttat tgcaaacatt gataagaaaa agaagttatt   29160
tcatgtgtga tgaaatatgg ataaatactg ttatttcatt ttttcttctt attatataag   29220
```

-continued

```
tcataaaatg ggcttttaaa ttggtataat atttatgtta cttcatttca cattataagc   29280
tatgcatttt ttgatctttt tcccctggta atataggtca atatggtcac ttctaaataa   29340
aatatattct atctaaaaca agacatatta taataatttt attttaatat acataaagtt   29400
tatgttagaa cttattttat cagtatttta aatttaaaat ccatgttaat tgaaaatatt   29460
tttaatatat tatactttgg attttagaaa aagttggaat atgtggagcc ataaacataa   29520
ggaagtaata aagataacaa ttcacaaata aatggcaaaa gtagtcatga tttagtttaa   29580
accaacaaaa ttatttttac ctttcaagga aaacctacca attaaaggct agcataggaa   29640
gagttttttc ctctactctc taaataacac ttctgtacaa cgtagttgcc tcagatggaa   29700
aaaggaactt gagatagata gggtgtctgt gtgtgtgtgt gtgtgtgtgt gtgtgtgtgt   29760
gtgtgtgctt tttggtattt ggttgtcaga taaagtttct acaaacgaaa gaaaatagta   29820
tcagccataa taccttcttt gcaattaaaa aaaggggaaa tacggaattg ggaggactaa   29880
tgattccaac tttctcagct cctcttgatt ttgtaggtgg aagggctaag tgaaacaagc   29940
agggcatagt ggctccacaa agaaatggga agtctgatgc cttaacaact agacctgcca   30000
atcccgcacc acagcccttt ctacaaattc gccttggctt cacccactct gtgaaaacac   30060
tcccccatgt tgctccttcc agtcctctta attagttgac tccctctgca cccccacacc   30120
cccagactcc ttctgtgaga gggagcctgt gttgtattct gcagatgcag agagcagaca   30180
ttaattggta cagaaaagag aaaatgaatt ggtttggacc acatgtgaaa aggagtttaa   30240
agcacaagag gcctacgttc agtttcaggc ttcctaagct ctgttatttt gttgtccctt   30300
ctcttatttt tcttttcaac cttcttcaga tgaagagaat gtggcagcaa gagcatcccc   30360
ggagccagaa ctccagctca ggccttacca aatggaagtt gcccagccag ccttggaagg   30420
gaagaatatc atcatctgcc tccctacagg gagtggaaaa accagagtgg ctgtttacat   30480
tgccaaggat cacttagaca agaagaaaaa agcatctgag cctggaaaag ttatagttct   30540
tgtcaataag gtattcaaag aacacataac actagttgat cattttcatt gtattattct   30600
gaaactttta tatgatggca tttgtgtcat tgactcacac atgtttagtt taattaagag   30660
taatgtcaaa ataagctctt tattttatct ttaatctttt ttaggtatat gtaatatcta   30720
agtgatgaac ctgaaaatag aaattttttca ataaaactag gacattatac caaatagcta   30780
taacttatgt agccccaaca cctgggagtt agttttgatt catctgcttc ctttattttcc   30840 cttatctggt cacaggttat atttacccag atatacttta aggttaacta gctaatttat   30900
cattgcaaat gaatatgaat gaccccaaaa tatcactgga atcaaggatc aaatattgtt   30960
ttttactttc tctttagctg ttgacccttta gtcaaagatg gcaagtcctc tttctccaga   31020
atacatataa tgtggtttgg agataaaatt aagtgaaggt ttggtatcta catcaagtta   31080
aatagatttt aaaatgctca agaagtatac atatatatat ataaaatata cacatattac   31140
attaaatgca actgaagttt tccttcaata atttatatct tagggtattt gaaggccatc   31200
ttcataagta aatatgtctg cttcaccgta aaacaaaatc tagtcatttg agctttattc   31260
agataaatga cagtttatta atttataaat atacaaattg gggatatgaa tatttactat   31320
tttatggaat aaaaatgagc atactttttcc ttgatcagaa agtctttttt ctgttcttat   31380
ctattccttt ataaaaaaaa gcagtagact gtaaaatatt ctattttta tttctattat   31440 gctaaaagtt ttagttacat cctgttttc agtacttaga atccatgatt tgaatgattc   31500
ctatcatgta gttccaaatg catttgtgt gcatctgcta agtccaaaga gctctccttt   31560
atacttgtat acttactatt aaaacacttt tatttatttt gctggtaatg gtgacacatt   31620
```

-continued

```
caaatttgtt tgccgataga cttgcatatg tattcccttt gtacaggata ttattttttt   31680
aaatgaaata ggtttgaatc ctatttctac ctaccggtac tttgaattag acaaattagt   31740
aacttctcta actttaattt cttcatctgc aaaatgaaca aaataataac taccctgctc   31800
tgaaatttca attggattat atatggccta gtaatgactc ctgcttttac tcttaaaatac  31860 tagctttctc ctgctccttt ctcttcacct tcataactca tgaaactaag taacataacc   31920
agggaggctt ttaagtgcca aatccaaaga aaagaaccaa gttaactgga ttcaaagcta   31980
cttaaactga taattttgaa accatttgag catctgccat tttctcaaac tcagcctcac   32040
catctaccct cccaaaggct cctcttcccc atttacctgt ctctttgtga gtaataccac   32100
ctcctccaaa gcatgcagcc cccacaccta ggagttagtt ttaattcatc tacttccttt   32160
atttccctta tctggtcaca gggacatagg ctaatagagt tgaaaagggg cttcgagatt   32220
cagctttctt cctttgcaga gtggttctct cacttctgca gggtaacttc ctaatatcaa   32280
ggaggtcccc ctactaacaa gacactgaca ctcttagaaa gccctatttg tattcatcca   32340
aatctgtttc tctggaatcc cacaatcacc ggttagagtt ccttcctctg caaccacacg   32400
aagtcctaat tctccagcct aatgacagcc cttcacatag acaaggcagc atcatgtggc   32460
tcctaagtta cttttttttg ttgttccttg gaataaatgt ccacagttcc tttaactgtt   32520
ttccatataa catggtttct aaacctgtca tcattcctag tgctcatact ccttcagaca   32580
tttttctggg acactcttaa atgcggtgtc cagagttggg caaaatacta cagataagat   32640
cataccagtg cagagcgtag gagacatgag atatgacacc cagcttatga ccgcatttgc   32700
ctctggcatc cacagactta tctggacctt gtcatagaat caaaatcctc agttcctttt   32760
tatttgaaaa tctcttaaac tagaacattc ttaatttatt tttgtgcagt cagtttctga   32820
gcctaaattc aaatacttag gtttatttct ttaactattg atcttttcaa gtctcatatt   32880
tttgtatgtg tctgatgcat cttcctttct ataatattcc cttctcttct caatgctata   32940
ttctagccag gaatctttca ttgcattgga tctacatgat tcttcggaat gcacatttat   33000
ggctatgttt aaatattaat ttatcctcat taattattca cattcactgc attgttgtgt   33060
ggacacctgg ggacttgact ctaattcctt attgcttttc tattgttttt ctccttagaa   33120
ttactagaaa tccctccact aattcttcca tctatgtcat aattgtttac tataccatct   33180
ttttgaattt taaattaatt tcagttttaa ttctttttga ttgagtcaga acacctctgg   33240
cccagtaagt ctaagtaacc tgaatcttgt gtttggccca acaacaaggt attgttaccc   33300
ttgatctaga aaaaagaaat cctgttctct aacaccattt actttcatct cccttcctcc   33360
gtcctttcca aagttatagc cttcgaatgc agagagaaat gaaaacacca cctgtgttcc   33420
cagactttcc atttcctatc tagggcttca acatcatgag agtaaaatcc caggttcctt   33480
cagatgctgc aatgcagccc catatgattc agcagaagtg ggtagcagtt gggtttgatt   33540
agtcttggca ggcactctgt cacatctcaa gaaaaggctc caagaggacc acacacctcc   33600
caattagcca tgtcagactt gcatctggct ttctctgtgt ccttcagtag gaagtcaaca   33660
ccacccagag cgagtatcag gatttccagc atctgctatc tcctgtgaca acttcttttt   33720
gttctgtaca tcagaaggtg cggcttcttt tgaagatttt tgactcacct tttatgggca   33780
gaattttgtg gtgcaatgtc actccataat acagagattc ttaattaaat cattcagcat   33840
gagtgtattt aaagacaaat caaatgtaga tcttgtcctc acgaaatata cagtctagaa   33900
gaaagatgag agatatatgt tgataatatg ataattaata ttttattgca ctttataaag   33960
```

-continued

```
cactctcaga tatattatct cattaaatct acacagcaac cccataaggt agtctttatt    34020
attctcattt tttcccatca gaaaactgaa gtttcaagac tttaattggc aattcaggga    34080
tcatccagcc aagaaacagc agaaatgaga cacgaacttt tatcttctga gtccactggt    34140
cttcctttgc cactgcaccc tccttctaga ataaaaggat tggtgaaata tcgtggaagt    34200
tttagtactg acaatacagc atcctctatt tcatttaatt ttcacaaccc tataataggt    34260
taacattatc ctcattttat taatctggaa attgagagca ttaagatgat tgagaccttg    34320
tccaaggtac aaagaagtaa gtggctggag tagctgtttt cagggctttc ttccctctgc    34380
atcatgctgt ctctttccac taaacttaat ttccattctt ttcctcagaa gccttctgtc    34440
ttgcataaat gaaatggaaa gaatacttct agaaaatgat tcaagaacgg ctttgtggaa    34500
gagagagaga agagcagagc tgtgactctc aaatttaaa ggcttaaatg tcattaaagt    34560
gaaggtttca agcctctgcc ccccagagat tgtccctaga ttcagtaatt cttgagtggg    34620
acttaggagt ctgcattttc taaacttctc aagcgtgttt gtaacaggta gattagagag    34680
actttacttt gaaaaaaaaa aagaactaaa tgaaagtttc tcttcttact ctttctaccc    34740
tttccacctt gtggtaaggt aatgttcttt cactcaccaa cttgattact gattttaagt    34800
ccactttgct tccttagaat ttatggattt cattttaact cttccccacc ccttcttcca    34860
gcccccagca cacctacttt tggaagcctc catcatttcc actaaataat aaagtaaacc    34920
agtgttcttc ataaggtagc tgttcccttt agccaggggg atcagccatt ccttatttaa    34980
cacctaagtg ggacttacct caagtaaaaa gatgaataac acaaaccta cagactagga    35040 gaaaggtaac cactgattgc atttctggta gaattatgga gagtgaataa tataatgggc    35100
attctttgaa gcttgccctt gaaactcttc ctgccaactc tctgtttccc atattgtaca    35160
ctgctgggct tccattgcat aaatcttcct aggatatgac cttcaagatg gccttatatt    35220
ttttctccta atccagaagg tattttgagt gactagtaat gtgtagcatt gaggtgtcaa    35280
cccagctacc ttcagcagat gttataacat acagaatcag ctgagaagga cccgaagttt    35340
ccacttcttt tgccaggtct actttcgggt ttgttctttc tcagccacca cagctattcc    35400
agcagctcat ttcttcactt cacatctgtt ctcctagtca atgccctaac tcctcacttg    35460
tggttccctg attcttccgg tcctgtgggc ctgttgcttc tggtctaatc caaaacaaac    35520
aacaggaata aatcacttca acagtacaac ttgtagggat cctgtaaact gttatactac    35580
atgtaaaata ctctgcttga tgtttgcagc cctttataac ctggcactgc tctacaaatt    35640
taaaaatgta tttcttattc aaccttagct tcagtttatc ttttcactga ctcatggctt    35700
actagattca aattccttca aattcccctt ttttgagtcg tcagttgctt cttctcttaa    35760
ctgtcacttt gtgtgtgttt ctaggtgagc attattacat tgtgttgtaa taatttgtct    35820
tgctttgttt agtcttggtc tgtatgatca gctagacaga gttcctcaga gttgtcaacc    35880
atatgttaaa tatctttgtg tcccagacat aaatgcccac acctaacaag ggtataatca    35940
gtgcttattg acagatgaat gaaaggagtg atgggaacgt tgttatgcct gattcactga    36000
taatgtaaac acctcttttc atgctggatg ccaaacaggc ctttgatcaa cactcttttg    36060
gcttcgacta actttctctc ttttaaaaaa tcttcacatt tttttaaggt actgctagtt    36120
gaacagctct tccgcaagga gttccaacca tttttgaaga aatggtatcg tgttattgga    36180
ttaagtggtg atacccaact gaaaatatca tttccagaag ttgtcaagtc ctgtgatatt    36240
attatcagta cagctcaaat ccttgaaaac tccctcttaa acttggaaaa tggagaagat    36300
gctggtgttc aattgtcagg tcagtttaag tgtttatttt tttaaaaaaa ttaatagtaa    36360
```

-continued

```
tattgatgat aacaaaggct gtatttgtta attttttaaa tgttcgtggc ttaaattgtc   36420
ttttattgct tatggtttta ttaaaatcct tctacttcct ggaggaaaca aaaaaagtaa   36480
gtttttaatt agaccacttt attctgcata agaataccat tattaaggca agcactcgct   36540
ggactttcca tttattctga caagttcctt tatttgctat tgaatgttgt tagatctgct   36600
tccctttccc atagaataaa aatacaaatc ttgtctttta tggggtatag gatgagaagg   36660
taggagaaag aatggaaaaa aataaaaata atttataata actaaatgca atgttaaaac   36720
aaggcaaaat tttccctctt taaatagtgt gttttcact tgatgtaata aaaataaaat   36780
tcaccaacct aaaattaaat attttattaa agaacaaaag taaaatcctg agatttgttt   36840
tgtaataagc cagggtgtga attccacatc taacgctttt tagctctgta aactttctga   36900
atcttatcta ttaaagaagg agaatgtcta acagggagtt tcatgattag tatatacgaa   36960
cgtctgtgtg tacaggtgct agtatagtta gatttccctc ctaaaaactg aaagtggact   37020
gctcttgtgt cgtgcccaag agaaggcatc cccaaggcag ctcaattact ggtctaaagc   37080
tattttctca ctgtagtgtg ctgatatgga gaaatgaact ctttgaattt tcttttaaga   37140
cttttccctc attatcattg atgaatgtca tcacaccaac aaagaagcag tgtataataa   37200
catcatgagg cattatttga tgcagaagtt gaaaaacaat agactcaaga aagaaaacaa   37260
accagtgatt cccttcctc agatactggg actaacagct tcacctggtg ttggaggggc   37320
cacgaagcaa gccaaagctg aagaacacat tttaaaagta agtcataatt ttatgtataa   37380
ccaatgaaag caaagctaaa acaaatgcca ggacttcttg gtcttattaa ataagattga   37440
gttcaagtgc tgtgatcatc agttaagtga aatctgtttg ctttagtaca ataaatatac   37500
tcagtcttct acagaatact aatatgcctt aataaatatc aataacacaa aatcatatca   37560
taaaaatgat ggagagtgat ataattaatg ggaagttgag ataaatagaa tgccttcttt   37620
tgaacatcta ctcttatggt taaatttaat gatctacctg atatagaaat atgcataaac   37680
tatgaaagtt tctagttgtc acacataata aagtcttact ccatgagttt caaaactgcg   37740
tattttctgt ccttcatatg ttattctagg aatctaggta attcaaatta aagggaaata   37800
gggatatgaa gatctttaaa gatgagcttg tcagctgccc cctaatggta acaccacata   37860
cagtgctact gttaatcttg agtgttaagt aaatcagagt agcccaagaa gtattttggt   37920
accaaggcaa ttgcatttga attttaagtc ccttacttta agttgaattc aatacaaatt   37980
atgtagagta gacacaacat tcagagatgc aattataggc tccaaaatat aatttattac   38040
tgggattaag gactaattcc aatctaataa tcaaggaaca tgactaagga tgctcccagc   38100
tttatgtgta gatgcctgct ttatgtgtag aagaaggtgg tagtatgatc cacggatgtc   38160
aagttgacct ttgatatgcc tcatgtaaca tggttatctc aaaatcattc tctgtcaatg   38220
atggtaaatt gttatactct ttccatgtca gttttccact tggaaaatgg aatttaagga   38280
atgaatatca atacaccttt ttctctgtta ttacaccaac ttgatttaga agctcctttt   38340
tcctatatta ggacaaatgt tgctgattgt gggttaatga gatccataat aaaacaatgt   38400
taaaatgcta tatttagcaa gcaatgctac atattacttt catgaaattt tataccacat   38460
atttatgcta caatttaatg ctacatattt tttacatgaa aaagagttct acgttgaata   38520
aagtgaaagg gaaaaataat tgcataaata ttgaaaaatg tctcttttcc agctatgtgc   38580
caatcttgat gcatttacta ttaaaactgt taaagaaaac cttgatcaac tgaaaaacca   38640
aatacaggag ccatgcaaga agtttgccat tgcagatgca accagagaac tatgggctta   38700
```

-continued

```
atgttttata tctattgatt gacaatacta cattcagtag aaagatggca aaggctattt   38760
tatactgacc atctgaaaaa tattatttaa aaattttagc aaacaagttt caggtttttt   38820
tttaattgat gttaggcagt aaagcactac agtgaattct cgcctctaga cctcttttag   38880
ttttctaatt tacatgagga atagcttatt cattgtttgt acatatgagt taaaaggggac  38940 agtgaggggc catgggcaga gggatgtgta actaagctgg aggggttatg acagttcgtt   39000
ttagcctttt taattttctt cgtgaattcc aggattgatt ttctgacatt ccacagagcc   39060
attttgttgc tatcaaatta catttggcaa tgataatggg aatcctatct aatttgcata   39120
cttgcatatt tactttctta ggaaaacagt gcaatggtaa agaagtgaaa tatttacttt   39180
aatgatgctt ttctgatgaa ttttttcagga attataagaa taaactgaga gtcaatttgg  39240
acattatggc cagtaaatta tgtcaatact ttattttgta aaatttagaa agcattacaa   39300
attctggcca tatgtacttg ataataccat tgaaaataag aatgttggga tcaaatgata   39360
tgaaatatgc atagtagata aaacaatgct tgaaatatag taggcactaa accaatgtta   39420
gtaactagcc tccgtatatc tcttttttta aattctgaaa aagactgcta tctactccag   39480
ctgcactagc acagttgaat atattttatt cactttcctt tttttgttac ttatttggtt   39540
ttacttgata attttaaatg catgtttcta ctcataaaga tttttaaaac taaatttctc   39600
aggtacattt tttaaaagaa tttgccattt tttaaactta ctttaatttt tttatatacc   39660
ttgaagcata acatacatac agaaaagtac aaattcatat gtgtactgat tgctgaattt   39720
tcctaaactg aatacacata tgtaaacaaa atccaaatca agagacagca cactgccagt   39780
atcctaaaag ctcctggctc cccccttccag tcaccatgcc ccaggaatca ctactatctt   39840
gacttctaaa acaaaaaatg agttttcact gattctgaac tttatataaa tggaatcata   39900
tagcatgcac tcctttattt ctggctttat tcagactcta cttcaacttt ttattttggt   39960
cgaaataata ctgaaaccag ttttacaaag gaggaatgtt tcttaaatta cactgtaagc   40020
tttctaaata attgtggcat taatgcaata tgtgttttct aagttacctt taacatacaa   40080
ggtttatata attcattaac tttacttttg ttaacctttt aagttggaga ttccagcaga   40140
ggtaacaggg tgttggtgtg ggtgtggctt gatggcaggc ttaaaagaga agctgacaaa   40200
aataaatgta cagacaagtg atgggacact aacctgttac tttgtctaaa caaagatgaa   40260
tcagatttat tataacctag aaattattct aacaaagata atgttattcc tttaacaata   40320
agaatacata agaataagtg tgtactttat ttttaggatc catttaaaga gaaacttcta   40380
gaaataatga caaggattca aacttattgt caaatgagtc caatgtcaga ttttggaact   40440
caaccctatg aacaatgggc cattcaaatg gaaaaaaaag gtaatttagg tttggaccta   40500
acacttagtt tatcccatgt ttataccaag attttagatg actatatcac agattccca   40560 aaaaatggaa agcaaaagta gttccaaata gaatttctgt gttctctgta ggacaagcat   40620
aataaacatg ttctaattcc tttttctaagg agagagattc caatgctatc caattttctc   40680
tttgtctcca gagtcttgag ataaacttta atagctctgt ctccaaaggc aaactcaact   40740
aatatatttt catgccattt ctctgtgcat cagctacatg tttttgctga ggcagaactc   40800
aagcagcaag tctaggagtt ggaaaacttg ccctgtttca gagctcagga cacattttga   40860
gccttaactt gcccatttta aaaccaaggt gaagccagtt ttgcagttag taacatatat   40920
tcaagtccat ggcacaattt tagggggttt atatgcttat tatttcactt acataaatata  40980 tttttttcaca gctgcaaaag aaggaaatcg caaagaacgt gtttgtgcag aacatttgag   41040
gaagtacaat gaggccctac aaattaatga cacaattcga atgatagatg cgtatactca   41100
```

-continued

```
tcttgaaact ttctataatg aagagaaaga taagaagttt gcagtcatag aagatgatag   41160
tgatgagggt ggtgatgatg agtattgtga tggtgatgaa gatgaggatg atttaaagaa   41220
acctttgaaa ctggatgaaa cagatagatt tctcatgact ttatttttg gtaagattca    41280 aagtaacata tactggtgtc attcatttac cttttcaaca tgaacttact gcttctcata   41340
agctctccaa aaagagaaat atcttttgaa agaagaaatc ccactcagat tggaactatt   41400
tctaatgata tgaccagatt agctaccagt tgtatgatca cagtcagtca tttggtcatt   41460
cagttttatt gtcaagacaa ttgtaatgaa tttatttatt aaaccatcct aattattaga   41520
tatagcgcaa gattgtagat gagccacaat tcatgaaacc ttctagtgta attcgttgta   41580
tgttttacta atttatactt ccaaatagtt tttaaattaa ttaattttta atcaataaaa   41640
ctgtatattt ttggtgtaca aaatgtttga tatatctgta cattgtggag tggctaaatc   41700
aagcttgtta acatatcaac tctaattatt tcttaaagaa aacaataaaa tgttgaaaag   41760
gctggctgaa aacccagaat atgaaaatga aaagctgacc aaattaagaa ataccataat   41820
ggagcaatat actaggactg aggaatcagc acgaggaata atctttacaa aaacacgaca   41880
gagtgcatat gcgctttccc agtggattac tgaaaatgaa aaatttgctg aagtaggagt   41940
caaagcccac catctgattg gagctggaca cagcagtgag ttcaaaccca tgacacaggt   42000
ataaatatcc ttttggacga cttcttttct tttctttctc ttttcttctt ctcttctctt   42060
cttctcttct tcttttcttt cagacgaggc ctcgctctgt cactcaggct gaagagcagt   42120
ggcatgatca agattcactg caccccttgac ctcctaggct caagcaatcc tccagccca   42180 gcctcctgag cagctgggac tctaggtgtg caccaccaca cccaactaat tttttatct    42240 tttttgtaga aaaggtgtcc cactatgttg tcctggcttg tcttaaactc ctgggctcaa   42300
gccatccttc tgcctctgcc ttccaaagta ttgagattat aggcacgagc cactgcgctc   42360
agcctggact tctttctta tgctgttatt actcttctca aattgttttt agtctttttc    42420
taccaatcct ctcaccaccc atgaatacat ttacaggata aaacacctgt tcttgaaata   42480
aaatctaagg ctaatagcaa tcaaatctgt ggtttttgag aggttaagtg ttgtttagg    42540 agtcattttt cccacataat aattggaaga actttctaag tttcccttgc aaaaataagt   42600
gacatgtaag cttaacaaca aagttcagaa atgattgcca tgtagtatca agtggaaaat   42660
tcaaactccc acaaaaatgt gttcgttata actagaacta tgcaaaatat atttacatag   42720
aatgagacct ctagggaaac ttgaaaaaac taaagaattt gatatattag agatttggga   42780
ttctggtaag taggttttct gttccatttt aaggtgtttt gttttacttt gtttacatgt   42840
tgcttactgt gggcatagta aaaaaacact tgggtaagaa aaaaaggcac tagtagacat   42900
tacaagcatg catgaagcaa tgatgccttg ttagagtaaa atattcttct gagggctaaa   42960
atcacattga ccctgagtct ttctggacaa atggatactt cctttctatt atagttatca   43020
ctattcaagc caatggagca aattaattct gtttcagtgt ttgctggaaa aaaattcttg   43080
aaatggttca ctataactct ttatataccc tctacatgca ctcctgtgag cattgccaat   43140
aaaattaatg ccagagaaag tactgttttc cttgggtaac aagtttgctt ccttcttttt   43200
gatgagatgt agtttgcttt atatgttttt ctttttgcct tagcttccag aaagctagca   43260
ggaaaaactc aagttcagtc tcacagcctc tgtgttgatt cttatgagtt ctgttttaa    43320 atttctatta tattaacttt agcgttgtga cttttattgt aagagggcta agcttctctg   43380
taaaaagagg tagagtgcaa atgaaaagcc tatgttcaag ctactttctg ctccttattc   43440
```

-continued

```
atttcaaacc aaggggctgt gtgccaaaat acagaacata ttcccttcct tccccactcc   43500
ttgtatcctc accttgtaaa ctggggtgga caaactcctt agcaatggtg ttaggcatct   43560
atgtgatgtg acttgaagat ctgacactgt ctggaatttt tgttattaaa gttactcctt   43620
caaattaaga cacaggcatc ttctgctaaa atccaagaac atgtaagttt ttatcgggag   43680
atgtgagggc cggagggaga aattttcaga gaagactcaa gagaggcctt tctacagggt   43740
tctccgacag ttaggagtag gagtcaaata aggactcaca ctgcctctga gaagaaaggg   43800
aaggggatgg aagaacatac ttttggtctg gcagctttat ttttgtttaa tgtatggggg   43860
caatagacag tgtggatgtg caccaaatgc caactggacc aacagctttg atgagagtgg   43920
ttatgaaaat aaaaccacat tgtccatatc aagctaggtt tgtgctcact catttctccc   43980
atgtaaggat gagaggtcat attttaattt atttatattg actttcaaaa ttcagagttt   44040
tttcatttga aaatagtttt atttacagtt gcataacctc ttctttcatt tttatttata   44100
ttgtcccttt gaattgataa tatatttacc tcattcaaaa ttaatgaggc acaaggcata   44160
ccactgacct ctagtcttcc agctcccctc cctagatgca gctgatgttt tcagtttctc   44220
ttgtgtcctt ttgggaatat tccatagctt ctaactcaaa tgattcttaa agtgaccaaa   44280
tgcatataca gtgtgcattt tctctgtgac tgaaaacaat atatcaaagc atctctgcat   44340
cttatcctct aaatagcaaa gattctgaag ttaatgtagt gggggaaaaa agcccatttt   44400
agcttctgat tgtcatatcc tcttctcaac cgacagctcc tcctttcttc ctctggagtc   44460
acccatcaat ttatttcctt ggcataaaat gtggtcttcc cacctccaga ctggatgatg   44520
gaaatatttt tgttattgtg tggtaatccc agattggaaa tcaaatgttg tctcaccatt   44580
atgtctttgt tcaatgccaa aaacagatgg caacaaatcc atgtatgatc taatcctttg   44640
atttacactg accagttgca atttattatt tcttcctcta attagaagat tttaatgtgt   44700
ttagcatcac aaaatttaat ttattaaaat gtttctacag aatgaacaaa aagaagtcat   44760
tagtaaattt cgcactggaa aaataaatct gcttatcgct accacagtgg cagaagaagg   44820
tctggatatt aaagaatgta acattgttat ccgttatggt ctcgtcacca atgaaatagc   44880
catggtccag gtacattcaa atacctctac ttactatgtt aatttttatt tgttgtgttc   44940
ctattttaat tgctttcttt tagttaaaca gcaaaaacat cttttttagtt tttaaaacaa   45000 agcctttttc ctgttaaaag agcattttta aaatgctgtg cactgttgcc tttcatattg   45060
ctgtcaattc atataataac cagatacctg ttgtatgttt aaacaacaac tcctctttag   45120
ctatttctgt accctaaggc tttccaggac catgacacta gccccatttg taagagtcaa   45180
aagcagcctc ctctttccta ggatgtctgt gagcccccag ctggaccagg aatctaaagt   45240
acactgtccc acaaatgtct gatgaagtaa catgcccaaa cctgagggag ccctgctgtt   45300
tctgcatttt cttcccttat cctttccaat tttctgtgtg tttagaagtt ttcatgataa   45360
aatgttggtt ggggggcagac ttataaatgt aaaaataaat aaaagagtga aatgttctgt   45420
tttcattcag atttcacttt atctcttacc cacctatgtt aatggcatta ttgtaacctg   45480
ttgagtaggc ataggtgtta tgctgattaa tagatacact attcttccta taaaattaac   45540
taaagggatt tttaaataac ttaaattgca tccttgaata aaaggcaagt catagaagac   45600
taagataacc agactgccat caaattagca aataatttta tttcaggagt ctatttgtaa   45660
gtcagtgata agcttagtaa tcaaacttag aatacatttt tccttgagga tactttttata   45720 gttgataggc tcctgggcca ggccacagaa gtttctatta atcaaaatat acctgaatat   45780
cactttcata aagaggcttg tagaaagtta tcaccatgtt aaatatgttc ccatgggaaa   45840
```

-continued

```
atgtgctaag aatgtaatgt aggatgccag aaactgacct gccttctcac cagccctagt 45900
gtcaaggtca gagatgaccc ttctctccat tcattcctcc cagcttccta ccaagaaaga 45960
cgactcctca gtccaagtca ttgatcgtgg ttctcatagt ttgagagaga agttctgaga 46020
gcaaaaagcc tggacaggat gatattatgt cattgaggcc taaccatcat cactctagaa 46080
cactttttct gtattaaagc atattataag tttcaaagag ctgacttaca agtaatggat 46140
taataactaa ctttactaac tttacccatt tgaagactgg catgctgaac aacccaatat 46200
catttcattc tgagcaagaa tatcattccc agaaaaaacc aggaggattt gtatcacaac 46260
gtaccctttc atttacttga tttatttgtg ttttcaggcc cgtggtcgag ccagagctga 46320
tgagagcacc tacgtcctgg ttgctcacag tggttcagga gttatcgaac atgagacagt 46380
taatgatttc cgagagaaga tgatgtataa agctatacat tgtgttcaaa atatgaaacc 46440
agaggagtat gctcataagg tattgttggt cacctctgaa tttgattttc atttaaaaat 46500
ggcggcatgt ggttgccatt gatatctctg tgactcattc tccagacaaa aattgtgctg 46560
aattataagt ttctgtttag tgaactgtgc ttaatccaga ttcacatgca gagaatcaag 46620
atccatggtg ggcaggaaat tatcagggag ccattcctca ttccagtaaa accaaccata 46680
aatttggata atataaattt agcctgcctt gttccagaaa gactgctgca actcactgat 46740
tcaatccaac atggtaattt tggtttgatc caatttgttt gtaaaggcac agttttttaa 46800
tttcagaaat gtagatgaaa cgcctactgt gtgccaggta accttatagg aacagccaac 46860
agaggaaaca aaacacataa gactcctgct gcacgaagtt tatatttcta gtgtgtgcct 46920
ggtgaagttt ggaggacaga aacagtaaac aaacattaaa agacaagaaa tataatatat 46980
caagataagt gaagagaatt agaataggat gatatgaaac aactgactag atggatactt 47040
tcttgttttt agtagttttt gaaattcttt ttttttcttat tatacttttaa gttctagcgt 47100 acatgtgcac aacgtgcagg tctgttacat atgtatacat gtgccatgtt ggtgtgctgt 47160
acccatttac ttgtcatta cattaggtat ttctcttaat gctatccctc tcccctcccc 47220
ccaccccacg acaggccctg gtgtgtaatg ttcccagccc tgtgtccaag tgttctcatt 47280
gttcaatttc cacctatgag tgagaacatg cggggtttgg ttttctgtcc ttgtgatagt 47340
ttgctcagaa tgatggtttt cagtttcatc catgtcccta caaaggacat gaactcatcc 47400
ttttttatgg ctgcatagac tagatggata cttttcaactg ggtggttgag gaaggtctct 47460
tagaaggagt gacagggaag ctgcatctga atgataagaa aatacagaat atgtcatcta 47520
gctacatctc aatttactaa cacacagtta tttgagttgt gcaaaggaat gcagtgaaga 47580
aagaatgtat ttctatagta tttcaggaaa tcccccatac cactgaatta aaaactgtaa 47640
ctactataat agcaaacaat ccatttagaa gaaaattcac accccttgcat atgggtgtga 47700 atgttagttt cttaacattg gaattggctc taccttaaat agagtttcac taaagggatg 47760
ctttcaaatt ggtgtgcatt gctattacca actccaaggt ttcctgacca ggtttctgca 47820
caaaacttta ttttaaaacc cctttaaata caaggcaaag caaatatttt agagtatcaa 47880
atcaaacttt tgtcaccaaa ttatgccact ggaaagttac tgcctcccag ttaatgtcct 47940
aagagaatta atcaagtaga tgtttacaaa gactgatgtt ttaagagtag ttttttgggg 48000
gtcaacacta ggacaatctc tggagtttaa gggtcaaatt cttccagaca ttctttagaa 48060
taagactctg tcccttttggg tgccccagaa tggactatat ttttaggtct cctttggcca 48120
agaaacctgc cctcctaaaa ctacttcagg tagatgaact tagagtagga gtggcaatgg 48180
```

-continued

```
ggaaggaggg ctacatgcca ccagtaatct gttcaaagcc tgtagaaaac attgctactg   48240
ggaagatgtt tactttcttc taatttgagc atctttctca acacaatctt cagacaacca   48300
ctaatgaatg atgagaattg acagataaga tgaaatcttt cttccatgtc ataaacacag   48360
tttaaacata acagagcttc ttaaaattaa atcagacttc taggagcaag ttgatcatca   48420
taaatgtttt tctctagcat tgattcaatt tttttgctac attattacac tttatttgga   48480
cttaggctga ttgtagctgt gcctcctgta tatttattat gagttctttt ttttgtttgt   48540
ttacccctct agttacttca aattccttta ctattttaga gttagtcttt tagcttctga   48600
tgtcctgatt acaaatccat acacttacct tggctttatt ttttttctga ctcattcata   48660
cacatttctt aattcccaca tgtatgtgat cctataatta ccttatcagc tcattgaact   48720
gtaaatgtct tataaaagta acctattaaa acttttaggg aaaaatattt cagtgtatta   48780
ttttgctata atttacatag gaaattaatc ttggtacttg tctgattaat ctattatata   48840
gcctccaggc ttgcttgcaa ggtttttattc tcttttctat gctatatatg gctgccttga   48900
agggagatct aaaatgtaga gttagaagcc aaagagatgg gctttgttca actgcactga   48960
tgacttactt ttactgaaaa tttctccctc ggtcttaaag aaaacaatta attcttccat   49020
aatttaatat aaatatgtca tctatgagag gtcagtttgg cggtaaatta ttcaagaacc   49080
agatttttct accgtgaagt tgtgttggta taaacactgt tcagtcccta tgtcaacttt   49140
catatgttac ataaactaga ttatttccat tataaaataa gtgctgctgc tagtcacaga   49200
gcatagaata aagaggttga tgggcatatt ctctcacaga aggaatctag gcagtattgg   49260
ctccatgaag ttatgaggaa tccaggcctt ttctctcctt tttatgctgt tatagcattg   49320
ggctttcatt ctcatggtcg aagatggctt ttagaatttc agctgccaca tcctcattct   49380
aggcaggaag taagaggaga atggaaaggg cgaaaggtac acatgccagc tatctaattt   49440
ttaagaagat tttctgaaaa ttccactcaa cagctttta catgtcattg actgctggtt   49500
tggaaatgta gtcatttagc tagcatattt ccacccagaa taaaattatg gttctgttag   49560
gaaaaatgga cactgaatga aaaactagtg gtttctgcta caaatgtgta aagagtagac   49620
tgattaagat ggtgaagggt ctgaaaatta taaagcatga aaaaagatta aaggcatttg   49680
ggtgcttagc atagattaga gaagacttgg taatgtaata acagtgttta gtaaagagat   49740
tccatgtgga aggaagttta gacctatttt atggaacaga attaaaacaa atgggtaggc   49800
tggcgcagtg gctcacacct gcaatcccag cactttgaga ggctgaggca ggtggatcac   49860
tgagatcaag aatttgagat cagcctgggc aacatggcaa aactccatct ctactaaaaa   49920
tatgaaaatt agctgagcat ggtggcaggt gcctggaatc ccagctactt gggagtctaa   49980
ggcagaagaa tcccttgaac ccaggagatg gaggttgcag tgacccgaga tagtaccaac   50040
acactccagc ctgggcagca gagcaagact ccatctcaat aaataaataa ataaataaat   50100
aacaaatggg taggctagac agagaattt tgttgaatat tgctaaggac tttctcacaa   50160
tagaactttt ctgaaatgga atgggctact ttttgaatac ctgaagactg cacattttca   50220
tggttacagg agatgattat ataccaaatt ctttgggggg tcattacctc attatttta   50280 tttcctagac cataagctaa gggtatattt tcacaactaa gacctccaaa tttcaggaga   50340
cttacttcta tgaaactgaa aaaagaaaac aaacctgaaa ccactaacta ttcctttctc   50400
tgtccagatt ttggaattac agatgcaaag tataatggaa agaaaatga aaaccaagag   50460 aaatattgcc aagcattaca agaataaccc atcactaata actttccttt gcaaaaactg   50520
cagtgtgcta gcctgttctg gggaagatat ccatgtaatt gagaaaatgc atcacgtcaa   50580
```

-continued

```
tatgacccca gaattcaagt gagtccagaa agacccattt ttacattttt ccacaagggg    50640
tgaagcaggt tgcattgtaa atgttctttc aaaatagtgc aaatgagatt catttatttt    50700
acaacttcct ctcctttagc ctctcaatta tattcctatt ttaaatgtct atgtttaaa     50760 taaactgcac tggggcagga aaagagaagt gtaagaacca aagccatttt gatccaaggc    50820
acgtattttt gtatgctcat catttgttct caaattttttg aacaactaaa gtcaagttaa    50880
tataaccaac agacttgaaa gaagttatga aaggcaacat gccccttgag aggtatgtgt    50940
agaagagaag cattgcctta gttgcaataa caagcctggg aagcaggagg aaggaagga     51000 atgccgtgta gaataccgca ggcatgcgga tgagctccag gtccaataac ccatgaacta    51060
cacactggta ttttgtcagt tctccatgat gattctttcc ctttgatact tatagggaac    51120
tttacattgt aagagaaaac aaagcactgc aaaagaagtg tgccgactat caaataaatg    51180
gtgaaatcat ctgcaaatgt ggccaggtga gtaaattgct gtgggccaga ttttacttta    51240
gccaacagga atgtttaatt gcatgtacat ttaattttcc tcttgctctc tcttttgttt    51300
tccaggcttg gggaacaatg atggtgcaca aaggcttaga tttgccttgt ctcaaaataa    51360
ggaattttgt agtggtttc aaaaataatt caacaaagaa acaatacaaa aagtgggtag    51420
aattacctat cacatttccc aatcttgact attcagaatg ctgtttattt agtgatgagg    51480
attagcactt gattgaagat tcttttaaaa tactatcagt taaacattta atatgattat    51540
gattaatgta ttcattatgc tacagaactg acataagaat caataaaatg attgtttttac    51600 tctgcattga a                                                        51611
```

<210> SEQ ID NO 3
<211> LENGTH: 3581
<212> TYPE: RNA
<213> ORGANISM: homo sapien

<400> SEQUENCE: 3

```
caaacucugu aagaacugcc ugacagaaag cuggacucaa agcuccuacc cgagugugca      60
gcaggaucgc cccgguccgg daccccaggc gcacaccgca gaguccaaag ugccgcgccu     120
gccggccgca ccugccugcc gcggccccgc gcgccgcccc gcugcccacc ugcccgccug     180
cccaccugcc caggugcgag ugcagccccg cgcgccggcc ugagagcccu guggacaacc     240
ucgucauugu caggcacaga gcgguagacc cugcuucucu aagugggcag cggacagcgg     300
cacgcacauu ucaccugucc cgcagacaac agcaccaucu gcuugggaga acccucuccc     360
uucucugaga aagaaagaug ucgaauggu auuccacaga cgagaauuuc cgcuaucuca     420
ucucgugcuu cagggccagg gugaaaaugu acauccaggu ggagccugug cuggacuacc     480
ugaccuuucu gccugcagag gugaaggagc agauucagag dacagucgcc accuccggga     540
acaugcaggc aguugaacug cugcugagca ccuuggagaa gggagucugg caccuugguu     600
ggacucggga uucguggag gccuccggga gaaccggcag cccucuggcc gcccgcuaca     660
ugaacccuga gcucacggac uugcccucuc caucguuuga gaacgcucau gaugaauauc     720
uccaacugcu gaaccuccuu cagcccacuc ugguggacaa gcuucuaguu agagacgucu     780
uggauaagug cauggaggag gaacuguuga caauugaaga cagaaaccgg auugcugcug     840
cagaaaacaa uggaaaugaa ucaggguaa gagagcuacu aaaaaggauu gugcagaaag     900
aaaacugguu cucugcauuu cugaauguuc uucgucaaac aggaaacaau gaacuugcc      960 aagaguuaac aggcucugau ugcucagaaa gcaaugcaga gauugagaau uuaucacaag    1020
```

-continued

```
uugaugguucc ucaaguggaa gagcaacuuc uuucaaccac aguucagcca aaucuggaga    1080
aggaggucug gggcauggag aauaacucau cagaaucauc uuuugcagau ucuucuguag    1140
uuucagaauc agacacaagu uuggcagaag gaagugucag cugcuuagau gaaagucuug    1200
gacauaacag caacaugggc agugauucag gcaccauggg aagugauuca gaugaagaga    1260
auguggcagc aagagcaucc ccggagccag aacuccagcu caggccuuac caaauggaag    1320
uugcccagcc agccuuggaa gggaagaaua ucaucaucug ccucccuaca gggaguggaa    1380
aaaccagagu ggcuguuuac auugccaagg aucacuuaga caagaagaaa aaagcaucug    1440
agccuggaaa aguuauaguu cuugucaaua agguacugcu aguugaacag cucuuccgca    1500
aggaguucca accauuuuug aagaaauggu aucguguuau uggauuaagu ggugauaccc    1560
aacugaaaau aucauuucca gaaguuguca agccugugu uauuauuauc aguacagcuc     1620
aaauccuuga aaacucccuc uuaaacuugg aaaauggaga agaugcuggu guucaauugu    1680
cagacuuuuc ccucauuauc auugaugaau gucaucacac caacaaagaa gcaguguaua    1740
auaacaucau gaggcauuau uugaugcaga aguugaaaaa caauagacuc aagaaagaaa    1800
acaaaccagu gauuccccuu ccucagauac ugggacuaac agcuucaccu ggguguugag    1860
gggccacgaa gcaagccaaa gcugaagaac acauuuaaaa acuaugugcc aaucuugaug    1920
cauuuacuau uaaaacuguu aaagaaaacc uugaucaacu gaaaaaccaa auacaggagc    1980
caugcaagaa guuugccauu gcagaugcaa ccagagaaga uccauuuaaa gagaaacuuc    2040
uagaaauaau gacaaggauu caaacuuauu gucaaaugag uccaauguca gauuuuggaa    2100
cucaacccua ugaacaaugg gccauucaaa uggaaaaaaa agcugcaaaa gaaggaaauc    2160
gcaaagaacg uguuugugca gaacauuuga ggaaguacaa ugaggcccua caaauuaaug    2220
acacaauucg aaugauagau gcguauacuc aucuugaaac uuucuauaau gaagagaaag    2280
auaagaaguu ugcagucaua gaagaugaua gugaugaggg uggugaugau gaguauugug    2340
auggugauga agaugaggau gauuuaaaga aaccuuugaa acuggaugaa acagauagau    2400
uucucaugac uuuauuuuuu gaaaacaaua aaauguugaa aaggcuggcu gaaaacccag    2460
aauaugaaaa ugaaaagcug accaaauuaa gaaauaccau aauggagcaa uauacuagga    2520
cugaggaauc agcacgagga auaaucuuua caaaaacacg acagagugca uaugcgcuuu    2580
cccaguggau uacugaaaau gaaaaauuug cugaaguagg agucaaagcc caccaucuga    2640
uuggagcugg acacagcagu gaguucaaac ccaugacaca gaaugaacaa aaagaaguca    2700
uuaguaaauu ucgcacugga aaaauaaauc ugcuuaucgc uaccacagug gcagaagaag    2760
gucuggauau uaaagaaugu aacauuguua uccguuaugg ucucgucacc aaugaaauag    2820
ccauggucca ggcccguggu cgagccgag cugaugagag caccuacguc cugguugcuc      2880
acagugguuc aggaguuauc gaacaugaga caguuaauga uuuccgagag aagaugaugu    2940
auaaagcuau acauuguguu caaaauauga aaccagagga guaugcucau aagauuuugg    3000
aauuacagau gcaaaguaua auggaaaaga aaaugaaaac caagagaaau auugccaagc    3060
auuacaagaa uaacccauca cuaauaacuu uccuuugcaa aaacugcagu gugcuagccu    3120 guucgggga agauauccau guaauugaga aaaugcauca cgucaauaug accccagaau      3180
ucaaggaacu uuacauugua agagaaaaca aagcacugca aaagaagugu gccgacuauc    3240
aaauaaaugg ugaaaucauc ugcaaaugug gccaggcuug gggaacaaug auggugcaca    3300
aaggcuuaga uuugccuugu cucaaaauaa ggaauuuugu aguggguuuc aaaaauaauu    3360
caacaaagaa acaauacaaa aaguggguag aauuaccuau cacauuuccc aaucuugacu    3420
```

-continued

```
auucagaaug cuguuuauuu agugaugagg auuagcacuu gauugaagau ucuuuuaaaa    3480
uacuaucagu uaaacauuua auaugauuau gauuaaugua uucauuaugc uacagaacug    3540
acauaagaau caauaaaaug auuguuuuac ucugcauuga a                        3581
```

<210> SEQ ID NO 4
<211> LENGTH: 3234
<212> TYPE: RNA
<213> ORGANISM: homo sapien

<400> SEQUENCE: 4

```
gcgcgccggc cugagagccc uguggacaac cucgucauug ucaggcacag agcgguagac      60
ccugcuucuc uaagugggca gcggacagcg gcacgcacau uucaccuguc ccgcagacaa     120
cagcaccauc ugcuugggag aacccucucc cuucucugag aaagaaagau gucgaauggg     180
uauuccacag acgagaauuu ccgcuaucuc aucucgugcu ucagggccag ggugaaaaug     240
uacauccagg uggagccugu gcuggacuac cugaccuuuc ugccugcaga ggugaaggag     300
cagauucaga ggacagucgc caccuccggg aacaugcagg caguugaacu gcugcugagc     360
accuuggaga agggagucug gcaccuuggu uggacucggg aauucgugga ggcccuccgg     420
agaaccggca gcccucuggc cgcccgcuac augaacccug agcucacgga cuugcccucu     480
ccaucguuug agaacgcuca ugaugaauau cuccaacugc ugaacccccu ucagcccacu     540
cugguggaca agcuucuagu uagagacguc uuggauaagu gcauggagga ggaacuguug     600
acaauugaag acagaaaccg gauugcugcu gcagaaaaca auggaaauga aucaggugua     660
agagagcuac uaaaaaggau ugugcagaaa gaaaacuggu ucucugcauu ucugaauguu     720
cuucgucaaa caggaaacaa ugaacuuguc caagaguuaa caggcucuga uugcucagaa     780
agcaaugcag agauugagaa uuuaucacaa guugaugguc ucaagugga gagcaacuu      840 cuuucaacca caguucagcc aaaucuggag aaggaggucu ggggcaugga gaauaacuca     900
ucagaaucau cuuuugcaga uucuucugua guuucagaau cagacacaag uuuggcagaa     960
ggaaguguca gcugcuuaga ugaaagucuu ggacauaaca gcaacauggg caguqauuca    1020 ggcaccaugg gaagugauuc agaugaagag aauguggcag caagagcauc cccggagcca    1080
gaacuccagc ucaggccuua ccaaauggaa guugcccagc cagccuugga agggaagaau    1140
aucaucaucu gccucccuac agggagugga aaaaccagag uggcuguuua cauugccaag    1200
gaucacuuag acaagaagaa aaaagcaucu gagccuggaa aaguuauagu ucuugucaau    1260
aagguacugc uaguugaaca gcucuuccgc aaggaguucc aaccauuuuu gaagaaaugg    1320
uaucguguua uuggauuaag uggugauacc caacugaaaa uaucauuucc agaaguuguc    1380
aaguccugug auauuauuau caguacagcu caaauccuug aaaacucccu cuuaaacuug    1440
gaaaauggag aagaugcugg uguucaauug ucagacuuuu cccucauuau cauugaugaa    1500
ugucaucaca ccaacaaaga agcaguguau aauaacauca ugaggcauua uuugaugcag    1560
aaguugaaaa acaauagacu caagaaagaa aacaaaccag ugauuccccu uccucagaua    1620
cugggacuaa cagcuucacc ugguguugga ggggccacga agcaagccaa agcugaagaa    1680
cacauuuuaa aagauccauu uaaagagaaa cuucuagaaa uaaugacaag gauucaaacu    1740
uauugucaaa ugaguccaau gucagauuuu ggaacucaac ccuaugaaca augggccauu    1800
caaauggaaa aaaagcugc aaaagaagga aaucgcaaag aacguguuug ucagaacau     1860 uugaggaagu acaaugaggc ccuacaaauu aaugacacaa uucgaaugau agaugcguau    1920
```

```
acucaucuug aaacuuucua uaaugaagag aaagauaaga aguuugcagu cauagaagau    1980
gauagugaug aggguggguga ugaugaguau ugugauggug augaagauga ggaugauuua    2040
aagaaaccuu ugaaacugga ugaaacagau agauuucuca ugacuuuauu uuuugaaaac    2100
aauaaaaugu ugaaaaggcu ggcugaaaac ccagaauaug aaaaugaaaa gcugaccaaa    2160
uuaagaaaua ccauaaugga gcaauauacu aggacugagg aaucagcacg aggaauaauc    2220
uuuacaaaaa cacgacagag ugcauaugcg cuuucccagu ggauuacuga aaaugaaaaa    2280
uuugcugaag uaggagucaa agcccaccau cugauuggag cuggacacag cagugaguuc    2340
aaacccauga cacagaauga acaaaaagaa gucauuagua aauuucgcac uggaaaaaua    2400
aaucugcuua ucgcuaccac aguggcagaa gaaggucugg auauuaaaga auguaacauu    2460
guuauccguu auggcucugu caccaaugaa auagccaugg uccaggcccg uggucgagcc    2520
agagcugaug agagcaccua cguccugguu gcucacagug guucaggagu uaucgaacau    2580
gagacaguua augauuuccg agagaagaug auguauaaag cuauacauug uguucaaaau    2640
augaaaccag aggaguaugc ucauaagauu uuggaauuac agaugcaaag uauaauggaa    2700
aagaaaauga aaaccaagag aaauauugcc aagcauuaca agaauaaccc aucacuaaua    2760
acuuuccuuu gcaaaaacug cagugugcua gccuguucug gggaagauau ccauguaauu    2820
gagaaaaugc aucacgucaa uaugacccca gaauucaagg aacuuuacau uguaagagaa    2880
aacaaagcac ugcaaaagaa gugugccgac uaucaaauaa auggugaaau caucugcaaa    2940
uguggccagg cuuggggaac aaugauggug cacaaaggcu uagauuugcc uugucucaaa    3000
auaaggaauu uuguaguggu uuucaaaaau aauucaacaa agaaacaaua caaaaagugg    3060
guagaauuac cuaucacauu ucccaaucuu gacuauucag aaugcuguuu auuuagugau    3120
gaggauuagc acuugauuga agauucuuuu aaaauacuau caguuaaaca uuuaauauga    3180
uuaugauuaa uguauucauu augcuacaga acugacauaa gaaucaauaa aaug          3234
```

<210> SEQ ID NO 5
<211> LENGTH: 1776
<212> TYPE: RNA
<213> ORGANISM: homo sapien

<400> SEQUENCE: 5

```
cacaaaccag ugauuccccu uccucagaua cugggacuaa cagcuucacc uggugguugga    60 ggggccacga agcaagccaa agcugaagaa cacauuuuaa aacuaugugc caaucuugau    120
gcauuuacua uuaaaacugu uaaagaaaac cuugaucaac ugaaaaacca aauacaggag    180
ccaugcaaga aguuugccau ugcagaugca accagagaag auccauuuaa agagaaacuu    240
cuagaaauaa ugacaaggau ucaaacuuau ugucaaauga guccaauguc agauuuugga    300
acucaacccu augaacaaug ggccauucaa auggaaaaaa aagcugcaaa agaaggaaau    360
cgcaaagaac guguuugugc agaacauuug aggaaguaca augaggcccu acaaauuaau    420
gacacaauuc gaaugauaga ugcguauacu caucuugaaa cuuucuauaa ugaagagaaa    480
gauaagaagu uugcagucau agaagaugau agugaugagg guggugauga ugaguauugu    540
gauggugaug aagaugagga ugauuuaaag aaaccuuuga aacuggauga aacagauaga    600
uuucucauga cuuuauuuuu ugaaaacaau aaaauguuga aaggcuggc ugaaaacccca    660 gaauaugaaa ugaaaagcu gaccaaauua agaaauacca uaauggagca auauacuagg    720
acugaggaau cagcacgagg aauaaucuuu acaaaaacac gacagagugc auaugcgcuu    780
ucccagugga uuacugaaaa ugaaaaauuu gcugaaguag gagucaaagc ccaccaucug    840
```

```
auuggagcug gacacagcag ugaguucaaa cccaugacac agaaugaaca aaaagaaguc      900
auuaguaaau uucgcacugg aagaauaaau cugcuuaucg cuaccacagu ggcagaagaa      960
ggucuggaua uuaaagaaug uaacauuguu auccguuaug gucucgucac caaugaaaua     1020
gccauggucc aggcccgugg ucgagccaga gcugaugaga gcaccuacgu ccugguugcu     1080
cacagugguu caggaguuau cgaacgugag acaguuaaug auuuccgaga gaagaugaug     1140
uauaaagcua uacauugugu ucaaaauaug aaaccagagg aguaugcuca uaagauuuug     1200
gaauuacaga ugcaaaguau aauggaaaag aaaaugaaaa ccaagagaaa uauugccaag     1260
cauuacaaga auaacccauc acuaauaacu uuccuuugca aaaacugcag ugugcuagcc     1320
uguucugggg aagauaucca uguaauugag aaaaugcauc acgucaauau gaccccagaa     1380
uucaaggaac uuuacauugu aagagaaaac aaaacacugc aaaagaagug ugccgacuau     1440
caaauaaaug gugaaaucau cugcaaaugu ggccaggcuu ggggaacaau gauggugcac     1500
aaaggcuuag auuugccuug ucucaaaaua aggaauuuug uagugguuuu caaaaauaau     1560
ucaacaaaga aacaauacaa aaagugggua gaauuaccua ucacauuucc caaucuugac     1620
uauucagaau gcuguuuauu uagugaugag gauuagcacu ugauugaaga uucuuuuaaa     1680
auacuaucag uuaaacauuu aauaugauua ugauuaaugu auucauuaug cuacagaacu     1740
gacauaagaa ucaauaaaau gauuguuuua cucugc                              1776
```

```
<210> SEQ ID NO 6
<211> LENGTH: 3380
<212> TYPE: RNA
<213> ORGANISM: homo sapien

<400> SEQUENCE: 6
```

```
gcgcgccggc cugagagccc uguggacaac cucgucauug ucaggcacag agcgguagac       60
ccugcuucuc uaagugggca gcggacagcg gcacgcacau uucaccuguc ccgcagacaa      120
cagcaccauc ugcuugggag aacccucucc cuucucugag aaagaaagau gucgaauggg      180
uauuccacag acgagaauuu ccgcuaucuc aucucgugcu ucagggccag ggugaaaaug      240
uacauccagu uggagccugu gcuggacuac cugacccuuc ugccugcaga ggugaaggag      300
cagauucaga ggacagucgc caccuccggg aacaugcagg caguugaacu gcugcugagc      360
accuuggaga agggagucug gcaccuuggu uggacucggg aauucgugga ggcccuccgg      420
agaaccggca gcccucuggc cgcccgcuac augaacccug agcucacgga cuugcccucu      480
ccaucguuug agaacgcuca ugaugaauau cuccaacugc ugaaccuccu ucagcccacu      540
cugguggaca agcuucuagu uagagacguc uuggauaagu gcauggagga ggaacuguug      600
acaauugaag acagaaaccg gauucugcu gcagaaaaca auggaaauga aucaggugua      660
agagagcuac uaaaaaggau ugugcagaaa gaaaacuggu ucucugcauu ucugaauguu      720
cuucgucaaa caggaaacaa ugaacuuguc caagaguuaa caggcucuga uugcucagaa      780 agcaaaugcag agauugagaa uuuaucacaa guugaugguc cucaagugga gagcaacuu      840 cuuucaacca caguucagcc aaaacuggag aaggagguc ggggcaugga gaauaacuca      900
ucagaaucau cuuuugcaga uucuucgua guuucagaau cagacacaag uuuggcagaa      960
ggaaguguca gcugcuuaga ugaaagucuu ggacauaaca gcaacauggg cagugauuca     1020
ggcaccaugg gaagugauuc agaugaagag aauuggcag caagagcauc cccgagcca      1080 gaacuccagc ucaggccuua ccaaauggaa guugcccagc cagccuugga agggaagaau     1140
```

```
aucaucaucu gccucccuac agggagugga aaaaccagag uggcuguuua cauugccaag    1200
gaucacuuag acaagaagaa aaaagcaucu gagccuggaa aaguuauagu ucuugucaau    1260
aagguacugc uaguugaaca gcucuuccgc aaggaguucc aaccauuuuu gaagaaaugg    1320
uaucguguua uuggauuaag uggugauacc caacugaaaa uaucauuucc agaaguuguc    1380
aaguccugug auauuauuau caguacagcu caaauccuug aaaacucccu cuuaaacuug    1440
gaaaauggag aagaugcugg uguucaauug ucagacuuuu ccccauuau cauugaugaa     1500 ugucaucaca ccaacaaaga agcaguguau aauaacauca ugaggcauua uuugaugcag    1560
aaguugaaaa acaauagacu caagaaagaa aacaaaccag ugauuccccu uccucagaua    1620
cugggacuaa cagcuucacc uggyguugga ggggccacga agcaagccaa agcugaagaa    1680
cacauuuuaa aacuaugugc caaucuugau gcauuuacua uuaaaacugu uaaagaaaac    1740
cuugaucaac ugaaaaacca aauacaggag ccaugcaaga aguuugccau ugcagaugca    1800
accagagaag auccauuuaa agagaaacuu cuagaaauaa ugacaaggau ucaaacuuau    1860
ugucaaauga guccaauguc agauuuugga acucaacccu augaacaaug ggccauucaa    1920
auggaaaaaa aagcugcaaa aaaaggaaau cgcaaagaac guguuugugc agaacauuug    1980
aggaaguaca augaggcccu acaaauuauu gacacaauuc gaaugauaga ugcguauacu    2040
caucuugaaa cuuucuauaa ugaagagaaa gauaagaagu uugcagucau agaagaugau    2100
agugaugagg guggugauga ugaguauugu gauggugaug aagaugagga ugauuuaaag    2160
aaaccuuuga aacuggauga aacagauaga uuucucauga cuuuauuuuu ugaaaacaau    2220
aaaauguuga aaaggcuggc ugaaaaccca gaauaugaaa augaaaagcu gaccaaauua    2280
agaaauacca uaauggagca auauacuagg acugaggaau cagcacgagg aauaaucuuu    2340
acaaaaacac gacagagugc auaugcgcuu ucccagugga uuacugaaaa ugaaaaauuu    2400
gcugaaguag gagucaaagc ccaccaucug auuggagcug gacacagcag ugaguucaaa    2460
cccaugacac agaaugaaca aaaagaaguc auuaguaaau uucgcacugg aaaaaucaau    2520
cugcuuaucg cuaccacagu ggcagaagaa ggucuggaua uuaaagaaug uaacauuguu    2580
auccguuaug gucucgucac caaugaaaua gccaugguuc aggcccgugg ucgagccaga    2640
gcugaugaga gcaccuacgu ccugguugcu cacagugguu caggaguuau cgaacaugag    2700
acaguuaaug auuuccgaga gaagaugaug uauaaagcua uacauugugu ucaaaauaug    2760
aaaccagagg aguaugcuca uaagauuuug gaauuacaga ugcaaaguau aauggaaaag    2820
aaaaugaaaa ccaagagaaa uauugccaag cauuacaaga auaacccauc acuaauaacu    2880
uuccuuugca aaaacugcag ugugcuagcc uguucugggg aagauaucca uguaauugag    2940
aaaaugcauc acgucaauau gaccccagaa uucaaggaac uuuacauugu aagagaaaac    3000
aaagcacugc aaaagaagug ugccgacuau caaauaaaug gugaaaucau cugcaaaugu    3060
ggccaggcuu ggggaacaau gauggugcac aaaggcuuag auuugccuug ucucaaaaua    3120
aggaauuuug uagugguuuu caaaaauaau ucaacaaaga aacaauacaa aaagugggua    3180
gaauuaccua ucacauuucc caaucuugac uauucagaau gcuguuuauu uagugaugag    3240
gauuagcacu ugauugaaga uucuuuuaaa auacuaucag uuaaacauuu aauaugauua    3300
ugauuaaugu auucauuaug cuacagaacu gacauaagaa ucaauaaaau gauuguuuua    3360
cucugaaaaa aaaaaaaaaa                                               3380
```

<210> SEQ ID NO 7
<211> LENGTH: 3373

```
<212> TYPE: RNA
<213> ORGANISM: homo sapien

<400> SEQUENCE: 7
gggcccugug dacaaccucg ucauugucag gcacagagcg guagacccug cuucucuaag        60
ugggcagcgg acagcggcac gcacauuuca ccugucccgc agacaacagc accaucugcu       120
ugggagaacc cucucccuuc ucugagaaag aaagaugucg aauggguauu ccacagacga       180
gaauuuccgc uaucucaucu cgugcuucag ggccaggg uug aaaauguaca uccaggugga      240
gccugugcug gacuaccuga ccuuucugcc ugcagaggug aaggagcaga uucagaggac       300
agucgccacc uccgggaaca ugcaggcagu ugaacugcug cugagcaccu uggagaaggg       360
agucuggcac cuugguugga cucgggaauu cguggaggcc cuccggagaa ccggcagccc       420
ucuggccgcc cgcuacauga acccugagcu cacggacuug cccucuccau cguuugagaa       480
cgcucaugau gaauaucucc aacugcugaa ccuccuucag cccacucugg uggacaagcu       540
ucuaguuaga dacgcucugg auaagugcau ggaggaggaa cuguugacaa uugaagacag       600
aaaccggauu gcugcugcag aaaacaaugg aaaugaauca gguguaagag agcuacuaaa       660
aaggauugug cagaaagaaa acugguucuc ugcauuucug aauguucuuc gucaaacagg       720
aaacaaugaa cuuguccaag aguuaacagg cucugauugc ucagaaagca augcagagau       780
ugagaauuua ucacaaguug augguccuca aguggaagag caacuucuuu caaccacagu       840
ucagccaaau cuggagaagg aggucugggg cauggagaau aacucaucag aaucaucuuu       900
ugcagauucu ucuguaguuu cagaaucaga cacaaguuug gcagaaggaa gugucagcug       960
cuuagaugaa agucuuggac auaacagcaa caugggcagu gauucaggca ccaugggaag      1020
ugauucagau gaagagaaug uggcagcaag agcaucccCg gagccagaac uccagcucag      1080
gccuuaccaa auggaaguug cccagccagc cuuggaaggg aagaauauca ucaucugccu      1140
cccuacaggg aguggaaaaa ccagaguggc uguuuacauu gccaaggauc acuuagacaa      1200
gaagaaaaaa gcaucugagc cuggaaaagu uauaguucuu gucaauaagg uacugcuagu      1260
ugaacagcuc uuccgcaagg aguuccaacc auuuuugaag aaaugguauc guguuauugg      1320
auuaaguggu gauacccaac ugaaaauauc auuuccagaa guugucaagu ccugugauau      1380
uauuaucagu acagcucaaa uccuugaaaa cucccucuua aacuuggaaa auggagaaga      1440 ugcuggugu u caauugucag acuuuuccuu cauuaucauu gaugaauguc aucacaccaa      1500
caaagaagca guguauaaua acaucaugag gcauuauuug augcagaagu ugaaaaacaa      1560
uagacucaag aaagaaaaca aaccagugau uccccuuccu cagauacugg gacuaacagc      1620
uucaccuggu guuggagggg ccacgaagca agccaaagcu gaagaacaca uuuuaaaacu      1680
augugccaau cuugaugcau uuacuauuaa aacuguuaaa gaaaaccuug ucaacugaa       1740 aaaccaauua caggagccau gcaagaaguu ugccauugca gaugcaacca gagaagaucc      1800
auuuaaagag aaacuucuag aaauaaugac aaggauucaa acuuauugc aaaugagucc       1860 aaugucagau uuuggaacuc aacccuauga acaaugggcc auucaaaugg aaaaaaaagc      1920
ugcaaaagaa ggaaaucgca agaaagugu u uugugcagaa cauuugagga aguacaauaa      1980
ggcccuacaa auuaaugaca caauucgaau gauagaugcg uauacucauc uugaaacuuu      2040
cuauaaugaa gagaaagaua agaaguuugc agucauagaa gaugauagug augagggugg      2100
ugaugaugag uauugugaug gugaugaaga ugaggaugau uuaaagaaac cuuugaaacu      2160
ggaugaaaca gauagauuuc ucaugacuuu auuuuuugaa aacaauaaaa uguugaaaag      2220
```

```
gcuggcugaa aacccagaau augaaaauga aaagcugacc aaauuaagaa auaccauaau      2280
ggagcaauau acuaggacug aggaaucagc acgaggaaua aucuuuacaa aaacacgaca      2340
gagugcauau gcgcuuuccc aguggauuac ugaaaaugaa aaauuugcug aaguaggagu      2400
caaagcccac caucugauug gagcuggaca cagcagugua uucaaacccca ugacacagaa      2460 ugaacaaaaa gaagucauua guaaauuucg cacuggaaaa auaaaucugc uuaucgcuac      2520
cacaguggca gaagaagguc uggauauuaa agaauguaac auuguuaucc guuaugguu      2580 cgucaccaau gaaauagcca ugguccaggc ccgggucga gccagagcug augagagcac      2640
cuacguccug guugcucaca gugguucagg aguuaucgaa cgugagacag uuaaugauu      2700 ccgagagaag augauguaua aagcuauaca uugugucaa aauaugaaac cagaggagua      2760
ugcucauaag auuuuggaau uacagaugca aaguauaaug gaaaagaaaa ugaaaaccaa      2820
gagaaauauu gccaagcauu acaagaauaa cccaucacua auaacuuucc uuugcaaaaa      2880
cugcagugug cuagccuguu cuggggaaga uauccaugua auugagaaaa ugcaucacgu      2940
caauaugacc ccagaauuca aggaacuuua cauuguaaga gaaaacaaag cacugcaaaa      3000
gaagugugcc gacuaucaaa uaaauggug aaucaucugc aaaugugcc aggcuugggg      3060 aacaaugaug gugcacaaag gcuuagauu gccuugcuc aaaauaagga auuuguagu      3120 gguuuucaaa aauaauucaa caaagaaaca auacaaaaag uggguagaau uaccuaucac      3180
auuucccaau cuugacuauu cagaaugcug uuuauuuagu gaugaggauu agcacuugau      3240
ugaagauucu uuuaaaauac uaucaguuaa acauuuaaua ugauuaugau uaauguauuc      3300
auuaugcuac agaacugaca uaagaaucaa uaaaaugauu guuuuacucu ccaaaaaaaa      3360
aaaaaaaaaa aaa                                                         3373
```

```
<210> SEQ ID NO 8
<211> LENGTH: 3244
<212> TYPE: RNA
<213> ORGANISM: homo sapien

<400> SEQUENCE: 8
uucaccuguc ccgcagacaa cagcaccauc ugcuugggag aacccucucc cuucucugag       60
aaagaaagau gucgaauggg uauuccacag acgagaauuu ccgcuaucuc aucucgugcu      120
ucagggccag ggugaaaaug uacauccagg uggagccugu gcuggacuac cugaccuuuc      180
ugccugcaga ggugaaggag cagauucaga ggacagucgc caccuccggg aacaugcagg      240
caguugaacu gcugcugagc accuuggaga agggagucug gcaccuuggu uggacucggg      300
aauucgugga ggcccuccgg agaaccggca gcccucuggc cgcccgcuac augaacccug      360
agcucacgga cuugcccucu ccaucguuug agaacgcuca ugaugaauau cuccaacugc      420
ugaaccuccu ucagcccacu cugguggaca agcuucuagu uagagacguc uuggauaagu      480
gcauggagga ggaacuguug acaauugaag acagaaaccg gauugcugcu gcagaaaaca      540
auggaaauga aucaggugua agagagcuac uaaaaaggau ugugcagaaa gaaaacuggu      600
ucucugcauu ucugaaugu cuucgucaaa caggaaacaa ugaacuuguc caagaguuaa      660
caggcucuga uugcucagaa agcaaugcag agauugagaa uuuaucacaa guugaugguc      720
cucaagugga agagcaacuu cuuucaacca caguucagcc aaaucuggag aaggagguu      780 ggggcaugga gaauaacuca ucagaaucau cuuuugcaga uucuucugua guuucagaau      840
cagacacaag uuuggcagaa ggaaguguca gcugcuuaga ugaaagucuu ggacauaaca      900
gcaacauggg caguggauca ggcaccaugg gaagugauuc agaugaagag aauguggcag      960
```

-continued

```
caagagcauc cccggagcca gaacuccagc ucaggccuua ccaaauggaa guugcccagc     1020
cagccuugga agggaagaau aucaucaucu gccucccuac agggagugga aaaaccagag     1080
uggcuguuua cauugccaag gaucacuuag acaagaagaa aaaagcaucu gagccuggaa     1140
aaguuauagu ucuugucaau aagguacugc uaguugaaca gcucuuccgc aaggaguucc     1200
aaccauuuuu gaagaaaugg uaucguguua uuggauuaag uggugauacc caacugaaaa     1260
uaucauuucc agaaguuguc aaguccugug auauuauuau caguacagcu caaauccuug     1320
aaaacucccu cuuaaacuug gaaaauggag aagaugcugg uguucaauug ucagacuuuu     1380
cccucauuau cauugaugaa ugucaucaca ccaacaaaga agcaguguau aauaacauca     1440
ugaggcauua uuugaugcag aaguugaaaa acaauagacu caagaaagaa aacaaaccag     1500
ugauuccccu uccucagaua cugggacuaa cagcuucacc ugguguugga ggggccacga     1560
agcaagccaa agcugaagaa cacauuuuaa aacuaugugc caaucuugau gcauuuacua     1620
uuaaaacugu uaaagaaaac cuugaucaac ugaaaaacca aauacaggag ccaugcaaga     1680
aguuugccau ugcagaugca accagagaag auccauuuaa agagaaacuu cuagaaauaa     1740
ugacaaggau ucaaacuuau ugucaaauga guccaauguc agauuuugga acucaacccu     1800
augaacaaug ggccauucaa auggaaaaaa aagcugcaaa agaaggaaau cgcaaagaac     1860
guguuugugc agaacauuug aggaaguaca augaggcccu acaaauuaau gacacaauuc     1920
gaaugauaga ugcguauacu caucuugaaa cuuucuauaa ugaagagaaa gauaagaagu     1980
uugcagucau agaagaugau agugaugagg guggugauga ugaguauugu gauggugaug     2040
aagaugagga ugauuuaaag aaaccuuuga aacuggauga aacagauaga uuucucauga     2100
cuuuauuuuu ugaaaacaau aaaaauguuga aaaggcuggc ugaaaaccca gaauaugaaa     2160
augaaaagcu gaccaaauua agaaauacca uaauggagca auauacuagg acugaggaau     2220
cagcacgagg aauaaucuuu acaaaaacac gacagagugc auaugcgcuu ucccagugga     2280
uuacugaaaa ugaaaaauuu gcugaaguag gagucaaagc ccaccaucug auuggagcug     2340
gacacagcag ugaguucaaa cccaugacac agaaugaaca aaaagaaguc auuaguaaau     2400
uucgcacugg aaaaauaaau cugcuuaucg cuaccacagu ggcagaagaa ggucuggaua     2460
uuaaagaaug uaacauuguu auccguuaug gucucgucac caaugaaaua gccauggucc     2520
aggcccgugg ucgagccaga gcugaugaga gcaccuacgu ccugguugcu cacagugguu     2580
caggaguuau cgaacgugag acaguuaaug auuuccgaga gaagaugaug uauaaagcua     2640
uacauugugu ucaaaauaug aaaccagagg aguaugcuca uaagauuuug gaauuacaga     2700
ugcaaaguau aauggaaaag aaaaugaaaa ccaagagaaa uauugccaag cauuacaaga     2760
auaacccauc acuaauaacu uuccuuugca aaaacugcag ugugcuagcc uguucuggggg     2820 aagauaucca uguaauugag aaaaugcauc acgucaauau gaccccagaa uucaaggaac     2880
uuuacauugu aagagaaaac aaaacacugc aaaagaagug ugccgacuau caaauaaaug     2940
gugaaaucau cugcaaaugu ggccaggcuu ggggaacaau gauggugcac aaaggcuuag     3000
auuugccuug ucucaaaaua aggaauuuug uagugguuuu caaaaauaau ucaacaaaga     3060
aacaauacaa aaagugggua gaauuaccua ucacauuucc caaucuugac uauucagaau     3120
gcuguuuauu uagugaugag gauuagcacu ugauugaaga uucuuuuaaa auacuaucag     3180
uuaaacauuu aauaugauua ugauuaaugu auucauuaug cuacagaacu gacauaagaa     3240
ucaa                                                                  3244
```

```
<210> SEQ ID NO 9
<211> LENGTH: 3452
<212> TYPE: RNA
<213> ORGANISM: homo sapien

<400> SEQUENCE: 9
acagaaacca aagucaggca aacucuguaa gaacugccug acagaaagcu ggacucaaag      60
cuccuacccg agugugcagc aggaucgccc cgguccggga ccccaggcgc acaccgcaga     120
guccaaagug ccgcgccugc cggccgcacc cgccggccug agagcccugu ggacaaccuc     180
gucauuguca ggcacagagc gguagacccu gcuucucuaa gugggcagcg gacagcggca     240
cgcacauuuc accugucccg cagacaacag caccaucugc uugggagaac ccucucccuu     300
cucugagaaa gaaagauguc gaaugggguau uccacagacg agaauuuccg cuaucucauc     360
ucgugcuuca gggccagggu gaaaauguac auccaggugg agccugugcu ggacuaccug     420
accuuucugc cugcagaggu gaaggagcag auucagagga cagucgccac cuccgggaac     480
augcaggcag uugaacugcu gcugagcacc uggagaagg gagucuggca ccuugguugg     540 acucgggau ucguggaggc ccuccggaga accggcagcc cucuggccgc ccgcuacaug     600
aacccugagc ucacggacuu gcccucucca ucguuugaga cgcucauga ugaauaucuc      660 caacugcuga accuccuuca gcccacucug guggacaagc uucuaguuag agacgucuug     720
gauaagugca uggaggagga acuguugaca auugaagaca gaaaccggau ugcugcugca     780
gaaaacaaug gaaaugaauc agguguaaga gagcuacuaa aaaggauugu gcagaaagaa     840
aacugguucu cugcauuucu gaauguucuu cgucaaacag gaaacaauga acuuguccaa     900
gaguuaacag gcucugauug cucagaaagc aaugcagaga uugagaauuu aucacaaguu     960
gaugguccuc aagugggaaga gcaacuucuu ucaaccacag uucagccaaa ucuggagaag    1020
gaggucuggg gcauggagaa uaacucauca gaaucaucuu uugcagauuc uucuguaguu    1080
ucagaaucag acacaaguuu ggcagaagga agugucagcu gcuuagauga aagucuugga    1140
cauaacagca acaugggcag ugauucaggc accgugggaa gugauucaga ugaagagaau    1200
guggcagcaa gagcaucccc ggagccagaa cuccagcuca ggccuuacca aauggaaguu    1260
gcccagccag ccuuggaagg gaagaauauc aucaucugcc ucccuacagg gaguggaaaa    1320
accagagugg cuguuuacau ugccaaggau cacuuagaca agaagaaaaa agcaucugag    1380
ccuggaaaag uuauaguucu ugucaauaag guacugcuag uugaacagcu cuuccgcaag    1440 gaguccaac cauuuuugaa gaaaugguau cgguuuauug gauuaagugg ugauacccaa    1500
cugaaaauau cauuuccaga aguugucaag uccugugaua uuauuaucag uacagcucaa    1560
auccuugaaa acucccucuu aaacuuggaa aauggagaag augcuggugu ucaauuguca    1620
gacuuuuccc ucauuaucau ugaugaaugu caucacacca caaagaagc aguguauaau    1680 aacaucauga ggcauuauuu gaugcagaag uugaaaaaca auagacucaa gaaagaaaac    1740
aaaccaguga uuccccuucc ucagauacug ggacuaacag cuucaccggg uguuggaggg    1800
gccacgaagc aagccaaagc ugaagaacac auuuuaaaac uaugugccaa ucuugaugca    1860
uuuacuauua aaacuguuaa agaaaaccuu gaucaacuga aaaaccaaau acaggagcca    1920
ugcaagaagu uugccauugc agaugcaacc agagaagauc cauuuaaaga gaaacuucua    1980
gaaauaauga caagggauuca aacuuauugu caaaugaguc caaugucaga uuuuggaacu    2040
caacccuaug aacaaugggc cauucaaaug gaaaaaaaag cugcaaaaga aggaaaucgc    2100
aaagaacgug uuugugcaga acauuugagg aaguacaaug aggcccuaca aauuaaugac    2160
```

-continued

```
acaauucgaa ugauagaugc guauacucau cuugaaacuu ucuauaauga agagaaagau    2220
aagaaguuug cagucauaga agaugauagu gaugaggGug gugaugauga guauugugau    2280
ggugaugaag augaggauga uuuaaagaaa ccuuugaaac uggaugaaac agauagauuu    2340
cucaugacuu uauuuuuuga aaacaauaaa auguugaaaa ggcuggcuga aaacccagaa    2400
uaugaaaaug aaaagcugac caaauuaaga aauaccauaa uggagcaaua uacuaggacu    2460
gaggaaucag cacgaggaau aaucuuuaca aaaacacgac agagugcaua ugcgcuuucc    2520
caguggauua cugaaaauga aaaauuugcu gaaguaggag ucaaagccca ccaucugauu    2580
ggagcuggac acagcaguga guucaaaccc augacacaga augaacaaaa agaagucauu    2640
aguaaauuuc gcacuggaaa aauaaaucug cuuaucgcua ccacaguggc agaagaaggu    2700
cuggauauua aagaauguaa cauuguuauc cguuaugguc ucgucaccaa ugaaauagcc    2760
augguccagg cccguggucg agccagagcu gaugagagca ccugcguccu gguugcucac    2820
agugguucag gaguuaucga acgugagaca guuaaugauu uccgagagaa gaugauguau    2880
aaagcuauac auuguguuca aaauaugaaa ccagaggagu augcucauaa gauuuuggaa    2940
uuacagaugc aaaguauaau ggaaaagaaa augaaaacca agagaaauau ugccaagcau    3000
uucaagaaua acccaucacu aauaacuuuc cuuugcaaaa acugcagugu gcuagccugu    3060
ucuggggaag auauccaugu aauugagaaa augcaucacg ucaauaugac cccagaauuc    3120
aaggaacuuu acauuguaag agaaaacaaa acacugcaaa agaagugugc cgacuaucaa    3180
auaaauggug aaaucaucug caaauguggc caggcuuggg aacaaugau ggugcacaaa    3240 ggcuuagauu ugccuugucu caaaauaagg aauuuuguag ugguuuucaa aaauaauuca    3300
acaaagaaac aauacaaaaa gugggUagaa uuaccuauca cauuucccaa ucuugacuau    3360
ucagaaugcu guuuauuuag ugaugaggau uagcacuuga uugaagauuc uuuuaaaaua    3420
cuaucaguua aacauuuaau augauuauga uu                                 3452
```

<210> SEQ ID NO 10
<211> LENGTH: 2540
<212> TYPE: RNA
<213> ORGANISM: homo sapien

<400> SEQUENCE: 10

```
cgccccgcug cccaccugcc cgccugccca ccugcccagg ugcgagugca gccccgcgcg      60
ccggccugag agcccugugg acaaccucgu cauugucagg cacagagcgg uagacccugc     120
uucucuaagu gggcagcgga cagcggcacg cacauuucac cugucccgca gacaacagca     180
ccaucugcuu gggagaaccc ucucccuucu cugagaaaga aagaugucga auggguauuc     240
cacagacgag aauuuccgcu aucucaucuc gugcuucagg gccagggUga aaauguacau     300
ccaggUggag ccugugcugg acuaccugac cuuucugccu gcagaggUga aggagcagau     360
ucagaggaca gucgccaccu ccgggaacau gcaggcaguu gaacugcugc ugagcaccuu     420
ggagaaggga gucuggcacc uugguuggac ucgggaauuc guggaggccc uccggagaac     480
cggcagcccu cuggccgccc gcuacaugaa cccugagcuc acggacuugc ccucuccauc     540
guuugagaac gcucaugaug aauaucucca acugcugaac cuccuucagc ccacucuggu     600
ggacaagcuu cuaguuagag acgucuugga uaagugcaug gaggaggaac uguugacaau     660
ugaagacaga aaccggauug cugcugcaga aaacaaugga aaugaaucag guguaagaga     720
gcuacuaaaa aggauugugc agaaagaaaa cugguucucu gcauuucuga auguucuucg     780
```
ucaaacagga aacaaugaac uuguccaaga guuaacaggc ucugauugcu cagaaagcaa     840
ugcagagauu gagaauuuau cacaaguuga ugguccucaa guggaagagc aacuucuuuc     900
aaccacaguu cagccaaauc uggagaagga ggucuggggc auggagaaua acucaucaga     960
aucaucuuuu gcagauucuu cuguaguuuc agaaucagac acaaguuugg cagaaggaag    1020
ugucagcugc uuagaugaaa gucuuggaca uaacagcaac augggcagug auucaggcac    1080
caugggaagu gauucagaug aagagaaugu ggcagcaaga gcauccccgg agccagaacu    1140
ccagcucagg ccuuaccaaa uggaaguugc ccagccagcc uuggaaggga agaauaucau    1200
caucugccuc ccuacaggga guggaaaaac cagaguggcu guuuacauug ccaaggauca    1260
cuuagacaag aagaaaaaag caucugagcc uggaaaaguu auaguucuug ucaauaaggu    1320
acugcuaguu gaacagcucu uccgcaagga guuccaacca uuuuugaaga aaugguaucg    1380
uguuauugga uuaaguggug auacccaacu gaaaauauca uuuccagaag uugucaaguc    1440
cugugauauu auuaucagua cagcucaaau ccuugaaaac ucccucuuaa acuuggaaaa    1500
uggagaagau gcugguguuc aauugucaga cuuuucccuc auuaucauug augaauguca    1560
ucacaccaac aaagaagcag uguauaauaa caucaugagg cauuauuuga ugcagaaguu    1620
gaaaaacaau agacucaaga agaaaaacaa accagugauu ccccuuccuc agauacuggg    1680
acuaacagcu ucaccuggug uuggagggggc cacgaagcaa gccaaagcug aagaacacau    1740
uuuaaaacua ugugccaauc uugaugcauu uacuauuaaa acuguuaaag aaaaccuuga    1800
ucaacugaaa aaccaaauac aggagccaug caagaaguuu gccauugcag augcaaccag    1860
agaagaucca uuuaaagaga aacuucuaga aauaaugaca aggauucaaa cuuauuguca    1920
aaugagucca augucagauu uuggaacuca acccaugaa caaugggcca uucaaaugga    1980
aaaaaaagcu gcaaaagaag gaaaucgcaa agaacguguu ugugcagaac auuugaggaa    2040
guacaaugag gcccuacaaa uuaaugacac aauucgaaug auagaugcgu auacucaucu    2100
ugaaacuuuc uauaaugaag agaaagauaa gaaguuugca gucauagaag augauaguga    2160
ugaggugguu gaugaugagu auugugaugg ugaugaagau gaggaugauu uaaagaaacc    2220
uuugaaacug gaugaaacag auagauuucu caugacuuua uuuuuugaaa acaauaaaau    2280
guugaaaagg cuggcugaaa acccagaaua ugaaaaugaa aagcugacca aauuaagaaa    2340
uaccauaaug gagcaauaua cuaggacuga ggaaucagca cgaggaauaa ucuuuacaaa    2400
aacacgacag agugcauaug cgcuuuccca guggauuacu gaaaaugaaa aauuugcuga    2460
aguaggaguc aaagcccacc aucugauugg agcuggacac agcagugagu ucaaacccau    2520
gacacaaaaa aaaaaaaaaa    2540

<210> SEQ ID NO 11
<211> LENGTH: 3581
<212> TYPE: DNA
<213> ORGANISM: homo sapien

<400> SEQUENCE: 11
caaactctgt aagaactgcc tgacagaaag ctggactcaa agctcctacc cgagtgtgca      60
gcaggatcgc cccggtccgg gaccccaggc gcacaccgca gagtccaaag tgccgcgcct     120
gccggccgca cctgcctgcc gcggccccgc gcgccgcccc gctgcccacc tgcccgcctg     180
cccacctgcc caggtgcgag tgcagccccg cgcgccggcc tgagagccct gtggacaacc     240
tcgtcattgt caggcacaga gcggtagacc ctgcttctct aagtgggcag cggacagcgg     300
cacgcacatt tcacctgtcc cgcagacaac agcaccatct gcttgggaga accctctccc     360

-continued

```
ttctctgaga aagaaagatg tcgaatgggt attccacaga cgagaatttc cgctatctca      420
tctcgtgctt cagggccagg gtgaaaatgt acatccaggt ggagcctgtg ctggactacc      480
tgacctttct gcctgcagag gtgaaggagc agattcagag gacagtcgcc acctccggga      540
acatgcaggc agttgaactg ctgctgagca ccttggagaa gggagtctgg caccttggtt      600
ggactcggga attcgtggag gccctccgga gaaccggcag ccctctggcc gcccgctaca      660
tgaaccctga gctcacggac ttgccctctc catcgtttga gaacgctcat gatgaatatc      720
tccaactgct gaacctcctt cagcccactc tggtggacaa gcttctagtt agagacgtct      780
tggataagtg catggaggag gaactgttga caattgaaga cagaaaccgg attgctgctg      840
cagaaaacaa tggaaatgaa tcaggtgtaa gagagctact aaaaaggatt gtgcagaaag      900
aaaactggtt ctctgcattt ctgaatgttc ttcgtcaaac aggaaacaat gaacttgtcc      960
aagagttaac aggctctgat tgctcagaaa gcaatgcaga gattgagaat ttatcacaag     1020
ttgatggtcc tcaagtggaa gagcaacttc tttcaaccac agttcagcca aatctggaga     1080
aggaggtctg gggcatggag aataactcat cagaatcatc ttttgcagat tcttctgtag     1140
tttcagaatc agacacaagt ttggcagaag gaagtgtcag ctgcttagat gaaagtcttg     1200
gacataacag caacatgggc agtgattcag gcaccatggg aagtgattca gatgaagaga     1260
atgtggcagc aagagcatcc ccggagccag aactccagct caggccttac caaatggaag     1320
ttgcccagcc agccttggaa gggaagaata tcatcatctg cctccctaca gggagtggaa     1380
aaaccagagt ggctgtttac attgccaagg atcacttaga caagaagaaa aaagcatctg     1440
agcctggaaa agttatagtt cttgtcaata aggtactgct agttgaacag ctcttccgca     1500
aggagttcca accatttttg aagaaatggt atcgtgttat tggattaagt ggtgataccc     1560
aactgaaaat atcatttcca gaagttgtca gtcctgtga tattattatc agtacagctc     1620
aaatccttga aaactccctc ttaaacttgg aaaatggaga agatgctggt gttcaattgt     1680
cagacttttc cctcattatc attgatgaat gtcatcacac caacaaagaa gcagtgtata     1740
ataacatcat gaggcattat ttgatgcaga agttgaaaaa caatagactc aagaaagaaa     1800
acaaaccagt gattcccctt cctcagatac tgggactaac agcttcacct ggtgttggag     1860
gggccacgaa gcaagccaaa gctgaagaac acattttaaa actatgtgcc aatcttgatg     1920
catttactat taaaactgtt aaagaaaacc ttgatcaact gaaaaaccaa atacaggagc     1980
catgcaagaa gtttgccatt gcagatgcaa ccagagaaga tccatttaaa gagaaacttc     2040
tagaaataat gacaaggatt caaacttatt gtcaaatgag tccaatgtca gattttggaa     2100
ctcaacccta tgaacaatgg gccattcaaa tggaaaaaaa agctgcaaaa gaaggaaatc     2160
gcaaagaacg tgtttgtgca gaacatttga ggaagtacaa tgaggcccta caaattaatg     2220
acacaattcg aatgatagat gcgtatactc atcttgaaac tttctataat gaagagaaag     2280
ataagaagtt tgcagtcata gaagatgata gtgatgaggg tggtgatgat gagtattgtg     2340
atggtgatga agatgaggat gatttaaaga aacctttgaa actggatgaa acagatagat     2400
ttctcatgac tttatttttt gaaaacaata aaatgttgaa aaggctggct gaaaacccag     2460
aatatgaaaa tgaaaagctg accaaattaa gaaataccat aatggagcaa tatactagga     2520
ctgaggaatc agcacgagga ataatcttta caaaaacacg acagagtgca tatgcgcttt     2580
cccagtggat tactgaaaat gaaaaatttg ctgaagtagg agtcaaagcc caccatctga     2640
ttggagctgg acacagcagt gagttcaaac ccatgacaca gaatgaacaa aaagaagtca     2700
```

-continued

```
ttagtaaatt tcgcactgga aaaataaatc tgcttatcgc taccacagtg gcagaagaag    2760
gtctggatat taaagaatgt aacattgtta tccgttatgg tctcgtcacc aatgaaaatag   2820 ccatggtcca ggcccgtggt cgagccagag ctgatgagag cacctacgtc ctggttgctc    2880
acagtggttc aggagttatc gaacatgaga cagttaatga tttccgagag aagatgatgt    2940
ataaagctat acattgtgtt caaaatatga aaccagagga gtatgctcat aagattttgg    3000
aattacagat gcaaagtata atggaaaaga aaatgaaaac caagagaaat attgccaagc    3060
attacaagaa taacccatca ctaataactt tcctttgcaa aaactgcagt gtgctagcct    3120
gttctgggga agatatccat gtaattgaga aaatgcatca cgtcaatatg accccagaat    3180
tcaaggaact ttacattgta agagaaaaca aagcactgca aaagaagtgt gccgactatc    3240
aaataaatgg tgaaatcatc tgcaaatgtg gccaggcttg gggaacaatg atggtgcaca    3300
aaggcttaga tttgccttgt ctcaaaataa ggaattttgt agtggttttc aaaaataatt    3360
caacaaagaa acaatacaaa aagtgggtag aattacctat cacatttccc aatcttgact    3420
attcagaatg ctgtttattt agtgatgagg attagcactt gattgaagat tcttttaaaa    3480
tactatcagt taaacattta atatgattat gattaatgta ttcattatgc tacagaactg    3540
acataagaat caataaaatg attgtttttac tctgcattga a                       3581
```

<210> SEQ ID NO 12
<211> LENGTH: 3234
<212> TYPE: DNA
<213> ORGANISM: homo sapien

<400> SEQUENCE: 12

```
gcgcgccggc ctgagagccc tgtggacaac ctcgtcattg tcaggcacag agcggtagac     60
cctgcttctc taagtgggca gcggacagcg gcacgcacat ttcacctgtc ccgcagacaa    120
cagcaccatc tgcttgggag aaccctctcc cttctctgag aaagaaagat gtcgaatggg    180
tattccacag acgagaattt ccgctatctc atctcgtgct tcagggccag ggtgaaaatg    240
tacatccagg tggagcctgt gctggactac ctgacctttc tgcctgcaga ggtgaaggag    300
cagattcaga ggacagtcgc cacctccggg aacatgcagg cagttgaact gctgctgagc    360
accttggaga agggagtctg gcaccttggt tggactcggg aattcgtgga ggccctccgg    420
agaaccggca gccctctggc cgcccgctac atgaaccctg agctcacgga cttgccctct    480
ccatcgtttg agaacgctca tgatgaatat ctccaactgc tgaacctcct tcagcccact    540
ctggtggaca agcttctagt tagagacgtc ttggataagt gcatggagga ggaactgttg    600
acaattgaag acagaaaccg gattgctgct gcagaaaaca tggaaatga atcaggtgta     660 agagagctac taaaaaggat tgtgcagaaa gaaaactggt tctctgcatt tctgaatgtt    720
cttcgtcaaa caggaaacaa tgaacttgtc caagagttaa caggctctga ttgctcagaa    780
agcaatgcag agattgagaa tttatcacaa gttgatggtc ctcaagtgga gagcaactt     840 ctttcaacca cagttcagcc aaatctggag aaggaggtct ggggcatgga gaataactca    900
tcagaatcat cttttgcaga ttcttctgta gtttcagaat cagacacaag tttggcagaa    960
ggaagtgtca gctgcttaga tgaaagtctt ggacataaca gcaacatggg cagtgattca   1020
ggcaccatgg gaagtgattc agatgaagag aatgtggcag caagagcatc cccggagcca   1080
gaactccagc tcaggcctta ccaaatggaa gttgcccagc cagccttgga agggaagaat   1140
atcatcatct gcctccctac agggagtgga aaaaccagag tggctgttta cattgccaag   1200
gatcacttag acaagaagaa aaaagcatct gagcctggaa aagttatagt tcttgtcaat   1260
```

-continued

```
aaggtactgc tagttgaaca gctcttccgc aaggagttcc aaccattttt gaagaaatgg      1320
tatcgtgtta ttggattaag tggtgatacc caactgaaaa tatcatttcc agaagttgtc      1380
aagtcctgtg atattattat cagtacagct caaatccttg aaaactccct cttaaacttg      1440
gaaaatggag aagatgctgg tgttcaattg tcagactttt ccctcattat cattgatgaa      1500
tgtcatcaca ccaacaaaga agcagtgtat aataacatca tgaggcatta tttgatgcag      1560
aagttgaaaa acaatagact caagaaagaa aacaaaccag tgattcccct tcctcagata      1620
ctgggactaa cagcttcacc tggtgttgga ggggccacga agcaagccaa agctgaagaa      1680
cacattttaa aagatccatt taaagagaaa cttctagaaa taatgacaag gattcaaact      1740
tattgtcaaa tgagtccaat gtcagatttt ggaactcaac cctatgaaca atgggccatt      1800
caaatggaaa aaaaagctgc aaaagaagga aatcgcaaag aacgtgtttg tgcagaacat      1860
ttgaggaagt acaatgaggc cctacaaatt aatgacacaa ttcgaatgat agatgcgtat      1920
actcatcttg aaactttcta taatgaagag aaagataaga agtttgcagt catagaagat      1980
gatagtgatg agggtggtga tgatgagtat tgtgatggtg atgaagatga ggatgattta      2040
aagaaacctt tgaaactgga tgaaacagat agatttctca tgactttatt ttttgaaaac      2100
aataaaatgt tgaaaaggct ggctgaaaac ccagaatatg aaaatgaaaa gctgaccaaa      2160
ttaagaaata ccataatgga gcaatatact aggactgagg aatcagcacg aggaataatc      2220
tttacaaaaa cacgacagag tgcatatgcg cttttcccagt ggattactga aaatgaaaaa      2280
tttgctgaag taggagtcaa agcccaccat ctgattggag ctggacacag cagtgagttc      2340
aaacccatga cacagaatga acaaaaagaa gtcattagta aatttcgcac tggaaaaata      2400
aatctgctta tcgctaccac agtggcagaa gaaggtctgg atattaaaga atgtaacatt      2460
gttatccgtt atggtctcgt caccaatgaa atagccatgg tccaggcccg tggtcgagcc      2520
agagctgatg agagcaccta cgtcctggtt gctcacagtg gttcaggagt tatcgaacat      2580
gagacagtta atgatttccg agagaagatg atgtataaag ctatacattg tgttcaaaat      2640
atgaaaccag aggagtatgc tcataagatt ttggaattac agatgcaaag tataatggaa      2700
aagaaaatga aaaccaagag aaatattgcc aagcattaca agaataaccc atcactaata      2760
actttccttt gcaaaaactg cagtgtgcta gcctgttctg gggaagatat ccatgtaatt      2820
gagaaaatgc atcacgtcaa tatgacccca gaattcaagg aactttacat tgtaagagaa      2880
aacaaagcac tgcaaaagaa gtgtgccgac tatcaaataa atggtgaaat catctgcaaa      2940
tgtggccagg cttggggaac aatgatggtg cacaaaggct tagatttgcc ttgtctcaaa      3000
ataaggaatt ttgtagtggt tttcaaaaat aattcaacaa agaaacaata caaaaagtgg      3060
gtagaattac ctatcacatt tcccaatctt gactattcag aatgctgttt atttagtgat      3120
gaggattagc acttgattga agattctttt aaaatactat cagttaaaca tttaatatga      3180
ttatgattaa tgtattcatt atgctacaga actgacataa gaatcaataa aatg          3234
```

<210> SEQ ID NO 13
<211> LENGTH: 1776
<212> TYPE: DNA
<213> ORGANISM: homo sapien

<400> SEQUENCE: 13

```
cacaaaccag tgattcccct tcctcagata ctgggactaa cagcttcacc tggtgttgga        60
ggggccacga agcaagccaa agctgaagaa cacattttaa aactatgtgc caatcttgat       120
```

```
gcatttacta ttaaaactgt taaagaaaac cttgatcaac tgaaaaacca aatacaggag      180
ccatgcaaga agtttgccat tgcagatgca accagagaag atccatttaa agagaaactt      240
ctagaaataa tgacaaggat tcaaacttat tgtcaaatga gtccaatgtc agattttgga      300
actcaaccct atgaacaatg ggccattcaa atggaaaaaa aagctgcaaa agaaggaaat      360
cgcaaagaac gtgtttgtgc agaacatttg aggaagtaca atgaggccct acaaattaat      420
gacacaattc gaatgataga tgcgtatact catcttgaaa cttctctaaa tgaagagaaa      480
gataagaagt ttgcagtcat agaagatgat agtgatgagg gtggtgatga tgagtattgt      540
gatggtgatg aagatgagga tgatttaaag aaacctttga aactggatga aacagataga      600
tttctcatga ctttatttt tgaaaacaat aaaatgttga aaaggctggc tgaaaaccca      660
gaatatgaaa atgaaaagct gaccaaatta agaaatacca taatggagca atatactagg      720
actgaggaat cagcacgagg aataatcttt acaaaaacac gacagagtgc atatgcgctt      780
tcccagtgga ttactgaaaa tgaaaaattt gctgaagtag gagtcaaagc ccaccatctg      840
attggagctg gacacagcag tgagttcaaa cccatgacac agaatgaaca aaaagaagtc      900
attagtaaat ttcgcactgg aagaataaat ctgcttatcg ctaccacagt ggcagaagaa      960
ggtctggata ttaaagaatg taacattgtt atccgttatg gtctcgtcac caatgaaata     1020
gccatggtcc aggcccgtgg tcgagccaga gctgatgaga gcacctacgt cctggttgct     1080
cacagtggtt caggagttat cgaacgtgag acagttaatg atttccgaga gaagatgatg     1140
tataaagcta tacattgtgt tcaaaatatg aaaccagagg agtatgctca taagattttg     1200
gaattacaga tgcaaagtat aatggaaaag aaaatgaaaa ccaagagaaa tattgccaag     1260
cattacaaga ataacccatc actaataact ttcctttgca aaaactgcag tgtgctagcc     1320
tgttctgggg aagatatcca tgtaattgag aaaatgcatc acgtcaatat gaccccagaa     1380
ttcaaggaac tttacattgt aagagaaaac aaaacactgc aaaagaagtg tgccgactat     1440
caaataaatg gtgaaatcat ctgcaaatgt ggccaggctt ggggaacaat gatggtgcac     1500
aaaggcttag atttgccttg tctcaaaata aggaattttg tagtggtttt caaaaataat     1560
tcaacaaaga aacaatacaa aaagtgggta gaattaccta tcacatttcc caatcttgac     1620
tattcagaat gctgtttatt tagtgatgag gattagcact tgattgaaga ttcttttaaa     1680
atactatcag ttaaacattt aatatgatta tgattaatgt attcattatg ctacagaact     1740
gacataagaa tcaataaaat gattgtttta ctctgc                               1776
```

```
<210> SEQ ID NO 14
<211> LENGTH: 3380
<212> TYPE: DNA
<213> ORGANISM: homo sapien

<400> SEQUENCE: 14
gcgcgccggc ctgagagccc tgtggacaac ctcgtcattg tcaggcacag agcggtagac       60
cctgcttctc taagtgggca gcggacagcg gcacgcacat ttcacctgtc ccgcagacaa      120
cagcaccatc tgcttgggag aaccctctcc cttctctgag aaagaaagat gtcgaatggg      180
tattccacag acgagaattt ccgctatctc atctcgtgct tcaggccag ggtgaaaatg      240 tacatccagg tggagcctgt gctggactac ctgacctttc tgcctgcaga ggtgaaggag      300
cagattcaga ggacagtcgc cacctccggg aacatgcagg cagttgaact gctgctgagc      360
accttggaga agggagtctg gcaccttggt tggactcggg aattcgtgga ggccctccgg      420
agaaccggca gccctctggc cgcccgctac atgaaccctg agctcacgga cttgccctct      480
```

-continued

```
ccatcgtttg agaacgctca tgatgaatat ctccaactgc tgaacctcct tcagcccact      540
ctggtggaca agcttctagt tagagacgtc ttggataagt gcatggagga ggaactgttg      600
acaattgaag acagaaaccg gattgctgct gcagaaaaca atggaaatga atcaggtgta      660
agagagctac taaaaaggat tgtgcagaaa gaaaactggt tctctgcatt tctgaatgtt      720
cttcgtcaaa caggaaacaa tgaacttgtc caagagttaa caggctctga ttgctcagaa      780
agcaatgcag agattgagaa tttatcacaa gttgatggtc ctcaagtgga agagcaactt      840
ctttcaacca cagttcagcc aaatctggag aaggaggtct ggggcatgga gaataactca      900
tcagaatcat cttttgcaga ttcttctgta gtttcagaat cagacacaag tttggcagaa      960
ggaagtgtca gctgcttaga tgaaagtctt ggacataaca gcaacatggg cagtgattca     1020
ggcaccatgg gaagtgattc agatgaagag aatgtggcag caagagcatc cccgagcca      1080 gaactccagc tcaggcctta ccaaatggaa gttgcccagc cagccttgga agggaagaat     1140
atcatcatct gcctccctac agggagtgga aaaaccagag tggctgtta cattgccaag      1200 gatcacttag acaagaagaa aaaagcatct gagcctggaa aagttatagt tcttgtcaat     1260
aaggtactgc tagttgaaca gctcttccgc aaggagttcc aaccattttt gaagaaatgg     1320
tatcgtgtta ttggattaag tggtgatacc caactgaaaa tatcatttcc agaagttgtc     1380
aagtcctgtg atattattat cagtacagct caaatccttg aaaactccct cttaaacttg     1440
gaaaatggag aagatgctgg tgttcaattg tcagactttt ccctcattat cattgatgaa     1500
tgtcatcaca ccaacaaaga agcagtgtat aataacatca tgaggcatta tttgatgcag     1560
aagttgaaaa acaatagact caagaaagaa aacaaaccag tgattcccct tcctcagata     1620
ctgggactaa cagcttcacc tggtgttgga ggggccacga agcaagccaa agctgaagaa     1680
cacattttaa aactatgtgc caatcttgat gcatttacta ttaaaactgt taaagaaaac     1740
cttgatcaac tgaaaaacca aatacaggag ccatgcaaga gtttgccat tgcagatgca      1800 accagagaag atccatttaa agagaaactt ctagaaataa tgacaaggat tcaaacttat     1860
tgtcaaatga gtccaatgtc agattttgga actcaaccct atgaacaatg ggccattcaa     1920
atggaaaaaa aagctgcaaa aaaaggaaat cgcaaagaac gtgtttgtgc agaacatttg     1980
aggaagtaca atgaggccct acaaattaat gacacaattc gaatgataga tgcgtatact     2040
catcttgaaa ctttctataa tgaagagaaa gataagaagt ttgcagtcat agaagatgat     2100
agtgatgagg gtggtgatga tgagtattgt gatggtgatg aagatgagga tgatttaaag     2160
aaacctttga aactggatga aacagataga tttctcatga ctttattttt tgaaaacaat     2220
aaaatgttga aaaggctggc tgaaaaccca gaatatgaaa atgaaaagct gaccaaatta     2280
agaaatacca taatggagca atatactagg actgaggaat cagcacgagg aataatcttt     2340
acaaaaacac gacagagtgc atatgcgctt tcccagtgga ttactgaaaa tgaaaaattt     2400
gctgaagtag gagtcaaagc ccaccatctg attggagctg gacacagcag tgagttcaaa     2460
cccatgacac agaatgaaca aaaagaagtc attagtaaat ttcgcactgg aaaaatcaat     2520
ctgcttatcg ctaccacagt ggcagaagaa ggtctggata ttaaagaatg taacattgtt     2580
atccgttatg gtctcgtcac caatgaaata gccatggtcc aggcccgtgg tcgagccaga     2640
gctgatgaga gcacctacgt cctggttgct cacagtggtt caggagttat cgaacatgag     2700
acagttaatg atttccgaga gaagatgatg tataaagcta tacattgtgt tcaaaatatg     2760
aaaccagagg agtatgctca taagattttg gaattacaga tgcaaagtat aatggaaaag     2820
```

-continued

```
aaaatgaaaa ccaagagaaa tattgccaag cattacaaga ataacccatc actaataact    2880
ttcctttgca aaaactgcag tgtgctagcc tgttctgggg aagatatcca tgtaattgag    2940
aaaatgcatc acgtcaatat gacccccagaa ttcaaggaac tttacattgt aagagaaaac   3000
aaagcactgc aaaagaagtg tgccgactat caaataaatg gtgaaatcat ctgcaaatgt    3060
ggccaggctt ggggaacaat gatggtgcac aaaggcttag atttgccttg tctcaaaata    3120
aggaattttg tagtggtttt caaaaataat tcaacaaaga aacaatacaa aaagtgggta    3180
gaattaccta tcacatttcc caatcttgac tattcagaat gctgtttatt tagtgatgag    3240
gattagcact tgattgaaga ttcttttaaa atactatcag ttaaacattt aatatgatta    3300
tgattaatgt attcattatg ctacagaact gacataagaa tcaataaaat gattgtttta    3360
ctctgaaaaa aaaaaaaaaa                                                 3380
```

```
<210> SEQ ID NO 15
<211> LENGTH: 3373
<212> TYPE: DNA
<213> ORGANISM: homo sapien

<400> SEQUENCE: 15
gggccctgtg acaacctcg tcattgtcag gcacagagcg gtagaccctg cttctctaag      60
tgggcagcgg acagcggcac gcacatttca cctgtcccgc agacaacagc accatctgct    120
tgggagaacc ctctcccttc tctgagaaag aaagatgtcg aatgggtatt ccacagacga    180
gaatttccgc tatctcatct cgtgcttcag ggccagggtg aaaatgtaca tccaggtgga    240
gcctgtgctg gactacctga cctttctgcc tgcagaggtg aaggagcaga ttcagaggac    300
agtcgccacc tccgggaaca tgcaggcagt tgaactgctg ctgagcacct ggagaaaggg    360
agtctggcac cttggttgga ctcgggaatt cgtggaggcc ctccgagaa ccggcagccc    420 tctggccgcc cgctacatga accctgagct cacggacttg ccctctccat cgtttgagaa    480
cgctcatgat gaatatctcc aactgctgaa cctccttcag cccactctgg tggacaagct    540
tctagttaga gacgtcttgg ataagtgcat ggaggaggaa ctgttgacaa ttgaagacag    600
aaaccggatt gctgctgcag aaaacaatgg aaatgaatca ggtgtaagag agctactaaa    660
aaggattgtg cagaaagaaa actggttctc tgcatttctg aatgttcttc gtcaaacagg    720
aaacaatgaa cttgtccaag agttaacagg ctctgattgc tcagaaagca atgcagagat    780 tgagaatttta tcacaagttg atggtcctca agtggaagag caacttcttt caaccacagt    840
tcagccaaat ctggagaagg aggtctgggg catggagaat aactcatcag aatcatcttt    900
tgcagattct tctgtagttt cagaatcaga cacaagtttg gcagaaggaa gtgtcagctg    960
cttagatgaa agtcttggac ataacagcaa catgggcagt gattcaggca ccatgggaag   1020
tgattcagat gaagagaatg tggcagcaag agcatccccg gagccagaac tccagctcag   1080
gccttaccaa atggaagttg cccagccagc cttggaaggg aagaatatca tcatctgcct   1140
ccctacaggg agtggaaaaa ccagagtggc tgtttacatt gccaaggatc acttagacaa   1200
gaagaaaaaa gcatctgagc ctggaaaagt tatagttctt gtcaataagg tactgctagt   1260
tgaacagctc ttccgcaagg agttccaacc atttttgaag aaatggtatc gtgttattgg   1320
attaagtggt gatacccaac tgaaaatatc atttccagaa gttgtcaagt cctgtgatat   1380
tattatcagt acagctcaaa tccttgaaaa ctccctctta aacttggaaa atggagaaga   1440
tgctggtgtt caattgtcag acttttcctt cattatcatt gatgaatgtc atcacaccaa   1500
caaagaagca gtgtataata acatcatgag gcattatttg atgcagaagt tgaaaaacaa   1560
```

```
tagactcaag aaagaaaaca aaccagtgat tccccttcct cagatactgg gactaacagc      1620
ttcacctggt gttggagggg ccacgaagca agccaaagct gaagaacaca tttttaaaact      1680 atgtgccaat cttgatgcat ttactattaa aactgttaaa gaaaaccttg atcaactgaa      1740
aaaccaaata caggagccat gcaagaagtt tgccattgca gatgcaacca gagaagatcc      1800
atttaaagag aaacttctag aaataatgac aaggattcaa acttattgtc aaatgagtcc      1860
aatgtcagat tttggaactc aaccctatga acaatgggcc attcaaatgg aaaaaaaagc      1920
tgcaaaagaa ggaaatcgca aagaaagtgt ttgtgcagaa catttgagga agtacaataa      1980
ggccctacaa attaatgaca caattcgaat gatagatgcg tatactcatc ttgaaacttt      2040
ctataatgaa gagaaagata agaagtttgc agtcatagaa gatgatagtg atgagggtgg      2100
tgatgatgag tattgtgatg gtgatgaaga tgaggatgat ttaaagaaac ctttgaaact      2160
ggatgaaaca gatagatttc tcatgacttt atttttttgaa aacaataaaa tgttgaaaag      2220
gctggctgaa aacccagaat atgaaaatga aaagctgacc aaattaagaa ataccataat      2280
ggagcaatat actaggactg aggaatcagc acgaggaata atctttacaa aaacacgaca      2340
gagtgcatat gcgctttccc agtggattac tgaaaatgaa aaatttgctg aagtaggagt      2400
caaagcccac catctgattg gagctggaca cagcagtgag ttcaaaccca tgacacagaa      2460
tgaacaaaaa gaagtcatta gtaaatttcg cactggaaaa ataaatctgc ttatcgctac      2520
cacagtggca gaagaaggtc tggatattaa agaatgtaac attgttatcc gttatggtct      2580
cgtcaccaat gaaatagcca tggtccaggc ccgtggtcga gccagagctg atgagagcac      2640
ctacgtcctg gttgctcaca gtggttcagg agttatcgaa cgtgagacag ttaatgattt      2700
ccgagagaag atgatgtata aagctataca ttgtgttcaa aatatgaaac cagaggagta      2760
tgctcataag attttggaat tacagatgca aagtataatg gaaaagaaaa tgaaaaccaa      2820
gagaaatatt gccaagcatt acaagaataa cccatcacta ataactttcc tttgcaaaaa      2880
ctgcagtgtg ctagcctgtt ctggggaaga tatccatgta attgagaaaa tgcatcacgt      2940
caatatgacc ccagaattca aggaacttta cattgtaaga gaaaacaaag cactgcaaaa      3000
gaagtgtgcc gactatcaaa taaatggtga aatcatctgc aaatgtggcc aggcttgggg      3060
aacaatgatg gtgcacaaag cttagatttt gccttgtctc aaaataagga attttgtagt      3120
ggttttcaaa aataattcaa caaagaaaca atacaaaaag tgggtagaat tacctatcac      3180
atttcccaat cttgactatt cagaatgctg tttatttagt gatgaggatt agcacttgat      3240
tgaagattct tttaaaatac tatcagttaa acatttaata tgattatgat taatgtattc      3300
attatgctac agaactgaca taagaatcaa taaaatgatt gttttactct ccaaaaaaaa      3360
aaaaaaaaaa aaa                                                          3373
```

<210> SEQ ID NO 16
<211> LENGTH: 3244
<212> TYPE: DNA
<213> ORGANISM: homo sapien

<400> SEQUENCE: 16

```
ttcacctgtc ccgcagacaa cagcaccatc tgcttgggag aaccctctcc cttctctgag        60
aaagaaagat gtcgaatggg tattccacag acgagaattt ccgctatctc atctcgtgct       120
tcagggccag ggtgaaaatg tacatccagg tggagcctgt gctggactac ctgacctttc       180
tgcctgcaga ggtgaaggag cagattcaga ggacagtcgc cacctccggg aacatgcagg       240
```

-continued

```
cagttgaact gctgctgagc accttggaga agggagtctg gcaccttggt tggactcggg      300
aattcgtgga ggccctccgg agaaccggca gccctctggc cgcccgctac atgaaccctg      360
agctcacgga cttgccctct ccatcgtttg agaacgctca tgatgaatat ctccaactgc      420
tgaacctcct tcagcccact ctggtggaca agcttctagt tagagacgtc ttggataagt      480
gcatggagga ggaactgttg acaattgaag acagaaaccg gattgctgct gcagaaaaca      540
atggaaatga atcaggtgta agagagctac taaaaaggat tgtgcagaaa gaaaactggt      600
tctctgcatt tctgaatgtt cttcgtcaaa caggaaacaa tgaacttgtc caagagttaa      660
caggctctga ttgctcagaa agcaatgcag agattgagaa tttatcacaa gttgatggtc      720
ctcaagtgga agagcaactt ctttcaacca cagttcagcc aaatctggag aaggaggtct      780
ggggcatgga gaataactca tcagaatcat cttttgcaga ttcttctgta gtttcagaat      840
cagacacaag tttggcagaa ggaagtgtca gctgcttaga tgaaagtctt ggacataaca      900
gcaacatggg cagtgattca ggcaccatgg gaagtgattc agatgaagag aatgtggcag      960
caagagcatc cccggagcca gaactccagc tcaggcctta ccaaatggaa gttgcccagc     1020
cagccttgga agggaagaat atcatcatct gcctccctac agggagtgga aaaaccagag     1080
tggctgttta cattgccaag gatcacttag acaagaagaa aaaagcatct gagcctggaa     1140
aagttatagt tcttgtcaat aaggtactgc tagttgaaca gctcttccgc aaggagttcc     1200
aaccattttt gaagaaatgg tatcgtgtta ttggattaag tggtgatacc caactgaaaa     1260
tatcatttcc agaagttgtc aagtcctgtg atattattat cagtacagct caaatccttg     1320
aaaactccct cttaaacttg gaaaatggag aagatgctgg tgttcaattg tcagactttt     1380
ccctcattat cattgatgaa tgtcatcaca ccaacaaaga agcagtgtat aataacatca     1440
tgaggcatta tttgatgcag aagttgaaaa acaatagact caagaagaa aacaaaccag     1500 tgattcccct tcctcagata ctgggactaa cagcttcacc tggtgttgga ggggccacga     1560
agcaagccaa agctgaagaa cacattttaa aactatgtgc caatcttgat gcatttacta     1620
ttaaaactgt taaagaaaac cttgatcaac tgaaaaacca aatacaggag ccatgcaaga     1680
agtttgccat tgcagatgca accagagaag atccatttaa agagaaactt ctagaaataa     1740
tgacaaggat tcaaacttat tgtcaaatga gtccaatgtc agattttgga actcaaccct     1800
atgaacaatg ggccattcaa atggaaaaaa aagctgcaaa agaaggaaat cgcaaagaac     1860
gtgtttgtgc agaacatttg aggaagtaca atgaggccct acaaattaat gacacaattc     1920
gaatgataga tgcgtatact catcttgaaa ctttctataa tgaagagaaa gataagaagt     1980
ttgcagtcat agaagatgat agtgatgagg gtggtgatga tgagtattgt gatggtgatg     2040
aagatgagga tgatttaaag aaaacctttga aactggatga aacagataga tttctcatga     2100
ctttattttt tgaaaacaat aaaatgttga aaaggctggc tgaaaaccca gaatatgaaa     2160
atgaaaagct gaccaaatta agaaatacca taatggagca atatactagg actgaggaat     2220
cagcacgagg aataatcttt acaaaaacac gacagagtgc atatgcgctt tcccagtgga     2280
ttactgaaaa tgaaaaattt gctgaagtag gagtcaaagc ccaccatctg attggagctg     2340
gacacagcag tgagttcaaa cccatgacac agaatgaaca aaaagaagtc attagtaaat     2400
ttcgcactgg aaaaataaat ctgcttatcg ctaccacagt ggcagaagaa ggtctggata     2460
ttaaagaatg taacattgtt atccgttatg gtctcgtcac caatgaaata gccatggtcc     2520
aggcccgtgg tcgagccaga gctgatgaga gcacctacgt cctggttgct cacagtggtt     2580
caggagttat cgaacgtgag acagttaatg atttccgaga gaagatgatg tataaagcta     2640
```

```
tacattgtgt tcaaaatatg aaaccagagg agtatgctca taagattttg gaattacaga     2700
tgcaaagtat aatggaaaag aaaatgaaaa ccaagagaaa tattgccaag cattacaaga     2760
ataacccatc actaataact ttcctttgca aaaactgcag tgtgctagcc tgttctgggg     2820
aagatatcca tgtaattgag aaaatgcatc acgtcaatat gaccccagaa ttcaaggaac     2880
tttacattgt aagagaaaac aaaacactgc aaaagaagtg tgccgactat caaataaatg     2940
gtgaaatcat ctgcaaatgt ggccaggctt ggggaacaat gatggtgcac aaaggcttag     3000
atttgccttg tctcaaaata aggaattttg tagtggtttt caaaaataat tcaacaaaga     3060
aacaatacaa aaagtgggta gaattaccta tcacatttcc caatcttgac tattcagaat     3120
gctgtttatt tagtgatgag gattagcact tgattgaaga ttcttttaaa atactatcag     3180
ttaaacattt aatatgatta tgattaatgt attcattatg ctacagaact gacataagaa     3240
tcaa                                                                  3244

<210> SEQ ID NO 17
<211> LENGTH: 3452
<212> TYPE: DNA
<213> ORGANISM: homo sapien

<400> SEQUENCE: 17
acagaaacca aagtcaggca aactctgtaa gaactgcctg acagaaagct ggactcaaag       60
ctcctacccg agtgtgcagc aggatcgccc cggtccggga ccccaggcgc acaccgcaga      120
gtccaaagtg ccgcgcctgc cggccgcacc cgccggcctg agagccctgt ggacaacctc      180
gtcattgtca ggcacagagc ggtagaccct gcttctctaa gtgggcagcg gacagcggca      240
cgcacatttc acctgtcccg cagacaacag caccatctgc ttgggagaac cctctccctt      300
ctctgagaaa gaaagatgtc gaatgggtat tccacagacg agaatttccg ctatctcatc      360
tcgtgcttca gggccagggt gaaaatgtac atccaggtgg agcctgtgct ggactacctg      420
acctttctgc ctgcagaggt gaaggagcag attcagagga cagtcgccac ctccgggaac      480
atgcaggcag ttgaactgct gctgagcacc ttggagaagg gagtctggca ccttggttgg      540
actcgggaat tcgtggaggc cctccggaga accggcagcc ctctggccgc ccgctacatg      600
aaccctgagc tcacggactt gccctctcca tcgtttgaga cgctcatga tgaatatctc      660 caactgctga acctccttca gcccactctg gtggacaagc ttctagttag agacgtcttg      720
gataagtgca tggaggagga actgttgaca attgaagaca gaaaccggat tgctgctgca      780
gaaaacaatg gaaatgaatc aggtgtaaga gagctactaa aaaggattgt gcagaaagaa      840
aactggttct ctgcatttct gaatgttctt cgtcaaacag gaaacaatga acttgtccaa      900
gagttaacag gctctgattg ctcagaaagc aatgcagaga ttgagaattt atcacaagtt      960
gatggtcctc aagtggaaga gcaacttctt tcaaccacag ttcagccaaa tctggagaag     1020
gaggtctggg gcatggagaa taactcatca gaatcatctt ttgcagattc ttctgtagtt     1080
tcagaatcag acacaagttt ggcagaagga agtgtcagct gcttagatga aagtcttgga     1140
cataacagca acatgggcag tgattcaggc accgtgggaa gtgattcaga tgaagagaat     1200
gtggcagcaa gagcatcccc ggagccagaa ctccagctca ggccttacca aatggaagtt     1260
gcccagccag ccttggaagg gaagaatatc atcatctgcc tccctacagg gagtggaaaa     1320
accagagtgg ctgtttacat tgccaaggat cacttagaca agaagaaaaa agcatctgag     1380
cctggaaaag ttatagttct tgtcaataag gtactgctag ttgaacagct cttccgcaag     1440
```

```
gagttccaac cattttttgaa gaaatggtat cgtgttattg gattaagtgg tgatacccaa          1500
ctgaaaatat catttccaga agttgtcaag tcctgtgata ttattatcag tacagctcaa          1560
atccttgaaa actccctctt aaacttggaa aatggagaag atgctggtgt tcaattgtca          1620 gactttttccc tcattatcat tgatgaatgt catcacacca acaaagaagc agtgtataat          1680
aacatcatga ggcattattt gatgcagaag ttgaaaaaca atagactcaa gaaagaaaac          1740
aaaccagtga ttcccccttcc tcagatactg ggactaacag cttcacctgg tgttggaggg          1800
gccacgaagc aagccaaagc tgaagaacac attttaaaac tatgtgccaa tcttgatgca          1860
tttactatta aaactgttaa agaaaacctt gatcaactga aaaaccaaat acaggagcca          1920
tgcaagaagt ttgccattgc agatgcaacc agagaagatc catttaaaga gaaacttcta          1980
gaaataatga caaggattca aacttattgt caaatgagtc caatgtcaga ttttggaact          2040
caaccctatg aacaatgggc cattcaaatg gaaaaaaaag ctgcaaaaga aggaaatcgc          2100
aaagaacgtg tttgtgcaga acatttgagg aagtacaatg aggccctaca aattaatgac          2160
acaattcgaa tgatagatgc gtatactcat cttgaaactt tctataatga agagaaagat          2220
aagaagtttg cagtcataga agatgatagt gatgagggtg gtgatgatga gtattgtgat          2280
ggtgatgaag atgaggatga tttaaagaaa cctttgaaac tggatgaaac agatagattt          2340
ctcatgactt tattttttga aaacaataaa atgttgaaaa ggctggctga aaacccagaa          2400
tatgaaaatg aaaagctgac caaattaaga aataccataa tggagcaata tactaggact          2460
gaggaatcag cacgaggaat aatctttaca aaaacacgac agagtgcata tgcgctttcc          2520
cagtggatta ctgaaaatga aaaatttgct gaagtaggag tcaaagccca ccatctgatt          2580
ggagctggac acagcagtga gttcaaaccc atgacacaga atgaacaaaa agaagtcatt          2640
agtaaatttc gcactggaaa aataaatctg cttatcgcta ccacagtggc agaagaaggt          2700
ctggatatta agaatgtaa cattgttatc cgttatggtc tcgtcaccaa tgaaatagcc          2760
atggtccagg cccgtggtcg agccagagct gatgagagca cctgcgtcct ggttgctcac          2820
agtggttcag gagttatcga acgtgagaca gttaatgatt ccgagagaa gatgatgtat          2880 aaagctatac attgtgttca aaatatgaaa ccagaggagt atgctcataa gattttggaa          2940
ttacagatgc aaagtataat ggaaaagaaa atgaaaacca agagaaatat tgccaagcat          3000
ttcaagaata acccatcact aataactttc ctttgcaaaa actgcagtgt gctagcctgt          3060 tctgggggaag atatccatgt aattgagaaa atgcatcacg tcaatatgac cccagaattc          3120
aaggaacttt acattgtaag agaaaacaaa acactgcaaa agaagtgtgc cgactatcaa          3180
ataaatggtg aaatcatctg caaatgtggc caggcttggg gaacaatgat ggtgcacaaa          3240
ggcttagatt tgccttgtct caaaataagg aattttgtag tggttttcaa aaataattca          3300
acaaagaaac aatacaaaaa gtgggtagaa ttacctatca catttcccaa tcttgactat          3360
tcagaatgct gtttatttag tgatgaggat tagcacttga ttgaagattc ttttaaaata          3420
ctatcagtta aacatttaat atgattatga tt                                         3452
```

<210> SEQ ID NO 18
<211> LENGTH: 2540
<212> TYPE: DNA
<213> ORGANISM: homo sapien

<400> SEQUENCE: 18

```
cgccccgctg cccacctgcc cgcctgccca cctgcccagg tgcgagtgca gccccgcgcg           60
ccggcctgag agccctgtgg acaacctcgt cattgtcagg cacagagcgg tagaccctgc          120
```

```
ttctctaagt gggcagcgga cagcggcacg cacatttcac ctgtcccgca gacaacagca    180
ccatctgctt gggagaaccc tctcccttct ctgagaaaga aagatgtcga atgggtattc    240
cacagacgag aatttccgct atctcatctc gtgcttcagg gccagggtga aaatgtacat    300
ccaggtggag cctgtgctgg actacctgac ctttctgcct gcagaggtga aggagcagat    360
tcagaggaca gtcgccacct ccgggaacat gcaggcagtt gaactgctgc tgagcacctt    420
ggagaaggga gtctggcacc ttggttggac tcgggaattc gtggaggccc tccgagaac    480 cggcagccct ctggccgccc gctacatgaa ccctgagctc acggacttgc cctctccatc    540
gtttgagaac gctcatgatg aatatctcca actgctgaac ctccttcagc ccactctggt    600
ggacaagctt ctagttagag acgtcttgga taagtgcatg gaggaggaac tgttgacaat    660
tgaagacaga aaccggattg ctgctgcaga aaacaatgga aatgaatcag gtgtaagaga    720
gctactaaaa aggattgtgc agaaagaaaa ctggttctct gcatttctga atgttcttcg    780
tcaaacagga aacaatgaac ttgtccaaga gttaacaggc tctgattgct cagaaagcaa    840
tgcagagatt gagaatttat cacaagttga tggtcctcaa gtggaagagc aacttctttc    900
aaccacagtt cagccaaatc tggagaagga ggtctggggc atggagaata actcatcaga    960
atcatctttt gcagattctt ctgtagtttc agaatcagac acaagtttgg cagaaggaag   1020
tgtcagctgc ttagatgaaa gtcttggaca taacagcaac atgggcagtg attcaggcac   1080
catgggaagt gattcagatg aagagaatgt ggcagcaaga gcatccccgg agccagaact   1140
ccagctcagg ccttaccaaa tggaagttgc ccagccagcc ttggaaggga agaatatcat   1200
catctgcctc cctacaggga gtggaaaaac cagagtggct gtttacattg ccaaggatca   1260
cttagacaag aagaaaaaag catctgagcc tggaaaagtt atagttcttg tcaataaggt   1320
actgctagtt gaacagctct ccgcaagga gttccaacca tttttgaaga aatggtatcg   1380
tgttattgga ttaagtggtg atacccaact gaaaatatca tttccagaag ttgtcaagtc   1440
ctgtgatatt attatcagta cagctcaaat ccttgaaaac tccctcttaa acttggaaaa   1500
tggagaagat gctggtgttc aattgtcaga cttttccctc attatcattg atgaatgtca   1560
tcacaccaac aaagaagcag tgtataataa catcatgagg cattatttga tgcagaagtt   1620
gaaaaacaat agactcaaga aagaaaacaa accagtgatt ccccttcctc agatactggg   1680
actaacagct tcacctggtg ttggaggggc cacgaagcaa gccaaagctg aagaacacat   1740
tttaaaacta tgtgccaatc ttgatgcatt tactattaaa actgttaaag aaaaccttga   1800
tcaactgaaa aaccaaatac aggagccatg caagaagttt gccattgcag atgcaaccag   1860
agaagatcca tttaaagaga aacttctaga ataatgaca aggattcaaa cttattgtca   1920
aatgagtcca atgtcagatt ttggaactca accctatgaa caatgggcca ttcaaatgga   1980
aaaaaaagct gcaaaagaag gaaatcgcaa agaacgtgtt tgtgcagaac atttgaggaa   2040
gtacaatgag gccctacaaa ttaatgacac aattcgaatg atagatgcgt atactcatct   2100
tgaaactttc tataatgaag agaaagataa gaagtttgca gtcatagaag atgatagtga   2160
tgagggtggt gatgatgagt attgtgatgg tgatgaagat gaggatgatt taaagaaacc   2220
tttgaaactg gatgaaacag atagatttct catgactttt ttttttgaaa acaataaaat   2280
gttgaaaagg ctggctgaaa acccagaata tgaaaatgaa aagctgacca aattaagaaa   2340
taccataatg gagcaatata ctaggactga ggaatcagca cgaggaataa tctttacaaa   2400
aacacgacag agtgcatatg cgctttccca gtggattact gaaaatgaaa aatttgctga   2460
```

```
agtaggagtc aaagcccacc atctgattgg agctggacac agcagtgagt tcaaacccat      2520
gacacaaaaa aaaaaaaaaa                                                  2540
```

<210> SEQ ID NO 19
<211> LENGTH: 1025
<212> TYPE: PRT
<213> ORGANISM: homo sapien

<400> SEQUENCE: 19

```
Met Ser Asn Gly Tyr Ser Thr Asp Glu Asn Phe Arg Tyr Leu Ile Ser
1               5                   10                  15

Cys Phe Arg Ala Arg Val Lys Met Tyr Ile Gln Val Glu Pro Val Leu
            20                  25                  30

Asp Tyr Leu Thr Phe Leu Pro Ala Glu Val Lys Glu Gln Ile Gln Arg
        35                  40                  45

Thr Val Ala Thr Ser Gly Asn Met Gln Ala Val Glu Leu Leu Leu Ser
    50                  55                  60

Thr Leu Glu Lys Gly Val Trp His Leu Gly Trp Thr Arg Glu Phe Val
65                  70                  75                  80

Glu Ala Leu Arg Arg Thr Gly Ser Pro Leu Ala Ala Arg Tyr Met Asn
            85                  90                  95

Pro Glu Leu Thr Asp Leu Pro Ser Pro Ser Phe Glu Asn Ala His Asp
            100                 105                 110

Glu Tyr Leu Gln Leu Leu Asn Leu Leu Gln Pro Thr Leu Val Asp Lys
        115                 120                 125

Leu Leu Val Arg Asp Val Leu Asp Lys Cys Met Glu Glu Glu Leu Leu
    130                 135                 140

Thr Ile Glu Asp Arg Asn Arg Ile Ala Ala Ala Glu Asn Asn Gly Asn
145                 150                 155                 160

Glu Ser Gly Val Arg Glu Leu Leu Lys Arg Ile Val Gln Lys Glu Asn
            165                 170                 175

Trp Phe Ser Ala Phe Leu Asn Val Leu Arg Gln Thr Gly Asn Asn Glu
            180                 185                 190

Leu Val Gln Glu Leu Thr Gly Ser Asp Cys Ser Glu Ser Asn Ala Glu
        195                 200                 205

Ile Glu Asn Leu Ser Gln Val Asp Gly Pro Gln Val Glu Glu Gln Leu
    210                 215                 220

Leu Ser Thr Thr Val Gln Pro Asn Leu Glu Lys Glu Val Trp Gly Met
225                 230                 235                 240

Glu Asn Asn Ser Ser Glu Ser Ser Phe Ala Asp Ser Ser Val Val Ser
            245                 250                 255

Glu Ser Asp Thr Ser Leu Ala Glu Gly Ser Val Ser Cys Leu Asp Glu
            260                 265                 270

Ser Leu Gly His Asn Ser Asn Met Gly Ser Asp Ser Gly Thr Met Gly
        275                 280                 285

Ser Asp Ser Asp Glu Glu Asn Val Ala Ala Arg Ala Ser Pro Glu Pro
    290                 295                 300

Glu Leu Gln Leu Arg Pro Tyr Gln Met Glu Val Ala Gln Pro Ala Leu
305                 310                 315                 320

Glu Gly Lys Asn Ile Ile Ile Cys Leu Pro Thr Gly Ser Gly Lys Thr
            325                 330                 335

Arg Val Ala Val Tyr Ile Ala Lys Asp His Leu Asp Lys Lys Lys Lys
            340                 345                 350

Ala Ser Glu Pro Gly Lys Val Ile Val Leu Val Asn Lys Val Leu Leu
```

-continued

```
             355                 360                 365

Val Glu Gln Leu Phe Arg Lys Glu Phe Gln Pro Phe Leu Lys Lys Trp
    370                 375                 380

Tyr Arg Val Ile Gly Leu Ser Gly Asp Thr Gln Leu Lys Ile Ser Phe
385                 390                 395                 400

Pro Glu Val Val Lys Ser Cys Asp Ile Ile Ile Ser Thr Ala Gln Ile
                405                 410                 415

Leu Glu Asn Ser Leu Leu Asn Leu Glu Asn Gly Glu Asp Ala Gly Val
                420                 425                 430

Gln Leu Ser Asp Phe Ser Leu Ile Ile Ile Asp Glu Cys His His Thr
                435                 440                 445

Asn Lys Glu Ala Val Tyr Asn Asn Ile Met Arg His Tyr Leu Met Gln
    450                 455                 460

Lys Leu Lys Asn Asn Arg Leu Lys Lys Glu Asn Lys Pro Val Ile Pro
465                 470                 475                 480

Leu Pro Gln Ile Leu Gly Leu Thr Ala Ser Pro Gly Val Gly Gly Ala
                485                 490                 495

Thr Lys Gln Ala Lys Ala Glu Glu His Ile Leu Lys Leu Cys Ala Asn
                500                 505                 510

Leu Asp Ala Phe Thr Ile Lys Thr Val Lys Glu Asn Leu Asp Gln Leu
                515                 520                 525

Lys Asn Gln Ile Gln Glu Pro Cys Lys Lys Phe Ala Ile Ala Asp Ala
    530                 535                 540

Thr Arg Glu Asp Pro Phe Lys Glu Lys Leu Leu Glu Ile Met Thr Arg
545                 550                 555                 560

Ile Gln Thr Tyr Cys Gln Met Ser Pro Met Ser Asp Phe Gly Thr Gln
                565                 570                 575

Pro Tyr Glu Gln Trp Ala Ile Gln Met Glu Lys Lys Ala Ala Lys Glu
                580                 585                 590

Gly Asn Arg Lys Glu Arg Val Cys Ala Glu His Leu Arg Lys Tyr Asn
                595                 600                 605

Glu Ala Leu Gln Ile Asn Asp Thr Ile Arg Met Ile Asp Ala Tyr Thr
    610                 615                 620

His Leu Glu Thr Phe Tyr Asn Glu Glu Lys Asp Lys Lys Phe Ala Val
625                 630                 635                 640

Ile Glu Asp Asp Ser Asp Glu Gly Gly Asp Asp Glu Tyr Cys Asp Gly
                645                 650                 655

Asp Glu Asp Glu Asp Asp Leu Lys Lys Pro Leu Lys Leu Asp Glu Thr
                660                 665                 670

Asp Arg Phe Leu Met Thr Leu Phe Phe Glu Asn Asn Lys Met Leu Lys
                675                 680                 685

Arg Leu Ala Glu Asn Pro Glu Tyr Glu Asn Glu Lys Leu Thr Lys Leu
    690                 695                 700

Arg Asn Thr Ile Met Glu Gln Tyr Thr Arg Thr Glu Glu Ser Ala Arg
705                 710                 715                 720

Gly Ile Ile Phe Thr Lys Thr Arg Gln Ser Ala Tyr Ala Leu Ser Gln
                725                 730                 735

Trp Ile Thr Glu Asn Glu Lys Phe Ala Glu Val Gly Val Lys Ala His
                740                 745                 750

His Leu Ile Gly Ala Gly His Ser Ser Glu Phe Lys Pro Met Thr Gln
                755                 760                 765

Asn Glu Gln Lys Glu Val Ile Ser Lys Phe Arg Thr Gly Lys Ile Asn
    770                 775                 780
```

-continued

```
Leu Leu Ile Ala Thr Thr Val Ala Glu Glu Gly Leu Asp Ile Lys Glu
785                 790             795             800

Cys Asn Ile Val Ile Arg Tyr Gly Leu Val Thr Asn Glu Ile Ala Met
                805             810             815

Val Gln Ala Arg Gly Arg Ala Arg Ala Asp Glu Ser Thr Tyr Val Leu
            820             825             830

Val Ala His Ser Gly Ser Gly Val Ile Glu His Glu Thr Val Asn Asp
            835             840             845

Phe Arg Glu Lys Met Met Tyr Lys Ala Ile His Cys Val Gln Asn Met
    850             855             860

Lys Pro Glu Glu Tyr Ala His Lys Ile Leu Glu Leu Gln Met Gln Ser
865             870             875             880

Ile Met Glu Lys Lys Met Lys Thr Lys Arg Asn Ile Ala Lys His Tyr
                885             890             895

Lys Asn Asn Pro Ser Leu Ile Thr Phe Leu Cys Lys Asn Cys Ser Val
                900             905             910

Leu Ala Cys Ser Gly Glu Asp Ile His Val Ile Glu Lys Met His His
            915             920             925

Val Asn Met Thr Pro Glu Phe Lys Glu Leu Tyr Ile Val Arg Glu Asn
    930             935             940

Lys Ala Leu Gln Lys Lys Cys Ala Asp Tyr Gln Ile Asn Gly Glu Ile
945             950             955             960

Ile Cys Lys Cys Gly Gln Ala Trp Gly Thr Met Met Val His Lys Gly
                965             970             975

Leu Asp Leu Pro Cys Leu Lys Ile Arg Asn Phe Val Val Val Phe Lys
            980             985             990

Asn Asn Ser Thr Lys Lys Gln Tyr  Lys Lys Trp Val Glu  Leu Pro Ile
            995             1000            1005

Thr Phe  Pro Asn Leu Asp Tyr  Ser Glu Cys Cys Leu  Phe Ser Asp
    1010            1015            1020

Glu Asp
1025

<210> SEQ ID NO 20
<211> LENGTH: 986
<212> TYPE: PRT
<213> ORGANISM: homo sapien

<400> SEQUENCE: 20

Met Ser Asn Gly Tyr Ser Thr Asp Glu Asn Phe Arg Tyr Leu Ile Ser
1               5               10              15

Cys Phe Arg Ala Arg Val Lys Met Tyr Ile Gln Val Glu Pro Val Leu
            20              25              30

Asp Tyr Leu Thr Phe Leu Pro Ala Glu Val Lys Glu Gln Ile Gln Arg
            35              40              45

Thr Val Ala Thr Ser Gly Asn Met Gln Ala Val Glu Leu Leu Leu Ser
    50              55              60

Thr Leu Glu Lys Gly Val Trp His Leu Gly Trp Thr Arg Glu Phe Val
65              70              75              80

Glu Ala Leu Arg Arg Thr Gly Ser Pro Leu Ala Ala Arg Tyr Met Asn
            85              90              95

Pro Glu Leu Thr Asp Leu Pro Ser Pro Ser Phe Glu Asn Ala His Asp
            100             105             110

Glu Tyr Leu Gln Leu Leu Asn Leu Leu Gln Pro Thr Leu Val Asp Lys
```

```
                 115                  120                  125

Leu Leu Val Arg Asp Val Leu Asp Lys Cys Met Glu Glu Glu Leu Leu
    130                  135                  140

Thr Ile Glu Asp Arg Asn Arg Ile Ala Ala Ala Glu Asn Asn Gly Asn
145                  150                  155                  160

Glu Ser Gly Val Arg Glu Leu Leu Lys Arg Ile Val Gln Lys Glu Asn
                 165                  170                  175

Trp Phe Ser Ala Phe Leu Asn Val Leu Arg Gln Thr Gly Asn Asn Glu
                 180                  185                  190

Leu Val Gln Glu Leu Thr Gly Ser Asp Cys Ser Glu Ser Asn Ala Glu
                 195                  200                  205

Ile Glu Asn Leu Ser Gln Val Asp Gly Pro Gln Val Glu Glu Gln Leu
    210                  215                  220

Leu Ser Thr Thr Val Gln Pro Asn Leu Glu Lys Glu Val Trp Gly Met
225                  230                  235                  240

Glu Asn Asn Ser Ser Glu Ser Ser Phe Ala Asp Ser Ser Val Val Ser
                 245                  250                  255

Glu Ser Asp Thr Ser Leu Ala Glu Gly Ser Val Ser Cys Leu Asp Glu
                 260                  265                  270

Ser Leu Gly His Asn Ser Asn Met Gly Ser Asp Ser Gly Thr Met Gly
                 275                  280                  285

Ser Asp Ser Asp Glu Glu Asn Val Ala Ala Arg Ala Ser Pro Glu Pro
    290                  295                  300

Glu Leu Gln Leu Arg Pro Tyr Gln Met Glu Val Ala Gln Pro Ala Leu
305                  310                  315                  320

Glu Gly Lys Asn Ile Ile Ile Cys Leu Pro Thr Gly Ser Gly Lys Thr
                 325                  330                  335

Arg Val Ala Val Tyr Ile Ala Lys Asp His Leu Asp Lys Lys Lys Lys
                 340                  345                  350

Ala Ser Glu Pro Gly Lys Val Ile Val Leu Val Asn Lys Val Leu Leu
                 355                  360                  365

Val Glu Gln Leu Phe Arg Lys Glu Phe Gln Pro Phe Leu Lys Lys Trp
    370                  375                  380

Tyr Arg Val Ile Gly Leu Ser Gly Asp Thr Gln Leu Lys Ile Ser Phe
385                  390                  395                  400

Pro Glu Val Val Lys Ser Cys Asp Ile Ile Ile Ser Thr Ala Gln Ile
                 405                  410                  415

Leu Glu Asn Ser Leu Leu Asn Leu Glu Asn Gly Glu Asp Ala Gly Val
                 420                  425                  430

Gln Leu Ser Asp Phe Ser Leu Ile Ile Ile Asp Glu Cys His His Thr
                 435                  440                  445

Asn Lys Glu Ala Val Tyr Asn Asn Ile Met Arg His Tyr Leu Met Gln
    450                  455                  460

Lys Leu Lys Asn Asn Arg Leu Lys Lys Glu Asn Lys Pro Val Ile Pro
465                  470                  475                  480

Leu Pro Gln Ile Leu Gly Leu Thr Ala Ser Pro Gly Val Gly Gly Ala
                 485                  490                  495

Thr Lys Gln Ala Lys Ala Glu Glu His Ile Leu Lys Asp Pro Phe Lys
                 500                  505                  510

Glu Lys Leu Leu Glu Ile Met Thr Arg Ile Gln Thr Tyr Cys Gln Met
                 515                  520                  525

Ser Pro Met Ser Asp Phe Gly Thr Gln Pro Tyr Glu Gln Trp Ala Ile
    530                  535                  540
```

Gln Met Glu Lys Lys Ala Ala Lys Glu Gly Asn Arg Lys Glu Arg Val
545                 550                 555                 560

Cys Ala Glu His Leu Arg Lys Tyr Asn Glu Ala Leu Gln Ile Asn Asp
                565                 570                 575

Thr Ile Arg Met Ile Asp Ala Tyr Thr His Leu Glu Thr Phe Tyr Asn
                580                 585                 590

Glu Glu Lys Asp Lys Lys Phe Ala Val Ile Glu Asp Asp Ser Asp Glu
                595                 600                 605

Gly Gly Asp Asp Glu Tyr Cys Asp Gly Asp Glu Asp Glu Asp Asp Leu
            610                 615                 620

Lys Lys Pro Leu Lys Leu Asp Glu Thr Asp Arg Phe Leu Met Thr Leu
625                 630                 635                 640

Phe Phe Glu Asn Asn Lys Met Leu Lys Arg Leu Ala Glu Asn Pro Glu
                645                 650                 655

Tyr Glu Asn Glu Lys Leu Thr Lys Leu Arg Asn Thr Ile Met Glu Gln
                660                 665                 670

Tyr Thr Arg Thr Glu Glu Ser Ala Arg Gly Ile Ile Phe Thr Lys Thr
                675                 680                 685

Arg Gln Ser Ala Tyr Ala Leu Ser Gln Trp Ile Thr Glu Asn Glu Lys
            690                 695                 700

Phe Ala Glu Val Gly Val Lys Ala His His Leu Ile Gly Ala Gly His
705                 710                 715                 720

Ser Ser Glu Phe Lys Pro Met Thr Gln Asn Glu Gln Lys Glu Val Ile
                725                 730                 735

Ser Lys Phe Arg Thr Gly Lys Ile Asn Leu Leu Ile Ala Thr Thr Val
                740                 745                 750

Ala Glu Glu Gly Leu Asp Ile Lys Glu Cys Asn Ile Val Ile Arg Tyr
                755                 760                 765

Gly Leu Val Thr Asn Glu Ile Ala Met Val Gln Ala Arg Gly Arg Ala
            770                 775                 780

Arg Ala Asp Glu Ser Thr Tyr Val Leu Val Ala His Ser Gly Ser Gly
785                 790                 795                 800

Val Ile Glu His Glu Thr Val Asn Asp Phe Arg Glu Lys Met Met Tyr
                805                 810                 815

Lys Ala Ile His Cys Val Gln Asn Met Lys Pro Glu Glu Tyr Ala His
                820                 825                 830

Lys Ile Leu Glu Leu Gln Met Gln Ser Ile Met Glu Lys Lys Met Lys
                835                 840                 845

Thr Lys Arg Asn Ile Ala Lys His Tyr Lys Asn Asn Pro Ser Leu Ile
            850                 855                 860

Thr Phe Leu Cys Lys Asn Cys Ser Val Leu Ala Cys Ser Gly Glu Asp
865                 870                 875                 880

Ile His Val Ile Glu Lys Met His His Val Asn Met Thr Pro Glu Phe
                885                 890                 895

Lys Glu Leu Tyr Ile Val Arg Glu Asn Lys Ala Leu Gln Lys Lys Cys
                900                 905                 910

Ala Asp Tyr Gln Ile Asn Gly Glu Ile Ile Cys Lys Cys Gly Gln Ala
            915                 920                 925

Trp Gly Thr Met Met Val His Lys Gly Leu Asp Leu Pro Cys Leu Lys
        930                 935                 940

Ile Arg Asn Phe Val Val Val Phe Lys Asn Asn Ser Thr Lys Lys Gln
945                 950                 955                 960

```
Tyr Lys Lys Trp Val Glu Leu Pro Ile Thr Phe Pro Asn Leu Asp Tyr
            965                 970                 975

Ser Glu Cys Cys Leu Phe Ser Asp Glu Asp
            980                 985

<210> SEQ ID NO 21
<211> LENGTH: 468
<212> TYPE: PRT
<213> ORGANISM: homo sapien

<400> SEQUENCE: 21

Met Thr Arg Ile Gln Thr Tyr Cys Gln Met Ser Pro Met Ser Asp Phe
1               5                   10                  15

Gly Thr Gln Pro Tyr Glu Gln Trp Ala Ile Gln Met Glu Lys Lys Ala
                20                  25                  30

Ala Lys Glu Gly Asn Arg Lys Glu Arg Val Cys Ala Glu His Leu Arg
            35                  40                  45

Lys Tyr Asn Glu Ala Leu Gln Ile Asn Asp Thr Ile Arg Met Ile Asp
        50                  55                  60

Ala Tyr Thr His Leu Glu Thr Phe Tyr Asn Glu Glu Lys Asp Lys Lys
65                  70                  75                  80

Phe Ala Val Ile Glu Asp Asp Ser Asp Glu Gly Gly Asp Asp Glu Tyr
                85                  90                  95

Cys Asp Gly Asp Glu Asp Glu Asp Leu Lys Lys Pro Leu Lys Leu
            100                 105                 110

Asp Glu Thr Asp Arg Phe Leu Met Thr Leu Phe Phe Glu Asn Asn Lys
            115                 120                 125

Met Leu Lys Arg Leu Ala Glu Asn Pro Glu Tyr Glu Asn Glu Lys Leu
        130                 135                 140

Thr Lys Leu Arg Asn Thr Ile Met Glu Gln Tyr Thr Arg Thr Glu Glu
145                 150                 155                 160

Ser Ala Arg Gly Ile Ile Phe Thr Lys Thr Arg Gln Ser Ala Tyr Ala
                165                 170                 175

Leu Ser Gln Trp Ile Thr Glu Asn Glu Lys Phe Ala Glu Val Gly Val
            180                 185                 190

Lys Ala His His Leu Ile Gly Ala Gly His Ser Ser Glu Phe Lys Pro
        195                 200                 205

Met Thr Gln Asn Glu Gln Lys Glu Val Ile Ser Lys Phe Arg Thr Gly
        210                 215                 220

Arg Ile Asn Leu Leu Ile Ala Thr Thr Val Ala Glu Glu Gly Leu Asp
225                 230                 235                 240

Ile Lys Glu Cys Asn Ile Val Ile Arg Tyr Gly Leu Val Thr Asn Glu
                245                 250                 255

Ile Ala Met Val Gln Ala Arg Gly Arg Ala Arg Ala Asp Glu Ser Thr
            260                 265                 270

Tyr Val Leu Val Ala His Ser Gly Ser Gly Val Ile Glu Arg Glu Thr
        275                 280                 285

Val Asn Asp Phe Arg Glu Lys Met Met Tyr Lys Ala Ile His Cys Val
        290                 295                 300

Gln Asn Met Lys Pro Glu Glu Tyr Ala His Lys Ile Leu Glu Leu Gln
305                 310                 315                 320

Met Gln Ser Ile Met Glu Lys Lys Met Lys Thr Lys Arg Asn Ile Ala
                325                 330                 335

Lys His Tyr Lys Asn Asn Pro Ser Leu Ile Thr Phe Leu Cys Lys Asn
            340                 345                 350
```

```
Cys Ser Val Leu Ala Cys Ser Gly Glu Asp Ile His Val Ile Glu Lys
        355                 360                 365

Met His His Val Asn Met Thr Pro Glu Phe Lys Glu Leu Tyr Ile Val
    370                 375                 380

Arg Glu Asn Lys Thr Leu Gln Lys Lys Cys Ala Asp Tyr Gln Ile Asn
385                 390                 395                 400

Gly Glu Ile Ile Cys Lys Cys Gly Gln Ala Trp Gly Thr Met Met Val
                405                 410                 415

His Lys Gly Leu Asp Leu Pro Cys Leu Lys Ile Arg Asn Phe Val Val
                420                 425                 430

Val Phe Lys Asn Asn Ser Thr Lys Lys Gln Tyr Lys Lys Trp Val Glu
                435                 440                 445

Leu Pro Ile Thr Phe Pro Asn Leu Asp Tyr Ser Glu Cys Cys Leu Phe
        450                 455                 460

Ser Asp Glu Asp
465
```

```
<210> SEQ ID NO 22
<211> LENGTH: 772
<212> TYPE: PRT
<213> ORGANISM: homo sapien

<400> SEQUENCE: 22

Met Ser Asn Gly Tyr Ser Thr Asp Glu Asn Phe Arg Tyr Leu Ile Ser
1                   5                   10                  15

Cys Phe Arg Ala Arg Val Lys Met Tyr Ile Gln Val Glu Pro Val Leu
                20                  25                  30

Asp Tyr Leu Thr Phe Leu Pro Ala Glu Val Lys Glu Gln Ile Gln Arg
            35                  40                  45

Thr Val Ala Thr Ser Gly Asn Met Gln Ala Val Glu Leu Leu Leu Ser
    50                  55                  60

Thr Leu Glu Lys Gly Val Trp His Leu Gly Trp Thr Arg Glu Phe Val
65                  70                  75                  80

Glu Ala Leu Arg Arg Thr Gly Ser Pro Leu Ala Ala Arg Tyr Met Asn
                85                  90                  95

Pro Glu Leu Thr Asp Leu Pro Ser Pro Ser Phe Glu Asn Ala His Asp
            100                 105                 110

Glu Tyr Leu Gln Leu Leu Asn Leu Leu Gln Pro Thr Leu Val Asp Lys
        115                 120                 125

Leu Leu Val Arg Asp Val Leu Asp Lys Cys Met Glu Glu Glu Leu Leu
    130                 135                 140

Thr Ile Glu Asp Arg Asn Arg Ile Ala Ala Ala Glu Asn Asn Gly Asn
145                 150                 155                 160

Glu Ser Gly Val Arg Glu Leu Leu Lys Arg Ile Val Gln Lys Glu Asn
                165                 170                 175

Trp Phe Ser Ala Phe Leu Asn Val Leu Arg Gln Thr Gly Asn Asn Glu
            180                 185                 190

Leu Val Gln Glu Leu Thr Gly Ser Asp Cys Ser Glu Ser Asn Ala Glu
        195                 200                 205

Ile Glu Asn Leu Ser Gln Val Asp Gly Pro Gln Val Glu Glu Gln Leu
    210                 215                 220

Leu Ser Thr Thr Val Gln Pro Asn Leu Glu Lys Glu Val Trp Gly Met
225                 230                 235                 240

Glu Asn Asn Ser Ser Glu Ser Ser Phe Ala Asp Ser Ser Val Val Ser
```

```
                 245              250              255

Glu Ser Asp Thr Ser Leu Ala Glu Gly Ser Val Ser Cys Leu Asp Glu
             260              265              270

Ser Leu Gly His Asn Ser Asn Met Gly Ser Asp Ser Gly Thr Met Gly
             275              280              285

Ser Asp Ser Asp Glu Glu Asn Val Ala Ala Arg Ala Ser Pro Glu Pro
             290              295              300

Glu Leu Gln Leu Arg Pro Tyr Gln Met Glu Val Ala Gln Pro Ala Leu
305              310              315              320

Glu Gly Lys Asn Ile Ile Ile Cys Leu Pro Thr Gly Ser Gly Lys Thr
                 325              330              335

Arg Val Ala Val Tyr Ile Ala Lys Asp His Leu Asp Lys Lys Lys Lys
                 340              345              350

Ala Ser Glu Pro Gly Lys Val Ile Val Leu Val Asn Lys Val Leu Leu
                 355              360              365

Val Glu Gln Leu Phe Arg Lys Glu Phe Gln Pro Phe Leu Lys Lys Trp
             370              375              380

Tyr Arg Val Ile Gly Leu Ser Gly Asp Thr Gln Leu Lys Ile Ser Phe
385              390              395              400

Pro Glu Val Val Lys Ser Cys Asp Ile Ile Ile Ser Thr Ala Gln Ile
                 405              410              415

Leu Glu Asn Ser Leu Leu Asn Leu Glu Asn Gly Glu Asp Ala Gly Val
                 420              425              430

Gln Leu Ser Asp Phe Ser Leu Ile Ile Ile Asp Glu Cys His His Thr
                 435              440              445

Asn Lys Glu Ala Val Tyr Asn Asn Ile Met Arg His Tyr Leu Met Gln
             450              455              460

Lys Leu Lys Asn Asn Arg Leu Lys Lys Glu Asn Lys Pro Val Ile Pro
465              470              475              480

Leu Pro Gln Ile Leu Gly Leu Thr Ala Ser Pro Gly Val Gly Gly Ala
                 485              490              495

Thr Lys Gln Ala Lys Ala Glu Glu His Ile Leu Lys Leu Cys Ala Asn
                 500              505              510

Leu Asp Ala Phe Thr Ile Lys Thr Val Lys Glu Asn Leu Asp Gln Leu
                 515              520              525

Lys Asn Gln Ile Gln Glu Pro Cys Lys Lys Phe Ala Ile Ala Asp Ala
             530              535              540

Thr Arg Glu Asp Pro Phe Lys Glu Lys Leu Leu Glu Ile Met Thr Arg
545              550              555              560

Ile Gln Thr Tyr Cys Gln Met Ser Pro Met Ser Asp Phe Gly Thr Gln
                 565              570              575

Pro Tyr Glu Gln Trp Ala Ile Gln Met Glu Lys Lys Ala Ala Lys Glu
             580              585              590

Gly Asn Arg Lys Glu Arg Val Cys Ala Glu His Leu Arg Lys Tyr Asn
             595              600              605

Glu Ala Leu Gln Ile Asn Asp Thr Ile Arg Met Ile Asp Ala Tyr Thr
             610              615              620

His Leu Glu Thr Phe Tyr Asn Glu Glu Lys Asp Lys Lys Phe Ala Val
625              630              635              640

Ile Glu Asp Asp Ser Asp Glu Gly Gly Asp Asp Glu Tyr Cys Asp Gly
                 645              650              655

Asp Glu Asp Glu Asp Asp Leu Lys Lys Pro Leu Lys Leu Asp Glu Thr
             660              665              670
```

```
Asp Arg Phe Leu Met Thr Leu Phe Phe Glu Asn Asn Lys Met Leu Lys
        675                 680                 685

Arg Leu Ala Glu Asn Pro Glu Tyr Glu Asn Glu Lys Leu Thr Lys Leu
        690                 695                 700

Arg Asn Thr Ile Met Glu Gln Tyr Thr Arg Thr Glu Glu Ser Ala Arg
705                 710                 715                 720

Gly Ile Ile Phe Thr Lys Thr Arg Gln Ser Ala Tyr Ala Leu Ser Gln
                725                 730                 735

Trp Ile Thr Glu Asn Glu Lys Phe Ala Glu Val Gly Val Lys Ala His
            740                 745                 750

His Leu Ile Gly Ala Gly His Ser Ser Glu Phe Lys Pro Met Thr Gln
        755                 760                 765

Lys Lys Lys Lys
    770
```

```
<210> SEQ ID NO 23
<211> LENGTH: 221
<212> TYPE: PRT
<213> ORGANISM: homo sapien

<400> SEQUENCE: 23

Met Ser Asn Gly Tyr Ser Thr Asp Glu Asn Phe Arg Tyr Leu Ile Ser
1               5                   10                  15

Cys Phe Arg Ala Arg Val Lys Met Tyr Ile Gln Val Glu Pro Val Leu
                20                  25                  30

Asp Tyr Leu Thr Phe Leu Pro Ala Glu Val Lys Glu Gln Ile Gln Arg
        35                  40                  45

Thr Val Ala Thr Ser Gly Asn Met Gln Ala Val Glu Leu Leu Leu Ser
    50                  55                  60

Thr Leu Glu Lys Gly Val Trp His Leu Gly Trp Thr Arg Glu Phe Val
65                  70                  75                  80

Glu Ala Leu Arg Arg Thr Gly Ser Pro Leu Ala Ala Arg Tyr Met Asn
                85                  90                  95

Pro Glu Leu Thr Asp Leu Pro Ser Pro Ser Phe Glu Asn Ala His Asp
            100                 105                 110

Glu Tyr Leu Gln Leu Leu Asn Leu Leu Gln Pro Thr Leu Val Asp Lys
        115                 120                 125

Leu Leu Val Arg Asp Val Leu Asp Lys Cys Met Glu Glu Glu Leu Leu
    130                 135                 140

Thr Ile Glu Asp Arg Asn Arg Ile Ala Ala Ala Glu Asn Asn Gly Asn
145                 150                 155                 160

Glu Ser Gly Val Arg Glu Leu Leu Lys Arg Ile Val Gln Lys Glu Asn
                165                 170                 175

Trp Phe Ser Ala Phe Leu Asn Val Leu Arg Gln Thr Gly Asn Asn Glu
            180                 185                 190

Leu Val Gln Glu Leu Thr Gly Ser Asp Cys Ser Glu Ser Asn Ala Gly
        195                 200                 205

Ile Cys Asn Phe Thr Glu Glu Asp Ser Ser Asn Ser Ala
    210                 215                 220
```

```
<210> SEQ ID NO 24
<211> LENGTH: 23
<212> TYPE: DNA
<213> ORGANISM: artificial sequence
<220> FEATURE:
<223> OTHER INFORMATION: gRNA Recognition Sequence
```

-continued

<400> SEQUENCE: 24
gcaatggcaa acttcttgca tgg                                                           23

<210> SEQ ID NO 25
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 25
agatgcaacc agagaagtat ggg                                                           23

<210> SEQ ID NO 26
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 26
cagatgcaac cagagaagta tgg                                                           23

<210> SEQ ID NO 27
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 27
tactacattc agtagaaaga tgg                                                           23

<210> SEQ ID NO 28
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 28
tcaactgaaa aaccaaatac agg                                                           23

<210> SEQ ID NO 29
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 29
ttctctggtt gcatctgcaa tgg                                                           23

<210> SEQ ID NO 30
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 30
attcagtaga aagatggcaa agg                                                           23

<210> SEQ ID NO 31

-continued

```
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 31
acattaagcc catacttctc tgg                                              23

<210> SEQ ID NO 32
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 32
tcttgcatgg ctcctgtatt tgg                                              23

<210> SEQ ID NO 33
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 33
tttggttttt cagttgatca agg                                              23

<210> SEQ ID NO 34
<211> LENGTH: 23
<212> TYPE: DNA
<213> ORGANISM: artificial sequence
<220> FEATURE:
<223> OTHER INFORMATION: gRNA Recognition Sequence

<400> SEQUENCE: 34
tttaaataat atttttcaga tgg                                              23
```